(12) United States Patent
Higgins et al.

(10) Patent No.: US 11,993,784 B2
(45) Date of Patent: *May 28, 2024

(54) TRANSPOSITION-BASED THERAPIES

(71) Applicant: Saliogen Therapeutics, Inc., Cambridge, MA (US)

(72) Inventors: Joseph J. Higgins, Cambridge, MA (US); Scott McMillan, Cambridge, MA (US); Ray Tabibiazar, Cambridge, MA (US)

(73) Assignee: Saliogen Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/192,382

(22) Filed: Mar. 29, 2023

(65) Prior Publication Data

US 2023/0250454 A1 Aug. 10, 2023

Related U.S. Application Data

(63) Continuation of application No. 18/058,486, filed on Nov. 23, 2022, which is a continuation of application No. 17/669,939, filed on Feb. 11, 2022, now Pat. No. 11,542,528, which is a continuation of application No. PCT/US2021/030729, filed on May 4, 2021.

(60) Provisional application No. 63/175,345, filed on Apr. 15, 2021, provisional application No. 63/058,200, filed on Jul. 29, 2020, provisional application No. 63/027,561, filed on May 20, 2020, provisional application No. 63/019,709, filed on May 4, 2020.

(51) Int. Cl.
*C12N 15/90* (2006.01)
*C12N 9/12* (2006.01)
*C12N 9/22* (2006.01)

(52) U.S. Cl.
CPC ........... *C12N 15/90* (2013.01); *C12N 9/1241* (2013.01); *C12N 9/22* (2013.01); *C07K 2319/80* (2013.01)

(58) Field of Classification Search
CPC ..... C12N 15/90–15/907; C12N 9/1241; C07K 2319/80
See application file for complete search history.

(56) References Cited

U.S. PATENT DOCUMENTS

| | | |
|---|---|---|
| 8,399,643 B2 | 3/2013 | Ostertag et al. |
| 8,420,782 B2 | 4/2013 | Bonas et al. |
| 8,470,973 B2 | 6/2013 | Bonas et al. |
| 8,586,526 B2 | 11/2013 | Gregory et al. |
| 8,912,138 B2 | 12/2014 | Gregory et al. |
| 9,017,967 B2 | 4/2015 | Bonas et al. |
| 9,200,045 B2 | 12/2015 | Liu et al. |
| 9,353,378 B2 | 5/2016 | Bonas et al. |
| 9,388,430 B2 | 7/2016 | Liu et al. |
| 9,428,767 B2 | 8/2016 | Minshull et al. |
| 9,453,054 B2 | 9/2016 | Bonas et al. |
| 9,493,750 B2 | 11/2016 | Gregory et al. |
| 9,534,234 B2 | 1/2017 | Minshull et al. |
| 9,574,209 B2 | 2/2017 | Minshull et al. |
| 9,580,697 B2 | 2/2017 | Minshull et al. |
| 9,670,503 B2 | 6/2017 | Craig |
| 9,783,790 B2 | 10/2017 | Craig |
| 9,809,628 B2 | 11/2017 | Bonas et al. |
| 10,041,077 B2 | 8/2018 | Minshull et al. |
| 10,131,885 B2 | 11/2018 | Ostertag et al. |
| 10,233,454 B2 | 3/2019 | Minshull et al. |
| 10,287,559 B2 | 5/2019 | Ostertag et al. |
| 10,344,285 B2 | 7/2019 | Minshull et al. |
| 10,415,022 B2 | 9/2019 | Craig |
| 10,435,696 B2 | 10/2019 | Minshull et al. |
| 10,533,190 B2 | 1/2020 | Doudna et al. |
| 10,550,407 B2 | 2/2020 | Doudna et al. |
| 10,793,878 B1 | 10/2020 | Doudna et al. |
| 10,900,054 B2 | 1/2021 | Doudna et al. |
| 10,927,384 B2 | 2/2021 | Minshull et al. |
| 11,060,086 B2 | 7/2021 | Minshull et al. |
| 11,060,098 B2 | 7/2021 | Minshull et al. |
| 11,060,109 B2 | 7/2021 | Minshull et al. |
| 11,162,102 B2 | 11/2021 | Minshull et al. |
| 2006/0210977 A1 | 9/2006 | Kaminski |
| 2009/0042297 A1 | 2/2009 | George, Jr. et al. |
| 2011/0047635 A1 | 2/2011 | Moisyadi et al. |

FOREIGN PATENT DOCUMENTS

| | | | |
|---|---|---|---|
| WO | WO 2008/100424 A2 | 8/2008 | |
| WO | WO 2010/085699 A2 | 7/2010 | |
| WO | WO 2010/099301 A2 | 9/2010 | |
| WO | WO 2013/012824 A2 | 1/2013 | |
| WO | WO 2015/157611 A2 | 10/2015 | |
| WO | WO 2016/172703 A2 | 10/2016 | |
| WO | WO-2018112415 A1 * | 6/2018 | ............. A61K 35/17 |
| WO | WO 2019/108932 A1 | 6/2019 | |
| WO | WO 2020/077357 A1 | 4/2020 | |
| WO | WO 2020/077360 A1 | 4/2020 | |
| WO | WO 2020/163755 A1 | 8/2020 | |
| WO | WO 2021/222653 A1 | 11/2021 | |
| WO | WO 2021/222654 A1 | 11/2021 | |

OTHER PUBLICATIONS

Schuitemaker et al. Clinical significance of HIV-1 coreceptor usage. Journal of Translational Medicine, vol. 9, Suppl 1, S5, 2010, printed as pp. 1/17-17/17. (Year: 2010).*

(Continued)

*Primary Examiner* — Jennifer Dunston

(74) *Attorney, Agent, or Firm* — Morgan, Lewis & Bockius LLP

(57) ABSTRACT

Gene therapy compositions and methods are provided that make use of novel transposases and/or chimeric transposases for targeted transposition.

28 Claims, 81 Drawing Sheets

Specification includes a Sequence Listing.

(56) References Cited

OTHER PUBLICATIONS

Pellenz et al. New human chromosomal sites with "Safe Harbor" potential for targeted transgene insertion. Human Gene Therapy, vol. 30, No. 7, pp. 814-828, Feb. 21, 2019. (Year: 2019).*
International Search Report & Written Opinion PCT Application No. PCT/US21/30729, dated Oct. 22, 2021, 12 pages.
Aboye, et al., "Biological Synthesis of Circular Polypeptides," The Journal of Biological Chemistry, vol. 287, No. 32, pp. 27026-27032, Aug. 2012.
Aguirre, "Concepts and Strategies in Retinal Gene Therapy," IOVS, vol. 58, No. 12, pp. 5399-5411, 2017.
Alexopoulou, et al., "The CMV early enhancer/chicken β actin (CAG) promoter can be used to drive transgene expression during the differentiation of murine embryonic stem cells into vascular progenitors," BMC Cell Biology, 2008, 9:2, 11 pages.
Balasubramanian, et al., "Generation of High Expressing Chinese Hamster Ovary Cell Pools Using the Leap-In Transposon System," Biotechnology Journal, vol. 13, No. 10, doi.org/10.1002/biot. 201700748, 2018.
Baldrick, "Pharmaceutical Excipient Development: The Need for Preclinical Guidance," Regulatory Toxicology and Pharmacology, vol. 32, No. 2, pp. 210-218, 2000.
Bejerano, et al., "Ultraconserved Elements in the Human Genome," Science, vol. 304, No. 5675, pp. 1321-1325, 2004.
Boch, et al., "TALEs of genome targeting," Nature Biotechnology, vol. 29, pp. 135-136, 2011.
Bouallègue, et al., "Molecular Evolution of piggyBac Superfamily: From Selfishness to Domestication," Genome Biol. Evol., vol. 9, No. 2, pp. 323-339, 2017.
Burnight, et al., "A Hyperactive Transposase Promotes Persistent Gene Transfer of a piggyBac DNA Transposon," Molecular Therapy—Nucleic Acids (2012) 1, e5.
Buskirk, et al., "Directed evolution of ligand dependence: Small-molecule-activated protein splicing," PNAS, vol. 101, No. 29, pp. 10505-10510, Jul. 2004.
Campos-Sanchez, et al., "Genomic Landscape of Human, Bat, and Ex Vivo DNA Transposon Integrations," Mol. Biol. Evol., vol. 31, No. 7, pp. 1816-1832, Apr. 2014.
Charman, "Lipids, Lipophilic Drugs, and Oral Drug Delivery—Some Emerging Concepts," Journal of Pharmaceutical Sciences, vol. 89, No. 8, pp. 967-978, 2000.
Chylinski, et al., "Classification and evolution of type II CRISPR-Cas systems," Nucleic Acid Research, vol. 42, No. 10, pp. 6091-6105, 2014.
De Palmenaer, et al., "IS4 family goes genomic," BMC Evolutionary Biology, 8:18, doi: 10.1186/1471-2148-8-18, Jan. 2008.
Di Polo, et al., "Transcriptional activation of the human rod cGMP-phosphodiesterase β-subunit gene is mediated by an upstream AP-1 element," Nucleic Acids Research, vol. 25, No. 19, pp. 3863-3867, 1997.
Dominguez, et al., "Beyond editing: repurposing CRISPR—Cas9 for precision genome regulation and interrogation," Nat Rev Mol Cell Biol., vol. 17, No. 1, pp. 5-15, Jan. 2016.
Fischer, et al., "Regulated transposition of a fish transposon in the mouse germ line," PNAS, vol. 98, No. 12, pp. 6759-6764, Jun. 2001.
Hernandez, et al., "Latent Adeno-Associated Virus Infection Elicits Humoral but Not Cell-Mediated Immune Responses in a Nonhuman Primate Model," Journal of Virology, vol. 73, No. 10, pp. 8549-8558, Oct. 1999.
Hew, et al., "RNA-guided piggyBac transposition in human cells," Synthetic Biology, vol. 4, No. 1, 12 pages, 2019.
Hockemeyer, et al., "Highly efficient gene targeting of expresses and silent genes in human ESCs and iPSCs using zinc finger nucleases," Nat Biotechnol., vol. 27, No. 9, pp. 851-857, Sep. 2009.
Hottentot, et al., "Targeted Locus Amplification and Next-Generation Sequencing," Genotyping, Methods in Molecular Biology, vol. 1492. Humana Press, New York, NY. https://doi.org/10.1007/978-1-4939-6442-0_13. 2017.

Ivics, et al., "Molecular Reconstruction of Sleeping Beauty, a Tc1-like Transposon from Fish, and Its Transposition in Human Cells," Cell. vol. 91, pp. 501-510, 1997.
Jebb, et al., "Six reference-quality genomes reveal evolution of bat adaptations," Nature, vol. 583, pp. 578-584, 2020.
Jin, et al., "The hyperactive Sleeping Beauty tranposase SB100X improves the genetic modification of T cells to express a chimeric antigen receptor," Gene Therapy, vol. 18, pp. 849-856, 2011.
Jinek, et al., "A Programmable Dual-RNA—Guided DNA Endonuclease in Adaptive Bacterial Immunity," Science, vol. 337, pp. 816-821, Aug. 2012.
Joung, et al., "TALENs: a widely applicable technology for targeted genome editing," Nat Rev Mol Cell Biol., vol. 14, No. 1, pp. 49-55, Jan. 2013.
Kan, et al., "The Evaluation of Novel Photoreceptor Specific Promoters in an EIAV Lentiviral Vector for TargetedGene Expression in the Photoreceptors of the Eye," Molecular Therapy, vol. 15, Suppl. 1, S258, May 1, 2007.
Kay, et al., "Transient immunomodulation with anti-CD40 ligand antibody and CTLA4Ig enhances persistence and secondary adenovirus-mediated gene transfer into mouse liver," PNAS, vol. 94, No. 9, pp. 4686-4691, Apr. 1997.
Kettlun, et al., "Manipulating piggyBac Transposon Chromosomal Integration Site Selection in Human Cells," Molecular Therapy, vol. 19, No. 9, pp. 1636-1644, 2011.
Khani, et al., "AAV-Mediated Expression Targeting of Rod and Cone Photoreceptors with a Human Rhodopsin Kinase Promoter," IOVS, vol. 48, pp. 3954-3961, 2007.
Klompe, et al., "Transposon-encoded CRISPR—Cas systems direct RNA-guided DNA integration," Nature, vol. 571, pp. 219-225, 2019.
Kosugi, et al., "Six Classes of Nuclear Localization Signals Specific to Different Binding Grooves of Importin α," The Journal of Biological Chemistry, vol. 284, No. 1, pp. 478-485, 2009.
Lestini, et al., "Surface modification of liposomes for selective cell targeting in cardiovascular drug delivery," Journal of Controlled Release, vol. 78, pp. 235-247, Jan. 2002.
Li, et al., "Cone-specific expression using a human red opsin promoter in recombinant AAV," Vision Research, vol. 48, pp. 332-338, 2008.
Lobritz, et al., "HIV-1 Entry, Inhibitors, and Resistance," Viruses 2010, vol. 2, pp. 1069-1105.
Luo, et al., "Comparative analysis of chimeric ZFP-, TALE- and Cas9-piggyBac transposases for integration into a single locus in human cells," Nucleic Acids Research, vol. 45, No. 14, pp. 8411-8422, 2017.
Mcdougald, et al., "CRISPR Activation Enhances In Vitro Potency of AAV Vectors Driven by Tissue-SpecificPromoters," Mol Ther Methods Clin Dev. Vol. 13, pp. 380-389, 2019.
Miller, et al., "A TALE nuclease architecture for efficient genome editing," Nature Biotechnology, vol. 29, pp. 143-148, 2011.
Mitra, et al., "piggyBac can bypass DNA synthesis during cut and paste transposition," The EMBO Journal, vol. 27, No. 7, pp. 1097-1109, 2008.
Mitra, et al., "Functional characterization of piggyBat from the bat Myotis lucifugus unveils an active mammalianDNA transposon," PNAS, vol. 110, No. 1, pp. 234-239, Jan. 2013.
Moldt, et al., "Cis-acting gene regulatory activities in the terminal regions of sleeping beauty DNA transposon-based vectors," Hum Gene Ther., vol. 18, No. 12, pp. 1193-1204, 2007.
Mootz, et al., "Protein Splicing Triggered by a Small Molecule," J. Am. Chem. Soc., vol. 124, No. 31, pp. 9044-9045, 2002.
Mootz, et al., "Conditional Protein Splicing: A New Tool to Control Protein Structure and Function in Vitro and in Vivo," J. Am. Chem. Soc., vol. 125, No. 35, pp. 10561-10569, 2003.
Nanda, et al., "Inteins in Science: Evolution to Application," Microorganisms, vol. 8, 20 pages, Dec. 2004.
Nathwani, et al., "Self-complementary adeno-associated virus vectors containing a novel liver-specific human factor IX expression cassette enable highly efficient transduction of murine and nonhuman primate liver," Blood, vol. 107, No. 7, pp. 2653-2661, Apr. 2006.

(56) References Cited

OTHER PUBLICATIONS

Owens, et al., "Chimeric piggyBac transposases for genomic targeting in human cells," Nucleic Acids Research, vol. 40, No. 14, pp. 6978-6991, 2012.
Owens, et al., "Transcription activator like effector (TALE)-directed piggyBac transposition in human cells," Nucelic Acids Research, vol. 41, No. 19, pp. 9197-9207, 2013.
Owens, et al., "Novel Piggybac Transposase Vectors For Safer Gene Addition Into Mammalian Genomes," Disseration, 177 pages, May 2014.
Papapetrou, et al., "Genomic safe harbors permit high β-globin transgene expression in thalassemia induced pluripotent stem cells," Nat Biotechnol., vol. 29, No. 1, pp. 73-78, Jan. 2011.
Patel, et al., "Lipid nanoparticles for delivery of messenger RNA to the back of the eye," Journal of Controlled Release, vol. 303, pp. 91-100, Jun. 2019.
Peck, et al., "Directed Evolution of a Small-Molecule-Triggered Intein with Improved Splicing Properties in Mammalian Cells," Chemistry & Biology, vol. 18, pp. 619-630, 2011.
Pellenz, et al., "New Human Chromosomal Sites with "Safe Harbor" Potential for Targeted Transgene Insertion," Human Gene Therapy, vol. 30, No. 7, pp. 814-828, Jul. 2019.
Plasterk, et al., "Resident aliens: the Tc1/mariner superfamily of transposable elements," Trends in Genetics, vol. 15, No. 8, pp. 326-332, 1999.
Powell, et al., "Compendium of excipients for parenteral formulations," PDA J Pharm Sci Technol. Vol. 52, No. 5, pp. 238-311, 1998.
Qi, et al., "Repurposing CRISPR as an RNA-Guided Platform for SequenceSpecific Control of Gene Expression," Cell, vol. 152, No. 5, pp. 1173-1183, Feb. 2013.
Ray, et al., "Bats with hATs: Evidence for Recent DNA Transposon Activity in Genus Myotis," Mol Biol Evol, vol. 24, No. 3, pp. 632-639, 2007. DOI: 10.1093/molbev/msl192.
Ray, et al., "Multiple waves of recent DNA transposon activity in the bat, Myotis lucifugus," Genome Research, vol. 18, pp. 717-728, 2008.
Rivel-Gervier, et al., "Kinetics and Epigenetics of Retroviral Silencing in Mouse Embryonic Stem Cells Defined by Deletion of the D4Z4 Element," Molecular Therapy, vol. 21, No. 8, pp. 1536-1550, 2013.
Sarmiento, et al., "Biotechnological applications of protein splicing," Curr Protein Pept Sci., vol. 20, No. 5, pp. 408-424, 2019.
Schwartz, et al., "Post-translational enzyme activation in an animal via optimized conditional protein splicing," Nature Chemical Biology, vol. 3, pp. 50-54, 2007.
Skretas, et al., "Regulation of protein activity with small-molecule-controlled inteins," Protein Science, vol. 14, pp. 523-532, 2005.
Streubel, et al., "TAL effector RVD specificities and efficiencies," Nature Biotechnology, vol. 30, pp. 593-595, 2012.
Tebas, et al., "Gene Editing of CCR5 in Autologous CD4 T Cells of Persons Infected with HIV," The New England Journal of Medicine, vol. 370, No. 10, pp. 901-910, 2014.
Tipanee, et al., "Moving Forward from Preclinical Studies to Clinical Trials," Human Gene Therapy, vol. 28, No. 11, pp. 1087-1104, 2017.
Truong, et al., "Development of an intein-mediated split—Cas9 system for gene therapy," Nucleic Acids Research, vol. 43, No. 13, pp. 6450-6458, Jun. 2015.
Urschitz, et al., "Helper-independent piggyBac plasmids for gene delivery approaches: Strategies for avoiding potential genotoxic effects," PNAS, vol. 107, No. 8, pp. 8117-8122, 2010.
Voight, et al., "Sleeping Beauty transposase structure allows rational design of hyperactive variants for genetic Engineering," Nature Communications. vol. 7, Article No. 11126, 2016.
Wang, "Lyophilization and development of solid protein pharmaceuticals," International Journal of Pharmaceutics, vol. 203, pp. 1-60, 2000.
Wang, et al., "CRISPR/Cas9 in Genome Editing and Beyond," Annu Rev Biochem., vol. 85, pp. 227-264, Jun. 2016.
Wilber, et al., "RNA as a Source of Transposase for Sleeping Beauty-Mediated Gene Insertion and Expression in Somatic Cells and Tissues," Molecular Therapy, vol. 13, No. 3, pp. 625-630, 2006.
Wood, et al., "Intein Applications: From Protein Purification and Labeling to Metabolic Control Methods," The Journal of Biological Chemistry, vol. 289, No. 21, pp. 14512-14519, May 2014.
Woodard, et al., "piggyBac-ing models and new therapeutic strategies," Trends Biotechnol., vol. 33, No. 9, pp. 525-533, 2015.
Ye, et al., "AL effectors mediate high-efficiency transposition of the piggyBac transposon in silkworm *Bombyx mori* L," Scientifice Reports, vol. 5:17172, 10 pages, doi: 10.1038/srep17172, Nov. 2015.
Yusa, et al., "A hyperactive piggyBac transposase for mammalian applications," PNAS, vol. 108, No. 4, pp. 1531-1536, Jan. 2011.

* cited by examiner

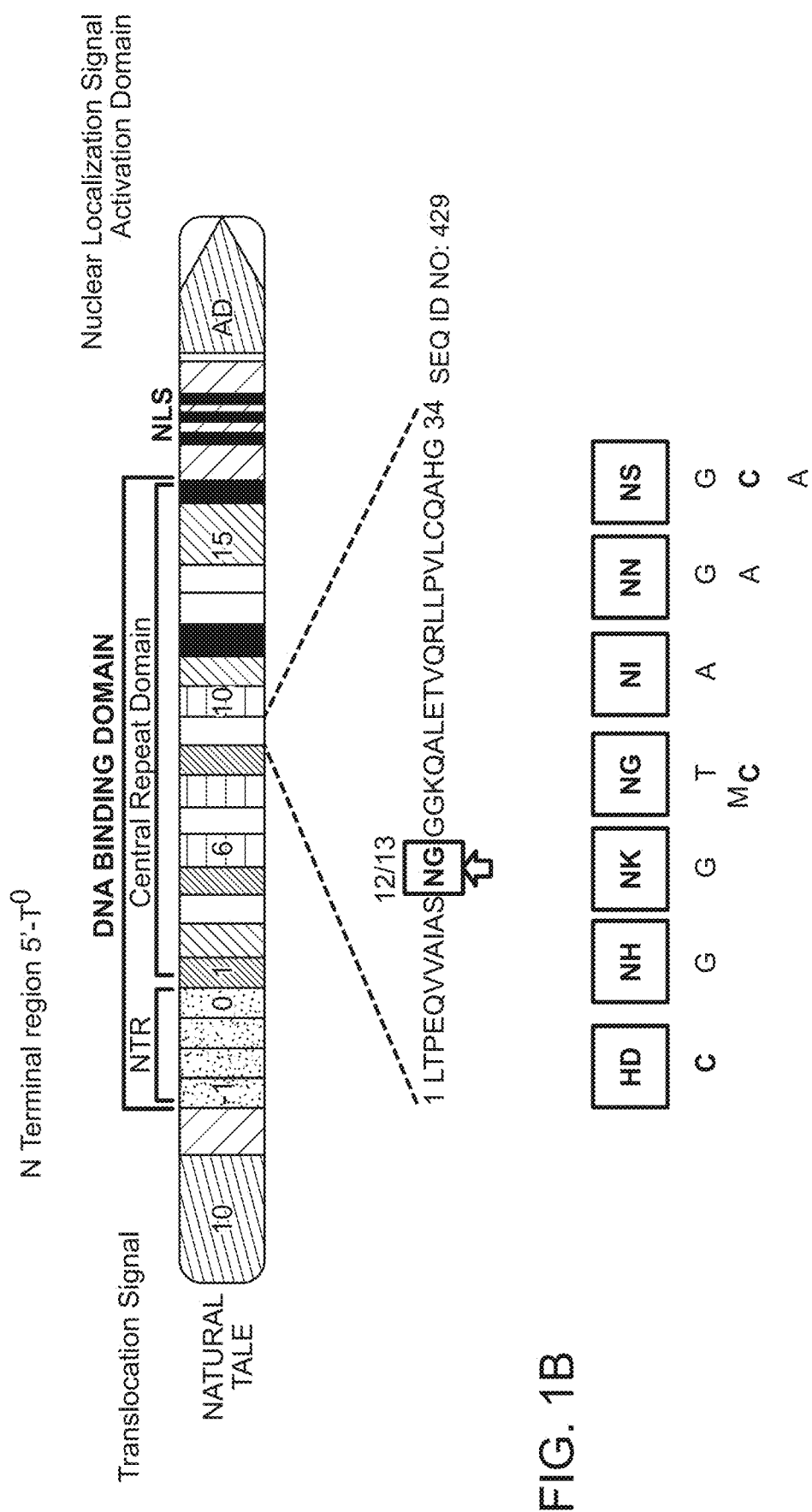

FIG. 3
DNA binding codes for human genomic safe harbor in areas of open chromatin

| GSHS | ID | Sequence | TALE (DNA binding code) |
|---|---|---|---|
| AAVS1 | 1 | TGGCCGGCCTGACCACTGG (SEQ ID NO: 23) | NH NH HD HD NH NH HD NG NH HD HD NI HD NG NH NH |
| AAVS1 | 2 | TGAAGGCCTGGCCGGCCTG (SEQ ID NO: 24) | NH NI NI NH NH HD NG NH NH HD HD NH HD NG NH |
| AAVS1 | 3 | TGAGCACTGAAGGCCTGGC (SEQ ID NO: 25) | NH NI NH HD NI NH HD NG NH NI NH NH HD HD NG NH NH HD |
| AAVS1 | 4 | TCCACTGAGCACTGAAGGC (SEQ ID NO: 26) | HD HD NI HD NG NH NI NH NI HD NG NH NI NH NH HD |
| AAVS1 | 5 | TGGTTTCCACTGAGCACTG (SEQ ID NO: 27) | NH NH NG NG NH NH HD HD NI HD NG NH NI HD NG NH |
| AAVS1 | 6 | TGGGGAAAATGACCCAACA (SEQ ID NO: 28) | NH NH NH NH NI NI NI NG NH HD HD HD NI HD NI |
| AAVS1 | 7 | TAGGACAGTGGGGAAAATG (SEQ ID NO: 29) | NI NH NH NH HD NI NH NG NH NH NH NI NI NG NH |
| AAVS1 | 8 | TCCAGGGACACGGTGCTAG (SEQ ID NO: 30) | HD HD NI NH NH NH HD NI HD NI HD NH NH NG NI NH |
| AAVS1 | 9 | TCAGAGCCAGGAGTCCTGG (SEQ ID NO: 31) | HD NI NH NI NH HD HD NI NH NH NI NH NG HD NG NH |
| AAVS1 | 10 | TCCTTCAGAGCCAGGAGTC (SEQ ID NO: 32) | HD HD NG NG HD NI NH NI NH HD HD NI NH NH NI NH HD |
| AAVS1 | 11 | TCCTCCTTCAGAGCCAGGA (SEQ ID NO: 33) | HD HD NG HD HD NG NG HD NI NH NI NH HD HD NH NH NI |
| AAVS1 | 12 | TCCAGCCCTCCTCCTTCA (SEQ ID NO: 34) | HD HD NI NH HD HD HD NG HD HD NG HD HD NG HD NG NI |
| AAVS1 | 13 | TCCGAGCTTGACCCTTGGA (SEQ ID NO: 35) | HD HD NH NI NH HD NG NG NH NI HD HD HD NG NG NH NI |
| AAVS1 | 14 | TGGTTTCCGAGCTTGACCC (SEQ ID NO: 36) | NH NH NG NG NG HD HD NH NI NH HD NG NG NI HD HD HD |

FIG. 3 (Cont.)

| Gene | Name | Sequence | RVDs |
|---|---|---|---|
| AAVS1 | 15 | TGGGGTGGTTCCGAGCTT (SEQ ID NO: 37) | NH NH NH NH NG NH NG NG HD NH NG HD NG NG |
| AAVS1 | 16 | TCTGCTGGGTGGTTTCCG (SEQ ID NO: 38) | HD NG NH HD NG NG NH NH NG NG NG HD NG NH |
| AAVS1 | 17 | TGCAGAGTATCTGCTGGGG (SEQ ID NO: 39) | NH HD NI NH NI NG HD NG NH HD NG NG NH NH NH |
| AAVS1 | AVS1 | CCAATCCCCTCAGT (SEQ ID NO: 40) | HD HD NI NI NG HD HD HD HD NG NI NH NG |
| AAVS1 | AVS2 | CAGTGCTCAGTGGAA (SEQ ID NO: 41) | HD NI NH NG NH HD NG HD NI NH NG NH NI NI |
| AAVS1 | AVS3 | GAAACATCCGGCGACTCA (SEQ ID NO: 42) | NH NI NI NI HD NI NG HD NH NH HD NH NH HD NG NG |
| hROSA26 | 1F | TCGCCCCTCAAATCTTACA (SEQ ID NO: 43) | HD NH HD HD HD HD NI NG HD NI NI NG HD NG NI HD NI |
| hROSA26 | 2F | TCAAATCTTACAGCTGCTC (SEQ ID NO: 44) | HD NI NI NI NG HD NG NI HD NI NH HD NG NH HD NG HD |
| hROSA26 | 3F | TCTTACAGCTGCTCACTCC (SEQ ID NO: 45) | HD NG NG NI HD NH HD NG NH HD NG HD NI HD NG HD HD |
| hROSA26 | 4F | TACAGCTGCTCACTCCCCT (SEQ ID NO: 46) | NI HD NI NH HD NG NH HD NG HD NI HD NG HD HD HD NG |
| hROSA26 | 5F | TGCTCACTCCCCTGCAGGG (SEQ ID NO: 47) | NH HD NG HD NI HD NG HD HD HD HD NG NH HD NI NH NH |
| hROSA26 | 6F | TCCCCTGCAGGGCAACGCC (SEQ ID NO: 48) | HD HD HD HD NG NH HD NI NH NH NH HD NI NI HD NH HD |
| hROSA26 | 7F | TGCAGGGCAACGCCCAGGG (SEQ ID NO: 49) | NH HD NI NH NH NH HD NI NI HD NH HD HD HD NI NH NH |
| hROSA26 | 8R | TCTCGATTATGGGCGGGAT (SEQ ID NO: 50) | HD NG HD NH NI NG NG NI NG NH NH NH HD NH NH NI NG |
| hROSA26 | 9R | TCGCTTCTCGATTATGGGC (SEQ ID NO: 51) | HD NH HD NG NH NG NH HD NG NH NI NG NG NI NG NH NH HD |

FIG. 3 (Cont.)

| | | | |
|---|---|---|---|
| hROSA26 | 10R | TGTCGAGTCGCTTCTCGAT (SEQ ID NO: 52) | NH NG HD NH NI NH NG HD NH HD NG NG HD NG NG NH HD NG NI NG |
| hROSA26 | 11R | TCCATGTCGAGTCGCTTCT (SEQ ID NO: 53) | HD HD NI NG NG HD NH NI NH NG HD NH NG HD NG NG NG HD NG |
| hROSA26 | 12R | TCGCCTCCATGTCGAGTCG (SEQ ID NO: 54) | HD NH HD NG HD HD NI NG NH NG HD NH NI NH NG HD NH |
| hROSA26 | 13R | TCGTCATCGCCTCCATGTC (SEQ ID NO: 55) | HD NI NG HD NI NG HD NH HD NG NI NG HD NG NI NH NG HD |
| hROSA26 | 14R | TGATCTCGTCATCGCCTCC (SEQ ID NO: 56) | NH NI NG HD NG NG HD NH NI NG HD NI NG HD NH HD HD HD |
| hROSA26 | ROSA1 | GCTTCAGCTTCCTA (SEQ ID NO: 57) | NH HD NG NG HD NI NH HD NG NG HD NG NI |
| hROSA26 | ROSA2 | CTGTGATCATGCCA (SEQ ID NO: 58) | HD NG NK NG NH NI NG HD NI NG NH HD NI |
| hROSA26 | TALER2 | ACAGTGGTACACACCT (SEQ ID NO: 59) | NI HD NI NN NG NN NN NG NI HD NI HD NI HD NG |
| hROSA26 | TALER3 | CCACCCCCACTAAG (SEQ ID NO: 60) | HD HD NI HD HD HD HD HD NI HD NG NI NN |
| hROSA26 | TALER4 | CATTGGCGGGCAC (SEQ ID NO: 61) | HD NI NG NG NN NN HD NN NN HD NI HD |
| hROSA26 | TALER5 | GCTTGAACCCAGGAGA (SEQ ID NO: 62) | NN HD NG NG NN NI NI HD HD NN NN NI NN NI |
| CCR5 | TALC3 | ACACCCGATCCACTGGG (SEQ ID NO: 63) | NI HD NI HD HD NN NI NG HD NG HD NN HD NG NN NN |
| CCR5 | TALC4 | GCTGCATCAACCCC (SEQ ID NO: 64) | NN HD NG NN HD NI NG HD NI NI HD HD HD |
| CCR5 | TALC5 | GCCACAAACAGAAATA (SEQ ID NO: 65) | NN NN HD NI HD NN NI NI HD NI NG NN HD NG HD |
| CCR5 | TALC7 | GGTGGCTCATGCCTG (SEQ ID NO: 66) | NN NN NG NN NN HD NG NI NG NN HD NG NN |

FIG. 3 (Cont.)

| CCR5 | TALC8 | | |
|---|---|---|---|
| Chr 2 | SHCHR2-1 | GATTTGCACAGCTCAT (SEQ ID NO: 67) | NN NI NG NG NG NN HD NI HD NI NN HD NG HD NI NG |
| Chr 2 | SHCHR2-2 | AAGCTCTGAGGAGCA (SEQ ID NO: 68) | NI NI NH HD NG HD NG NH NI NH NH NI NH HD |
| Chr 2 | SHCHR2-3 | CCCTAGCTGTCCC (SEQ ID NO: 69) | HD HD HD NG NI NK HD NG NH NG HD HD HD |
| Chr 2 | SHCHR2-4 | GCCTAGCATGCTAG (SEQ ID NO: 70) | NH HD HD NG NI NH HD NI NG NH HD NG NH |
| Chr 2 | SHCHR4-1 | ATGGGCTTCACGGAT (SEQ ID NO: 71) | NI NG NH NH NH HD NG NG HD NI HD NH NH NI NG |
| Chr 4 | SHCHR4-1 | GAAACTATGCCTGC (SEQ ID NO: 72) | NH NI NI NI HD NG NI NG NH HD HD NG NH HD |
| Chr 4 | SHCHR4-2 | GCACCATTGCTCCC (SEQ ID NO: 73) | NH HD HD HD NI NG NG NH HD NG HD HD |
| Chr 4 | SHCHR4-3 | GACATGCAACTCAG (SEQ ID NO: 74) | NH NI HD NG NH HD NI HD NG HD NI NH |
| Chr 6 | SHCHR6-1 | ACACCACTAGGGGT (SEQ ID NO: 75) | NI HD NI HD HD NI HD NG NI NH NH NH NG |
| Chr 6 | SHCHR6-2 | GTCTGCTAGACAGG (SEQ ID NO: 76) | NH NG HD NG NH HD NG NI NH NI HD NI NH NH |
| Chr 6 | SHCHR6-3 | GGCCTAGACAGGCTG (SEQ ID NO: 77) | NH NH HD HD NG NI NH NI HD NI NH HD NG NH |
| Chr 6 | SHCHR6-4 | GAGGCATTCTTATCG (SEQ ID NO: 78) | NH NI NH NH HD NI NG NG HD NG NG NI NG HD NH |
| Chr 10 | SHCHR10-1 | GCCTGGAAACGTTCC (SEQ ID NO: 79) | NN HD HD NG NN NN NI NI HD NG NG NG HD HD |
| Chr 10 | SHCHR10-2 | GTGCTCTGACAATA (SEQ ID NO: 80) | NN NG NN HD NG NG NN HD NI NG NI |
| Chr 10 | SHCHR10-3 | GTTTTGCAGCCTCC (SEQ ID NO: 81) | NN NG NG NG NN HD NI NN HD NG HD HD |

FIG. 3 (Cont.)

| | | | |
|---|---|---|---|
| Chr 10 | SHCHR10-4 | ACAGCTGTGGAACGT (SEQ ID NO: 82) | NI HD NI NN HD NG NG NN NG NN NN NI NI HD NN NG |
| Chr 10 | SHCHR10-5 | GGCTCTCTTCCTCCT (SEQ ID NO: 83) | HD NI NI NN HD NI HD NN NI NI HD NI HD NG NN HD NG NN |
| Chr 11 | SHCHR11-1 | CTATCCCAAAACTCT (SEQ ID NO: 84) | HD NG NI NG HD HD NI NI NI HD NG NG |
| Chr 11 | SHCHR11-2 | GAAAAACTATGTAT (SEQ ID NO: 85) | NH NI NI NI NI HD NG NI NG NH NG NG |
| Chr 11 | SHCHR11-3 | AGGCAGGCTGGTTGA (SEQ ID NO: 86) | NI NH NH HD NI NH NH HD NG NH NH NG NG NH NI |
| Chr 17 | SHCHR17-1 | CAATACAACCACGC (SEQ ID NO: 87) | HD NI NI NG NI HD NI HD HD NI HD NN HD |
| Chr 17 | SHCHR17-2 | ATGACGGACTCAACT (SEQ ID NO: 88) | NI NG NN NI HD NN NN NI HD NG HD NI NI HD NG |
| Chr 17 | SHCHR17-3 | CACAACATTTGTAA (SEQ ID NO: 89) | HD NI HD NI HD NI HD NG NG NG NN NG NI NI |
| Chr 17 | SHCHR17-4 | ATTTCCAGTGCACA (SEQ ID NO: 90) | NI NG NG NG HD HD NI NN NG NN HD NI HD NI |

FIG. 3 (Cont.)

Code:

| RVD | Nucleotide | RVD | Nucleotide |
|---|---|---|---|
| HD | C | NI | A |
| NH | G | NN | G, A |
| NK | G | NS | G, C, A |
| NG | T, mC | | |

FIG. 4

Guide RNAs to target human genomic safe harbor sites using dCas in areas of open chromatin

| GSHS | Identifier | Sequence |
|---|---|---|
| AAVS1 | 14F | CACCGGGAGCCACGAAAACAGATCC (SEQ ID NO: 99) |
| AAVS1 | 15F | CACCGCGAAAACAGATCCAGGACA (SEQ ID NO: 100) |
| AAVS1 | 16F | CACCGAGATCCAGGACACGGTGCT (SEQ ID NO: 101) |
| AAVS1 | 17F | CACCGGACACGGTGCTAGGACAGTG (SEQ ID NO: 102) |
| AAVS1 | 18F | CACCGGAAAATGACCCAACAGCCTC (SEQ ID NO: 103) |
| AAVS1 | 19F | CACCGCCTGGCCGGCCTGACCACT (SEQ ID NO: 104) |
| AAVS1 | 20F | CACCGCTGAGCACTGAAGGCCTGGC (SEQ ID NO: 105) |
| AAVS1 | 21F | CACCGTGGTTCCACTGAGCACTGA (SEQ ID NO: 106) |
| AAVS1 | 22F | CACCGGATAGCCAGGAGTCCTTTCG (SEQ ID NO: 107) |
| AAVS1 | 23F | CACCGCGTTCCAGTGCTCAGACT (SEQ ID NO: 108) |
| AAVS1 | 24F | CACCGCAGTGCTCAGACTAGGGAAG (SEQ ID NO: 109) |
| AAVS1 | 25F | CACCGCCCCTCCTTCAGAGCCAGCC (SEQ ID NO: 110) |
| AAVS1 | 26F | CACCGTCCTTCAGAGCCAGGAGTCC (SEQ ID NO: 111) |
| AAVS1 | 27F | CACCGTGGTTTCCGAGCTTGACCCT (SEQ ID NO: 112) |
| AAVS1 | 28F | CACCGCTGCAGAGTATCTGCTGGGG (SEQ ID NO: 113) |
| AAVS1 | 29F | CACCGGGTTCCTGCAGAGTATCTGC (SEQ ID NO: 114) |
| AAVS1 | 14R | AAACGGATCTGTTTTCGTGGCTCCC (SEQ ID NO: 115) |
| AAVS1 | 15R | AAACTGTCCCTGGATCTGTTTTCGC (SEQ ID NO: 116) |
| AAVS1 | 16R | AAACAGCACCGTGTCCTGGATCTC (SEQ ID NO: 117) |
| AAVS1 | 17R | AAACCACTGTCCTAGCACCGTGTCC (SEQ ID NO: 118) |
| AAVS1 | 18R | AAACGAGGCTGTTGGGTCATTTTCC (SEQ ID NO: 119) |
| AAVS1 | 19R | AAACAGTGGTCAGGCCGGCCAGGCC (SEQ ID NO: 120) |
| AAVS1 | 20R | AAACGCCAGGCCTTCAGTGCTCAGC (SEQ ID NO: 121) |

FIG. 4 (Cont.)

| | | |
|---|---|---|
| AAVS1 | 21R | AAACTCAGTGCTCAGTGGAAACCAC (SEQ ID NO: 122) |
| AAVS1 | 22R | AAACCGAAAGGACTCCTGGCTATCC (SEQ ID NO: 123) |
| AAVS1 | 23R | AAACAGTCTGAGCACTGGAAGCGCC (SEQ ID NO: 124) |
| AAVS1 | 24R | AAACCTTCCCTAGTCTGAGCACTGC (SEQ ID NO: 125) |
| AAVS1 | 25R | AAACGGCTCTGAAGGAGGAGGGGCC (SEQ ID NO: 126) |
| AAVS1 | 26R | AAACGGACTCCTGGCTCTGAAGGAC (SEQ ID NO: 127) |
| AAVS1 | 27R | AAACAGGGTCAAGCTCCAGGAAACC (SEQ ID NO: 128) |
| AAVS1 | 28R | AAACCCCAGCAGATACTCTGCAGC (SEQ ID NO: 129) |
| AAVS1 | 29R | AAACGCAGATACTCTGCAGGAACGC (SEQ ID NO: 130) |
| AAVS1 | AAVS1 | TCCCCTCCCAGAAAGACCTG (SEQ ID NO: 131) |
| AAVS1 | gAAVS2 | TGGGCTCCAAGCAATCCTGG (SEQ ID NO: 132) |
| AAVS1 | gAAVS3 | GTGGCTCAGGAGGTACCTGG (SEQ ID NO: 133) |
| AAVS1 | gAAVS4 | GAGCCACGAAAACAGATCCA (SEQ ID NO: 134) |
| AAVS1 | gAAVS5 | AAGTGAACGGGGAAGGGGAGG (SEQ ID NO: 135) |
| AAVS1 | gAAVS6 | GACAAAAGCCGAAGTCCAGG (SEQ ID NO: 136) |
| AAVS1 | gAAVS7 | GTGGTTGATAAACCCACGTG (SEQ ID NO: 137) |
| AAVS1 | gAAVS8 | TGGAACAGCCACAGCAGGG (SEQ ID NO: 138) |
| AAVS1 | gAAVS9 | GCAGGGGAACGGGGATGCAG (SEQ ID NO: 139) |
| AAVS1 | gAAVS10 | GAGATGGTGACGAGGAAGG (SEQ ID NO: 140) |
| AAVS1 | gAAVS11 | GAGATGGCTCCAGGAAATGG (SEQ ID NO: 141) |
| AAVS1 | gAAVS12 | TAAGGAATCTGCCTAACAGG (SEQ ID NO: 142) |

FIG. 4 (Cont.)

| | | |
|---|---|---|
| AAVS1 | gAAVS13 | TCAGGAGACTAGGAAGGAGG (SEQ ID NO: 143) |
| AAVS1 | gAAVS14 | TATAAGGTGGTCCCAGCTCG (SEQ ID NO: 144) |
| AAVS1 | gAAVS15 | CTGGAAGATGCCATGACAGG (SEQ ID NO: 145) |
| AAVS1 | gAAVS16 | GCACAGACTAGAGAGGTAAG (SEQ ID NO: 146) |
| AAVS1 | gAAVS17 | ACAGACTAGAGAGGTAAGGG (SEQ ID NO: 147) |
| AAVS1 | gAAVS18 | GAGAGGTGACCCGAATCCAC (SEQ ID NO: 148) |
| AAVS1 | gAAVS19 | GCACAGGCCCCAGAAGGAGA (SEQ ID NO: 149) |
| AAVS1 | gAAVS20 | CCGGAGAGGACCCAGACACG (SEQ ID NO: 150) |
| AAVS1 | gAAVS21 | GAGAGGACCCAGACACGGGG (SEQ ID NO: 151) |
| AAVS1 | gAAVS22 | GCAACACAGCAGAGAGCAAG (SEQ ID NO: 152) |
| AAVS1 | gAAVS23 | GAAGAGGGAGTGGAGAAGA (SEQ ID NO: 153) |
| AAVS1 | gAAVS24 | AAGACGGAACCTGAAGGAGG (SEQ ID NO: 154) |
| AAVS1 | gAAVS25 | AGAAAGCGGCACAGGCCCAG (SEQ ID NO: 155) |
| AAVS1 | gAAVS26 | GGGAAACAGTGGGCCAGAGG (SEQ ID NO: 156) |
| AAVS1 | gAAVS27 | GTCCGGACTCAGGAGGAGAGA (SEQ ID NO: 157) |
| AAVS1 | gAAVS28 | GGCACAGCAAGGGCACTCGG (SEQ ID NO: 158) |
| AAVS1 | gAAVS29 | GAAGAGGGGAAGTCGAGGGA (SEQ ID NO: 159) |
| AAVS1 | gAAVS30 | GGGAATGGTAAGGAGGCCTG (SEQ ID NO: 160) |
| AAVS1 | gAAVS31 | GCAGAGTGGTCAGCACAGAG (SEQ ID NO: 161) |
| AAVS1 | gAAVS32 | GCACAGAGTGGCTAAGCCCA (SEQ ID NO: 162) |
| AAVS1 | gAAVS33 | GACGGGTGTCAGCATAGGG (SEQ ID NO: 163) |
| AAVS1 | gAAVS34 | GCCCAGGGCCAGAACGACG (SEQ ID NO: 164) |
| AAVS1 | gAAVS35 | GGTGGGAGTCCAGCACGGGC (SEQ ID NO: 165) |
| AAVS1 | gAAVS36 | ACAGGCCGCCAGGAACTCGG (SEQ ID NO: 166) |

FIG. 4 (Cont.)

| | | |
|---|---|---|
| AAVS1 | gAAVS37 | ACTAGGAAGTGTGTAGCACC (SEQ ID NO: 167) |
| AAVS1 | gAAVS38 | ATGAATAGCAGACTGCCCCG (SEQ ID NO: 168) |
| AAVS1 | gAAVS39 | ACACCCCTAAAAGCACAGTG (SEQ ID NO: 169) |
| AAVS1 | gAAVS40 | CAAGGAGTTCCAGCAGGTGG (SEQ ID NO: 170) |
| AAVS1 | gAAVS41 | AAGGAGTTCCAGCAGGTGGG (SEQ ID NO: 171) |
| AAVS1 | gAAVS42 | TGGAAAGAGGAGGAAGAGG (SEQ ID NO: 172) |
| AAVS1 | gAAVS43 | TCGAATTCCTAACTGCCCCG (SEQ ID NO: 173) |
| AAVS1 | gAAVS44 | GACCTGCCCAGCACACCCTG (SEQ ID NO: 174) |
| AAVS1 | gAAVS45 | GGAGCAGCTGCGGCAGTGGG (SEQ ID NO: 175) |
| AAVS1 | gAAVS46 | GGGAGGGAGAGCTTGGCAGG (SEQ ID NO: 176) |
| AAVS1 | gAAVS47 | GTTACGTGGCCAAGAAGCAG (SEQ ID NO: 177) |
| AAVS1 | gAAVS48 | GCTGAACAGAGAAGAGAGCTGG (SEQ ID NO: 178) |
| AAVS1 | gAAVS49 | TCTGAGGGTGGAGGGACTGG (SEQ ID NO: 179) |
| AAVS1 | gAAVS50 | GGAGAGGTGAGGGACTTGGG (SEQ ID NO: 180) |
| AAVS1 | gAAVS51 | GTGAACCAGGCAGACAACGA (SEQ ID NO: 181) |
| AAVS1 | gAAVS52 | CAGGTACCTCCTGAGCCACG (SEQ ID NO: 182) |
| AAVS1 | gAAVS53 | GGGGAGTAGGGCATGCAG (SEQ ID NO: 183) |
| hROSA26 | gHROSA26-1 | GCAAATGGCCAGCAAGGGTG (SEQ ID NO: 184) |
| hROSA26 | gHROSA26-2 | CAAATGGCCAGCAAGGGTGG (SEQ ID NO: 309) |
| hROSA26 | gHROSA26-3 | GCAGAACCTGAGGATATGGA (SEQ ID NO: 310) |
| hROSA26 | gHROSA26-3 | AATACACAGAATGAAAATAG (SEQ ID NO: 311) |
| hROSA26 | gHROSA26-4 | CTGGTGACTAGAATAGGCAG (SEQ ID NO: 312) |
| hROSA26 | gHROSA26-5 | TGGTGACTAGAATAGGCAGT (SEQ ID NO: 313) |
| hROSA26 | gHROSA26-6 | TAAAAGAATGTGAAAAGATG (SEQ ID NO: 314) |
| hROSA26 | gHROSA26-7 | TCAGGAGTTCAAGACCACCC (SEQ ID NO: 315) |

FIG. 4 (Cont.)

| hROSA26 | gHROSA26-8  | TGTAGTCCCAGTTATGCAGG (SEQ ID NO: 316) |
| --- | --- | --- |
| hROSA26 | gHROSA26-9  | GGGTTCACACCACAAATGCA (SEQ ID NO: 317) |
| hROSA26 | gHROSA26-10 | GGCAAATGGCCAGCAAGGGT (SEQ ID NO: 318) |
| hROSA26 | gHROSA26-11 | AGAAACCAATCCCAAAGCAA (SEQ ID NO: 319) |
| hROSA26 | gHROSA26-12 | GCCAAGGACACCAAAACCCA (SEQ ID NO: 320) |
| hROSA26 | gHROSA26-13 | AGTGGTGATAAGGCAACAGT (SEQ ID NO: 321) |
| hROSA26 | gHROSA26-14 | CCTGAGACAGAAGTATTAAG (SEQ ID NO: 322) |
| hROSA26 | gHROSA26-15 | AAGGTCACACAATGAATAGG (SEQ ID NO: 323) |
| hROSA26 | gHROSA26-16 | CACCATACTAGGGAAGAAGA (SEQ ID NO: 324) |
| hROSA26 | gHROSA26-17 | CAATACCCTGCCCTTAGTGG (SEQ ID NO: 327) |
| hROSA26 | gHROSA26-18 | AATACCCTGCCCTTAGTGGG (SEQ ID NO: 325) |
| hROSA26 | gHROSA26-19 | TTAGTGGGGGGTGGAGTGGG (SEQ ID NO: 326) |
| hROSA26 | gHROSA26-20 | GTGGGGGGTGGAGTGGGGGG (SEQ ID NO: 328) |
| hROSA26 | gHROSA26-21 | GGGGGGTGGAGTGGGGGGTG (SEQ ID NO: 329) |
| hROSA26 | gHROSA26-22 | GGGTGGAGTGGGGGGTGGG (SEQ ID NO: 330) |
| hROSA26 | gHROSA26-23 | GGGTGGAGTGGGGGGTGGGG (SEQ ID NO: 331) |
| hROSA26 | gHROSA26-24 | GGGGTGGGGAAAGACATCG (SEQ ID NO: 332) |
| hROSA26 | gHROSA26-25 | GCAAATGGCCAGCAAGGGTG (SEQ ID NO: 184) |
| hROSA26 | gHROSA26-26 | CAAATGGCCAGCAAGGGTGG (SEQ ID NO: 309) |
| hROSA26 | gHROSA26-27 | GCAGAACCTGAGGATATGGA (SEQ ID NO: 310) |
| hROSA26 | gHROSA26-28 | AATACACAGAATGAAAATAG (SEQ ID NO: 311) |
| hROSA26 | gHROSA26-29 | CTGGTGACTAGAATAGGCAG (SEQ ID NO: 312) |
| hROSA26 | gHROSA26-30 | TGGTGACTAGAATAGGCAGT (SEQ ID NO: 313) |

FIG. 4 (Cont.)

| | | |
|---|---|---|
| hROSA26 | gHROSA26-31 | TAAAAGAATGTGAAAAGATG (SEQ ID NO: 314) |
| hROSA26 | gHROSA26-32 | TCAGGAGTTCAAGACCACCC (SEQ ID NO: 315) |
| hROSA26 | gHROSA26-33 | TGTAGTCCCAGTTATGCAGG (SEQ ID NO: 316) |
| hROSA26 | gHROSA26-34 | GGGTTCACACCACAAATGCA (SEQ ID NO: 317) |
| hROSA26 | gHROSA26-35 | GGCAAATGGCCAGCAAGGGT (SEQ ID NO: 318) |
| hROSA26 | gHROSA26-36 | AGAAACCAATCCCAAAGCAA (SEQ ID NO: 319) |
| hROSA26 | gHROSA26-37 | GCCAAGGACCACCAAAACCCA (SEQ ID NO: 320) |
| hROSA26 | gHROSA26-38 | AGTGGTGATAAGGCAACAGT (SEQ ID NO: 321) |
| hROSA26 | gHROSA26-39 | CCTGAGACAGAAGTATTAAG (SEQ ID NO: 322) |
| hROSA26 | gHROSA26-40 | AAGGTCACACACAATGAATAGG (SEQ ID NO: 323) |
| hROSA26 | gHROSA26-41 | CACCATACTAGGGAAGAAGA (SEQ ID NO: 324) |
| hROSA26 | gHROSA26-42 | CAATACCCTGCCCTTAGTGG (SEQ ID NO: 327) |
| hROSA26 | gHROSA26-43 | AATACCCTGCCCTTAGTGGG (SEQ ID NO: 325) |
| hROSA26 | gHROSA26-44 | TTAGTGGGGGGTGGAGTGGG (SEQ ID NO: 326) |
| hROSA26 | gHROSA26-45 | GTGGGGGGTGGAGTGGGGGG (SEQ ID NO: 328) |
| hROSA26 | gHROSA26-46 | GGGGGGTGGAGTGGGGGGTG (SEQ ID NO: 329) |
| hROSA26 | gHROSA26-47 | GGGGTGGAGTGGGGGGTGGG (SEQ ID NO: 330) |
| hROSA26 | gHROSA26-48 | GGTGGAGTGGGGGGTGGGG (SEQ ID NO: 331) |
| hROSA26 | gHROSA26-49 | GGGGTGGGGAAAGACATCG (SEQ ID NO: 332) |
| hROSA26 | gHROSA26-50 | GCAGCTGTGAATTCTGATAG (SEQ ID NO: 333) |
| hROSA26 | gHROSA26-51 | GAGATCAGAGAACCAGATG (SEQ ID NO: 334) |
| hROSA26 | gHROSA26-52 | TCTATACTGATTGCAGCCAG (SEQ ID NO: 335) |
| hROSA26 | gHROSA26-1 | GCAAATGGCCAGCAAGGGTG (SEQ ID NO: 184) |
| hROSA26 | 44F | CACCGAATCGAGAAGCGACTCGACA (SEQ ID NO: 185) |
| hROSA26 | 45F | CACCGTCCCTGGGCGTTGCCCTGC (SEQ ID NO: 186) |
| hROSA26 | 46F | CACCGCCCTGGGCGTTGCCCTGCAG (SEQ ID NO: 187) |

FIG. 4 (Cont.)

| | | |
|---|---|---|
| hROSA26 | 1nF | CACCGCCCGTGGGAAGATAAACTAAT (SEQ ID NO: 188) |
| hROSA26 | 2nF | CACCGTCCCCTGCAGGGCAACGCCC (SEQ ID NO: 189) |
| hROSA26 | 3nF | CACCGTCGAGTGCGCTTCTCCGATTA (SEQ ID NO: 190) |
| hROSA26 | 4nF | CACCGGTCGCTGCCTCCCGTCTTGTA (SEQ ID NO: 191) |
| hROSA26 | 5nF | CACCGGAGTGCCGCAATACCTTTAT (SEQ ID NO: 192) |
| hROSA26 | 6nF | CACCGACACTTTGGTGGTGCAGCAA (SEQ ID NO: 193) |
| hROSA26 | 7nF | CACCGTCTCAAATGGTATAAAACTC (SEQ ID NO: 194) |
| hROSA26 | 8nF | CACCGCCGTGGGAAGATAAACTAAT (SEQ ID NO: 188) |
| hROSA26 | 9F | CACCGAATCCCGCCCATAATCGAGA (SEQ ID NO: 195) |
| hROSA26 | 10F | CACCGTCCCGCCCATAATCGAGAAG (SEQ ID NO: 196) |
| hROSA26 | 11F | CACCGCCATAATCGAGAAGCGACT (SEQ ID NO: 197) |
| hROSA26 | 12F | CACCGGAGAAGCGACTCGACATGGA (SEQ ID NO: 198) |
| hROSA26 | 13F | CACCGGAAGCGACTCGACATGGAGG (SEQ ID NO: 199) |
| hROSA26 | 14F | CACCGGCGACTCGAGTGCGACATGGAGGCGA (SEQ ID NO: 200) |
| hROSA26 | 44F | AAACTGTGTCGAGTCGCTTCTCGATTC (SEQ ID NO: 201) |
| hROSA26 | 45F | AAACGCAGGGCAACGCCCAGGGACC (SEQ ID NO: 202) |
| hROSA26 | 46F | AAACCTGCAGGGCAACGCCAGGGC (SEQ ID NO: 203) |
| hROSA26 | 1nR | AAACATTAGTTTATCTTCCCACGGC (SEQ ID NO: 204) |
| hROSA26 | 2nR | AAACGGGCGTTGCCCTGCAGGGGAC (SEQ ID NO: 205) |
| hROSA26 | 3nR | AAACTAATCGAGAAGCGACTCGACC (SEQ ID NO: 206) |
| hROSA26 | 4nR | AAACTACAAGACGGGAGGCAGCAGC (SEQ ID NO: 207) |
| hROSA26 | 5nR | AAACATAAAGGTATTGCGGCACTCC (SEQ ID NO: 208) |

FIG. 4 (Cont.)

| hROSA26 | 6nR | AAACTTGCTGCACCACCAAAGTGTC (SEQ ID NO: 209) |
|---|---|---|
| hROSA26 | 7nR | AAACGAGTTTTATACCATTTGAGAC (SEQ ID NO: 210) |
| hROSA26 | 8nR | AAACATTAGTTTATCTTCCCACGGC (SEQ ID NO: 204) |
| hROSA26 | 9R | AAACTCTCGATTATGGGCGGGATTC (SEQ ID NO: 211) |
| hROSA26 | 10R | AAACCTTCTCGATTATGGGCGGGAC (SEQ ID NO: 212) |
| hROSA26 | 11R | AAACAGTCGCTTCTCGATTATGGGC (SEQ ID NO: 213) |
| hROSA26 | 12R | AAACTCCATGTCGAGTCGCTTCTCC (SEQ ID NO: 214) |
| hROSA26 | 13R | AAACCCTCCATGTCGAGTCGCTTCC (SEQ ID NO: 215) |
| hROSA26 | 14R | AAACTCGCCTCCATGTCGAGTCGCC (SEQ ID NO: 216) |
| CCR5 | 1F | CACCGACAGGGTTAATGTGAAGTCC (SEQ ID NO: 217) |
| CCR5 | 2F | CACCGTCCCCTCTCACATTTAAAGT (SEQ ID NO: 218) |
| CCR5 | 3F | CACCGCATTTAAAGTTGGTTTAAGT (SEQ ID NO: 219) |
| CCR5 | 4F | CACCGTTAGAAAATATAAAGAATAA (SEQ ID NO: 220) |
| CCR5 | 5 | CACCGTAAAATGCTTACTGGTTTGAA (SEQ ID NO: 221) |
| CCR5 | 6F | CACCGTCCTGGGTCCAGAAAAAGAT (SEQ ID NO: 222) |
| CCR5 | 7F | CACCGTTGGGGTGGTGAGCATCTGTG (SEQ ID NO: 223) |
| CCR5 | 8F | CACCGGGGAGAGTGGAGAAAAAG (SEQ ID NO: 224) |
| CCR5 | 9F | CACCGGTTAAAACTCTTTAGACAAC (SEQ ID NO: 225) |
| CCR5 | 10F | CACCGGAAAATCCCCACTAAGATCC (SEQ ID NO: 226) |
| CCR5 | 1R | AAACGGACTTCACATTAACCCTGTC (SEQ ID NO: 227) |
| CCR5 | 2R | AAACACTTTAAATGTGAGAGGGGAC (SEQ ID NO: 228) |
| CCR5 | 3R | AAACACTTAAACCAACTTAAATGC (SEQ ID NO: 229) |
| CCR5 | 4R | AAACTTATTCTTTATATTTTCTAAC (SEQ ID NO: 230) |
| CCR5 | 5R | AAACTTCAAACCAGTAAGCATTTAC (SEQ ID NO: 231) |
| CCR5 | 6R | AAACATCTTTTTCTGGACCCAGGAC (SEQ ID NO: 232) |
| CCR5 | 7R | AAACCACAGATGCTCACCACCCAAC (SEQ ID NO: 233) |

FIG. 4 (Cont.)

| | | | |
|---|---|---|---|
| CCR5 | 8R | | AAACCTTTTCTCCACTCTCCCCGC (SEQ ID NO: 234) |
| CCR5 | 9R | | AAACGTTGTCTAAAGAGTTTTAACC (SEQ ID NO: 235) |
| CCR5 | 10R | | AAACGGATCTTAGTGGGGATTTTCC (SEQ ID NO: 236) |
| CCR5 | gCCR5-1 | | AGTAGCAGTAATGAAGCTGG (SEQ ID NO: 237) |
| CCR5 | gCCR5-2 | | ATACCCAGACGAGAAAGCTG (SEQ ID NO: 238) |
| CCR5 | gCCR5-3 | | TACCCAGAACGAGAAAGCTGA (SEQ ID NO: 239) |
| CCR5 | gCCR5-4 | | GGTGGTGAGCATCTGTGTGG (SEQ ID NO: 240) |
| CCR5 | gCCR5-5 | | AAATGAGAAGAAGAGGCACA (SEQ ID NO: 241) |
| CCR5 | gCCR5-6 | | CTTGTGGCCTGGGAGGAGCTG (SEQ ID NO: 242) |
| CCR5 | gCCR5-7 | | GCTGTAGAAGGAGACAGAGC (SEQ ID NO: 243) |
| CCR5 | gCCR5-8 | | GAGCTGGTTGGGAAGACATG (SEQ ID NO: 244) |
| CCR5 | gCCR5-9 | | CTGGTTGGGAAGACATGGGG (SEQ ID NO: 245) |
| CCR5 | gCCR5-10 | | CGTGAGGATGGGAAGGAGGG (SEQ ID NO: 246) |
| CCR5 | gCCR5-11 | | ATGCAGAGTCAGCAGAACTG (SEQ ID NO: 247) |
| CCR5 | gCCR5-12 | | AAGACATCAAGCACAGAAGG (SEQ ID NO: 248) |
| CCR5 | gCCR5-13 | | TCAAGCACAGAAGGAGGAGG (SEQ ID NO: 249) |
| CCR5 | gCCR5-14 | | AACCGTCAATAGGCAAAGGG (SEQ ID NO: 250) |
| CCR5 | gCCR5-15 | | CCGTATTTCAGACTGAATGG (SEQ ID NO: 251) |
| CCR5 | gCCR5-16 | | GAGAGGACAGGTGCTACAGG (SEQ ID NO: 252) |
| CCR5 | gCCR5-17 | | AACCAAGGAAGGGCAGGAGG (SEQ ID NO: 253) |
| CCR5 | gCCR5-18 | | GACCTCTGGGTGGAGACAGA (SEQ ID NO: 254) |
| CCR5 | gCCR5-19 | | CAGATGACCATGACAAGCAG (SEQ ID NO: 255) |
| CCR5 | gCCR5-20 | | AACACCAGTGAGTAGAGCGG (SEQ ID NO: 256) |

FIG. 4 (Cont.)

| | | |
|---|---|---|
| CCR5 | gCCR5-21 | AGGACCTTGAAGCACAGAGA (SEQ ID NO: 257) |
| CCR5 | gCCR5-22 | TACAGAGGCAGACTAACCCA (SEQ ID NO: 258) |
| CCR5 | gCCR5-23 | ACAGAGGCAGAGACTAACCCAG (SEQ ID NO: 259) |
| CCR5 | gCCR5-24 | TAAATGACGTGCTAGACCTG (SEQ ID NO: 260) |
| CCR5 | gCCR5-25 | AGTAACCACTCAGGACACAGGG (SEQ ID NO: 261) |
| chr2 | gchr2-1 | ACCACAAAACAGAAACACCA (SEQ ID NO: 262) |
| chr2 | gchr2-2 | GTTTGAAGACAAGCCTGAGG (SEQ ID NO: 263) |
| chr4 | gchr4-1 | GCTGAACCCCAAAAGACAGG (SEQ ID NO: 264) |
| chr4 | gchr4-2 | GCAGCTGAGACACACACCAG (SEQ ID NO: 265) |
| chr4 | gchr4-3 | AGGACACCCCAAAGAAGCTG (SEQ ID NO: 266) |
| chr4 | gchr4-4 | GGACACCCCAAAGAAGCTGA (SEQ ID NO: 267) |
| chr6 | gchr6-1 | CCAGTGCAATGGACACAGAGA (SEQ ID NO: 268) |
| chr6 | gchr6-2 | AGAGAGGAGCCTGCAAGT (SEQ ID NO: 269) |
| chr6 | gchr6-3 | GTGTTTGGGCCCTAGAGCGA (SEQ ID NO: 270) |
| chr6 | gchr6-4 | CATGTGCCTGGTGTCAATGCA (SEQ ID NO: 271) |
| chr6 | gchr6-5 | TACAAAGAGGAAGATAAGTG (SEQ ID NO: 272) |
| chr6 | gchr6-6 | GTCACAGAATACACCACTAG (SEQ ID NO: 273) |
| chr6 | gchr6-7 | GGGTTACCCTGGACATGGAA (SEQ ID NO: 274) |
| chr6 | gchr6-8 | CATGGAAGGGTATTCACTCG (SEQ ID NO: 275) |
| chr6 | gchr6-9 | AGAGTGGCCTAGACAGGCTG (SEQ ID NO: 276) |
| chr6 | gchr6-10 | CATGCTGGACAGCTCGGCAG (SEQ ID NO: 277) |
| chr6 | gchr6-11 | AGTGAAAGAAGAGAAAATTC (SEQ ID NO: 278) |
| chr6 | gchr6-12 | TGGTAAGTCTAAGAAACCTA (SEQ ID NO: 279) |
| chr6 | gchr6-13 | CCCACAGCCTAACCACCCTA (SEQ ID NO: 280) |
| chr6 | gchr6-14 | AATATTTCAAAGCCCTAGGG (SEQ ID NO: 281) |

FIG. 4 (Cont.)

| | | |
|---|---|---|
| chr6 | gchr6-15 | GCACTCGGAACAGGGTCTGG (SEQ ID NO: 282) |
| chr6 | gchr6-16 | AGATAGGAGCTCCAACAGTG (SEQ ID NO: 283) |
| chr6 | gchr6-17 | AAGTTAGAGCAGCAGCCAGGAAA (SEQ ID NO: 284) |
| chr6 | gchr6-18 | TAGAGCAGCCAGGAAAGGGA (SEQ ID NO: 285) |
| chr6 | gchr6-19 | TGAATACCCTTCCATGTCCA (SEQ ID NO: 286) |
| chr6 | gchr6-20 | CCTGCATTGCACCAGGCACA (SEQ ID NO: 287) |
| chr6 | gchr6-21 | TCTAGGGCCCAAACACACCT (SEQ ID NO: 288) |
| chr6 | gchr6-22 | TCCCTCCATCTATCAAAAGG (SEQ ID NO: 289) |
| chr10 | gchr10-1 | AGCCCTGAGACAGAAGCAGG (SEQ ID NO: 290) |
| chr10 | gchr10-2 | GCCCTGAGACAGAAGCAGGT (SEQ ID NO: 291) |
| chr10 | gchr10-3 | AGGAGATGCAGTGATACGCA (SEQ ID NO: 292) |
| chr10 | gchr10-4 | ACAATACCAAGGTATCCGG (SEQ ID NO: 293) |
| chr10 | gchr10-5 | TGATAAAGAAAACAAAGTGA (SEQ ID NO: 294) |
| chr10 | gchr10-6 | AAAGAAAACAAAGTGAGGGA (SEQ ID NO: 295) |
| chr10 | gchr10-7 | GTGGCAAGTGGAGAAATTGA (SEQ ID NO: 296) |
| chr10 | gchr10-8 | CAAGTGGAGAAATTGAGGGA (SEQ ID NO: 297) |
| chr10 | gchr10-9 | GTGGTGATGATTGCAGCTGG (SEQ ID NO: 298) |
| chr11 | gchr11-1 | CTATGTGCCTGACACACAGG (SEQ ID NO: 299) |
| chr11 | gchr11-2 | GGGTTGGGACCAGGAAAGAGG (SEQ ID NO: 300) |
| chr17 | gchr17-1 | GATGCCTGGAAAAGGAAAGA (SEQ ID NO: 301) |
| chr17 | gchr17-2 | TAGTATGCACCTGCAAGAGG (SEQ ID NO: 302) |
| chr17 | gchr17-3 | TATGCACCTGCAAGAGGCGG (SEQ ID NO: 303) |
| chr17 | gchr17-4 | AGGGGAGAAGAAGAAGCAGA (SEQ ID NO: 304) |
| chr17 | gchr17-5 | GCTGAATCAAGAGACAAGCG (SEQ ID NO: 305) |
| chr17 | gchr17-6 | AAGCAAATAAATCTCCTGGG (SEQ ID NO: 306) |
| chr17 | gchr17-7 | AGATGAGTGCTAGAGACTGG (SEQ ID NO: 307) |
| chr17 | gchr17-8 | CTGATGGTTGAGCACAGCAG (SEQ ID NO: 308) |

FIG. 5A
Hyperactive MLT mutants from transposase DNA and transposase protein

| Nucleotide change | Amino Acid Change |
|---|---|
| T13C | S5P |
| T22C | S8P |
| T22C/T37C | S8P/C13R |
| A26G | D9G |
| A29G | D10G |
| A32G | E11G |
| T37C | C13R |
| C41T | A14V |
| A106G | S36G |
| G161A | S54N |
| T375G | N125K |
| A389C | K130T |
| G715A | G239S |
| A880G | T294A |
| A898G | T300A |
| A1033G | I345V |
| G1280A | R427H |
| A1424G | D475G |
| A1441G | M481V |
| C1472A | P491Q |
| G1558A | A520T |
| G1681A | A561T |

FIG. 5B

Excision positive and Integration deficient MLT mutants from transposase DNA and transposase protein

| MLT Backbone | MLT Mutant 1 | MLT Mutant 2 | MLT Mutant 3 |
|---|---|---|---|
| S8P/C13R | R164N | 0 | 0 |
| S8P/C13R | W168V | 0 | 0 |
| S8P/C13R | W168V | K369A | 0 |
| S8P/C13R | M278A | 0 | 0 |
| S8P/C13R | K286A | 0 | 0 |
| S8P/C13R | R287A | 0 | 0 |
| S8P/C13R | R333A | 0 | 0 |
| S8P/C13R | R333A | E284A | 0 |
| S8P/C13R | R333A | E284A | R336A |
| S8P/C13R | K334A | 0 | 0 |
| S8P/C13R | N335A | 0 | 0 |
| S8P/C13R | K349A | 0 | 0 |
| S8P/C13R | K350A | 0 | 0 |
| S8P/C13R | K368A | 0 | 0 |
| S8P/C13R | K369A | 0 | 0 |
| S8P/C13R | D416N | 0 | 0 |
| S8P/C13R | D416N | K286A | 0 |
| S8P/C13R | D416N | R287A | 0 |
| S8P/C13R | D416N | R333A | 0 |
| S8P/C13R | D416N | K334A | 0 |
| S8P/C13R | D416N | R336A | 0 |
| S8P/C13R | D416N | K349A | 0 |
| S8P/C13R | D416N | K350A | 0 |

FIG. 5B (Cont.)

| S8P/C13R | D416N | K368A | 0 |
|---|---|---|---|
| S8P/C13R | D416N | K369A | 0 |
| S8P/C13R | D416N | N310A | 0 |

Three Dimensional Model of MLT Using Phyre² Showing DNA Binding Domains

DNA Binding Domains

Secondary structure prediction for MLT, generated using Phyre2

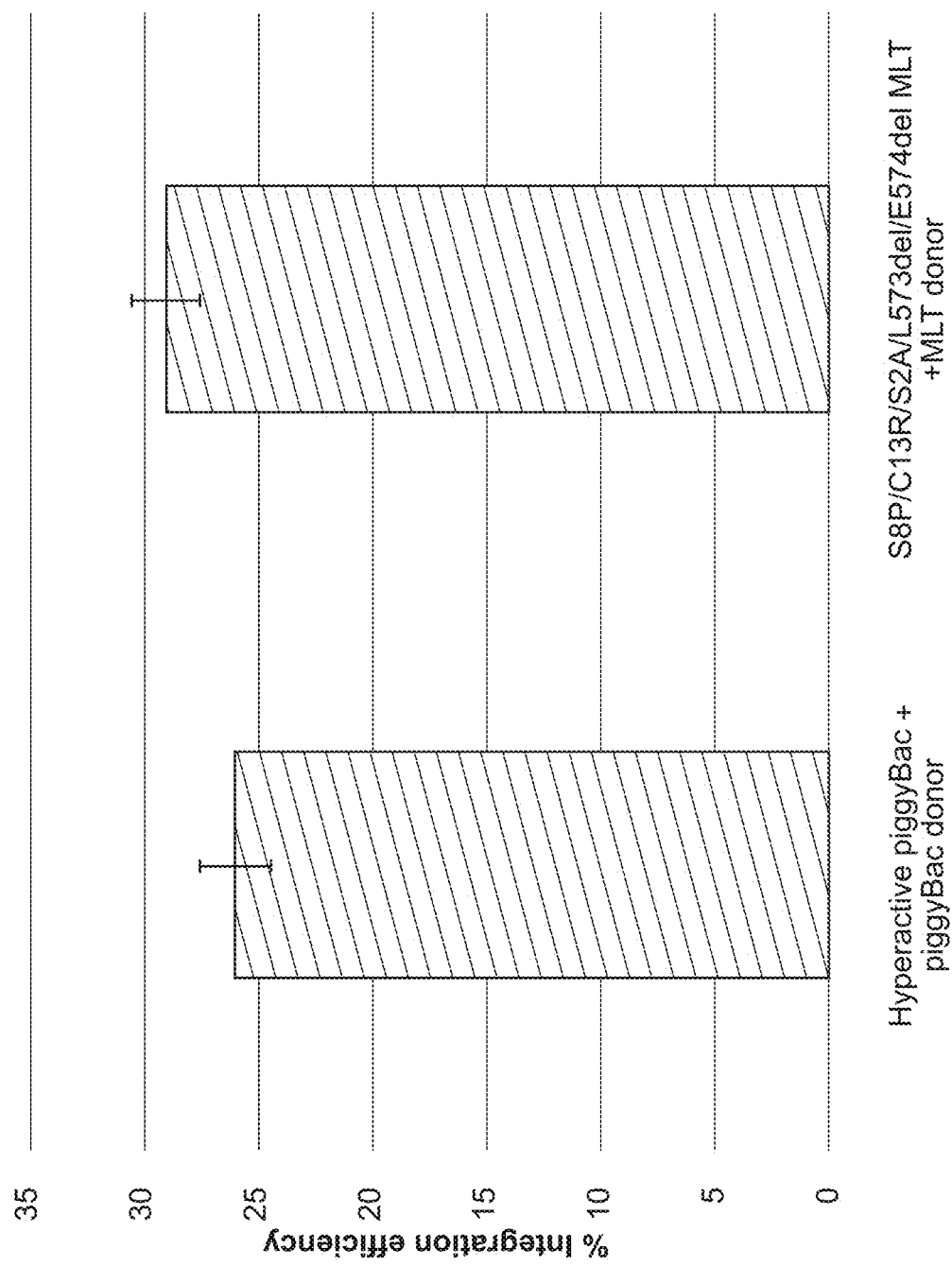

FIG. 10
Nucleotide sequence alignment of engineered MLT (SEQ ID NO: 337, human codon-optimized, "MLT") and published sequence by Mitra et al. (SEQ ID NO: 336, Identity 77.67%, Gaps 1.44%)

```
MLT            78  ATGGCCCAGCACACAGCGACTACCCCGACGACGAGTTCAGAGCCGATAAGCT
Mitra et al.    1  ATGGCGCAACACTCAGATTACTCCGACGATGAATTTTGCTGACAAACT MLT           128  GAGTAACTA--CAGCTGCGACACAGCGACCTGGAAAACGCCAGCACATCCGA
Mitra et al.   51  GTCCAATTATTCA--TGCGATAGCGACCTCGAAAACGCTTCCACGTCTGA MLT           176  CGAGGACAGCTCTGACGACGAGGTGATGGTGCGGCCCAGAACCCTGAGAC
Mitra et al.   99  TGAAGATAGCAGCGATGATGAAGTAATGGTGAGGCCTCGCACCCTCCGCC MLT           226  GGAGAAGAATCAGC------AGCTCTAGCAGCGACTCTGAATCCGACATC
Mitra et al.  149  GTCGCCGCATCAGCTCTTCGAGCTCT-----GATTCTGAATCCGATATT MLT           270  GAGGGCGGCCCGGGAAGAGTGGAGCCACGTGGACAACCCTCCTGTTCTGGA
Mitra et al.  193  GAGGGTGGCCCGCGGAGGAGTGGTCCCACGTAGACAATCCGCCGGTGCTGGA MLT           320  AGATTTTCTGGGCCATCAGGGCCTGAACACCGACGCCGTGATCAACAACA
Mitra et al.  243  GGACTTCCTAGGCCACCAAGGTCTGAACACTGACGCAGTAATCAACAATA
```

FIG. 10 (cont.)

```
MLT            370  TCGAGGATGCCGTGAAGCTGTGTTCATAGGAGATGATTTCTTTGAGTTCCTG
Mitra et al.   293  TCGAAGATGCAGTGAAACTGTTTATCGGTGACGATTTCTTCGAGTTTCTG MLT            420  GTCGAGGAATCCAACCGCTATTACAACCAGAATAGAAACAACTTCAAGCT
Mitra et al.   343  GTGGAGGAATCTAACCGGTACTATAACCAGAATCGTAATAACTTCAAGCT MLT            470  GAGCAAGAAAAG--CCTGAAGTGGAAGGACATCACCCCTCAGGAGATGAA
Mitra et al.   393  CTCTA--AAAAGTCTCTGAAGTGGAAGGACATCACCCCCCAGGAGATGAA MLT            518  AAAGTTCCTGGGACTGATCGTTCTGATGGGACCGAGACCCCTTACTTTGGC
Mitra et al.   441  AAAGTTCCTCCGGTCTGATCGTTCTGATGGGCCAAGTTCGCAAGGATCGTC MLT            568  GGGATGATTACTGGACAACCGAACCTTGGACCGAGACAGATTCAGAGACCT
Mitra et al.   491  GTGACGACTATTGGACTACCGAACCGTGACGGAAACTCCATACTTTGGC MLT            618  AAGACCATGACCGTCGTGACCGTTTCCGTCAGATCTGGAAAGCCTGGCACTT
Mitra et al.   541  AAGACCATGACTCGTGACTGTCAACGAGTCTGATCTGGAAGGCCTGGCACTT MLT            668  CAACAACAATGCTGATATCGTGAACGAGTCTGATAGACTGTGTAAAGTGC
Mitra et al.   591  CAATAACAACGCTGACATTGTCAACGAGTCTGATCGTCTGTGTAAGGTTC MLT            718  GGCCAGTGTTGGATTACTTCGTGCCTAAGTTCATCAACATCTATAAGCCT
Mitra et al.   641  GCCCTGTGCTGGATTACTTCGTTCCAAAATTCATTAACATTTACAAACCA
```

FIG. 10 (cont.)

| | | |
|---|---|---|
| MLT | 768 | CACCAGCAGCTGAGCCTGGATGAAGGCATCGTGCCCTGGCGGGGCAGACT |
| Mitra et al. | 691 | CATCAGCAGCTGTCCCTGGATGAGGGCATCGTGCCGTGCCGGGCGGGCCT |
| MLT | 818 | GTTCTTCAGAGTGTACAAATGCTGGCAAGATCGTCAAATACGGCATCCCTGG |
| Mitra et al. | 741 | GTTCTTCCGTGTCTATAAATGCTGGCAAGATTGTGAAGTACGGTATCCCTGG |
| MLT | 868 | TGCGCCTTCTGTGCGAGAGCGATACACAGGCTACACATCTGTAATATGGAAATC |
| Mitra et al. | 791 | TTCGCCTGCTGTGCGGAAAGCGACACTGGCTACACATCTGTAACATGGAGATC |
| MLT | 918 | TACTGCGGCGAGGGCAAAAGACTGCTGGAAACCATCCAGACCCGTCGTTTC |
| Mitra et al. | 841 | TACTGCGGGCGAGGGCAAAACGTCTCCCTGGAAACTATCCAGACCCGTCGTGTC |
| MLT | 968 | CCCTTATACCGACAGCTGGTACCACATCTACATGGACAACTACTACAATT |
| Mitra et al. | 891 | TCCATACACGGATTCCTGGTATCATATTACATGGATAACTATTATAACA |
| MLT | 1018 | CTGTGGCCAACTGCGAGCCCTGATGAAGAACAAGTTTAGAATCTGCGGC |
| Mitra et al. | 941 | GCGTGGCTAACTGTGAAGCTCTGATGAAAGAATAAGTTCCGTATTTGCGGT |
| MLT | 1068 | ACAATCAGAAAAAAACAGAGGCATCCCTAAGGACTTCCAGACCATCTCTCT |
| Mitra et al. | 991 | ACTATCCGTAAGAATCGTGAAGAATTCCGAAAGATTTCCAGACCATCTCCCT |
| MLT | 1118 | GAAGAAGGGCCGAAACCAAGTTCATCAGAAACGAAAACGACATCCTGCTCCAAG |
| Mitra et al. | 1041 | GAAAAAGGGTGAAACTAAGTTCATTCGCAAAAACGACATCCTCCTGCAAG |

FIG. 10 (cont.)

```
MLT          1168  TGTGGCAGTCCAAGAAACCCGTGTACCTGATCAGCAGC-ATCCATAGCGC
Mitra et al. 1091  TCTGGCAGTCTAAAAAGCCTGTATATCTGATC-TCATCTATTCACAGCGC MLT          1217  CGAGATGGAAGAAAAGCCAGACATCGAACAGAACAAGCAAGAAGAAGATCG
Mitra et al. 1140  TGAAATGGAAGAAATCTCAGAACATTGATCGCCACCTCCAAGAAAAGATCG MLT          1267  TGAAGCCCAATGCTCTCTGATCGACTACAAGCACAAGCACATGAAAGGCGTGGAC
Mitra et al. 1190  TCAAACCGAATGCATTGATTGATTACAACAAGCACATGAAGGGCGTTGAT MLT          1317  CGGGCCCGACCAGTACCTGTCTTATTACTCTATCCTGAGAAGAACAGTGAA
Mitra et al. 1240  CGTGCTGACCAGTACCTGTCTCGCTATGTACATGAATTGTGCGCTACTGTGAA MLT          1367  ATGGACCAAGAGACTGGCCATGTACATGATCAATTGCGCCCCTGTTCAACA
Mitra et al. 1290  GTGGACTAAACGTCTCGCTATTGTACATGATTAATTGTGCGCTGTTCAATT MLT          1417  GCTACGCCGTGTACAAGTCCGTGCCGACAAAGAAAAATGGGATTCAAGATG
Mitra et al. 1340  CTTACGCTGTGTATAAAGCGTGCGTCAGCGCAAAATGGGCTTTAAAATG MLT          1467  TTCCTGAAGCAGACAGCCATCCACTGGCTGACAGACATTCCTGAGGA
Mitra et al. 1390  TTCCTGAAGCAGCAGGCTATTCACTGGCTGACCGACGATATTCCGGAAGA MLT          1517  CATGGACATTGTGCCAGATCTGCAACCTCTGTGCCCAGCCACCCTCTGGTATGA
Mitra et al. 1440  TATGGACATTGTCCCGGATCTCCAGCCTATCCACCGCCGAGCACCGGTATGC
```

FIG. 10 (cont.)

```
MLT           1567 GAGCTAAGCCTCCCACCAGGCGATCCTCCATGTAGACTGAGCATGGACATG
Mitra et al.  1490 GTGCTAAACCTCCGACTAGTGATCCGCCTTGCCGTCTGTCTATGGATATG MLT           1617 CGGAAGCACACCCTGCAGGCCATCGTCGGCAGCGGCAAGAAGAAGAACAT
Mitra et al.  1540 CGTAAGCATACCCTGCAGGCAATTGTGGGCTCTGGCAAAAAGAAAATAT MLT           1667 CCTTAGACGGTGCAGGGTGTGCAGGCGTGCACAAGCTGCGGGAGCGAGACTC
Mitra et al.  1590 CCTGCGTCGTTGCCGTATGCTCTGTACACAAACTGCGTTCTGAGACTC MLT           1717 GGTACACATGTGCAAGTTTTGCAACATTCCCCTGCACAAGGGAGCCTGCTTC
Mitra et al.  1640 GTTATATGTGTAAATTTTGCAATATTCCACTCCACAAGGGTGCCTGCTTC MLT           1767 GAGAAGTACCACACCCTGAAGAATTA-CTAG--
Mitra et al.  1690 GAGAAGTACCATACGCTGAAGAACTATCTCCGAG
```

FIG. 11

Nucleotide alignment of engineered MLT ("MLT", SEQ ID NO: 338) and the sequence from WO2010085699 (SEQ ID NO: 339, Identity 73.68%, Gaps 1.16%)

```
MLT            1   ATGGCCCAGCA--CAGCGACTACCCCGACGACGAGTTCAGAGCCGATAAGCTGAGTAACTACAGCTGCGACAGCGACCTG
WO 2010085699  1   ATGTCGCAGCATTCA--GACTATACTCATGATGAGTTTTGTCAGACAAGTTGTCCAATTATTCTTGTGATAGCGATCTT

MLT           79   GAAAACGCCAGCACCATCCGACGAGGA---CAGCTCTGACGAGGTGATGGTGCGGCCCAGAACCCTGAGACGGAGAAG
WO 2010085699 79   GAAAATGCGAGTACAAGTGATGAAGATTCTAG---TGATGATGAAGTAATGGTGCGTCCAAGAACATTGAGGCGACGAAG

MLT          156   AATCAGCAGCTCTAGCAGCGACTCTGAATCCGAGGGCCTGAGGGCCTGAGGGCCGTGATCAACAACCGACGCCCTCTG
WO 2010085699 156  AATTTCGAGCTCCAGCTCTGACTCAGAGTCAGATATAGAAGCGGGAGAGAAGATGGTCGCATGTTGATAATCCACCGG

MLT          236   TTCTGGAAGATTTTCTGGGCATCAGGGCCTGAACACCGACTGATCAACAACATCGAGGATGCCGTGAAGCTGTTC
WO 2010085699 236  TCTTAGAAGATTTTTTTAGGGCATCAAGGATTAAAACACAGATGCTGTTATAAATAATATAGAAGAAGATGCCGTGAAATTATTT

MLT          316   ATAGGAGATGATTTCTTTGAGTTCCTGGTCGAGGAATCCAACCGCTATTACAACCAGAATAGAAACAACTTCAAGCTGAG
WO 2010085699 316  ATCGGAGATGATTGATTTTTTTTTGAATTTCTTGTAGAGGAGTCAAACAGGAGTATTATCAAAATAGGAATAATTTCAAACTTTC

MLT          396   CAAGAAAAGCCTGAAGTGGAAGGACATCACCCCTCAGGAGATGAAAAAGTTCCTGGACTGTTCTGATGGACAGG
WO 2010085699 396  AAAAAAAAGCCTAAAGTGGAAGATGTGGAAGATGAAGATGAAGAGTTTTTAGGGTTAATTGTTCTCATGGGACAGG

MLT          476   TGCGGGAAGGACAGAAGGGGATGATTACTGGACAACCGAACCCTTACTTTTGGCAAGACCATGACCAGA
WO 2010085699 476  TGCGCAAAGATAGAAGACATATTGGACGACGAGCCATGGCCATATTTTGGTAAAACGATGACGAGA

MLT          556   GACAGATTCAGACAGATCTGGAAAGCCTGGCACTTCAACAACAATGCTGATATCGTGAACAGTCTGATAGACTCTGTAA
WO 2010085699 556  GACAGGTTCCGACAGATATGGAAAGCTTGGCACTTCAATTAAATAATGCGGATATCGTAAATGAATCAGATAGACTTTGCAA
```

FIG. 11 (cont.)

| | | |
|---|---|---|
| MLT | 636 | AGTCCGGCCAGTGTTGGATTACTTCGTGCCTAAGTTCATCAACATCTATAAGCCTCACCAGCAGCTGAGC-CTGGATGAA |
| WO 2010085699 | 636 | AGTGAGACCAGTACTAGATTATTTGTGCCTAAATTTATAAATTTACAAACCTCATCAGCA-ATTATCACTAGATGAA |
| MLT | 715 | GGCATCGTGCCCTGGCGGGCAGACTGTTCTTCAGAGTGTACAATGCTGGCAAGATCGTCAAATACGGCATCCTGGTGCG |
| WO 2010085699 | 715 | GGGATCGTGTACCTTGGAGGGGAAGATTATTCTTTAGGGTATATAAATGCTGGCAAGATCGTTAAATATGGAATATTGGTTCG |
| MLT | 795 | CCTTCGTGCGAGAGCGATACAGGCTACATCTGTAATATGGAAATTCTACTGCGGGCGAGGGCAAAAGACTGCTGGAAACCA |
| WO 2010085699 | 795 | TTTGTTGTGCGAAAGTGATACAGGATATATCTGTAACATGGAAATTTATTGCGGGAAGGAAAGCGATTATTGGAAACGA |
| MLT | 875 | TCCAGACCGTCGTTCCCCCTTATACCGACAGCTGGTACCACATCTACATGGACAACTACTACAATTCTGTGGCCAACTGC |
| WO 2010085699 | 875 | TACAAACAGTAGTGTCTCCATACACTGATTCGTGGTACCATATATATATATGGACAATTATTATATAATAGCGTCGCAAATTGT |
| MLT | 955 | GAGGCCCTGATGAAGAACAAGTTTAGAATCTGCGGCACAATCAGAAAAAAACAGAGGCATCCCTAAGGACTTCCAGACCAT |
| WO 2010085699 | 955 | GAAGCACTTATGAAAAACAAATTCAGAATATGTGGAACAATCCGGAACAATCGAGGTATACCTAAAGATTTTCAAACAAT |
| MLT | 1035 | CTCTCCTGAAGAGGGCGAACCAAGTTCATCAGAAGTTATAAGGCCAGTCCAAGAAACCCGTGT |
| WO 2010085699 | 1035 | TTCTTTGAAAAAAGTGAAAATTGAAAATGAAAAAAAATTTATAAGGAAGATGGCAATCAAAAAGCCTGTAT |
| MLT | 1115 | ACCTGA--TCAGCAGCATCCATAGCGCCGAGATGAAGCCAGAACATCGACAGAACAAGCACACATGAAAAGAAGATCGTGA |
| WO 2010085699 | 1115 | ACCTGATTTCTTC---GATTCATTCTGCGGAGATGGAAGATATTGACAGAATATTGAAGAACATCAAAAAGAAATTGTCA |
| MLT | 1193 | AGCCCAATGCTCTGATCGACTACAACAAGCACACTGAAAGGCCGTGGACCCGGGCCCGACCAGTACCTGTCTTATTACTCTATC |
| WO 2010085699 | 1193 | AACCGAATGCACTCATTGACTACAATAAACATATGAAAGGTGTTGACCGGCCGACCAATACCTTTCATATTATTCGATA |

FIG. 11 (cont.)

```
MLT            1273 CTGAGAAGAACAGTGAAATGGACCAAGAGACTGGCCATGTACATGATCATTGCGCCCTGTTCAACAGCTACGCCGTGTA
WO 2010085699  1273 TTGCGGGAGGACGGTCAAATGGACAAAAAGGTTGGCCATGTACATGATATGATAAATTGCGCATTATTTAATTCTTATGCAGTTTA

MLT            1353 CAAGTCCGTGCCGACAAAGAAAAAATGGATTCAAGATGTTCCTGAAGCAGCAGCCATCCACTGGCTGACAGACGACATTC
WO 2010085699  1353 CAAATCAGTGAGGCAAAGAAAGAAAAATGGGTTTTAAAATGTTTTGAAACAAACAGCTATCCACTGGTTGACGGATGATATTC

MLT            1433 CTGAGGACATGGACATTGTGCCCAGATCTGCCAACCTGTGCCCAGCACCTCTGGTATGAGAGCTAAGCCTCCCACCAGC-GA
WO 2010085699  1433 CAGAGGACATGGACATTGTTCCAGACCTTCAACCAGTTACCGTCTCTACTTCTGGAATGCGGGCTAAACCACCTA-CATCTGA

MLT            1512 TCCTCCACCATGTAGACTGAGC-ATGGACACTGAAGCAGGCCATCGTCCAGGCCACACCCTGCAGGCCACAAGCATC
WO 2010085699  1512 TCCACCATGCAGCT-ATCGATGGACATGAGAGAACATAGTTACAGGCAATTGTCGGAAGTGAAAAAGAAATAAAACATT

MLT            1591 CTTAGACGGTGCAGGGTGTGCAGCCGGTGCACAAGCTGCGGAGACTCGGTACATGTGCAAGTTTTGCAACATTCCCCT
WO 2010085699  1591 TTGAGAAGGTGTCGCGTATGTTCCGCAGTGACACGCTACACATGTGCAAATTTTGCAATATATACCTCT

MLT            1671 GCACAAGGGAGCCTGCTTCCGAGAAGTACCACACCCTGAAGAATTACTAG
WO 2010085699  1671 ACATAAAGGGGCGTGTTTTGAAAAATATCATACGCTAAAAAACTAT---
```

FIG. 12

Amino acid alignment of engineered MLT (SEQ ID NO: 340, L573del/E574del/S2A, with S8P, C13R, and N125K mutations, "MLT") and a published sequence by Mitra et al. (SEQ ID NO: 341, Mitra contained 2 extra amino acids on C-terminus)

```
MLT            MAQHSDYPDEEFRADKLSNYSCDSDLENASTSDEDSSDDEVMVRPRTLRRRISSSSDS  60
Mitra et al.   MAQHSDY DDEF ADKLSNYSCDSDLENASTSDEDSSDDEVMVRPRTLRRRISSSSDS  60

MLT            ESDIEGGREEWSHVDNPPVLEDELGHQLNTDAVINNIEDAVKLFIGDDFEEFLVEESNR 120
Mitra et al.   ESDIEGGREEWSHVDNPPVLEDELGHQLNTDAVINNIEDAVKLFIGDDFEEFLVEESNR 120

MLT            YYNQKRNNFKLSKKSLKWKDITPQEMKKFLGLIVLMGQVRKDRRDDYWTTEPWTETPYFG 180
Mitra et al.   YYNQNRNNFKLSKKSLKWKDITPQEMKKFLGLIVLMGQVRKDRRDDYWTTEPWTETPYFG 180

MLT            KTMTRDRERQIWKAWHFNNNADIVNESDRLCKVRPVLDYFVPKFINIYKPHQQLSLDEGI 240
Mitra et al.   KTMTRDRERQIWKAWHFNNNADIVNESDRLCKVRPVLDYFVPKFINIYKPHQQLSLDEGI 240

MLT            VPWRGRLFFRVYNAGKIVKYGILVRLLCESDTGYICNMEIYCGEGKRLLETIQTVVSPYT 300
Mitra et al.   VPWRGRLFFRVYNAGKIVKYGILVRLLCESDTGYICNMEIYCGEGKRLLETIQTVVSPYT 300
```

FIG. 12 (cont.)

```
MLT          DSWYHIYMDNYNSVANCEALMKNKFRICGTTIRKNRGIPKDFQTISLKKGETKFIRKNDI   360
Mitra et al. DSWYHIYMDNYNSVANCEALMKNKFRICGTTIRKNRGIPKDFQTISLKKGETKFIRKNDI   360

MLT          LLQVWQSKKPVYLISSIHSAEMEESQNIDRTSKKKIVKPNALIDYNKHMKGVDRADQYLS   420
Mitra et al. LLQVWQSKKPVYLISSIHSAEMEESQNIDRTSKKKIVKPNALIDYNKHMKGVDRADQYLS   420

MLT          YYSILRRTVKWTKRLAMYMINCALFNSYAVYKSVRQRKMGFKMFLKQTAIHWLTDDIPED   480
Mitra et al. YYSILRRTVKWTKRLAMYMINCALFNSYAVYKSVRQRKMGFKMFLKQTAIHWLTDDIPED   480

MLT          MDIVPDLQPVPSTSGMRAKPPTSDPPCRLSMDMRKHTLQAIVGSGKKKNILRRCRVCSVH   540
Mitra et al. MDIVPDLQPVPSTSGMRAKPPTSDPPCRLSMDMRKHTLQAIVGSGKKKNILRRCRVCSVH   540

MLT          KLRSETRYMCKFCNIPLHKGACFEKYHTLKNY*                              572
Mitra et al. KLRSETRYMCKFCNIPLHKGACFEKYHTLKNY LE                            574
```

FIG. 13

Comparison of an amino acid of engineered MLT (SEQ ID NO: 9, L573del/E574del/S2A, with S8P and C13R mutations, "MLT") and the sequence from WO2010085699 (SEQ ID NO: 343)

```
MLT            MAQHSDYPDDEFRADKLSNYSCDSDLENASTSDEDSSDDEVMVRPRTLRRRRISSSSSDS    60
WO 2010085699  M++QHSDY DDEF ADKLSNYSCDSDLENASTSDEDSSDDEVMVRPRTLRRRRISSSSSDS    60
WO 2010085699  MSQHSDYSDDEFCADKLSNYSCDSDLENASTSDEDSSDDEVMVRPRTLRRRRISSSSSDS

MLT            ESDIEGGREEWSHVDNPPVLEDFLGHQGLNTDAVINNIEDAVKLFIGDDFEEFLVEESNR   120
WO 2010085699  ESDIEGGREEWSHVDNPPVLEDFLGHQGLNTDAVINNIEDAVKLFIGDDFEEFLVEESNR   120

MLT            YNQNRNNFKLSKKSLKWKDITPQEMKKFLGLIVLMGQVRKDRRDDYWTTEPWTETPYFG    180
WO 2010085699  YNQNRNNFKLSKKSLKWKDITPQEMKKFLGLIVLMGQVRKDRRDDYWTTEPWTETPYFG    180

MLT            KTMTRDRFRQIWKAWHFNNNADIVNESDRLCKVRPVLDYFVPKFINIYKPHQQLSLDEGI   240
WO 2010085699  KTMTRDRFRQIWKAWHFNNNADIVNESDRLCKVRPVLDYFVPKFINIYKPHQQLSLDEGI   240
```

FIG. 13 (cont.)

```
MLT              VPWRGRLFFRVYNAGKIVKYGILVRLLCESDTGYICNMEIYCGEGKRLLETIQTVVSPYT  300
WO 2010085699    VPWRGRLFFRVYNAGKIVKYGILVRLLCESDTGYICNMEIYCGEGKRLLETIQT  SPYT
                 VPWRGRLFFRVYNAGKIVKYGILVRLLCESDTGYICNMEIYCGEGKRLLETIQT-WSPYT  299

MLT              DSWYHIYMDNYYNSVANCEALMKNKFRICGTIRKNRGIPKDFQTISLKKGETKFIRKNDI  360
WO 2010085699    DSWYHIYMDNYYNSVANCEALMKNKFRICGTIRKNRGIPKDFQTISLKKGETKFIRKNDI
                 DSWYHIYMDNYYNSVANCEALMKNKFRICGTIRKNRGIPKDFQTISLKKGETKFIRKNDI  359

MLT              LLQVWQSKKPVYLISSIHSAEMEESQNIDRTSKKKIVKPNALIDYNKHMKGVDRADQYLS  420
WO 2010085699    LLQVWQSKKPVYLISS  HSAEMEESQNIDRTSKKKIVKPNALIDYNKHMKGVDRADQYLS
                 LLQVWQSKKPVYLISS-HSAEMEESQNIDRTSKKKIVKPNALIDYNKHMKGVDRADQYLS  418
```

FIG. 13 (cont.)

```
MLT              YYSILRRTVKWTKRLAMYMINCALFNSYAVYKSVRQRKMGFKMFLKQTAIHWLTDDIPED  480
                 YYSILRR  KWTKRLAMYMINCALFNSYAVYKSVRQRKMGFKMFLKQTA HWLTDDIPED
WO 2010085699    YYSILRRW-KWTKRLAMYMINCALFNSYAVYKSVRQRKMGFKMFLKQTA-HWLTDDIPED  476

MLT              MDIVPDLQPVPSTSGMRAKPPTSDPPCRLSMDMRKHTLQAIVGSGKKKNILRRCRVCSVH  540
                 MDIVPDLQPVPSTSGMRAKPPTSDPPCRLSMDMRKHTLQAIVGSGKKKNILRRCRVCSVH
WO 2010085699    MDIVPDLQPVPSTSGMRAKPPTSDPPCRLSMDMRKHTLQAIVGSGKKKNILRRCRVCSVH  536

MLT              KLRSETRYMCKFCNIPLHKGACFEKYHTLKNY*  572
                 KLRSETRYMCKFCNIPLHKGACFEKYHTLKN
WO 2010085699    KLRSETRYMCKFCNIPLHKGACFEKYHTLKN   567
```

FIG. 14

Comparison of a terminal left end of MLT to a published sequence (Ray et al., piggyBac1_ML)

```
LEFT END (RAY ET AL.)    1   TTAACACTTGGATTGCGGGAAACGAGTTAAGTCGGCTCGCCGTGAATTGCCGTACTCCGC
MLT Left End             1   TTAACACTTGGATTGCGGGAAACGAGTTAAGTCGGCTCGCCGTGAATTGCCGTACTCCGC LEFT END (RAY ET AL.)   61   GGGAGCCGTCTTAACTCGGTTCATATAGATTTGCGGTGGAGTGCGGGAAACGTGTAAACT
MLT Left End            61   GGGAGCCGTCTTAACTCGGTTCATATAGATTTGCGGTGGAGTGCGGGAAACGTGTAAACT LEFT END (RAY ET AL.)  121   CGGGCCGATTGTAACTGCGTATTACCAAATATTTGTT    SEQ ID NO: 430
MLT Left End           121   CGGGCCGATTGTAACTGCGTATTACCAAATATTTGTT    SEQ ID NO: 431
```

FIG. 15

Comparison of a terminal right end of MLT to a published sequence (Ray et al. piggyBac1_ML)

```
RIGHT END (RAY ET AL.)   2423   AATTATTTATGTACTGAATAGATAAAAAAAATGTCTGTGATTGAATAAATTTTCATTTTTT
MLT Right End               1   AATTATTTATGTACTGAATAGATAAAAAAaaTGTCTGTGATTGAATAAATTTTCATTTTTT RIGHT END (RAY ET AL.)   2483   ACACAAGAAACCGAAAATTTCATTTCAATCGAACCCATACTTCAAAAGATATAGGCATTT
MLT Right End              61   ACACAAGAAACCGAAAATTTCATTTCAATCGAACCCATACTTCAAAAGATATAGGCATTT RIGHT END (RAY ET AL.)   2453   TAAACTAACTCTGATTTTGCGCGGGAAACCTAAATAATTGCCCGCGCCATCTTATATTTT
MLT Right End             121   TAAACTAACTCTGATTTTGCGCGGGAAACCTAAATAATTGCCCGCGCCATCTTATATTTT RIGHT END (RAY ET AL.)   2603   GGCGGGAAATTCACCCGACACCGTAGTGTTAA    SEQ ID NO: 432
MLT Right End             181   GGCGGGAAATTCACCCGACACCGTAGTGTTAA    SEQ ID NO: 433
```

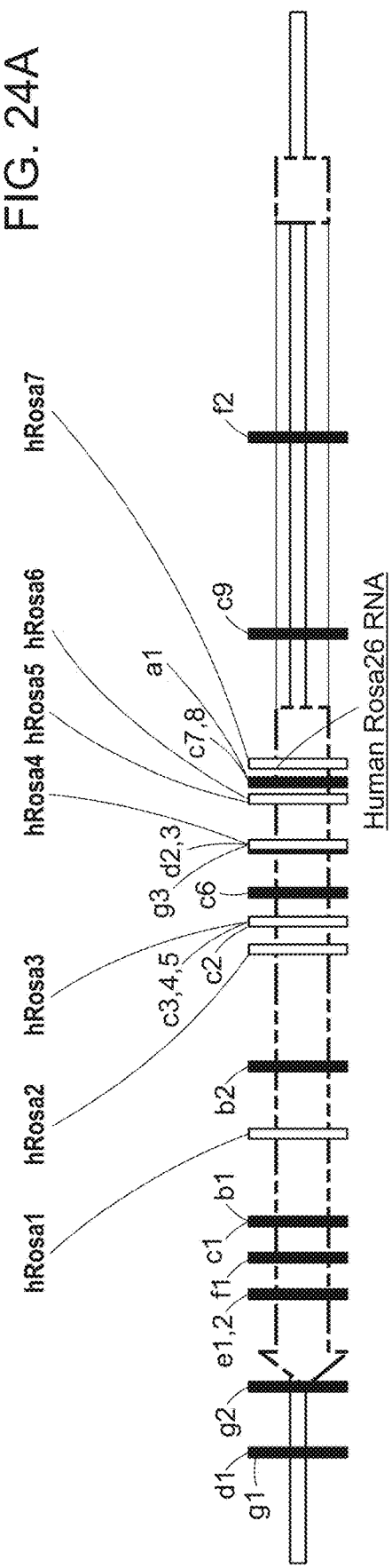
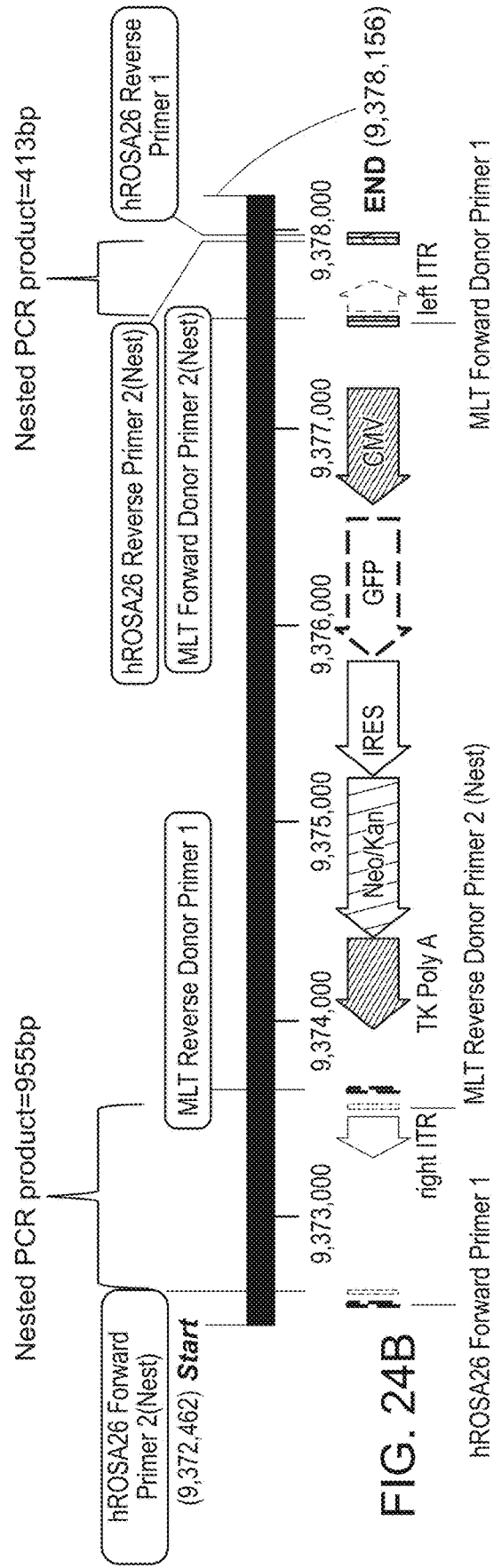
FIG. 24A
FIG. 24B

TRANSPOSITION-BASED THERAPIES

PRIORITY

The present application is a continuation of U.S. application Ser. No. 18/058,486, filed Nov. 23, 2022, which is a continuation of U.S. application Ser. No. 17/669,939, filed Feb. 11, 2022, now U.S. Pat. No. 11,542,528 and is a continuation of International Application No. PCT/US21/30729, filed May 4, 2021, which claims priority to and benefit from U.S. Provisional Patent Application No. 63/019,709, filed May 4, 2020, the U.S. Provisional Patent Application No. 63/027,561, filed May 20, 2020, U.S. Provisional Patent Application No. 63/058,200, filed Jul. 29, 2020, and U.S. Provisional Patent Application No. 63/175,345, filed Apr. 15, 2021, the entirety of each which is incorporated by reference herein.

FIELD OF THE INVENTION

The present invention relates, in part, to a dual system using enzymes capable of transposition (e.g., engineered transposases and/or chimeric transposases) and transposons for targeting human genomic safe harbor sites (GSHS).

DESCRIPTION OF THE TEXT FILE SUBMITTED ELECTRONICALLY

This application contains a Sequence Listing in XML format submitted electronically herewith via EFS-Web. The contents of the XML copy, created on Mar. 6, 2024, is named "SAL-003C3_126933-5003_Sequence_Listing.XML" and is 492,348 bytes in size. The Sequence Listing is incorporated herein by reference in its entirety.

BACKGROUND

Human gene therapy is a promising approach that delivers genes for treating and mitigating various diseases and conditions, including inherited and acquired diseases. Gene therapy involves replacing or complementing a mutated gene (which causes a disease) with a healthy copy of the gene, inactivating or silencing a mutated gene that is functioning improperly (or any other gene), or introducing a new gene into chromosomes. The ability to safely and efficiently integrate genes into a host genome is essential for successful gene therapy in humans.

Currently, the most commonly used vectors for permanent or transient transfer of genes in gene therapy trials are virus-based. Although it is possible to achieve stable genomic integration with high-efficiency using viral vectors, multiple studies have shown serious disadvantages and safety concerns. Thus, adenoviruses and adeno-associated viruses (AAV) have been shown to evoke host human responses that limit administration or re-administration, while retroviruses/lentiviruses preferentially integrate transgenes into euchromatin thereby increasing the risk of insertional mutagenesis or oncogenesis. Viral systems are also limited in cargo size, restricting the size and number of transgenes and their regulatory elements. Viral vector-host interaction can include immunogenicity, and integration of a viral vector DNA in a host genome may have genotoxic effects. Also, because the AAV genome mainly persists in an episomal form in the nucleus of the infected cells, it can be lost in conditions of cell proliferation (such as, e.g. liver growth or other organ growth), limiting therapeutic efficacy. Accordingly, limitations of viral vectors such as pathogenicity, expensive production, and systemic instability have proved to be major obstacles to the use of viral-based systems. In fact, re-administration of viral-based vectors can promote immune responses that can result in life threatening systemic effects and limit gene-transfer efficacy. See Kay et al. *Proc Natl Acad Sci USA* 1997; 94:4686-91; Hernandez et al., *J Virol* 1999; 73:8549-58.

Non-viral vectors (i.e., lipid-based, polymer-based, lipid-polymer based, and poly-lysine) are synthetic tools for encapsulating transgenic DNA or RNA until it reaches the cellular target. Compared to viral vectors, non-viral vectors are generally safer to prepare, and the risk of pathogenic and immunologic complications is diminished. Non-viral vectors have been designed by modifying the surface of a non-viral vector for targeted therapy. See, e.g., Lestini et al., *J Control Release* 2002; 78:235-47.

Nucleases are also being evaluated for use in non-viral human gene therapy. Clustered regularly interspaced short palindromic repeats (CRISPR)/CRISPR associated (Cas9) and transcription activator-like effector (TALE) nuclease (TALEN) systems induce double-stranded DNA breaks (DSBs). The DSBs enhance homologous recombination to insert transgenes at specific sequences but off-target DNA cleavages at unknown remote sites cause inadvertent mutations that require complex genotoxicity screens for detection. The CRISPR system uses Cas9 complexed with a user-defined guide RNA (gRNA) to recognize and cut complementary sequences. TALEN and CRISPR both use host homology-directed repair to introduce a co-delivered donor template at the desired sequence. The TALEN and CRISPR approaches demonstrate efficient gene transfer, but concerns about their cyto- and genotoxic effects remain significant obstacles for clinical applications. Furthermore, gene addition using homology-directed repair requires replication, thus limiting nuclease technology to dividing tissues (i.e. not effective in non-diving tissue such as the central nervous system). Other gene editing techniques, such as prime editing and base pair editing, are limited to correcting base pairs or small nucleotide stretches. These features limit the in vivo and ex vivo application of this technology to diseases with a single common pathogenic nucleotide variant. However, most genetic disorders have hundreds or even thousands of pathogenic nucleotide variants in one or more genes.

A recombinase recognizes and binds specific sequences at the ends of a transposon, mediates synaptic interactions between the ends to bring them together, interacts with the target DNA, and executes the DNA breakage and joining reactions that underlie recombination. An integrase is a recombinase enzyme that is capable of integrating DNA (e.g., of a virus), into another piece of DNA, usually the host chromosome.

DNA transposons are mobile elements that use a "cut-and-paste" mechanism. DNA is excised by double strand cleavage from the donor molecule and integrated into the acceptor molecule. Transposons move from one position on DNA to a second position on DNA in the presence of a transposase, an enzyme that binds to the end of a transposon and catalyzes its movement to a specific genomic location in a host.

A main concern in transposase-based gene therapy is insertional mutagenesis due to random integration, albeit mostly at known sequences (e.g. TTAA sequences), near or within loci that activate oncogenes, interrupt tumor-suppressor genes, or disrupt the transcription of normal genes. Thus, while non-viral, transposon gene therapy approaches have great promise for treating individuals with genetic disorders, the challenge is to reduce the risk of random insertion.

Accordingly, there is a clinical need to improve the safety of enzymes capable of transposition, such as, e.g., transposases, to reduce the risk of insertional mutagenesis and oncogenesis.

SUMMARY OF THE INVENTION

Therefore, the present invention provides, in part, novel transposase compositions that have particular use in therapies yet avoid limitations of existing transposases.

In aspects, there is provided a mammalian transposase which is suitable for use in gene therapy, and advantageously gene therapy with large payloads (e.g. a transposon) which is durable. In aspects, the mammalian transposase is an engineered version of an *Myotis lucifugus* transposase (MLT transposase) that has been designed to have an N-terminal amino acid substitution and C-terminal amino acid deletions. In embodiments, the MLT transposase has an amino acid sequence of SEQ ID NO: 2, or a variant thereof. In embodiments, the MLT transposase is further engineered to have amino acid substitutions to improve activity, e.g. at positions corresponding to positions S8, C13, and/or N125 of SEQ ID NO: 2.

In aspects, a composition is provided comprising a transposase enzyme (e.g., an MLT transposase) or nucleic acid encoding the transposase enzyme, wherein the transposase enzyme comprises an amino acid sequence having at least about 80% sequence identity to SEQ ID NO: 2, wherein the transposase enzyme comprises an amino acid substitution at the position corresponding to position S2 of SEQ ID NO: 2.

The present invention provides a gene transfer system or construct comprising a monomer or a head-to-tail dimer enzyme capable of genomic integration by transposition and a DNA binding domain (DBD), such as a transcription activator-like effector protein (TALE) DBD or inactive (dCas9) programmed by a guide RNA (gRNA) (referred to as a dCas9/gRNA complex) as shown in FIGS. 1A-D or in FIG. 2. These chimeric systems, having a DBD fused to an enzyme capable of transposition (e.g., a recombinase, an integrase, or a transposase), direct binding of the enzyme to a specific sequence [e.g. TALE repeat variable di-residues (RVD) or gRNA] near a transposase recognition site such that the transposase is prevented from binding to random recognition sites. In some embodiments, an enzyme (e.g., transposase) of the gene transfer system binds to human genomic safe harbor sites (GSHS). TALEs described herein can physically sequester the enzyme to GSHS and promote transposition to nearby TTAAsequences in close proximity to the RVD TALE nucleotide sequences. GSHSs in open chromatin sites are specifically targeted based on the predilection for transposases to insert into open chromatin. In addition, dCas9 (i.e. deficient for nuclease activity) is programmed with gRNAs directed to bind at a desired sequence of DNA in GSHS.

In some aspects, a composition is provided that comprises an enzyme capable of transposition comprising (a) a TALE DBD or a dCas9/gRNA DBD; (b) an enzyme capable of targeted genomic integration by transposition, the enzyme being capable of inserting a transposon at a TA dinucleotide site or a TTAA tetranucleotide site in a GSHS sequence in a nucleic acid molecule; and (c) a linker that connects the TALE or Cas/gRNA DBD and the enzyme.

In some embodiments, the enzyme, e.g., a transposase or a transposase enzyme, is in a dimeric form (e.g. a head to tail dimer). In some embodiments, the enzyme is in a tetrameric form or in another multimeric form. In some embodiments, the enzyme is in a monomeric form.

In some embodiments, the composition is suitable for causing insertion of the transposon in the GSHS when contacted with a biological cell. The TALE DBD or dCas/gRNA complex can be suitable for directing the transposase enzyme to the GSHS sequence. In embodiments, the composition comprises a dCas/gRNA complex.

In some embodiments, a composition is provided that comprises an enzyme capable of transposition comprising (a) a dCas9/gRNA complex; (b) an enzyme capable of targeted genomic integration by transposition, the enzyme being capable of inserting a transposon at a TA dinucleotide site or a TTAA tetranucleotide site in a GSHS sequence in a nucleic acid molecule; and (c) a linker that connects the dCas/gRNA complex and the enzyme.

In embodiments, the GSHS is in an open chromatin location in a chromosome. In some embodiments, the GSHS is selected from adeno-associated virus site 1 (AAVS1), chemokine (C-C motif) receptor 5 (CCR5) gene, HIV-1 coreceptor, and human Rosa26 locus. In some embodiments, the GSHS is located on human chromosome 2, 4, 6, 10, 11, or 17.

In some embodiments, the GSHS is selected from sites listed in FIG. 3 and FIG. 4, or a variant thereof (e.g. having about 1, or about 2, or about 3, or about 4, or about 5 mutations, independently selected from an insertion, substitution or deletion). In some embodiments, the TALE DBD comprises a sequence of FIG. 3 or a variant thereof (e.g. having about 1, or about 2, or about 3, or about 4, or about 5 mutations, independently selected from an insertion, substitution or deletion). In some embodiments, the dCas/gRNA DBD comprises a sequence of FIG. 4, or a variant thereof (e.g. having about 1, or about 2, or about 3, or about 4, or about 5 mutations, independently selected from insertion, substitution or deletion).

In some embodiments, the GSHS is within about 25, or about 50, or about 100, or about 150, or about 200, or about 300, or about 500 nucleotides of the TA dinucleotide site or TTAA tetranucleotide site. In some embodiments, the GSHS is greater than 500 nucleotides from the TA dinucleotide site or TTAA tetranucleotide site.

In embodiments, the TALE DBD comprises one or more repeat sequences. In some embodiments, the TALE DBD or repeat variable di-residue (RVD) comprises about 14, or about 15, or about, 16, or about 17, or about 18, or about 18.5 amino acid repeat sequences. In some embodiments, the RVD is included within TALE amino acid repeat sequences comprising 33 or 34 amino acids.

In some embodiments, the one or more of the TALE DBD repeat sequences comprise an RVD at residue 12 or 13 of the 33 or 34 amino acids. The RVD can recognize certain base pair(s) or residue(s) of the target DNA. In some embodiments, the RVD recognizes one base pair in the nucleic acid molecule. In some embodiments, the RVD recognizes a "C" residue in the nucleic acid molecule and the RVD is selected from HD, N(gap), HA, ND, and HI. In some embodiments, the RVD recognizes a "G" residue in the nucleic acid molecule and the RVD is selected from NN, NH, NK, HN, and NA. In some embodiments, the RVD recognizes an "A" residue in the nucleic acid molecule and the RVD is selected from NI and NS. In some embodiments, the RVD recognizes a "T" residue in the nucleic acid molecule and the RVD is selected from NG, HG, H(gap), and IG. In embodiments, the enzyme (e.g., without limitation, a transposase enzyme) is capable of inserting a transposon at a TA dinucleotide site.

In some embodiments, the enzyme is capable of inserting a transposon at a TTAA tetranucleotide site.

In embodiments, a nucleic acid encoding the enzyme capable of targeted genomic integration by transposition comprises an intein. In embodiments, the nucleic acid encodes the enzyme in the form of first and second portions with the intein encoded between the first and second portions, such that the first and second portions are fused into a functional enzyme upon post-translational excision of the intein from the enzyme.

In embodiments, the enzyme is a recombinase or an integrase. In embodiments, the recombinase is an integrase. In embodiments, the integrase is a transposase or the recombinase is a transposase.

In embodiments, the transposase has one or more mutations that confer hyperactivity. In embodiments, the transposase is a mammal-derived transposase, optionally encoded by a helper RNA.

In embodiments, the enzyme is derived from *Bombyx mori, Xenopus tropicalis, Trichoplusia ni*, or *Myotis lucifugus*. In embodiments, the enzyme is an engineered version, including but not limited to an enzyme that is a monomer, dimer, tetramer (or another multimer), hyperactive, or has a reduced interaction with non-TTAA recognitions sites (Int-), derived from *Bombyx mori, Xenopus tropicalis, Trichoplusia ni*, or *Myotis lucifugus*. In some embodiments, the transposase enzyme is a *Myotis lucifugus* transposase (referred to herein as MLT or an MLT transposase), which can be either the wild type, monomer, dimer, tetramer (or another multimer), hyperactive, an Int-mutant, or any other variant.

In embodiments, a hyperactive form or Int- form of an MLT transposase has one or more mutations selected from L573X, E574X, and S2X, wherein X is any amino acid or no amino acid, optionally X is A, G, or a deletion, optionally the mutations are L573del, E574del, and S2A.

In embodiments, an MLT transposase, referred to herein as a corrected, engineered MLT transposase, has L573del, E574del, and S2A mutations. Such MLT transposase comprises an amino acid sequence of SEQ ID NO: 2, or a variant having at least about 90%, or at least about 93%, or at least about 95%, or at least about 97%, or at least about 98%, or at least about 99% identity thereto. In embodiments, the MLT transposase is encoded by a nucleotide sequence of SEQ ID NO: 3, or a variant having at least about 90%, or at least about 93%, or at least about 95%, or at least about 97%, or at least about 98%, or at least about 99% identity thereto.

In embodiments, an MLT transposase has the amino acid of SEQ ID NO: 4, or an amino acid sequence having at least about 90%, or at least about 93%, or at least about 95%, or at least about 97%, or at least about 98%, or at least about 99% identity thereto. In some embodiments, the MLT transposase is encoded by the nucleotide sequence of SEQ ID NO: 5, or a nucleotide acid sequence having at least about 90%, or at least about 93%, or at least about 95%, or at least about 97%, or at least about 98%, or at least about 99% identity thereto.

In embodiments, a hyperactive, Int-, or other forms of an MLT transposase include a mutation from FIGS. 5A and 5B, e.g. without limitation, about 1, or about 2, or about 3, or about 4, or about 5 mutations. In embodiments, the transposase can include any of the mutations depicted in FIGS. 5A and 5B, or equivalents thereof.

In embodiments, an MLT transposase in accordance with embodiments of the present disclosure comprises one or more hyperactive mutations that confer hyperactivity upon the MLT transposase. In embodiments, hyperactive mutants comprise one or more substitutions at S8, C13, and N125. In embodiments, hyperactive mutations comprise one or more of S8P, C13R, and N125K mutations.

In embodiments, an MLT transposase has an amino acid sequence having hyperactive mutations at positions which correspond to at least one of S8P, C13R, and N125K mutations relative to the amino acid sequence of SEQ ID NO: 2. In embodiments, an MLT transposase has an amino acid sequence of SEQ ID NO: 7, which has a mutation at a position which corresponds to hyperactive N125K mutation relative to the amino acid sequence of SEQ ID NO: 2.

In embodiments, an MLT transposase has an amino acid sequence of SEQ ID NO: 9, which comprises mutations at positions which correspond to hyperactive S8P and C13R mutations relative to the amino acid sequence of SEQ ID NO: 2.

In embodiments, an MLT transposase has an amino acid sequence having hyperactive mutations at positions which correspond to at least one of S8P, C13R, and N125K mutations relative to the amino acid sequence of SEQ ID NO: 2. It should be appreciated that the MLT transposase having the amino acid sequence of SEQ ID NO: 2 can have two hyperactive mutations (S8P and C13R), without the N125K mutation, or the MLT transposase having the amino acid sequence of SEQ ID NO: 2 can have any other mutation(s) (e.g., any one or more of mutations in FIGS. 5A and 5B). In embodiments, an MLT transposase has an amino acid sequence of SEQ ID NO: 340, which comprises hyperactive mutations at positions which correspond to S8P, C13R, and N125K mutations relative to the amino acid sequence of SEQ ID NO: 2.

In embodiments, the transposase enzyme is derived from *Bombyx mori, Xenopus tropicalis, Trichoplusia ni, Myotis lucifugus, Rhinolophus ferrumequinum, Rousettus aegyptiacus, Phyllostomus discolor, Myotis myotis, Pteropus vampyrus, Pipistrellus kuhlii, troglodytes, Molossus molossus*, or *Homo sapiens*. In embodiments, the transposase enzyme is derived from any of *Trichoplusia ni, Myotis lucifugus, Myotis myotis, Pan troglodytes*, or *Pteropus vampyrus* (see FIG. 7). The transposases can have one or more hyperactive and/or integration deficient mutations selected from FIGS. 5A and 5B, or equivalents thereof. One skilled in the art can correspond such mutants to transposases from any of *Trichoplusia ni, Myotis lucifugus, Myotis myotis*, or *Pteropus vampyrus*, with reference to FIG. 7. Also, one skilled in the art can correspond such mutants to transposases from *Bombyx mori, Xenopus tropicalis, Trichoplusia ni, Myotis lucifugus, Rhinolophus ferrumequinum, Rousettus aegyptiacus, Phyllostomus discolor, Myotis myotis, Pteropus vampyrus, Pipistrellus kuhlii, troglodytes, Molossus molossus*, or *Homo sapiens*.

In some embodiments, the enzyme (e.g., without limitation, a transposase) has a nucleotide sequence having at least about 90%, or at least about 93%, or at least about 95%, or at least about 97%, or at least about 98%, or at least about 99% identity to a nucleotide sequence of any of *Rhinolophus ferrumequinum, Rousettus aegyptiacus, Phyllostomus discolor, Myotis myotis, Pteropus vampyrus, Pipistrellus kuhlii*, and *Molossus molossus*. In some embodiments, the transposase enzyme can have an amino acid sequence having at least about 90%, or at least about 93%, or at least about 95%, or at least about 97%, or at least about 98%, or at least about 99% identity to an amino acid sequence of any of *Rhinolophus ferrumequinum, Rousettus aegyptiacus, Phyllostomus discolor, Myotis myotis, Pteropus vampyrus, Pipistrellus kuhlii*, and *Molossus molossus*.

In embodiments, the enzyme (e.g., without limitation, a transposase) is an engineered version, including but not limited to a transposase enzyme that is a monomer, dimer, tetramer, hyperactive, or has a reduced interaction with non-TTAA recognitions sites (Int-), derived from any of *Bombyx mori, Xenopus tropicalis, Trichoplusia ni, Myotis lucifugus, Rhinolophus ferrumequinum, Rousettus aegyptiacus, Phyllostomus discolor, Myotis myotis, Pteropus vampyrus, Pipistrellus kuhlii, Pan troglodytes, Molossus molossus*, and *Homo sapiens*. The transposase enzyme can be either the wild type, monomer, dimer, tetramer or another multimer, hyperactive, or an Int-mutant.

In some embodiments, the linker that connects the TALE DBD and the enzyme capable of targeted genomic integration by transposition is a flexible linker. In some embodiments, the flexible linker is substantially comprised of glycine and serine residues, optionally wherein the flexible linker comprises $(Gly_4Ser)_n$, where n is from about 1 to about 12. The flexible linker can be of about 20, or about 30, or about 40, or about 50, or about 60 amino acid residues.

A composition comprising an enzyme capable of transposition in accordance with embodiments of the present disclosure can include one or more non-viral vectors. Also, the enzyme (e.g., a chimeric transposase) can be disposed on the same (cis) or different vector (trans) than a transposon with a transgene. Accordingly, in some embodiments, the chimeric transposase and the transposon encompassing a transgene are in cis configuration such that they are included in the same vector. In some embodiments, the chimeric transposase and the transposon encompassing a transgene are in trans configuration such that they are included in different vectors. The vector is any non-viral vector in accordance with the present disclosure.

In some aspects, a nucleic acid encoding an enzyme capable of targeted genomic integration by transposition (e.g., a chimeric transposase) in accordance with embodiments of the present disclosure is provided. The nucleic acid can be DNA or RNA. In some embodiments, the nucleic acid encoding the enzyme is DNA. In some embodiments, the nucleic acid encoding the enzyme capable of targeted genomic integration by transposition (e.g., a chimeric transposase) is RNA such as, e.g., helper RNA. In embodiments, the chimeric transposase is incorporated into a vector. In some embodiments, the vector is a non-viral vector.

In embodiments, a nucleic acid encoding a transposon is a DNA, referred to as a "donor DNA." In embodiments, a nucleic acid encoding an enzyme capable of targeted genomic integration by transposition (e.g., a chimeric transposase) is helper RNA. In embodiments, the donor DNA is incorporated into a plasmid. In embodiments, the donor DNA is a plasmid. In some aspects, a host cell comprising the nucleic acid in accordance with embodiments of the present disclosure is provided.

In some embodiments, a composition or a nucleic acid in accordance with embodiments of the present disclosure is provided wherein the composition is in the form of a lipid nanoparticle (LNP).

In embodiments, a nucleic acid encoding the enzyme and a nucleic acid encoding the transposon are contained within the same lipid nanoparticle (LNP). In some embodiments, the nucleic acid encoding the enzyme and the nucleic acid encoding the transposon are a mixture incorporated into or associated with the same LNP. In some embodiments, the nucleic acid encoding the enzyme and the nucleic acid encoding the transposon are in the form of a co-formulation incorporated into or associated with the same LNP.

In embodiments, the LNP is selected from 1,2-dioleoyl-3-trimethylammonium propane (DOTAP), a cationic cholesterol derivative mixed with dimethylaminoethane-carbamoyl (DC-Chol), phosphatidylcholine (PC), triolein (glyceryl trioleate), and 1,2-distearoyl-sn-glycero-3-phosphoethanolamine-N-[carboxy(polyethylene glycol)-2000] (DSPE-PEG), 1,2-dimyristoyl-rac-glycero-3-methoxypolyethyleneglycol—2000 (DMG-PEG 2K), and 1,2 distearol-sn-glycerol-3phosphocholine (DSPC) and/or comprising of one or more molecules selected from polyethylenimine (PEI) and poly(lactic-co-glycolic acid) (PLGA), and N-Acetylgalactosamine (GalNAc).

In some embodiments, an LNP can be as described, e.g. in Patel et al., *J Control Release* 2019; 303:91-100. The LNP can comprise one or more of a structural lipid (e.g. DSPC), a PEG-conjugated lipid (CDM-PEG), a cationic lipid (MC3), cholesterol, and a targeting ligand (e.g. GalNAc).

In some aspects, a method for inserting a gene into the genome of a cell is provided that comprises contacting a cell with an enzyme (e.g., without limitation, a chimeric transposase) in accordance with embodiments of the present disclosure. The method can be in vivo or ex vivo method.

In some embodiments, the cell is contacted with a nucleic acid encoding the enzyme (e.g., without limitation, a chimeric transposase). In some embodiments, the cell is contacted with an RNA encoding the chimeric transposase, and/or with a construct comprising a transposon with flanking insulators such as, e.g. HS4 and D4Z4. In some embodiments, the cell is contacted with a DNA encoding the chimeric transposase.

In some embodiments, the transposon is flanked by one or more inverted terminal ends. The transposon can be under control of a tissue-specific promoter. In some embodiments, the transposon is an ATP Binding Cassette Subfamily A Member 4 gene (ABC) transporter gene (ABCA4), or functional fragment thereof. As another example, in some embodiments, the transposon is a very low-density lipoprotein receptor gene (VLDLR) or a low-density lipoprotein receptor gene (LDLR), or a functional fragment thereof.

In embodiments, the enzyme is a transposase such as a chimeric transposase, and the method provides reduced insertional mutagenesis or oncogenesis as compared to a method with a non-chimeric transposase.

In embodiments, the method is used to treat an inherited or acquired disease in a patient in need thereof.

For example, in some embodiments, the method is used for treating and/or mitigating a class of Inherited Macular Degeneration (IMDs) (also referred to as Macular dystrophies (MDs), including Stargardt disease (STGD), Best disease, X-linked retinoschisis, pattern dystrophy, Sorsby fundus dystrophy and autosomal dominant drusen. The STGD can be STGD Type 1 (STGD1). In some embodiments, the STGD can be STGD Type 3 (STGD3) or STGD Type 4 (STGD4) disease. The IMD can be characterized by one or more mutations in one or more of ABCA4, ELOVL4, PROM1, BEST1, and PRPH2. The gene therapy can be performed using transposon-based vector systems, with the assistance by chimeric transposases in accordance with the present disclosure, which are provided on the same vector as the gene to be transferred (cis) or on a different vector (trans) or as RNA. The transposon can comprise an ATP binding cassette subfamily A member 4 (ABCA4), or functional fragment thereof, and the transposon-based vector systems can operate under the control of a retina-specific promoter.

In some embodiments, the method is used for treating and/or mitigating familial hypercholesterolemia (FH), such as homozygous FH (HoFH) or heterozygous FH (HeFH) or disorders associated with elevated levels of low-density lipoprotein cholesterol (LDL-C). The gene therapy can be performed using transposon-based vector systems, with the assistance by enzymes (e.g., without limitation, chimeric transposases) in accordance with the present disclosure, which are provided on the same vector (cis) as the gene to be transferred or on a different vector (trans, e.g., a donor DNA/helper RNA system). The transposon can comprise a very low-density lipoprotein receptor gene (VLDLR) or a low-density lipoprotein receptor gene (LDLR), or a functional fragment thereof. The transposon-based vector systems can operate under control of a liver-specific promoter. In some embodiments, the liver-specific promoter is an LP1 promoter. The LP1 promoter can be a human LP1 promoter, which can be constructed as described, e.g., in Nathwani et al. *Blood* vol. 107(7) (2006):2653-61.

It should be appreciated that any other inherited or acquired diseases can be treated and/or mitigated using the method in accordance with the present disclosure.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF DRAWINGS

FIGS. 1A-D depict non-limiting representations of chimeric, monomer or head-to-tail dimer transposases that are designed to target human GSHS using TALE and Cas9/guide RNA DNA binders. FIG. 1A. TALEs include nuclear localization signals (NLS) and an activation domain (AD) to function as transcriptional activators. The DNA binding domain has approximately 16.5 repeats of 33-34 amino acids with a residual variable di-residue (RVD) at position 12-13. FIG. 1B. RVDs are shown that have specificity for one or several nucleotides. Only bases of the DNA leading strand are shown. FIG. 1C. A chimeric transposase construct comprising a TALE DNA-binding protein fused thereto by a linker that is greater than 23 amino acids in length (top) and a chimeric transposase construct comprising dCas9 linked to one or more guide RNAs (bottom). FIG. 1D. A schematic diagram showing that chimeric transposases form dimers or tetramers at open chromatin to insert donor DNA at TTAA recognition sites near DNA binding regions targeted by TALEs or dCas9/gRNA. Binding of the TALE or dCas9/gRNA to GSHS physically sequesters the transposase as a monomer or dimer to the same location and promotes transposition to the nearby TTAA sequences (FIG. 3 and FIG. 4) near repeat variable di-residues (RVD) nucleotide sequences. All RVDs are preceded by a thymine (T) to bind to the NTR shown in FIG. 1A).

FIGS. 3 and 4 depict DNA binding codes for human genomic safe harbor sites in areas of open chromatin (FIG. 3) and guide RNAs to target human genomic safe harbor sites using dCas in areas of open chromatin (FIG. 4). Genomic locations for chromosomes 2, 4, 6, and 11 are adapted from Pellenz et al. (*Hum Gene Ther* 2019; 30:814-28) and chromosomes 10 and 17 from Papapetrou et al. (*Nat Biotechnol* 2011; 29:73-8). Sequences were downloaded from the UCSC Genome browser using hg18 or hg19 and evaluated with E-TALEN, a software tool to design and evaluate TALE DBD and WU-CRISPR, a software tool to design guide RNAs.

FIG. 5A depicts hyperactive MLT mutants.

FIG. 5B depicts excision positive and integration deficient (Int-) MLT mutants.

FIG. 7 depicts an amino acid sequence alignment of PiggyBac™ ("Tni") transposase to MLT ("bat") transposase and other bat transposases (*Trichoplusia ni*, *Myotis lucifugus*, *Myotis myotis*, and *Pteropus vampyrus*). Amino acid sequence alignment of PiggyBac™ transposase (SEQ ID NO: 10) versus MLT and other mammalian transposases (SEQ ID NO: 14 (*Myotis lucifugus*), SEQ ID NO: 12 (*Myotis myotis* 2a), SEQ ID NO: 13 (*Myotis myotis* 1), SEQ ID NO: 11 (*Pteropus vampyrus*), SEQ ID NO: 14 (*Myotis lucifugus* 2), SEQ ID NO: 15 (*Myotis myotis* 2), and SEQ ID NO: 16 (*Myotis myotis* 2b), appear in the order listed below under "Consensus" (SEQ ID NO: 436).

FIG. 8A depicts a plasmid construct template that transcribes transposase RNA that is later processed with a 5'-m7G cap1 and pseudouridine substitution. FIG. 8B depicts a generic MLT donor DNA construct template for use with any transgene.

FIG. 9A is a bar chart illustrating integration efficiency of hyperactive PiggyBac™ transposase versus hyperactive MLT variants (S8P/C13R double mutant; L573del E574del) using sequences from Yusa et al. (2010).

FIG. 10 depicts a nucleotide sequence alignment of MLT (human codon-optimized for RNA) and a published sequence by Mitra et al. (*Proc Natl Acad Sci USA*. 2013 Jan. 2; 110(1):234-9) (Identity 77.67%, Gaps 1.44%).

FIG. 11 depicts a nucleotide sequence alignment of MLT and a sequence from WO2010085699 (Identity 73.68%, Gaps 1.16%).

FIG. 12 depicts an amino acid sequence alignment of MLT (L573del/E574del/S2A, with S8P, C13R, and N125K mutations) and published sequence by Mitra et al. (Mitra contained 2 extra amino acids on C-terminus).

FIG. 13 depicts comparison of an amino acid of an engineered MLT (L573del/E574del/S2A, with S8P and C13R mutations, "MLT") and the sequence from WO2010085699.

FIG. 14 depicts comparison of a terminal left end of MLT to a published sequence (Ray et al., piggyBac1_ML).

FIG. 15 depicts comparison of a terminal right end of MLT to a published sequence (Ray et al. piggyBac1_ML).

FIG. 17A shows that mammalian transposon (Ts) variants S8P, C13R, N125K and S8P/C13R have higher excision frequency that the native enzyme. FIG. 17B shows functional transgene expression in Hela cells transfected with a donor neomycin transgene, 1:20 serial dilutions. The mammalian MLT transposase variant S8P/C13R showed comparable relative integration to the insect PiggyBac™ transposase in Hela cells.

FIG. 19A shows analysis of purified MBP-MLT transposase fusion protein by an amylose-resin column. A major protein band of 100+kDa was identified by SDS-PAGE after purification of the expressed protein (MBP-MLT transposase) from the supernatant of the sonicated bacteria on a column of amylose resin. In FIG. 19B, shows a 67.5 kDa MLT transposase-specific band was shown after overnight cleavage of the MBP tag by TEV protease and heparin elution.

FIG. 22A shows % of integration activity for no MLT, MLT-dCas9, MLT-dCas12j, hyperacive PiggyBac™ transposase-dCas 12j, hyperacive PiggyBac™ transposase-dCas9, hyperacive PiggyBac™ transposase, and MLT. FIG. 22B shows % of excision activity for no MLT, MLT-Intein-N-terminus, MLT1, and MLT2. FIG. 22C shows % of integration activity for no MLT, MLT-Intein-N-terminus, MLT1, and MLT2. FIG. 22D shows % of excision activity for no MLT, MLT-dCas12j, MLT-dCas9, MLT-Intein-N-terminus dCas9, MLT-Intein-N-terminus, MLT-Intein-N-terminus TALE, MLT-TALE10, and MLT. MLT-TALE10 in 27 bp and 49 bp from TTAA sites in hROSA29.

FIG. 24A depicts positive clonal lines containing targeted insertions to human ROSA26 using hyperactive PiggyBac™ transposase donor and helper with Cas9/gRNA, identified in the present disclosure.

FIG. 24B depicts a nested PCR strategy to detect the insertion of a donor MLT at a specific TTAA site in human ROSA26 locus using MLT helper with Cas9 and two different sets of gRNA (Set 1: AATCGAGAAGCGACTCGACA (SEQ ID NO: 425), TGCCCTGCAGGGGAGTGAGC (SEQ ID NO: 426); Set 2: GAAGCGACTCGACATGGAGG (SEQ ID NO: 427), CCTGCAGGGGAGTGAGCAGC (SEQ ID NO: 428)) that were 61 bp and 62 bp respectively, from the TTAA targeted site.

FIG. 30A shows all cells, FIG. 30B shows single cells, and FIG. 30C shows live cells. FIG. 30D shows GFP single-positive cells, mCherry single-positive cells, double-positive cells, and double-negative cells.

DETAILED DESCRIPTION OF THE INVENTION

Figure 1C:
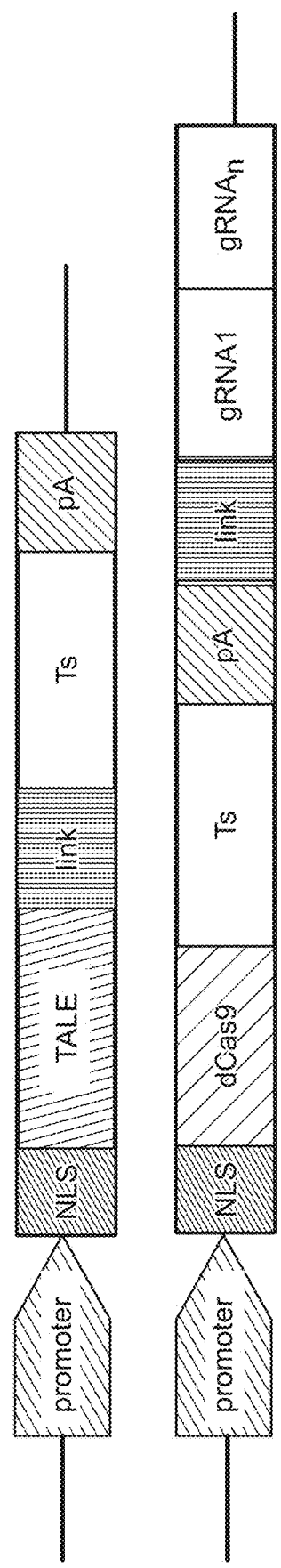

The present invention is based, in part, on the discovery of an engineered transposase enzyme capable of gene insertion that finds use, e.g., in therapy. In aspects, there is provided an engineered MLT enzyme (occasionally referred to as "engineered", "corrected," "the present MLT", "MLT1" or "MLT2").

The present invention is based, in part, on the discovery that an enzyme capable of targeted genomic integration by transposition (e.g., a recombinase, an integrase, or a transposase enzyme), as a monomer or a dimer, can be fused with a transcription activator-like effector proteins (TALE) DNA binding domain (DBD) or a dCas9/gRNA to thereby create a chimeric enzyme capable of a site- or locus-specific transposition. The enzyme (e.g., without limitation, a chimeric transposase) utilizes the specificity of TALE DBD to certain sites within a host genome, which allows using DBDs to target any desired location in the genome. In this way, the chimeric transposase in accordance with the present disclosure allows achieving targeted integration of a transgene.

In embodiments, the enzyme capable of targeted genomic integration by transposition is a recombinase or an integrase. In embodiments, the recombinase is an integrase. In embodiments, the integrase is a transposase or the recombinase is a transposase.

In embodiments, the transposase has one or more mutations that confer hyperactivity. In embodiments, the transposase is a mammal-derived transposase, optionally a helper RNA transposase. Thus, the present compositions and methods for gene transfer utilize a dual transposon/transposase system. Transposable elements are non-viral gene delivery vehicles found ubiquitously in nature. Transposon-based vectors have the capacity of stable genomic integration and long-lasting expression of transgene constructs in cells. Generally speaking, dual transposon and transposase systems work via a cut-and-paste mechanism whereby transposon DNA containing a transgene(s) of interest is integrated into chromosomal DNA by a transposase enzyme at a repetitive sequence site. Dual transposon/transposase (or "donor/helper") plasmid systems insert a transgene flanked by inverted terminal ends ("ends"), such as TTAA tetranucleotide sites, without leaving a DNA footprint in the human genome. The transposase enzyme is transiently expressed (on the same or a different vector from a vector encoding the transposon) and it catalyzes the insertion events from the donor plasmid to the host genome. Genomic insertions primarily target introns but may target other TTAA sites and integrate into approximately 50% of human genes.

Selection of a transposon system for gene therapy depends on the system's integration site preference. For example, PiggyBac™ (PB) transposon has preference for transcription units, with insertions primarily targeting introns. Some transposases require certain sites in the host DNA for catalytic activity even if the DNA-enzyme complex is brought into the vicinity of the host-DNA. For example, Tc1/mariner transposon integrates into a TA dinucleotide (Fischer et al., *Proc Natl Acad Sci USA* 2001; 98:6759-64), and PiggyBac™ (PB) transposon integrates into a TTAA tetranucleotide (Mitra et al., *EMBO J* 2008; 27:1097-109). A benefit of using transposase-based genomic targeting over nuclease-based techniques is that integration via the cut-and-paste mechanism is readily identified by assaying the copy number of transposon insertions (e.g. (nr)LAM-PCR). Therefore, a single insertion clone is not expected to have additional DNA modifications. In comparison, targetable nucleases are capable of mutating genome without introducing an identifiable insert. Therefore, it may be challenging to confirm the DNA integrity of modified cells. Genomic screens to identify off-target nuclease mutations are complex and limited in sequence coverage.

As discussed above, viral (e.g. AAV, lentivirus, etc.) and nuclease-based (e.g. CRISPR/Cas, prime editing base editing) gene therapies are typically limited by mutagenesis risk, and also have drawbacks such as immunogenicity, manufacturing costs, cargo size, and reversibility. Transposons are less likely to activate a proto-oncogene than lentivirus or other retroviruses but cause insertional mutagenesis when a transgene is inserted in one or more locations in a host genome other than the intended locations. In particular, the genomic sites recognized by transposases, such as a TA dinucleotide site or a TTAA tetranucleotide site, can be found in multiple locations in a genome such that a transgene can be inserted in unintended locations within the genome and have disruptive, often severe effects on the host. For example, the insertional mutagenesis can affect a function of a metabolic gene. Accordingly, to improve the function of a dual transposon/transposase system as a safe and efficient gene therapy tool, it is desired to increase and control the specificity of a transposase's binding and insertion.

Accordingly, in some aspects, a composition is provided that comprises an enzyme capable of transposition, comprising (a) a TALE DBD or a dCas9/gRNA complex; (b) an enzyme capable of targeted genomic integration by transposition, the enzyme being capable of inserting a transposon at a TA dinucleotide site or a TTAA tetranucleotide site in a GSHS in a nucleic acid molecule; and (c) a linker that connects the TALE DBD or the dCas9/gRNA complex and the enzyme. In embodiments, the enzyme (e.g., a transposase enzyme) is a head to tail dimer. In some embodiments, the enzyme is a tetramer. In some embodiments, the enzyme is a monomer.

In embodiments, TALE or dCas9/gRNA DBDs cause the enzyme capable of transposition (e.g., without limitation, a chimeric transposase) to bind specifically to human GSHS. In embodiments, the TALEs or dCas9/gRNA DBD sequester the transposase to GSHS and promote transposition to nearby TA dinucleotide or TTAA tetranucleotide sites which can be located in proximity to the repeat variable di-residues (RVD) TALE or gRNA nucleotide sequences. The GSHS regions are located in open chromatin sites that are susceptible to transposase activity. Accordingly, the transposase does not only operate based on its ability to recognize TA or TTAA sites, but it also directs a transposon (having a transgene) to specific locations in proximity to a TALE or dCas9/gRNA DBD. The chimeric transposase in accordance with embodiments of the present disclosure has negligible risk of genotoxicity and exhibits superior features as compared to existing gene therapies.

In embodiments, the gRNA, e.g. to be associated with dCas9 is AATCGAGAAGCGACTCGACA (SEQ ID NO: 425) and/or TGCCCTGCAGGGGAGTGAGC (SEQ ID NO: 426). In embodiments, the gRNA, e.g. to be associated with dCas9 is GAAGCGACTCGACATGGAGG (SEQ ID NO: 427) and/or CCTGCAGGGGAGTGAGCAGC (SEQ ID NO: 428).

In some embodiments, a chimeric transposase is mutated to be characterized by reduced or inhibited binding of off-target sequences and consequently reliant on a DBD fused thereto, such as a TALE or dCas9/gRNA DBD, for transposition.

The described compositions and methods allow reducing random vector and transgene insertion, which increase a mutagenic risk. The described compositions and methods make use of a transposome system that reduces genotoxicity compared to viral- and nuclease-mediated gene therapies. The dual system is designed to avoid the persistence of an active transposase and efficiently transfect human cell lines without significant cytotoxicity.

In some embodiments, the composition is suitable for causing insertion of the transposon in the GSHS when contacted with a cell comprising a GSHS.

In some embodiments, the TALE or dCas9/gRNA DBD can be suitable for directing the transposase enzyme to the GSHS sequence.

In embodiments, TALE or dCas9/gRNA DBDs are customizable, such as a TALE or dCas9/gRNA DBD can be selected for targeting a specific genomic location. In some embodiments, the genomic location is in proximity to a TA dinucleotide site or a TTAA tetranucleotide site.

In embodiments, CRISPR (Clustered Regularly Interspaced Short Palindromic Repeat) associated protein 9 (Cas9), or a variant thereof, targets the enzyme to a locus of interest. Cas9 is a generic nuclease, and a guide RNA (gRNA) confers sequence specificity on Cas9 by carrying an identical complementary sequence to a genomic region of interest. Jinek et al. (2012) *Science* 337:816-821. A CRISPR/Cas9 tool only requires Cas9 nuclease for DNA cleavage and a single-guide RNA (sgRNA) for target specificity. See Jinek et al. (2012); Chylinski et al. (2014) *Nucleic Acids Res* 42, 6091-6105. The inactivated form of Cas9, which is a nuclease-deficient (or inactive, or "catalytically dead") Cas9, is typically denoted as "dCas9" and has no substantial nuclease activity. Qi, L. S. et al. (2013). *Cell* 152, 1173-1183. CRISPR/dCas9 binds precisely to specific genomic sequences through targeting of guide RNA (gRNA) sequences. See Dominguez et al., *Nat Rev Mol Cell Biol.* 2016; 17:5-15; Wang et al., *Annu Rev Biochem.* 2016; 85:227-64. dCas9 is utilized to edit gene expression when applied to the transcription binding site of a desired site and/or locus in a genome. When the dCas9 protein is coupled to guide RNA (gRNA) to create dCas9 guide RNA complex, dCas9 prevents the proliferation of repeating codons and DNA sequences that might be harmful to an organism's genome. Essentially, when multiple repeat codons are produced, it elicits a response, or recruits an abundance of dCas9 to combat the overproduction of those codons and results in the shut-down of transcription. Thus, dCas9 works synergistically with gRNA and directly affects the DNA polymerase Il from continuing transcription.

In embodiments, the gene-editing system comprises a nuclease-deficient Cas enzyme guide RNA complex. In some embodiments, the gene-editing system comprises a nuclease-deficient (or inactive, or "catalytically dead" Cas9, typically denoted as "dCas9") guide RNA complex.

In embodiments, the dCas9/gRNA complex comprises a guide RNA selected from: GTTTAGCTCACCCGTGAGCC (SEQ ID NO: 91), CCCAATATTATTGTTCTCTG (SEQ ID NO: 92), GGGGTGGGATAGGGGATACG (SEQ ID NO: 93), GGATCCCCCTCTACATTTAA (SEQ ID NO: 94), GTGATCTTGTACAAATCATT (SEQ ID NO: 95), CTACACAGAATCTGTTAGAA (SEQ ID NO: 96), TAAGCTAGAGAATAGATCTC (SEQ ID NO: 97), and TCAATACACTTAATGATTTA (SEQ ID NO: 98), wherein the guide RNA directs the enzyme to a chemokine (C-C motif) receptor 5 (CCR5) gene.

In embodiments, the dCas9/gRNA complex comprises a guide RNA selected from:
CACCGGGAGCCACGAAAACAGATCC (SEQ ID NO: 99); CACCGCGAAAACAGATCCAGGGACA (SEQ ID NO: 100); CACCGAGATCCAGGGACACGGTGCT (SEQ ID NO: 101); CACCGGACACGGTGCTAGGACAGTG (SEQ ID NO: 102); CACCGGAAAATGACCCAACAGCCTC (SEQ ID NO: 103); CACCGGCCTGGCCGGCCTGACCACT (SEQ ID NO: 104); CACCGCTGAGCACTGAAGGCCTGGC (SEQ ID NO: 105); CACCGTGGTTTCCACTGAGCACTGA (SEQ ID NO: 106); CACCGGATAGCCAGGAGTCCTTTCG (SEQ ID NO: 107); CACCGGCGCTTCCAGTGCTCAGACT (SEQ ID NO: 108); CACCGCAGTGCTCAGACTAGGGAAG (SEQ ID NO: 109); CACCGGCCCCTCCTCCTTCAGAGCC (SEQ ID NO: 110); CACCGTCCTTCAGAGCCAGGAGTCC (SEQ ID NO: 111); CACCGTGGTTTCCGAGCTTGACCCT (SEQ ID NO: 112); CACCGCTGCAGAGTATCTGCTGGGG (SEQ ID NO: 113); CACCGCGTTCCTGCAGAGTATCTGC (SEQ ID NO: 114); AAACGGATCTGTTTTCGTGGCTCCC (SEQ ID NO: 115); AAACTGTCCCTGGATCTGTTTTCGC (SEQ ID NO: 116); AAACAGCACCGTGTCCCTGGATCTC (SEQ ID NO: 117); AAACCACTGTCCTAGCACCGTGTCC (SEQ ID NO: 118); AAACGAGGCTGTTGGGTCATTTTCC (SEQ ID NO: 119); AAACAGTGGTCAGGCCGGCCAGGCC (SEQ ID NO: 120); AAACGCCAGGCCTTCAGTGCTCAGC (SEQ ID NO: 121); AAACTCAGTGCTCAGTGGAAACCAC (SEQ ID NO: 122); AAACCGAAAGGACTCCTGGCTATCC (SEQ ID NO: 123); AAACAGTCTGAGCACTGGAAGCGCC (SEQ ID NO: 124); AAACCTTCCCTAGTCTGAGCACTGC (SEQ ID NO: 125); AAACGGCTCTGAAGGAGGAGGGGCC (SEQ ID NO: 126); AAACGGACTCCTGGCTCTGAAGGAC (SEQ ID NO: 127); AAACAGGGTCAAGCTCGGAAACCAC (SEQ ID NO: 128); AAACCCCCAGCAGATACTCTGCAGC (SEQ ID NO: 129); AAACGCAGATACTCTGCAGGAACGC (SEQ ID NO: 130); TCCCCTCCCAGAAAGACCTG (SEQ ID NO: 131); TGGGCTCCAAGCAATCCTGG (SEQ ID NO: 132); GTGGCTCAGGAGGTACCTGG (SEQ ID NO: 133); GAGCCACGAAAACAGATCCA (SEQ ID NO: 134); AAGTGAACGGGGAAGGGAGG (SEQ ID NO: 135); GACAAAAGCCGAAGTCCAGG (SEQ ID NO: 136); GTGGTTGATAAACCCACGTG (SEQ ID NO: 137); TGGAACAGCCACAGCAGGG (SEQ ID NO: 138); GCAGGGGAACGGGGATGCAGG (SEQ ID NO: 139); GAGATGGTGGACGAGGAAGG (SEQ ID NO: 140); GAGATGGCTCCAGGAAATGG (SEQ ID NO: 141); TAAGGAATCTGCCTAACAGG (SEQ ID NO: 142); TCAGGAGACTAGGAAGGAGG (SEQ ID NO: 143); TATAAGGTGGTCCAGCTCG (SEQ ID NO: 144); CTGGAAGATGCCATGACAGG (SEQ ID NO: 145); GCACAGACTAGAGAGGTAAG (SEQ ID NO: 146); ACAGACTAGAGAGGTAAGGG (SEQ ID NO: 147); GAGAGGTGACCCGAATCCAC (SEQ ID NO: 148); GCACAGGCCCCAGAAGGAGA (SEQ ID NO: 149); CCGGAGAGGACCCAGACACG (SEQ ID NO: 150); GAGAGGACCCAGACACGGGG (SEQ ID NO: 151); GCAACACAGCAGAGAGCAAG (SEQ ID NO: 152); GAAGAGGGAGTGGAGGAAGA (SEQ ID NO: 153); AAGACGGAACCTGAAGGAGG (SEQ ID NO: 154); AGAAAGCGGCACAGGCCCAG (SEQ ID NO: 155); GGGAAACAGTGGGCCAGAGG (SEQ ID NO: 156); GTCCGGACTCAGGAGAGAGA (SEQ ID NO: 157); GGCACAGCAAGGGCACTCGG (SEQ ID NO: 158); GAAGAGGGGAAGTCGAGGGA (SEQ ID NO: 159); GGGAATGGTAAGGAGGCCTG (SEQ ID NO: 160); GCAGAGTGGTCAGCACAGAG (SEQ ID NO: 161); GCACAGAGTGGCTAAGCCCA (SEQ ID NO: 162); GACGGGGTGTCAGCATAGGG (SEQ ID NO: 163); GCCCAGGGCCAGGAACGACG (SEQ ID NO: 164); GGTGGAGTCCAGCACGGCGC (SEQ ID NO: 165); ACAGGCCGCCAGGAACTCGG (SEQ ID NO: 166); ACTAGGAAGTGTGTAGCACC (SEQ ID NO: 167); ATGAATAGCAGACTGCCCCG (SEQ ID NO: 168); ACACCCCTAAAAGCACAGTG (SEQ ID NO: 169); CAAGGAGTTCCAGCAGGTGG (SEQ ID NO: 170); AAGGAGTTCCAGCAGGTGGG (SEQ ID NO: 171); TGGAAAGAGGAGGGAAGAGG (SEQ ID NO: 172); TCGAATTCCTAACTGCCCCG (SEQ ID NO: 173); GACCTGCCCAGCACACCCTG (SEQ ID NO: 174); GGAGCAGCTGCGGCAGTGGG (SEQ ID NO: 175); GGGAGGGAGAGCTTGGCAGG (SEQ ID NO: 176); GTTACGTGGCCAAGAAGCAG (SEQ ID NO: 177); GCTGAACAGAGAAGAGCTGG (SEQ ID NO: 178); TCTGAGGGTGGAGGGACTGG (SEQ ID NO: 179); GGAGAGGTGAGGGACTTGGG (SEQ ID NO: 180); GTGAACCAGGCAGACAACGA (SEQ ID NO: 181); CAGGTACCTCCTGAGCCACG (SEQ ID NO: 182); GGGGGAGTAGGGCATGCAG (SEQ ID NO: 183); GCAAATGGCCAGCAAGGGTG (SEQ ID NO: 184); CAAATGGCCAGCAAGGGTGG (SEQ ID NO: 309); GCAGAACCTGAGGATATGGA (SEQ ID NO: 310); AATACACAGAATGAAAATAG (SEQ ID NO: 311); CTGGTGACTAGAATAGGCAG (SEQ ID NO: 312); TGGTGACTAGAATAGGCAGT (SEQ ID NO: 313); TAAAAGAATGTGAAAAGATG (SEQ ID NO: 314); TCAGGAGTTCAAGACCACCC (SEQ ID NO: 315); TGTAGTCCCAGTTATGCAGG (SEQ ID NO: 316); GGGTTCACACCACAAATGCA (SEQ ID NO: 317); GGCAAATGGCCAGCAAGGGT (SEQ ID NO: 318); AGAAACCAATCCCAAAGCAA (SEQ ID NO: 319); GCCAAGGACACCAAAACCCA (SEQ ID NO: 320); AGTGGTGATAAGGCAACAGT (SEQ ID NO: 321); CCTGAGACAGAAGTATTAAG (SEQ ID NO: 322); AAGGTCACACAATGAATAGG (SEQ ID NO: 323); CACCATACTAGGGAAGAAGA (SEQ ID NO: 324); CAATACCCTGCCCTTAGTGG (SEQ ID NO: 327); AATACCCTGCCCTTAGTGGG (SEQ ID NO: 325); TTAGTGGGGGGTGGAGTGGG (SEQ ID NO: 326); GTGGGGGGTGGAGTGGGGGG (SEQ ID NO: 328); GGGGGGTGGAGTGGGGGGTG (SEQ ID NO: 329); GGGGTGGAGTGGGGGGTGGG (SEQ ID NO: 330); GGGTGGAGTGGGGGGTGGGG (SEQ ID NO: 331); GGGGGGGGGAAAGACATCG (SEQ ID NO: 332); GCAGCTGTGAATTCTGATAG (SEQ ID NO: 333); GAGATCAGAGAAACCAGATG (SEQ ID NO: 334); TCTATACTGATTGCAGCCAG (SEQ ID NO: 335); CACCGAATCGAGAAGCGACTCGACA (SEQ ID NO: 185); CACCGGTCCCTGGGCGTTGCCCTGC (SEQ ID NO: 186); CACCGCCCTGGGCGTTGCCCTGCAG (SEQ ID NO: 187); CACCGCCGTGGGAAGATAAACTAAT (SEQ ID NO: 188); CACCGTCCCTGCAGGGCAACGCCC (SEQ ID NO: 189); CACCGGTCGAGTCGCTTCTCGATTA (SEQ ID NO: 190); CACCGCTGCTGCCTCCGTCTTGTA (SEQ ID NO: 191); CACCGGAGTGCCGCAATACCTTTAT (SEQ ID NO: 192); CACCGACACTTTGGTGGTGCAGCAA (SEQ ID NO: 193); CACCGTCTCAAATGGTATAAAACTC (SEQ ID NO: 194); CACCGAATCCCGCCCATAATCGAGA (SEQ ID NO: 195); CACCGTCCCGCCCATAATCGAGAAG (SEQ ID NO: 196); CACCGCCCATAATCGAGAAGCGACT (SEQ ID NO: 197); CACCGGAGAAGCGACTCGACATGGA (SEQ ID NO: 198); CACCGGAAGCGACTCGACATGGAGG (SEQ ID NO: 199); CACCGGCGACTCGACATGGAGGCGA (SEQ ID NO: 200); AAACTGTCGAGTCGCTTCTCGATTC (SEQ ID NO: 201); AAACGCAGGGCAACGCCCAGGGACC (SEQ ID NO: 202); AAACCTGCAGGGCAACGCCCAGGGC (SEQ ID NO: 203); AAACATTAGTTTATCTTCCCACGGC (SEQ ID NO: 204); AAACGGGCGTTGCCCTGCAGGGGAC (SEQ ID NO: 205); AAACTAATCGAGAAGCGACTCGACC (SEQ ID NO: 206); AAACTACAAGACGGGAGGCAGCAGC (SEQ ID NO: 207); AAACATAAAGGTATTGCGGCACTCC (SEQ ID NO: 208); AAACTTGCTGCACCACCAAAGTGTC (SEQ ID NO: 209); AAACGAGTTTTATACCATTTGAGAC (SEQ ID NO: 210); AAACTCTCGATTATGGGGGGATTC (SEQ ID NO: 211); AAACCTTCTCGATTATGGGGGGGAC (SEQ ID NO: 212); AAACAGTCGCTTCTCGATTATGGGC (SEQ ID NO: 213); AAACTCCATGTCGAGTCGCTTCTCC (SEQ ID NO: 214); AAACCCTCCATGTCGAGTCGCTTCC (SEQ ID NO: 215); AAACTCGCCTCCATGTCGAGTCGCC (SEQ ID NO: 216); CACCGACAGGGTTAATGTGAAGTCC (SEQ ID NO: 217); CACCGTCCCCTCTACATTTAAAGT (SEQ ID NO: 218); CACCGCATTTAAAGTTGGTTTAAGT (SEQ ID NO: 219); CACCGTTAGAAAATATAAAGAATAA (SEQ ID NO: 220); CACCGTAAATGCTTACTGGTTTGAA (SEQ ID NO: 221); CACCGTCCTGGGTCCAGAAAAAGAT (SEQ ID NO: 222); CACCGTTGGGTGGTGAGCATCTGTG (SEQ ID NO: 223); CACCGCGGGGAGAGTGGAGAAAAAG (SEQ ID NO: 224); CACCGGTTAAAACTCTTTAGACAAC (SEQ ID NO: 225); CACCGGAAAATCCCCACTAAGATCC (SEQ ID NO: 226); AAACGGACTTCACATTAACCCTGTC (SEQ ID NO: 227); AAACACTTTAAATGTAGAGGGGAC (SEQ ID NO: 228); AAACACTTAAACCAACTTTAAATGC (SEQ ID NO: 229); AAACTTATTCTTTATATTTTCTAAC (SEQ ID NO: 230); AAACTTCAAACCAGTAAGCATTTAC (SEQ ID NO: 231); AAACATCTTTTTCTGGACCCAGGAC (SEQ ID NO: 232); AAACCACAGATGCTCACCACCCAAC (SEQ ID NO: 233); AAACCTTTTTCTCCACTCTCCCGC (SEQ ID NO: 234); AAACGTTGTCTAAAGAGTTTTAACC (SEQ ID NO: 235); AAACGGATCTTAGTGGGATTTTCC (SEQ ID NO: 236); AGTAGCAGTAATGAAGCTGG (SEQ ID NO: 237); ATACCCAGACGAGAAAGCTG (SEQ ID NO: 238); TACCCAGACGAGAAAGCTGA (SEQ ID NO: 239); GGTGGTGAGCATCTGTGTGG (SEQ ID NO: 240); AAATGAGAAGAAGAGGCACA (SEQ ID NO: 241); CTTGTGGCCTGGGAGAGCTG (SEQ ID NO: 242); GCTGTAGAAGGAGACAGAGC (SEQ ID NO: 243); GAGCTGGTTGGGAAGACATG (SEQ ID NO: 244); CTGGTTGGGAAGACATGGGG (SEQ ID NO: 245); CGTGAGGATGGGAAGGAGGG (SEQ ID NO: 246); ATGCAGAGTCAGCAGAACTG (SEQ ID NO: 247); AAGACATCAAGCACAGAAGG (SEQ ID NO: 248); TCAAGCACAGAAGGAGGAGG (SEQ ID NO: 249); AACCGTCAATAGGCAAAGGG (SEQ ID NO: 250); CCGTATTTCAGACTGAATGG (SEQ ID NO: 251); GAGAGGACAGGTGCTACAGG (SEQ ID NO: 252); AACCAAGGAAGGGCAGGAGG (SEQ ID NO: 253); GACCTCTGGGTGGAGACAGA (SEQ ID NO: 254); CAGATGACCATGACAAGCAG (SEQ ID NO: 255); AACACCAGTGAGTAGAGCGG (SEQ ID NO: 256); AGGACCTTGAAGCACAGAGA (SEQ ID NO: 257); TACAGAGGCAGACTAACCCA (SEQ ID NO: 258); ACAGAGGCAGACTAACCCAG (SEQ ID NO: 259); TAAATGACGTGCTAGACCTG (SEQ ID NO: 260); AGTAACCACTCAGGACAGGG (SEQ ID NO: 261); ACCACAAAACAGAAACACCA (SEQ ID NO: 262); GTTTGAAGACAAGCCTGAGG (SEQ ID NO: 263); GCTGAACCCCAAAAGACAGG (SEQ ID NO: 264); GCAGCTGAGACACACACCAG (SEQ ID NO: 265); AGGACACCCCAAAGAAGCTG (SEQ ID NO: 266); GGACACCCCAAAGAAGCTGA (SEQ ID NO: 267); CCAGTGCAATGGACAGAAGA (SEQ ID NO: 268); AGAAGAGGGAGCCTGCAAGT (SEQ ID NO: 269); GTGTTTGGGCCCTAGAGCGA (SEQ ID NO: 270); CATGTGCCTGGTGCAATGCA (SEQ ID NO: 271); TACAAAGAGGAAGATAAGTG (SEQ ID NO: 272); GTCACAGAATACACCACTAG (SEQ ID NO: 273); GGGTTACCCTGGACATGGAA (SEQ ID NO: 274); CATGGAAGGGTATTCACTCG (SEQ ID NO: 275); AGAGTGGCCTAGACAGGCTG (SEQ ID NO: 276); CATGCTGGACAGCTCGGCAG (SEQ ID NO: 277); AGTGAAAGAAGAGAAAATTC (SEQ ID NO: 278); TGGTAAGTCTAAGAAACCTA (SEQ ID NO: 279); CCCACAGCCTAACCACCCTA (SEQ ID NO: 280); AATATTTCAAAGCCCTAGGG (SEQ ID NO: 281); GCACTCGGAACAGGGTCTGG (SEQ ID NO: 282); AGATAGGAGCTCCAACAGTG (SEQ ID NO: 283); AAGTTAGAGCAGCCAGGAAA (SEQ ID NO: 284); TAGAGCAGCCAGGAAAGGGA (SEQ ID NO: 285); TGAATACCCTTCCATGTCCA (SEQ ID NO: 286); CCTGCATTGCACCAGGCACA (SEQ ID NO: 287); TCTAGGGCCCAAACACACCT (SEQ ID NO: 288); TCCCTCCATCTATCAAAAGG (SEQ ID NO: 289); AGCCCTGAGACAGAAGCAGG (SEQ ID NO: 290); GCCCTGAGACAGAAGCAGGT (SEQ ID NO: 291); AGGAGATGCAGTGATACGCA (SEQ ID NO: 292); ACAATACCAAGGGTATCCGG (SEQ ID NO: 293); TGATAAAGAAAACAAAGTGA (SEQ ID NO: 294); AAAGAAAACAAAGTGAGGGA (SEQ ID NO: 295); GTGGCAAGTGGAGAAATTGA (SEQ ID NO: 296); CAAGTGGAGAAATTGAGGGA (SEQ ID NO: 297); GTGGTGATGATTGCAGCTGG (SEQ ID NO: 298); CTATGTGCCTGACACACAGG (SEQ ID NO: 299); GGGTTGGACCAGGAAAGAGG (SEQ ID NO: 300); GATGCCTGGAAAAGGAAAGA (SEQ ID NO: 301); TAGTATGCACCTGCAAGAGG (SEQ ID NO: 302); TATGCACCTGCAAGAGGCGG (SEQ ID NO: 303); AGGGGAAGAAGAGAAGCAGA (SEQ ID NO: 304); GCTGAATCAAGAGACAAGCG (SEQ ID NO: 305); AAGCAAATAAATCTCCTGGG (SEQ ID NO: 306); AGATGAGTGCTAGAGACTGG (SEQ ID NO: 307); and CTGATGGTTGAGCACAGCAG (SEQ ID NO: 308). See FIG. 4.

Embodiments of the present disclosure make use of the ability of TALE or dCas9/gRNA DBDs to target specific sites in a host genome. The DNA targeting ability of a TALE or dCas9/gRNA DBD is provided by TALE repeat sequences (e.g., modular arrays) or gRNA which are linked together to recognize flanking DNA sequences. Each TALE or gRNA can recognize certain base pair(s) or residue(s).

TALE nucleases (TALENs) are a known tool for genome editing and introducing targeted double-stranded breaks. TALENs comprise endonucleases, such as FokI nuclease domain, fused to a customizable DBD. This DBD is composed of highly conserved repeats derived from TALEs, which are proteins secreted by *Xanthomonas* bacteria to alter transcription of genes in host plant cells. The DBD includes a repeated highly conserved 33-34 amino acid sequence with divergent 12th and 13th amino acids. These two positions, referred to as the RVD, are highly variable and show a strong correlation with specific base pair or nucleotide recognition. This straightforward relationship between amino acid sequence and DNA recognition has allowed for the engineering of specific DBDs by selecting a combination of repeat segments containing the appropriate RVDs. Boch et al. *Nature Biotechnology*. 2011; 29 (2): 135-6.

Accordingly, TALENs can be readily designed using a "protein-DNA code" that relates modular DNA-binding TALE repeat domains to individual bases in a target-binding site. See Joung et al. *Nat Rev Mol Cell Biol.* 2013; 14(1): 49-55. doi:10.1038/nrm3486. FIG. 3, for example, shows such code.

It has been demonstrated that TALENs can be used to target essentially any DNA sequence of interest in human cell. Miller et al. *Nat Biotechnol.* 2011; 29:143-148. Guidelines for selection of potential target sites and for use of particular TALE repeat domains (harboring NH residues at the hypervariable positions) for recognition of G bases have been proposed. See Streubel et al. *Nat Biotechnol.* 2012; 30:593-595.

Accordingly, in some embodiments, the TALE DBD comprises one or more repeat sequences. In some embodiments, the TALE DBD comprises about 15, or about, 16, or about 17, or about 18, or about 18.5 repeat sequences. In some embodiments, the TALE DBD repeat sequences comprise 33 or 34 amino acids.

In some embodiments, the one or more of the TALE DBD repeat sequences comprise an RVD at residue 12 or 13 of the 33 or 34 amino acids. The RVD can recognize certain base pair(s) or residue(s). In some embodiments, the RVD recognizes one base pair in the nucleic acid molecule. In some embodiments, the RVD recognizes a "C" residue in the nucleic acid molecule and is selected from HD, N(gap), HA, ND, and HI. In some embodiments, the RVD recognizes a "G" residue in the nucleic acid molecule and is selected from NN, NH, NK, HN, and NA. In some embodiments, the RVD recognizes an "A" residue in the nucleic acid molecule and is selected from NI and NS. In some embodiments, the RVD recognizes a "T" residue in the nucleic acid molecule and is selected from NG, HG, H(gap), and IG.

In embodiments, the GSHS is in an open chromatin location in a chromosome. In some embodiments, the GSHS is selected from adeno-associated virus site 1 (AAVS1), chemokine (C-C motif) receptor 5 (CCR5) gene, HIV-1 coreceptor; and human Rosa26 locus. In some embodiments, the GSHS is located on human chromosome 2, 4, 6, 10, 11, or 17.

In some embodiments, the GSHS is selected from TALC1, TALC2, TALC3, TALC4, TALC5, TALC7, TALC8, AVS1, AVS2, AVS3, ROSA1, ROSA2, TALER1, TALER2, TALER3, TALER4, TALER5, SHCHR2-1, SHCHR2-2, SHCHR2-3, SHCHR2-4, SHCHR4-1, SHCHR4-2, SHCHR4-3, SHCHR6-1, SHCHR6-2, SHCHR6-3, SHCHR6-4, SHCHR10-1, SHCHR10-2, SHCHR10-3, SHCHR10-4, SHCHR10-5, SHCHR11-1, SHCHR11-2, SHCHR11-3, SHCHR17-1, SHCHR17-2, SHCHR17-3, and SHCHR17-4.

In some embodiments, the GSHS comprises one or more of TGGCCGGCCTGACCACTGG (SEQ ID NO: 23), TGAAGGCCTGGCCGGCCTG (SEQ ID NO: 24), TGAGCACTGAAGGCCTGGC (SEQ ID NO: 25), TCCACTGAGCACTGAAGGC (SEQ ID NO: 26), TGGTTTCCACTGAGCACTG (SEQ ID NO: 27), TGGGGAAAATGACCCAACA (SEQ ID NO: 28), TAGGACAGTGGGGAAAATG (SEQ ID NO: 29), TCCAGGGACACGGTGCTAG (SEQ ID NO: 30), TCAGAGCCAGGAGTCCTGG (SEQ ID NO: 31), TCCTTCAGAGCCAGGAGTC (SEQ ID NO: 32), TCCTCCTTCAGAGCCAGGA (SEQ ID NO: 33), TCCAGCCCTCCTCCTTCA (SEQ ID NO: 34), TCCGAGCTTGACCCTTGGA (SEQ ID NO: 35), TGGTTTCCGAGCTTGACCC (SEQ ID NO: 36), TGGGGTGGTTTCCGAGCTT (SEQ ID NO: 37), TCTGCTGGGGTGGTTTCCG (SEQ ID NO: 38), TGCAGAGTATCTGCTGGGG (SEQ ID NO: 39), CCAATCCCCTCAGT (SEQ ID NO: 40), CAGTGCTCAGTGGAA (SEQ ID NO: 41), GAAACATCCGGCGACTCA (SEQ ID NO: 42), TCGCCCCTCAAATCTTACA (SEQ ID NO: 43), TCAAATCTTACAGCTGCTC (SEQ ID NO: 44), TCTTACAGCTGCTCACTCC (SEQ ID NO: 45), TACAGCTGCTCACTCCCCT (SEQ ID NO: 46), TGCTCACTCCCCTGCAGGG (SEQ ID NO: 47), TCCCCTGCAGGGCAACGCC (SEQ ID NO: 48), TGCAGGGCAACGCCCAGGG (SEQ ID NO: 49), TCTCGATTATGGGCGGGAT (SEQ ID NO: 50), TCGCTTCTCGATTATGGGC (SEQ ID NO: 51), TGTCGAGTCGCTTCTCGAT (SEQ ID NO: 52), TCCATGTCGAGTCGCTTCT (SEQ ID NO: 53), TCGCCTCCATGTCGAGTCG (SEQ ID NO: 54), TCGTCATCGCCTCCATGTC (SEQ ID NO: 55), TGATCTCGTCATCGCCTCC (SEQ ID NO: 56), GCTTCAGCTTCCTA (SEQ ID NO: 57), CTGTGATCATGCCA (SEQ ID NO: 58), ACAGTGGTACACACCT (SEQ ID NO: 59), CCACCCCCCACTAAG (SEQ ID NO: 60), CATTGGCCGGGCAC (SEQ ID NO: 61), GCTTGAACCCAGGAGA (SEQ ID NO: 62), ACACCCGATCCACTGGG (SEQ ID NO: 63), GCTGCATCAACCCC (SEQ ID NO: 64), GCCACAAACAGAAATA (SEQ ID NO: 65), GGTGGCTCATGCCTG (SEQ ID NO: 66), GATTTGCACAGCTCAT (SEQ ID NO: 67), AAGCTCTGAGGAGCA (SEQ ID NO: 68), CCCTAGCTGTCCC (SEQ ID NO: 69), GCCTAGCATGCTAG (SEQ ID NO: 70), ATGGGCTTCACGGAT (SEQ ID NO: 71), GAAACTATGCCTGC (SEQ ID NO: 72), GCACCATTGCTCCC (SEQ ID NO: 73), GACATGCAACTCAG (SEQ ID NO: 74), ACACCACTAGGGGT (SEQ ID NO: 75), GTCTGCTAGACAGG (SEQ ID NO: 76), GGCCTAGACAGGCTG (SEQ ID NO: 77), GAGGCATTCTTATCG (SEQ ID NO: 78), GCCTGGAAACGTTCC (SEQ ID NO: 79), GTGCTCTGACAATA (SEQ ID NO: 80), GTTTTGCAGCCTCC (SEQ ID NO: 81), ACAGCTGTGGAACGT (SEQ ID NO: 82), GGCTCTCTTCCTCCT (SEQ ID NO: 83), CTATCCCAAAACTCT (SEQ ID NO: 84), GAAAAACTATGTAT (SEQ ID NO: 85), AGGCAGGCTGGTTGA (SEQ ID NO: 86), CAATACAACCACGC (SEQ ID NO: 87), ATGACGGACTCAACT (SEQ ID NO: 88), CACAACATTTGTAA (SEQ ID NO: 89), and ATTTCCAGTGCACA (SEQ ID NO: 90).

In some embodiments, the TALE DBD binds to one of TGGCCGGCCTGACCACTGG (SEQ ID NO: 23), TGAAGGCCTGGCCGGCCTG (SEQ ID NO: 24), TGAGCACTGAAGGCCTGGC (SEQ ID NO: 25), TCCACTGAGCACTGAAGGC (SEQ ID NO: 26), TGGTTTCCACTGAGCACTG (SEQ ID NO: 27), TGGGGAAAATGACCCAACA (SEQ ID NO: 28), TAGGACAGTGGGGAAAATG (SEQ ID NO: 29), TCCAGGGACACGGTGCTAG (SEQ ID NO: 30), TCAGAGCCAGGAGTCCTGG (SEQ ID NO: 31), TCCTTCAGAGCCAGGAGTC (SEQ ID NO: 32), TCCTCCTTCAGAGCCAGGA (SEQ ID NO: 33), TCCAGCCCTCCTCCTTCA (SEQ ID NO: 34), TCCGAGCTTGACCCTTGGA (SEQ ID NO: 35), TGGTTTCCGAGCTTGACCC (SEQ ID NO: 36), TGGGGTGGTTTCCGAGCTT (SEQ ID NO: 37), TCTGCTGGGGTGGTTTCCG (SEQ ID NO: 38), TGCAGAGTATCTGCTGGGG (SEQ ID NO: 39), CCAATCCCCTCAGT (SEQ ID NO: 40), CAGTGCTCAGTGGAA (SEQ ID NO: 41), GAAACATCCGGCGACTCA (SEQ ID NO: 42), TCGCCCCTCAAATCTTACA (SEQ ID NO: 43), TCAAATCTTACAGCTGCTC (SEQ ID NO: 44), TCTTACAGCTGCTCACTCC (SEQ ID NO: 45), TACAGCTGCTCACTCCCCT (SEQ ID NO: 46), TGCTCACTCCCCTGCAGGG (SEQ ID NO: 47), TCCCCTGCAGGGCAACGCC (SEQ ID NO: 48), TGCAGGGCAACGCCCAGGG (SEQ ID NO: 49), TCTCGATTATGGGGGGAT (SEQ ID NO: 50), TCGCTTCTCGATTATGGGC (SEQ ID NO: 51), TGTCGAGTCGCTTCTCGAT (SEQ ID NO: 52), TCCATGTCGAGTCGCTTCT (SEQ ID NO: 53), TCGCCTCCATGTCGAGTCG (SEQ ID NO: 54), TCGTCATCGCCTCCATGTC (SEQ ID NO: 55), TGATCTCGTCATCGCCTCC (SEQ ID NO: 56), GCTTCAGCTTCCTA (SEQ ID NO: 57), CTGTGATCATGCCA (SEQ ID NO: 58), ACAGTGGTACACACCT (SEQ ID NO: 59), CCACCCCCCACTAAG (SEQ ID NO: 60), CATGGCCGGGCAC (SEQ ID NO: 61), GCTTGAACCCAGGAGA (SEQ ID NO: 62), ACACCCGATCCACTGGG (SEQ ID NO: 63), GCTGCATCAACCCC (SEQ ID NO: 64), GCCACAAACAGAAATA (SEQ ID NO: 65), GGTGGCTCATGCCTG (SEQ ID NO: 66), GATTTGCACAGCTCAT (SEQ ID NO: 67), AAGCTCTGAGGAGCA (SEQ ID NO: 68), CCCTAGCTGTCCC (SEQ ID NO: 69), GCCTAGCATGCTAG (SEQ ID NO: 70), ATGGGCTTCACGGAT (SEQ ID NO: 71), GAAACTATGCCTGC (SEQ ID NO: 72), GCACCATTGCTCCC (SEQ ID NO: 73), GACATGCAACTCAG (SEQ ID NO: 74), ACACCACTAGGGGT (SEQ ID NO: 75), GTCTGCTAGACAGG (SEQ ID NO: 76), GGCCTAGACAGGCTG (SEQ ID NO: 77), GAGGCATTCTTATCG (SEQ ID NO: 78), GCCTGGAAACGTTCC (SEQ ID NO: 79), GTGCTCTGACAATA (SEQ ID NO: 80), GTTTTGCAGCCTCC (SEQ ID NO: 81), ACAGCTGTGGAACGT (SEQ ID NO: 82), GGCTCTCTTCCTCCT (SEQ ID NO: 83), CTATCCCAAAACTCT (SEQ ID NO: 84), GAAAAACTATGTAT (SEQ ID NO: 85), AGGCAGGCTGGTTGA (SEQ ID NO: 86), CAATACAACCACGC (SEQ ID NO: 87), ATGACGGACTCAACT (SEQ ID NO: 88), CACAACATTTGTAA (SEQ ID NO: 89), and ATTTCCAGTGCACA (SEQ ID NO: 90).

In some embodiments, the TALE DBD comprises one or more of

NH NH HD HD NH NH HD HD NG NH NI HD HD NI HD NG NH NH,

NH NI NI NH NH HD HD NG NH NH HD HD NH NH HD HD NG NH,

NH NI NH HD NI HD NG NH NI NI NH NH HD HD NG NH NH HD,

HD HD NI HD NG NH NI NH HD NI HD NG NH NI NI NH NH HD,

NH NH NG NG NG HD HD NI HD NG NH NI NH HD NI HD NG NH,

NH NH NH NH NI NI NI NI NG NH NI HD HD HD NI NI HD NI,

NI NH NH NI HD NI NH NG NH NH NH NH NI NI NI NI NG NH,

HD HD NI NH NH NH NI HD NI HD NH NH NG NH HD NG NI NH,

HD NI NH NI NH HD HD NI NH NH NI NH NG HD HD NG NH NH,

HD HD NG NG HD NI NH NI NH HD HD NI NH NH NI NH NG HD,

HD HD NG HD HD NG NG HD NI NH NI NH HD HD NI NH NH NI,

HD HD NI NH HD HD HD HD NG HD HD NG HD HD NG NG HD NI,

HD HD NH NI NH HD NG NG NH NI HD HD HD NG NG NH NH NI,

NH NH NG NG NG HD HD NH NI NH HD NG NG NH NI HD HD HD,

NH NH NH NH NG NH NH NG NG NG HD HD NH NI NH HD NG NG,

HD NG NH HD NG NH NH NH NH NG NH NH NG NG NG HD HD NH,

NH HD NI NH NI NH NG NI NG HD NG NH HD NG NH NH NH NH,

HD HD NI NI NG HD HD HD HD NG HD NI NH NG,

HD NI NH NG NH HD NG HD NI NH NG NH NH NI NI,

NH NI NI NI HD NI NG HD HD NH NH HD NH NI HD NG HD NI,

HD NH HD HD HD NG HD NI NI NI NG HD NG NG NI HD NI,

HD NI NI NI NG HD NG NG NI HD NI NH HD NG NH HD NG HD,

HD NG NG NI HD NI NH HD NG NH HD NG HD NI HD NG HD HD,

NI HD NI NH HD NG NH HD NG HD NI HD NG HD HD HD HD NG,

NH HD NG HD NI HD NG HD HD HD HD NG NH HD NI NH NH NH,

HD HD HD HD NG NH HD NI NH NH NH HD NI NI HD NH HD HD,

NH HD NI NH NH NH HD NI NI HD NH HD HD HD NI NH NH NH,

HD NG HD NH NI NG NG NI NG NH NH NH HD NH NH NH NI NG,

HD NH HD NG NG HD NG HD NH NI NG NG NI NG NH NH NH HD,

NH NG HD NH NI NH NG HD NH HD NG NG HD NG HD NH NI NG,

HD HD NI NG NH NG HD NH NI NH NG HD NH HD NG NG HD NG,

HD NH HD HD NG HD HD NI NG NH NG HD NH NI NH NG HD NH,

HD NH NG HD NI NG HD NH HD HD NG HD HD NI NG NH NG HD,

NH NI NG HD NG HD NH NG HD NI NG HD NH HD HD NG HD HD,

NH HD NG NG HD NI NH HD NG NG HD HD NG NI,

HD NG NK NG NH NI NG HD NI NG NH HD HD NI,

NI HD NI NN NG NN NN NG NI HD NI HD NI HD HD NG,

HD HD NI HD HD HD HD HD NI HD NG NI NI NN,

HD NI NG NG NN NN HD NN NN NN HD NI HD,

NN HD NG NG NN NI NI HD HD HD NI NN NN NI NN NI,

NI HD NI HD HD HD NN NI NG HD HD NI HD NG NN NN NN,

NN HD NG NN HD NI NG HD NI NI HD HD HD HD,

NN NN HD NI HD NN NI NI NI HD NI HD HD HD NG HD HD,

NN NN NG NN NN HD NG HD NI NG NN HD HD NG NN,

NN NI NG NG NG NN HD NI HD NI NN HD NG HD NI NG,

NI NI NH HD NG HD NG NH NI NH NH NI NH HD,

HD HD HD NG NI NK HD NG NH NG HD HD HD HD,

NH HD HD NG NI NH HD NI NG NH HD NG NI NH,

NI NG NH NH NH HD NG NG HD NI HD NH NH NI NG,

NH NI NI NI HD NG NI NG NH HD HD NG NH HD,

NH HD NI HD HD NI NG NG NH HD NG HD HD HD,

NH NI HD NI NG NH HD NI NI HD NG HD NI NH,

NI HD NI HD HD NI HD NG NI NH NH NH NH NG,

NH NG HD NG NH HD NG NI NH NI HD NI NH NH,

NH NH HD HD NG NI NH NI HD NI NH NH HD NG NH,

-continued

NH NI NH NH HD NI NG NG HD NG NG NI NG HD NH,

NN HD HD NG NN NN NI NI NI HD NN NG NG HD HD,

NN NG NN HD NG HD NG NN NI HD NI NI NG NI,

NN NG NG NG NG NN HD NI NN HD HD NG HD HD,

NI HD NI NN HD NG NN NG NN NN NI NI HD NN NG,

HD NI NI NN NI HD HD NN NI NN HD NI HD NG NN HD NG NN,

HD NG NI NG HD HD HD NI NI NI NI HD NG HD NG,

NH NI NI NI NI NI HD NG NI NG NH NG NI NG,

NI NH NH HD NI NH NH HD NG NH NH NG NG NH NI,

HD NI NI NG NI HD NI NI HD HD NI HD NN HD,

NI NG NN NI HD NN NN NI HD NG HD NI NI HD NG,

HD NI HD NI NI HD NI NG NG NG NN NG NI NI,
and

NI NG NG NG HD HD NI NN NG NN HD NI HD NI.

In some embodiments, the GSHS is selected from sites listed in FIG. 3 and the TALE DBD comprises a sequence of FIG. 3.

In some embodiments, the TALE DBD comprises one or more of the sequences of FIG. 3 or a sequence having at least about 90%, or at least about 93%, or at least about 95%, or at least about 97%, or at least about 98%, or at least about 99% identity thereto.

In some embodiments, the GSHS and the TALE DBD sequences are selected from:

(SEQ ID NO: 23)
TGGCCGGCCTGACCACTGG
and

NH NH HD HD NH NH HD HD NG NH NI HD HD NI HD NG NH NH;

(SEQ ID NO: 24)
TGAAGGCCTGGCCGGCCTG
and

NH NI NI NH NH HD HD NG NH NH HD HD NH NH HD HD NG NH;

(SEQ ID NO: 25)
TGAGCACTGAAGGCCTGGC
and

NH NI NH HD NI HD NG NH NI NI NH NH HD HD NG NH NH HD;

(SEQ ID NO: 26)
TCCACTGAGCACTGAAGGC
and

HD HD NI HD NG NH NI NH HD NI HD NG NH NI NI NH NH HD;

```
TGGTTTCCACTGAGCACTG                              (SEQ ID NO: 27)
and

NH NH NG NG NG HD HD NI HD NG NH NI NH HD NI HD
NG NH;

TGGGGAAAATGACCCAACA                              (SEQ ID NO: 28)
and

NH NH NH NH NI NI NI NI NG NH NI HD HD HD NI NI
HD NI;

TAGGACAGTGGGGAAAATG                              (SEQ ID NO: 29)
and

NI NH NH NI HD NI NH NG NH NH NH NH NI NI NI NI
NG NH;

TCCAGGGACACGGTGCTAG                              (SEQ ID NO: 30)
and

HD HD NI NH NH NH NI HD NI HD NH NH NG NH HD NG
NI NH;

TCAGAGCCAGGAGTCCTGG                              (SEQ ID NO: 31)
and

HD NI NH NI NH HD HD NI NH NH NI NH NG HD HD NG
NH NH;

TCCTTCAGAGCCAGGAGTC                              (SEQ ID NO: 32)
and

HD HD NG NG HD NI NH NI NH HD HD NI NH NH NI NH
NG HD;

TCCTCCTTCAGAGCCAGGA                              (SEQ ID NO: 33)
and

HD HD NG HD HD NG NG HD NI NH NI NH HD HD NI NH
NH NI;

TCCAGC

```
                                                    (SEQ ID NO: 47)
TGCTCACTCCCCTGCAGGG
and

NH HD NG HD NI HD NG HD HD HD NG NH HD NI NH

NH NH;

(SEQ ID NO: 48)
TCCCCTGCAGGGCAACGCC
and

HD HD HD HD NG NH HD NI NH NH NH HD NI NI HD NH

HD HD;

(SEQ ID NO: 49)
TGCAGGGCAACGCCCAGGG
and

NH HD NI NH NH NH HD NI NI HD NH HD HD HD NI NH

NH NH;

(SEQ ID NO: 50)
TCTCGATTATGGGCGGGAT
and

HD NG HD NH NI NG NG NI NG NH NH NH HD NH NH NH

NI NG;

(SEQ ID NO: 51)
TCGCTTCTCGATTATGGGC
and

HD NH HD NG NG HD NG NH NI NG NG NI NG NH NH

NH HD;

(SEQ ID NO: 52)
TGTCGAGTCGCTTCTCGAT
and

NH NG HD NH NI NH NG HD NH HD NG NG HD NG HD NH

NI NG;

(SEQ ID NO: 53)
TCCATGTCGAGTCGCTTCT
and

HD HD NI NG NH NG HD NH NI NH NG HD NH HD NG NG

HD NG;

(SEQ ID NO: 54)
TCGCCTCCATGTCGAGTCG
and

HD NH HD HD NG HD HD NI NG NH NG HD NH NI NH NG

HD NH;

(SEQ ID NO: 55)
TCGTCATCGCCTCCATGTC
and

HD NH NG HD NI NG NH HD HD NG HD HD NI NG NH

NG HD;

(SEQ ID NO: 56)
TGATCTCGTCATCGCCTCC
and

NH NI NG HD NG HD NH NG HD NI NG HD NH HD HD NG

HD HD;

(SEQ ID NO: 57)
GCTTCAGCTTCCTA
and

NH HD NG NG HD NI NH HD NG NG HD HD NG NI;

(SEQ ID NO: 58)
CTGTGATCATGCCA
and

HD NG NK NG NH NI NG HD NI NG NH HD HD NI;

(SEQ ID NO: 59)
ACAGTGGTACACACCT
and

NI HD NI NN NG NN NN NG NI HD NI HD NI HD HD NG;

(SEQ ID NO: 60)
CCACCCCCCACTAAG
and

HD HD NI HD HD HD HD HD NI HD NG NI NI NN;

(SEQ ID NO: 61)
CATTGGCCGGGCAC
and

HD NI NG NG NN NN HD HD NN NN NN HD NI HD;

(SEQ ID NO: 62)
GCTTGAACCCAGGAGA
and

NN HD NG NG NN NI NI HD HD NI NN NN NI NN NI;

(SEQ ID NO: 63)
ACACCCGATCCACTGGG
and

NI HD NI HD HD HD NN NI NG HD HD NI HD NG NN NN

NN;

(SEQ ID NO: 64)
GCTGCATCAACCCC
and

NN HD NG NN HD NI NG HD NI NI HD HD HD HD;

(SEQ ID NO: 65)
GCCACAAACAGAAATA
and

NN NN HD NI HD NN NI NI NI HD NI HD HD HD NG HD

HD;

(SEQ ID NO: 66)
GGTGGCTCATGCCTG
and

NN NN NG NN NN HD NG HD NI NG NN HD HD NG NN;

(SEQ ID NO: 67)
GATTTGCACAGCTCAT
and

NN NI NG NG NG NN HD NI HD NI NN HD NG HD NI NG;

(SEQ ID NO: 68)
AAGCTCTGAGGAGCA
and

NI NI NH HD NG HD NG NH NI NH NH NI NH HD;

(SEQ ID NO: 69)
CCCTAGCTGTCCC
and

HD HD HD NG NI NK HD NG NH NG HD HD HD HD;
```

```
                               (SEQ ID NO: 70)
GCCTAGCATGCTAG
and

NH HD HD NG NI NH HD NI NG NH HD NG NI NH;

(SEQ ID NO: 71)
ATGGGCTTCACGGAT
and

NI NG NH NH NH HD NG NG HD NI HD NH NH NI NG;

(SEQ ID NO: 72)
GAAACTATGCCTGC
and

NH NI NI NI HD NG NI NG NH HD HD NG NH HD;

(SEQ ID NO: 73)
GCACCATTGCTCCC
and

NH HD NI HD HD NI NG NG NH HD NG HD HD HD;

(SEQ ID NO: 74)
GACATGCAACTCAG
and

NH NI HD NI NG NH HD NI NI HD NG HD NI NH;

(SEQ ID NO: 75)
ACACCACTAGGGGT
and

NI HD NI HD HD NI HD NG NI NH NH NH NH NG;

(SEQ ID NO: 76)
GTCTGCTAGACAGG
and

NH NG HD NG NH HD NG NI NH NI HD NI NH NH;

(SEQ ID NO: 77)
GGCCTAGACAGGCTG
and

NH NH HD HD NG NI NH NI HD NI NH NH HD NG NH;

(SEQ ID NO: 78)
GAGGCATTCTTATCG
and

NH NI NH NH HD NI NG NG HD NG NG NI NG HD NH;

(SEQ ID NO: 79)
GCCTGGAAACGTTCC
and

NN HD HD NG NN NN NI NI NI HD NN NG NG HD HD;

(SEQ ID NO: 80)
GTGCTCTGACAATA
and

NN NG NN HD NG HD NG NN NI HD NI NI NG NI;

(SEQ ID NO: 81)
GTTTTGCAGCCTCC
and

NN NG NG NG NG NN HD NI NN HD HD NG HD HD;

(SEQ ID NO: 82)
ACAGCTGTGGAACGT
and

NI HD NI NN HD NG NN NG NN NN NI NI HD NN NG;

(SEQ ID NO: 83)
GGCTCTCTTCCTCCT
and

HD NI NI NN NI HD HD NN NI NN HD NI HD NG NN HD
NG NN;

(SEQ ID NO: 84)
CTATCCCAAAACTCT
and

HD NG NI NG HD HD HD NI NI NI NI HD NG HD NG;

(SEQ ID NO: 85)
GAAAAACTATGTAT
and

NH NI NI NI NI NI HD NG NI NG NH NG NI NG;

(SEQ ID NO: 86)
AGGCAGGCTGGTTGA
and

NI NH NH HD NI NH NH HD NG NH NH NG NG NH NI;

(SEQ ID NO: 87)
CAATACAACCACGC
and

HD NI NI NG NI HD NI NI HD HD NI HD NN HD;

(SEQ ID NO: 88)
ATGACGGACTCAACT
and

NI NG NN NI HD NN NN NI HD NG HD NI NI HD NG;
and (SEQ ID NO: 89)
CACAACATTTGTAA
and

HD NI HD NI NI HD NI NG NG NG NN NG NI NI.
```

In some embodiments, the GSHS is within about 25, or about 50, or about 100, or about 150, or about 200, or about 300, or about 500 nucleotides of the TA dinucleotide site or TTAA tetranucleotide site.

In some embodiments, guide RNAs (gRNAs) for targeting human genomic safe harbor sites using dCas in areas of open chromatin are as shown in FIG. 4.

In embodiments, the enzyme (e.g., without limitation, a transposase enzyme) is capable of inserting a transposon at a TA dinucleotide site. In some embodiments, the enzyme (e.g., without limitation, a transposase enzyme) is capable of inserting a transposon at a TTAA tetranucleotide site.

Figure 1D:
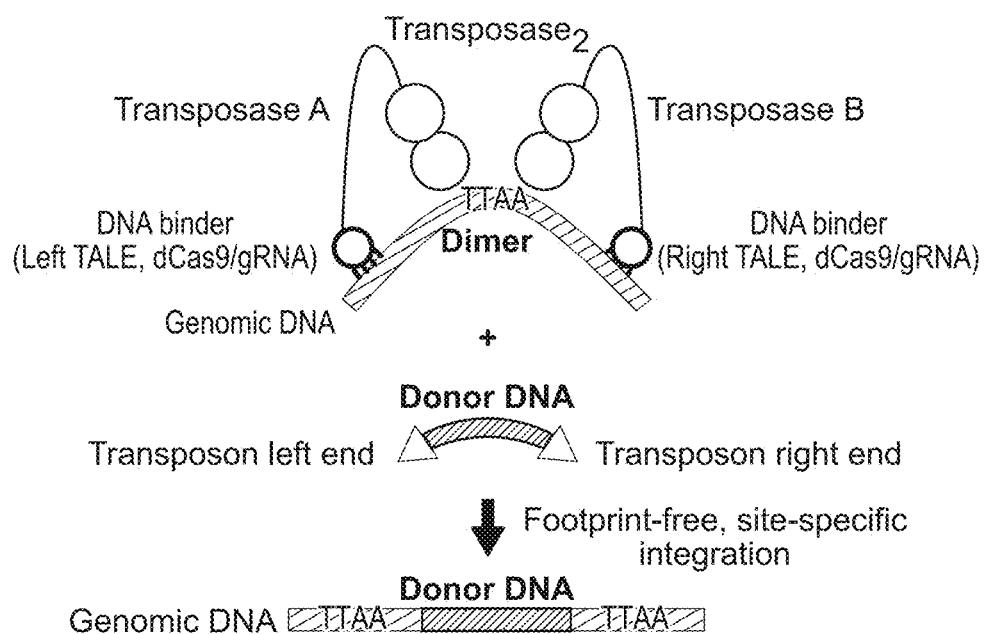
Figure 2:
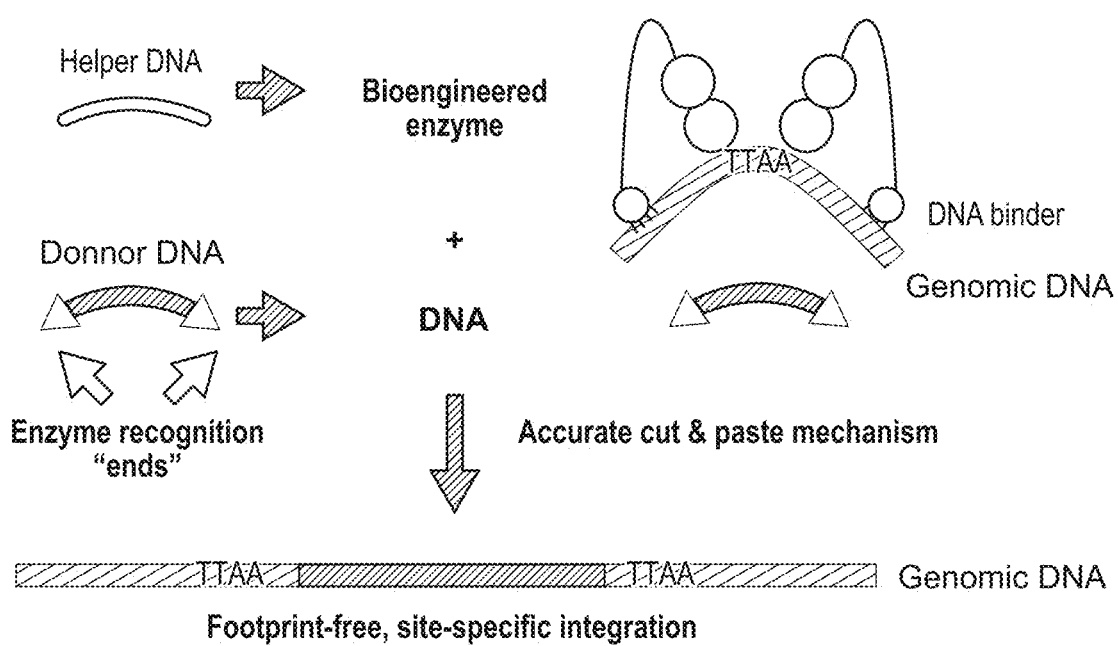
FIG. 2 is a non-limiting representation of a system in accordance with embodiments of the present disclosure comprising a nucleic acid (e.g., helper RNA) encoding an enzyme capable of targeted genomic integration by transposition and a nucleic acid encoding a transposase (donor DNA). The helper RNA is translated into a bioengineered enzyme (e.g., integrase, recombinase, or transposase) that recognizes specific ends and seamlessly inserts the donor DNA into the human genome in a site-specific manner without a footprint. The enzyme can form a dimer or a tetramer at open chromatin to insert donor DNA at TTAA recognition sites near DNA binding regions targeted by dCas9/gRNA or TALEs. Binding of the dCas9/gRNA to TALE GSHS physically sequesters the enzyme to the same location and promotes transposition to the nearby TTAA sequences (see FIG. 3 and FIG. 4).

In embodiments, the composition comprises a system having nucleic acids encoding the enzyme and the transposon, respectively. FIGS. 1A-1D show examples of a system in accordance with embodiments of the present disclosure. For example, as shown in FIG. 2, in some embodiments, the system comprises a nucleic acid (e.g., helper RNA) encoding an enzyme capable of targeted genomic integration by transposition, and a nucleic acid encoding a transposase (e.g., donor DNA). The helper RNA is translated into a bioengineered enzyme (e.g., integrase, recombinase, or transposase) that recognizes specific ends and seamlessly inserts the donor DNA into the human genome in a site-specific manner without a footprint.

In embodiments, an enzyme capable of targeted genomic integration by transposition is encoded by a first nucleic acid, and the transposon is encoded by a second, non-viral nucleic acid. The transposon comprises a transgene and is flanked by ends recognized by the enzyme, and the enzyme causes the transgene be inserted in a certain genomic locus and/or site (e.g., at a TA dinucleotide site or a TTAA tetranucleotide site in a genomic safe harbor site (GSHS) of a nucleic acid molecule. In some embodiments, the first nucleic acid is RNA, for example, helper RNA; and the second, non-viral nucleic acid is DNA. In embodiments, inteins (also referred to as splicing domains) are used to synthesize a recombinant enzyme (e.g., without limitation, an MLT fusion protein) that includes desired internal DNA biding domains (DNA binders) that target specific sites within the human genome for integration of a donor transgene. Inteins (INTervening protEINS) are mobile genetic elements that are protein domains, found in nature, with the capability to carry out the process of protein splicing. See Sarmiento & Camarero (2019) *Current protein & peptide science*, 20(5), 408-424, which is incorporated by reference herein in its entirety. Protein spicing is a post-translation biochemical modification which results in the cleavage and formation of peptide bonds between precursor polypeptide segments flanking the intein. Id. Inteins apply standard enzymatic strategies to excise themselves post-translationally from a precursor protein via protein splicing. Nanda et al., *Microorganisms* vol. 8,12 2004. 16 Dec. 2020, doi: 10.3390/microorganisms8122004. An intein can splice its flanking N- and C-terminal domains to become a mature protein and excise itself from a sequence. For example, split inteins have been used to control the delivery of heterologous genes into transgenic organisms. See Wood & Camarero (2014) *J Biol Chem.* 289(21): 14512-14519. This approach relies on splitting the target protein into two segments, which are then post-translationally reconstituted in vivo by protein trans-splicing (PTS). See Aboye & Camarero (2012) *J. Biol. Chem.* 287, 27026-27032. More recently, an intein-mediated split-Cas9 system has been developed to incorporate Cas9 into cells and reconstitute nuclease activity efficiently. Truong et al., *Nucleic Acids Res.* 2015, 43 (13), 6450-6458. The protein splicing excises the internal region of the precursor protein, which is then followed by the ligation of the N-extein and C-extein fragments, resulting in two polypeptides—the excised intein and the new polypeptide produced by joining the C- and N-exteins. Sarmiento & Camarero (2019).

In embodiments, intein-mediated incorporation of DNA binders such as, without limitation, dCas9, dCas12j, or TALEs, allows creation of a split-MLT transposase system that permits reconstitution of the full-length MLT transposase from two smaller fragments. This allows avoiding the need to express DNA binders at the N- or C-terminus of an MLT transposase. In this approach, the two portions of an MLT transposase are fused to the intein and, after co-expression, the intein allows producing a full-length MLT transposase by post-translation modification. Thus, in embodiments, a nucleic acid encoding the enzyme capable of targeted genomic integration by transposition comprises an intein. In embodiments, the nucleic acid encodes the enzyme in the form of first and second portions with the intein encoded between the first and second portions, such that the first and second portions are fused into a functional enzyme upon post-translational excision of the intein from the enzyme.

In embodiments, an intein can be a suitable ligand-dependent intein, for example, an intein selected from those described in U.S. Pat. No. 9,200,045; Mootz et al., *J. Am. Chem. Soc.* 2002; 124, 9044-9045; Mootz et al., *J. Am. Chem. Soc.* 2003; 125, 10561-10569; Buskirk et al., *Proc. Natl. Acad. Sci. USA.* 2004; 101, 10505-10510; Skretas & Wood. *Protein Sci.* 2005; 14, 523-532; Schwartz, et al., *Nat. Chem. Biol.* 2007; 3, 50-54; Peck et al., *Chem. Biol.* 2011; 18 (5), 619-630; the entire contents of each of which are hereby incorporated by reference herein.

In embodiments the intein is NpuN (Intein-N) (SEQ ID NO: 423) and/or NpuC (Intein-C) (SEQ ID NO: 424), or a variant thereof, e.g. a sequence having at least about 90%, or at least about 93%, or at least about 95%, or at least about 97%, or at least about 98%, or at least about 99% identity thereto.

In embodiments, an enzyme capable of targeted genomic integration by transposition is, without limitation, a transposase enzyme. In embodiments, the transposase enzyme is derived from *Bombyx mori, Xenopus tropicalis*, or *Trichoplusia ni*. In embodiments, the enzyme (e.g., without limitation, a transposase enzyme) is an engineered version of a transposase enzyme, including but not limited to monomers, dimers, tetramers, hyperactive, or Int-forms, derived from *Bombyx mori, Xenopus tropicalis*, or *Trichoplusia ni*.

In embodiments, the transposase enzyme is an engineered version, including but not limited to a transposase enzyme that is a monomer, dimer, tetramer, hyperactive, or has a reduced interaction with non-TTAA recognitions sites (Int-), derived from any of *Bombyx mori, Xenopus tropicalis, Trichoplusia ni, Rhinolophus ferrumequinum, Rousettus aegyptiacus, Phyllostomus discolor, Myotis myotis, Myotis lucifugus, Pipistrellus kuhlii, Pteropus vampyrus*, and *Molossus molossus Bombyx mori, Xenopus tropicalis, Trichoplusia ni* or *Myotis lucifugus*. The transposase enzyme can be either the wild type, monomer, dimer, tetramer, hyperactive, or an Int-mutant.

In some embodiments, the linker that connects the TALE DBD or dCas9/gRNA and the transposase enzyme is a flexible linker. In some embodiments, the flexible linker is substantially comprised of glycine and serine residues, optionally wherein the flexible linker comprises $(Gly_4Ser)_n$, where n is from about 1 to about 12. The flexible linker can be about 20, or about 30, or about 40, or about 50, or about 60 amino acid residues.

In some aspects, a nucleic acid encoding a chimeric transposase in accordance with embodiments of the present disclosure is provided. The nucleic acid can be DNA or RNA. In some embodiments, the chimeric transposase is incorporated into a vector. In some embodiments, the vector is a non-viral vector.

In some aspects, a host cell comprising the nucleic acid in accordance with embodiments of the present disclosure is provided.

In some embodiments, a composition or a nucleic acid in accordance with embodiments of the present disclosure is provided wherein the composition is in the form of a lipid nanoparticle (LNP). The composition can comprise one or more lipids selected from 1,2-dioleoyl-3-trimethylammonium propane (DOTAP), a cationic cholesterol derivative mixed with dimethylaminoethane-carbamoyl (DC-Chol), phosphatidylcholine (PC), triolein (glyceryl trioleate), and 1,2-distearoyl-sn-glycero-3-phosphoethanolamine-N-[carboxy(polyethylene glycol)-2000] (DSPE-PEG), 1,2-dimyristoyl-rac-glycero-3-methoxypolyethyleneglycol—2000 (DMG-PEG 2K), and 1,2 distearol-sn-glycerol-3phosphocholine (DSPC) and/or comprising of one or more molecules selected from polyethylenimine (PEI) and poly(lactic-co-glycolic acid) (PLGA), and N-Acetylgalactosamine (GalNAc).

In some aspects, a method for inserting a gene into the genome of a cell is provided that comprises contacting a cell with a chimeric transposase in accordance with embodiments of the present disclosure. The method can be an in vivo or ex vivo method.

In some embodiments, the cell is contacted with a nucleic acid encoding the chimeric transposase in accordance with embodiments of the present disclosure. In some embodiments, the cell is contacted with an RNA encoding the chimeric transposase. In some embodiments, the cell is contacted with a construct comprising a transposon. In some embodiments, the cell is contacted with a DNA encoding the chimeric transposase.

In embodiments, the present method for inserting a gene into the genome of a cell utilizes the present MLT transposase, e.g. with an amino acid sequence of SEQ ID NO: 2, or a variant thereof (and optionally one or more hyperactive mutations), or the described chimera thereof, at a ratio of about 0.5:1, or a ratio of about 1:1 or a ratio of about 2:1, or a ratio of about 1:0.5, or a ratio of about 1:2, the ratio being the amount of transposon (or payload/transgene) to amount of MLT transposase or the described chimera thereof (e.g. weight: weight, concentration: concentration).

In embodiments, the present method for inserting a gene into the genome of a cell utilizes an immortalized cell line. In embodiments, the present method for inserting a gene into the genome of a cell utilizes a cell derived from a human subject (e.g. the method is performed ex vivo or invitro). In embodiments, the present method for inserting a gene into the genome of a cell utilizes a kidney cell, or a ovary cell, or an immune cell, e.g. a T cell).

In embodiments, the present method for inserting a gene into the genome allows for expression of the inserted gene. In embodiments, the present method for inserting a gene into the genome provides expression of the inserted gene for at least 7 days, or at least 8 days, or at least 9 days, or at least 10 days, or at least 14 days, or at least 21 days, or at least about 7-21 days, or at least about 7-14 days, or at least about 7-10 days, or at least about 10-14 days.

In embodiments, the present method for inserting a gene into the genome does not substantially effect recipient cell viability (e.g. at least about 95%, or at least about 90%, or at least about 85%, or at least about 80%, or at least about 75%, or at least about 50% of cells remain viable after insertion).

As would be appreciated in the art, a transposon often includes an open reading frame that encodes a transgene at the middle of transposon and terminal repeat sequences at the 5' and 3' end of the transposon. The translated transposase binds to the 5' and 3' sequence of the transposon and carries out the transposition function.

In embodiments, a transposon is used interchangeably with transposable elements, which are used to refer to polynucleotides capable of inserting copies of themselves into other polynucleotides. The term transposon is well known to those skilled in the art and includes classes of transposons that can be distinguished on the basis of sequence organization, for example inverted terminal sequences at each end, and/or directly repeated long terminal repeats (LTRs) at the ends. In some embodiments, the transposon as described herein may be described as a PiggyBac™ transposase like element, e.g. a transposon element that is characterized by its traceless excision, which recognizes TTAA sequence and restores the sequence at the insert site back to the original TTAA sequence after removal of the transposon.

In embodiments, the transposon includes a MLT transposase. In embodiments, the MLT transposase is a transposase having an amino acid sequence of SEQ ID NO: 2, or an amino acid sequence having at least about 90%, or at least about 93%, or at least about 95%, or at least about 97%, or at least about 98%, or at least about 99% identity thereto. In embodiments, the MLT transposase is a transposase having an amino acid sequence of SEQ ID NO: 4, or an amino acid sequence having at least about 90%, or at least about 93%, or at least about 95%, or at least about 97%, or at least about 98%, or at least about 99% identity thereto.

In embodiments, the transposase can act on an MLT left terminal end, or a sequence having at least about 90%, or at least about 93%, or at least about 95%, or at least about 97%, or at least about 98%, or at least about 99% identity thereto, wherein the nucleotide sequence of the MLT left terminal end (5' to 3') is as follows:

(SEQ ID NO: 21)
TTAACACTTGGATTGCGGGAAACGAGTTAAGTCGGCTCGCGTGAATTGCG

CGTACTCCGCGGGAGCCGTCTTAACTCGGTTCATATAGATTTGCGGTGGA

GTGCGGGAAACGTGTAAACTCGGGCCGATTGTAACTGCGTATTACCAAAT

ATTTGTT.

In embodiments, the transposase can act on an MLT right terminal end, or a sequence having at least about 90%, or at least about 93%, or at least about 95%, or at least about 97%, or at least about 98%, or at least about 99% identity thereto, wherein the nucleotide sequence of the MLT right terminal end (5' to 3') is as follows:

(SEQ ID NO: 22)
AATTATTTATGTACTGAATAGATAAAAAAATGTCTGTGATTGAATAAATT

TTCATTTTTTACACAAGAAACCGAAAATTTCATTTCAATCGAACCCATAC

TTCAAAAGATATAGGCATTTTAAACTAACTCTGATTTTGCGCGGGAAACC

TAAATAATTGCCCGCGCCATCTTATATTTTGGCGGGAAATTCACCCGACA

CCGTAGTGTTAA.

In some embodiments, the transposon is flanked by one or more terminal ends. In some embodiments, the transposon is or comprises a gene encoding a compete polypeptide. In some embodiments, the transposon is or comprises a gene which is defective or substantially absent in a disease state.

In embodiments, the transposon can encode various genes. For example, in some embodiments, the transposon is an ATP Binding Cassette Subfamily A Member 4 gene (ABC) transporter gene (ABCA4), or functional fragment thereof. As another example, in some embodiments, the transposon is a very low-density lipoprotein receptor gene (VLDLR) or a low-density lipoprotein receptor gene (LDLR) or a functional fragment thereof.

In some embodiments, a therapeutic gene is inserted into a GSHS location in a host genome. GSHSs can be defined as loci well-suited for gene transfer, as integrations within these sites are not associated with adverse effects such as proto-oncogene activation, tumor suppressor inactivation, or insertional mutagenesis. GSHSs can defined by the following criteria: 1) distance of at least 50 kb from the 5' end of any gene, (2) distance of at least 300 kb from any cancer-related gene, (3) distance of at least 300 kb from any microRNA (miRNA), (4) location outside a transcription unit, and (5) location outside ultra-conserved regions (UCRs) of the human genome. See Papapetrou et al. *Nat Biotechnol* 2011; 29:73-8; Bejerano et al. *Science* 2004; 304:1321-5.

Furthermore, the use of GSHS locations can allow stable transgene expression across multiple cell types. One such site, chemokine C-C motif receptor 5 (CCR5) has been identified and used for integrative gene transfer. CCR5 is a member of the beta chemokine receptor family and is required for the entry of R5 tropic viral strains involved in primary infections. A homozygous 32 bp deletion in the CCR5 gene confers resistance to HIV-1 virus infections in humans. Disrupted CCR5 expression, naturally occurring in about 1% of the Caucasian population, does not appear to result in any reduction in immunity. Lobritz at al., *Viruses* 2010; 2:1069-105. A clinical trial has demonstrated safety and efficacy of disrupting CCR5 via targetable nucleases. Tebas at al., HIV. *N Engl J Med* 2014; 370:901-10.

The transposon can be under control of a tissue-specific promoter. The tissue-specific promoter can be, e.g., a liver-specific promoter. In some embodiments, the liver-specific promoter is an LP1 promoter that, in some embodiments, is a human LP1 promoter. The LP1 promoter is described, e.g., in Nathwani et al. *Blood* vol. 2006; 107(7):2653-61, and it can be constructed as described in Nathawani et al. In some embodiments, the tissue-specific promoter is retina-specific promoter, such as, e.g. a retinal pigment epithelium (RPE) promoter, which can be RPE65, IRBP, or VMD2 promoter. The RPE65, IRBP, and VMD2 promoters are described in, e.g., Aguirre. *Invest Ophthalmol Vis Sci.* 2017; 58(12):5399-5411. doi:10.1167/iovs.17-22978. In some embodiments, the retina-specific promoter is a photoreceptor promoter, optionally selected from β-phosphodiesterase (PDE) (see, e.g. Di Polo et al., *Nucleic Acids Res.* 1997; 25(19):3863-3867), rhodopsin kinase (GRK1) (see, e.g. Khani et al., 2007; McDougald et al., *Mol Ther Methods Clin Dev.* 2019; 13:380-389. Published 2019 Mar. 28), CAR (cone arrestin) (see, e.g. McDougald et al., *Mol Ther Methods Clin Dev.* 2019; 13:380-389. Published 2019 Mar. 28), retinitis pigmentosa 1 (RP1), and L-opsin (see, e.g. Kan et al., *Molecular Therapy*, vol. 15, Suppl. 1, S258, May 1, 2007; Lee et al., *Vision Res.* 2008 February; 48(3):332-8).

It should be appreciated however that a variety of promoters can be used, including other tissue-specific promoters, inducible promoters, constitutive promoters, etc.

The chimeric transposase can be incorporated into a vector such as a non-viral vector. The chimeric transposase can be encoded on the same vector as a vector encoding a transposon, or it can be encoded on a separate vector plasmid or RNA.

Furthermore, various transposase enzymes can be used to construct a chimeric transposase.

In some embodiments, the transposase is from a Tc1/mariner transposon system. See, e.g. Plasterk et al. *Trends in Genetics.* 1999; 15(8):326-32.

In some embodiments, the promoter is a cytomegalovirus (CMV) enhancer fused to the chicken ß-actin (CAG) promoter. See Alexopoulou et al., *BMC Cell Biol.* 2008; 9:2, published online Jan. 11, 2008.

In some embodiments, the transposase is from a Sleeping Beauty transposon system (see, e.g., Cell. 1997; 91:501-510), e.g. a hyperactive form of Sleeping Beauty (hypSB), e.g. SB100X (see Gene Therapy volume 18, pages 849-856 (2011), or a PiggyBac™ (PB) transposon system (see, e.g. *Trends Biotechnol.* 2015 September; 33(9):525-33, which is incorporated herein by reference in its entirety), e.g. a hyperactive form of PB transposase (hypPB), e.g. with seven amino acid substitutions (e.g. I30V, S103P, G165S, M282V, S509G, N570S, N538K on mPB, or functional equivalents in non-mPB, see *Mol Ther Nucleic Acids.* 2012 October; 1(10): e50, which is incorporated herein by reference in its entirety); see also Yusa et al., *PNAS Jan.* 25, 2011 108 (4) 1531-1536; Voigt et al., *Nature Communications* volume 7, Article number: 11126 (2016).

The PiggyBac™ transposases belong to the IS4 transposase family. De Palmenaer et al., *BMC Evolutionary Biology.* 2008; 8:18. doi: 10.1186/1471-2148-8-18. The PiggyBac™ transposase family includes a large diversity of transposons, and any of these transposons can be used in embodiments of the present disclosure. See, e.g., Bouallègue et al., *Genome Biol* Evol. 2017; 9(2):323-339. The founding member of the PiggyBac™ transposase (super)family, insect PiggyBac™ transposase, was originally identified in the cabbage looper moth (*Trichoplusiani ni*) and studied both in vivo and in vitro. Insect PiggyBac™ transposase is known to transpose by a canonical cut-and-paste mechanism promoted by an element-encoded transposase with a catalytic site resembling the RNase H fold shared by many recombinases. The insect PiggyBac™ transposon system has been shown to be highly active in a wide range of animals, including *Drosophila* and mice, where it has been developed as a powerful tool for gene tagging and genome engineering. Other transposons affiliated to the PiggyBac™ transposase superfamily are common in arthropods and vertebrates including *Xenopus* and *Bombyx*. Mammalian PiggyBac™ transposons and transposases, including hyperactive mammalian PiggyBac™ transposase variants, which can be used in embodiments of the present disclosure, are described, e.g., in International Application WO2010085699, which is incorporated herein by reference in its entirety.

In some embodiments, the transposase is from a MLT transposon system that is based on a cut-and-paste MLT element obtained from the little brown bat (*Myotis lucifugus*) or other bat transposases, such as *Rhinolophus ferrumequinum, Rousettus aegyptiacus, Phyllostomus discolor, Myotis myotis, Pipistrellus kuhlii and Molossus molossus.* See Mitra et al., *Proc Natl Acad Sci USA.* 2013 Jan. 2; 110(1):234-9; Jebb et al., *Nature*, volume 583, pages 578-584 (2020), which is incorporated by reference herein in its entirety. In some embodiments, hyperactive forms of a bat transposase is used. The MLT transposase has been shown to be capable of transposition in bat, human, and yeast cells. The hyperactive forms of the MLT transposase enhance the transposition process. In addition, chimeric MLT transposases are capable of site-specific excision without genomic integration.

Furthermore, in embodiments, the engineered and/or corrected MLT transposase is used that has certain mutations relative to the wild-type MLT transposase. In embodiments, hyperactive forms of the corrected MLT transposase are used.

In embodiments, the transposase enzyme is derived from any of *Bombyx mori, Xenopus tropicalis, Trichoplusia ni, Rhinolophus ferrumequinum, Rousettus aegyptiacus, Phyllostomus discolor, Myotis myotis, Myotis lucifugus, Pipistrellus kuhlii, Pteropus vampyrus,* and *Molossus molossus.* In embodiments, the transposase enzyme is derived from any of *Trichoplusia ni, Myotis lucifugus, Myotis myotis,* or *Pteropus vampyrus* (see FIG. 7). The transposases can have one or more hyperactive and/or integration deficient mutations selected from FIGS. 5A and 5B, or equivalents thereof. One skilled in the art can correspond such mutants to transposases from any of *Trichoplusia ni, Myotis lucifugus, Myotis myotis,* or *Pteropus vampyrus,* with reference to FIG. 7.

The amino acid sequences shown in the alignment of FIG. 7 are as follows (where notations in parentheses are for distinguishing between different types of sequences only):

*Trichnoplusia ni*
(SEQ ID NO: 10)
```
  1 MGSSLDDEHI LSALLQSDDE LVGEDSDSEI SDHVSEDDVQ SDTEEAFIDE VHEVQPTSSG
 61 SEILDEQNVI EQPGSSLASN KILTLPQRTI RGKNKHCWST SKSTRRSRVS ALNIVRSQRG
121 PTRMCRNIYD PLLCFKLFFT DEIISEIVKW TNAEISLKRR ESMTGATFRD TNEDEIYAFF
181 GILVMTAVRK DNHMSTDDLF DRSLSMVYVS VMSRDRFDFL IRCLRMDDKS IRPTLRENDV
241 FTPVRKIWDL FIHQCIQNYT PGAHLTIDEQ LLGFRGRCPF RMYIPNKPSK YGIKILMMCD
301 SGTKYMINGM PYLGRGTQTN GVPLGEYYVK ELSKPVRGSC RNITCDNWFT SIPLAKNLLQ
361 EPYKLTIVGT VRSNKREIPE VLKNSRSRPV GTSMFCFDGP LTLVSYKPKP AKMVYLLSSC
421 DEDASINEST GKPQMVMYYN QTKGGVDTLD QMCSVMTCSR KTNRWPMALL YGMINIACIN
481 SFIIYSHNVS SKGEKVQSRK KFMRNLYMSL TSSFMRKRLE APTLKRYLRD NISNILPNEV
541 PGTSDDSTEE PVTKKRTYCT YCPSKIRRKA NASCKKCKKV ICREHNIDMC QSCF
```

*Pteropus vampyrus*
(SEQ ID NO: 11)
```
  1 MSNPRKRSIP TCDVNFVLEQ LLAEDSFDES DFSEIDDSDD FSDSASEDYT VRPPSDSESD
 61 GNSPTSADSG RALKWSTRVM IPRQRYDFTG TPGRKVDVSD TTDPLQYFEL FFTEELVSKI
121 TSEMNAQAAL LASKPPGPKG FSRMDKWKDT DNDELKVFFA VMLLQGIVQK PELEMFWSTR
181 PLLDIPYLRQ IMTGERFLLL LRCLHFVNNS SISAGQSKAQ ISLQKIKPVF DFLVNKFSTV
241 YTPNRNIAVD ESLMLFKGRL AMKQYIPTKM LKKDSADGLK
```

*Myotis myotis* ("2a")
(SEQ ID NO: 12)
```
  1 MDLRCQHTVL SIRESRGLLP NLKMKTSRMK KGDIIFSRKG DILLLAWKDK RVVRMISIHD
 61 TSVSTTGKKN RKTGENIVKP ACIKEYNAHM KGVDRADQFL SCCSILRKMM KWTKKVVLYL
121 INCGLFNSFR VYNVLNPQAK MKYKQFLLSV ARDWIMDDNN EGSPEPETNL SSPSPGGARR
181 APRKDPPKRL SGDMKQHEPT CIPASGKKKF PTRACRVCAH GKRSESRYLC KFCLVPLHRG
241 KCFTQYHTLK KY
```

*Myotis myotis* ("1")
(SEQ ID NO: 13)
```
  1 MKAFLGVILN MGVLNHPNLQ SYWSMDFESH IPFFRSVFKR ERFLQIFWML HLKNDQKSSK
 61 DLRTRTEKVN CFLSYLEMKF RERFCPGREI AVDEAVVGFK GKIHFITYNP KKPTKWGIRL
121 YVLSDSKCGY VHSFVPYYGG ITSETLVRPD LPFTSRIVLE LHERLKNSVP GSQGYHFFTD
181 RYYTSVTLAK ELFKEKTHLT GTIMPNRKDN PPVIKHQKLK KGEIVAFRDE NVMLLAWKDK
241 RIVTLSTWDS ETESVERRVG GGKEIVLKPK VVTNYTKFMG GVDIADYTST YCFMRKTLKW
301 WRTLFFWGLE VSVVNSYILY KECQKRKNEK PITHVKFIRK LVHDLVGEFR DGTLTSRGRL
361 LSTNLEQRLD GKLHIITPHP NKKHKDCVVC SNRKIKGGRR ETIYICETCE CKPGLHVGEC
421 FKKYHTMKNY RD
```

*Myotis luciifugus* ("2")
(SEQ ID NO: 14)
```
  1 MPSLRKRKET NETDTLPEVF NDNLSDIPSE IEDADDCFDD SGDDSTDSTD SEIIRPVRKR
 61 KVAVLSSDSD TDEATDNCWS EIDTPPRLQM FEGHAGVTTF PSQCDSVPSV TNLFFGDELF
121 EMLCKELSNY HDQTAMKRKT PSRTLKWSPV TQKDIKKFLG LIILMGQTRK DSLKDYWSTD
181 PLICTPIFPQ TMSRHRFEQI WTFWHFNDNA KMDSRSGRLF KIQPVLDYFL HKFRTIYKPK
241 QQLSLDEGMI PWRGRFKFRT YNPAKITKYG LLVRMVCESD TGYICSMEIY TAEGRKLQET
301 VLSVLGPYLG IWHHIYQDNY YNATSTAELL LQNKTRVCGT IRESRGLPPN LEMKTSRMKK
361 GDIIFSRKGD ILLLAWKDKR VVRMISTIHD TSVSTTGKKN RKTGENIVKP TCIKEYNAHM
421 KGVDRADQFL SCCSILRKTM KWTKKVVLYL INCGLFNSFR VYNVLNPQAK MKYKQFLLSV
```

```
481 ARDWITDDNN EGSPEPETNL SSPSPGGARR APRKDPPKRL AGDMKQHEPT CIPASGKKKF

541 PTRACRVCAA HGKRSESRYL CKGCLCPLHR GKCFTQYHTL KKYMDLRCQH TVLSTCGRGY

601 SVLARFKPRT NERTGSSHCH VQVPAGGQGP PSTIIANGCG CKLEPMVRTR SPTCLVIEFG

661 CM
```

Myotis myotis ("2")

(SEQ ID NO: 15)
```
  1 MPSLRKRKET NETDTLPEVF NDNLSDIPSE IEDADDCFDD SGDDSTDSTE SEIIRPVRKR

61 KVAVLSSDSN TDEATDNCWS EIDTPPRLQM FEGHAGVTTF PSQCDSVPSV TNLFFGDELF

121 EMLCKELSNY HDQTAMKRKT PSRTLKWSPV TQKDIKKFLG LIILMGQTRK DSWKDYWSTD

181 PLICTPIFPQ TMSRHRFEQI WTFWHFNDNA KMDSCSGRLF KIQPVLDYFL HKFRTIYKPK

241 QQLSLDEGMI PWRGRLKFTY NPAITKYGLL VRMVCESDTG YICNMEIYTA ERKKLQETVL

301 SVLGPYLGIW HHIYQDNYYN ATSTAELLLQ NKTRVCGTIR ESRGLPPNLK MKTSRMKKGD

361 IIFSRKGDIL LLAWKDKRVV RMISTIHDTS VSTTGKKNRK TGENIVKPTC IKEYNAHMKG

421 VDRADQFLSC CSILRKTTKW TKKVVLYLIN CGLFNSFRVY NILNPQAKMK YKQFLLSVAR

481 DWITDDNNEG SPEPETNLSS PSSGGARRAP RKDQPKRLSG DMKQHEPTCI PASGKKKFPT

541 ACRVCAAHGK RSESRYLRKF CFVPLRGKCF MYHTLKKYSE LFSLIVVSKI QNVIIYKTTK

601 VYMRYVMRSH CPLSFLVFAP SVKDRSRVFS FFTRHLLWTL DVNTLSCPHR MKRSHWWKPC

661 RSIYEKLYNC TNP
```

Myotis myotis ("2b")

(SEQ ID NO: 16)
```
  1 MDLRCQHTVL SIRESRGLPP NLKMKTSRMK KGDIIFSRKG DILLLAWKDK RVVSMISTIH

61 DTSVSTTGKK NRKTGENIVK PACIKEYNAH MKGVDRADQF LSCCSILRKT MKWTKKVVLY

121 LINCGLFNSF RVYNVLNPQA KMKYKQFLLS VARDWITDDN NEGSPEPETN LSSPSPGGAR

181 RAPRKDPPKR LSGDMKQHEP TCIPASGKKK FPTRACRVCA AHGKRSESRY LCKFCLVPLH

241 RGKCFTQYHT LKKY
```

In embodiments, one skilled in the art can correspond such mutants to transposases from any of *Bombyx mori, Xenopus tropicalis, Trichoplusia ni, Rhinolophus ferrumequinum, Rousettus aegyptiacus, Phyllostomus discolor, Myotis myotis, Myotis lucifugus, Pipistrellus kuhlii, Pteropus vampyrus*, and *Molossus molossus*.

In some embodiments, the transposase enzyme can have a nucleotide sequence having at least about 90%, or at least about 93%, or at least about 95%, or at least about 97%, or at least about 98%, or at least about 99% identity to a nucleotide sequence of any of *Rhinolophus ferrumequinum, Rousettus aegyptiacus, Phyllostomus discolor, Myotis myotis, Myotis lucifugus, Pteropus vampyrus, Pipistrellus kuhlii, Pan troglodytes, Molossus molossus,* or *Homo sapiens*. In some embodiments, the transposase enzyme can have an amino acid sequence having at least about 90%, or at least about 93%, or at least about 95%, or at least about 97%, or at least about 98%, or at least about 99% identity to an amino acid sequence of any of *Rhinolophus ferrumequinum, Rousettus aegyptiacus, Phyllostomus discolor, Myotis myotis, Myotis lucifugus, Pteropus vampyrus, Pipistrellus kuhlii, Pan troglodytes, Molossus molossus,* or *Homo sapiens*. See Jebb, et al. (2020).

In some embodiments, a wild type MLT transposase is encoded by the following nucleotide sequence:

(SEQ ID NO: 5)
```
ATGTCGCAGCATTCAGACTATTCTCATGATGAGTTTTGTGCAGACAAGTT
GTCCAATTATTCTTGTGATAGCGATCTTGAAAATGCGAGTACAAGTGATG
AAGATTCTAGTGATGATGAAGTAATGGTGCGTCCCAGGACATTGAGGCGA
CGAAGAATTTCGAGCTCCAGCTCTGACTCAGAGTCAGATATAGAAGGCGG
GAGAGAAGAATGGTCGCATGTTGATAATCCACCGGTCTTAGAAGATTTTT
TAGGGCATCAAGGATTAAACACAGATGCTGTTATAAATAATATAGAAGAT
GCCGTGAAATTATTTATCGGAGATGATTTTTTTGAATTTCTTGTAGAGGA
GTCAAACAGGTATTATAATCAAAATAGGAATAATTTCAAACTTTCAAAAA
AAAGCCTAAAGTGGAAAGATATAACCCCTCAAGAGATGAAGAAGTTTTTA
GGGTTAATTGTTCTCATGGGACAGGTGCGCAAAGATAGAAGAGATGACTA
TTGGACCACGGAGCCATGGACGGAGACGCCATATTTTGGTAAAACGATGA
CGAGAGACAGGTTCCGACAGATATGGAAAGCTTGGCACTTCAATAATAAT
GCGGATATCGTAAATGAATCAGATAGACTTTGCAAAGTGAGACCAGTACT
AGATTATTTTGTGCCTAAATTTATAAATATTTACAAACCTCATCAGCAAT
```

-continued

```
TATCACTAGATGAAGGGATCGTACCTTGGAGGGGAAGATTATTCTTTAGG

GTATATAATGCTGGCAAGATCGTTAAATATGGAATATTGGTTCGTTTGTT

GTGCGAAAGTGATACAGGATATATCTGTAACATGGAAATTTATTGCGGCG

AAGGAAAGCGATTATTGGAAACGATACAAACAGTAGTGTCTCCATACACT

GATTCGTGGTACCATATATATATGGACAATTATTATAATAGCGTCGCAAA

TTGTGAAGCACTTATGAAAAACAAATTCAGAATATGTGGAACAATCCGGA

AAAATCGAGGTATACCTAAAGATTTTCAAACAATTTCTTTGAAAAAAGGT

GAAACAAAATTTATAAGGAAAAATGATATATTGTTACAAGTGTGGCAATC

AAAAAAGCCTGTATACCTGATTTCTTCGATTCATTCTGCGGAGATGGAAG

AAAGTCAGAATATTGACAGAACATCAAAAAAGAAAATTGTCAAACCGAAT

GCACTCATTGACTACAATAAACATATGAAAGGTGTTGACCGGGCCGACCA

ATACCTTTCATATTATTCGATATTGCGGAGGACGGTCAAATGGACAAAAA

GGTTGGCAATGTATATGATAAATTGCGCATTATTTAATTCTTATGCAGTT

TACAAATCAGTGAGGCAAAGAAAAATGGGTTTTAAAATGTTTTTGAAACA

AACAGCTATCCACTGGTTGACGGATGATATTCCAGAGGACATGGACATTG

TTCCAGACCTTCAACCAGTACCGTCTACTTCTGGAATGCGGGCTAAACCA

CCTACATCTGATCCACCATGCAGGCTATCGATGGACATGAGAAAGCATAC

GTTACAGGCAATTGTCGGAAGTGGAAAAAAGAAAAACATTTTGAGAAGGT

GTCGCGTATGTTCCGTTCATAAATTGCGCAGTGAGACACGCTACATGTGC

AAATTTTGCAATATACCTCTACATAAAGGGGCGTGTTTTGAAAAATATCA

TACGCTAAAAAACTAT,
``` or a nucleotide sequence having at least about 90%, or at least about 93%, or at least about 95%, or at least about 97%, or at least about 98%, or at least about 99% identity thereto.

In some embodiments, a wild type MLT transposase, encoded by the nucleotide sequence of SEQ ID NO: 5 (above), has the following amino acid sequence:

(SEQ ID NO: 4)
```
MSQHSDYSDDEFCADKLSNYSCDSDLENASTSDEDSSDDEVMVRPRTLRR

RRISSSSSDSESDIEGGREEWSHVDNPPVLEDFLGHQGLNTDAVINNIED

AVKLFIGDDFFEFLVEESNRYYNQNRNNFKLSKKSLKWKDITPQEMKKFL

GLIVLMGQVRKDRRDDYWTTEPWTETPYFGKTMTRDRFRQIWKAWHFNNN

ADIVNESDRLCKVRPVLDYFVPKFINIYKPHQQLSLDEGIVPWRGRLFFR

VYNAGKIVKYGILVRLLCESDTGYICNMEIYCGEGKRLLETIQTWSPYTD

SWYHIYMDNYYNSVANCEALMKNKFRICGTIRKNRGIPKDFQTISLKKGE

TKFIRKNDILLQVWQSKKPVYLISS1HSAEMEESQNIDRTSKKKIVKPNA

LIDYNKHMKGVDRADQYLSYYSILRRWKWTKRLAMYMINCALFNSYAVYK

SVRQRKMGFKMFLKQTA1HWLTDDIPEDMDIVPDLQPVPSTSGMRAKPPT

SDPPCRLSMDMRKHTLQAIVGSGKKKNILRRCRVCSVHKLRSETRYMCKF

CNIPLHKGACFEKYHTLKNY,
``` or an amino acid sequence having at least about 90%, or at least about 93%, or at least about 95%, or at least about 97%, or at least about 98%, or at least about 99% identity thereto.

In some embodiments, an MLT transposase has the immediately above amino acid sequence (SEQ ID NO: 4) and includes a hyperactive mutation selected from FIG. 5A or FIG. 5B. For example, a MLT transposase can include about 1, or about 2, or about 3, or about 4, or about 5 hyperactive mutations selected from FIG. 5A or FIG. 5B, or combinations thereof.

In embodiments, an MLT transposase comprises one or more mutations selected from L573X, E574X, and S2X, wherein X is any amino acid or no amino acid, optionally X is A, G, or a deletion, optionally the mutations are L573del, E574del, and S2A.

In embodiments, an MLT transposase comprises L573del, E574del, and S2A mutations, and comprises an amino acid sequence of SEQ ID NO: 2:

(SEQ ID NO: 2)
```
MAQHSDYSDDEFCADKLSNYSCDSDLENASTSDEDSSDDEVMVRPRTLRR

RRISSSSSDSESDIEGGREEWSHVDNPPVLEDFLGHQGLNTDAVINNIED

AVKLFIGDDFFEFLVEESNRYYNQNRNNFKLSKKSLKWKDITPQEMKKFL

GLIVLMGQVRKDRRDDYWTTEPWTETPYFGKTMTRDRFRQIWKAWHFNNN

ADIVNESDRLCKVRPVLDYFVPKFINIYKPHQQLSLDEGIVPWRGRLFFR

VYNAGKIVKYGILVRLLCESDTGYICNMEIYCGEGKRLLETIQTVVSPYT

DSWYHIYMDNYYNSVANCEALMKNKFRICGTIRKNRGIPKDFQTISLKKG

ETKFIRKNDILLQVWQSKKPVYLISSIHSAEMEESQNIDRTSKKKIVKPN

ALIDYNKHMKGVDRADQYLSYYSILRRTVKWTKRLAMYMINCALFNSYAV

YKSVRQRKMGFKMFLKQTAIHWLTDDIPEDMDIVPDLQPVPSTSGMRAKP

PTSDPPCRLSMDMRKHTLQAIVGSGKKKNILRRCRVCSVHKLRSETRYMC

KFCNIPLHKGACFEKYHTLKNY,
``` or an amino acid sequence having at least about 90%, or at least about 93%, or at least about 95%, or at least about 97%, or at least about 98%, or at least about 99% identity thereto.

The MLT transposase comprising the amino acid sequence of SEQ ID NO: 2, or a variant thereof, was engineered to improve upon the enzymes of Mitra et al. (*Proc Natl Acad Sci USA*. 2013 Jan. 2; 110(1):234-9) and WO2010085699, which are both incorporated by reference herein in their entireties. The MLT transposase comprising the amino acid sequence of SEQ ID NO: 2, or a variant thereof (with mutations L573del, E574del, and S2A), is referred to herein as an "engineered" and/or "corrected" MLT transposase.

In some embodiments, an MLT transposase comprising the amino acid sequence of SEQ ID NO: 2 is encoded by the following nucleotide sequence:

(SEQ ID NO: 3)
```
ATGGCCCAGCACAGCGACTACAGCGACGACGAGTTCTGTGCCGATAAGCT

GAGTAACTACAGCTGCGACAGCGACCTGGAAAACGCCAGCACATCCGACG

AGGACAGCTCTGACGACGAGGTGATGGTGCGGCCCAGAACCCTGAGACGG

AGAAGAATCAGCAGCTCTAGCAGCGACTCTGAATCCGACATCGAGGGCGG

CCGGGAAGAGTGGAGCCACGTGGACAACCCTCCTGTTCTGGAAGATTTTC

TGGGCCATCAGGGCCTGAACACCGACGCCGTGATCAACAACATCGAGGAT

GCCGTGAAGCTGTTCATAGGAGATGATTTCTTTGAGTTCCTGGTCGAGGA
```

-continued

```
ATCCAACCGCTATTACAACCAGAATAGAAACAACTTCAAGCTGAGCAAGA

AAAGCCTGAAGTGGAAGGACATCACCCCTCAGGAGATGAAAAAGTTCCTG

GGACTGATCGTTCTGATGGGACAGGTGCGGAAGGACAGAAGGGATGATTA

CTGGACAACCGAACCTTGGACCGAGACCCCTTACTTTGGCAAGACCATGA

CCAGAGACAGATTCAGACAGATCTGGAAAGCCTGGCACTTCAACAACAAT

GCTGATATCGTGAACGAGTCTGATAGACTGTGTAAAGTGCGGCCAGTGTT

GGATTACTTCGTGCCTAAGTTCATCAACATCTATAAGCCTCACCAGCAGC

TGAGCCTGGATGAAGGCATCGTGCCCTGGCGGGGCAGACTGTTCTTCAGA

GTGTACAATGCTGGCAAGATCGTCAAATACGGCATCCTGGTGCGCCTTCT

GTGCGAGAGCGATACAGGCTACATCTGTAATATGGAAATCTACTGCGGCG

AGGGCAAAAGACTGCTGGAAACCATCCAGACCGTCGTTTCCCCTTATACC

GACAGCTGGTACCACATCTACATGGACAACTACTACAATTCTGTGGCCAA

CTGCGAGGCCCTGATGAAGAACAAGTTTAGAATCTGCGGCACAATCAGAA

AAAACAGAGGCATCCCTAAGGACTTCCAGACCATCTCTCTGAAGAAGGGC

GAAACCAAGTTCATCAGAAAGAACGACATCCTGCTCCAAGTGTGGCAGTC

CAAGAAACCCGTGTACCTGATCAGCAGCATCCATAGCGCCGAGATGGAAG

AAAGCCAGAACATCGACAGAACAAGCAAGAAGAAGATCGTGAAGCCCAAT

GCTCTGATCGACTACAACAAGCACATGAAAGGCGTGGACCGGGCCGACCA

GTACCTGTCTTATTACTCTATCCTGAGAAGAACAGTGAAATGGACCAAGA

GACTGGCCATGTACATGATCAATTGCGCCCTGTTCAACAGCTACGCCGTG

TACAAGTCCGTGCGACAAAGAAAAATGGGATTCAAGATGTTCCTGAAGCA

GACAGCCATCCACTGGCTGACAGACGACATTCCTGAGGACATGGACATTG

TGCCAGATCTGCAACCTGTGCCCAGCACCTCTGGTATGAGAGCTAAGCCT

CCCACCAGCGATCCTCCATGTAGACTGAGCATGGACATGCGGAAGCACAC

CCTGCAGGCCATCGTCGGCAGCGGCAAGAAGAAGAACATCCTTAGACGGT

GCAGGGTGTGCAGCGTGCACAAGCTGCGGAGCGAGACTCGGTACATGTGC

AAGTTTTGCAACATTCCCCTGCACAAGGGAGCCTGCTTCGAGAAGTACCA

CACCCTGAAGAATTACTAG,
``` or a nucleotide sequence having at least about 90%, or at least about 93%, or at least about 95%, or at least about 97%, or at least about 98%, or at least about 99% identity thereto.

In some embodiments, a MLT transposase comprising the amino acid sequence of SEQ ID NO: 2 includes one or more hyperactive mutations selected from FIG. 5A or FIG. 5B. For example, a MLT transposase can include about 1, or about 2, or about 3, or about 4, or about 5 hyperactive mutations selected from FIG. 5A or FIG. 5B, or combinations thereof.

In some embodiments, a MLT transposase comprising the amino acid sequence of SEQ ID NO: 2 includes one or more hyperactive mutations selected from a substitution or deletion at one or more of positions S5, S8, D9, D10, E11, C13, A14, S36, S54, N125, K130, G239, T294, T300, I345, R427, D475, M481, P491, A520, and A561.

In some embodiments, a MLT transposase comprising the amino acid sequence of SEQ ID NO: 2 includes one or more hyperactive mutations selected from S5P, S8P, S8P/C13R, D9G, D10G, E11G, C13R, A14V, S36G, S54N, N125K, K130T, G239S, T294A, T300A, I345V, R427H, D475G, M481V, P491Q, A520T, and A561T.

In embodiments, the MLT transposase comprises one or more of hyperactive mutants selected from S8$X_1$, C13$X_2$ and/or N125$X_3$ (e.g., all of S8$X_1$, C13$X_2$ and N125$X_3$, S8$X_1$ and C13$X_2$, S8$X_1$ and N125$X_3$, and C13$X_2$ and N125$X_3$), where $X_1$, $X_2$, and $X_3$ is each independently any amino acid, or $X_1$ is a non-polar aliphatic amino acid, selected from G, A, V, L, I and P, $X_2$ is a positively charged amino acid selected from K, R, and H, and/or $X_3$ is a positively charged amino acid selected from K, R, and H. In embodiments, $X_1$ is P, $X_2$ is R, and/or $X_3$ is K.

In some embodiments, an MLT transposase is encoded by a nucleotide sequence (SEQ ID NO: 6) that corresponds to an amino acid (SEQ ID NO: 7) having the N125K mutation relative to the amino acid sequence of SEQ ID NO: 2 or a functional equivalent thereof:

```
                                               (SEQ ID NO: 6)
   1 atggcccagc acagcgacta cagcgacgac gagttctgtg
     ccgataagct gagtaactac 61 agctgcgaca gcgacctgga aaacgccagc acatccgacg
     aggacagctc tgacgacgag 121 gtgatggtgc ggcccagaac cctgagacgg agaagaatca
     gcagctctag cagcgactct 181 gaatccgaca tcgagggcgg ccgggaagag tggagccacg
     tggacaaccc tcctgttctg 241 gaagattttc tgggccatca gggcctgaac accgacgccg
     tgatcaacaa catcgaggat 301 gccgtgaagc tcttcatagg agatgatttc tttgagttcc
     tggtcgagga atccaaccgc 361 tattacaacc agaagagaaa caacttcaag ctgagcaaga
     aaagcctgaa gtggaaggac 421 atcacccctc aggagatgaa aaagttcctg ggactgatcg
     ttctgatggg acaggtgcgg 481 aaggacagaa gggatgatta ctggacaacc gaaccttgga
     ccgagacccc ttactttggc 541 aagaccatga ccagagacag attcagacag atctggaaag
     cctggcactt caacaacaat 601 gctgatatcg tgaacgagtc tgatagactg tgtaaagtgc
     ggccagtgtt ggattacttc 661 gtgcctaagt tcatcaacat ctataagcct caccagcagc
     tgagcctgga tgaaggcatc 721 gtgccctggc ggggcagact gttcttcaga gtgtacaatg
     ctggcaagat cgtcaaatac 781 ggcatcctgg tgcgccttct gtgcgagagc gatacaggct
     acatctgtaa tatggaaatc 841 tactgcggcg agggcaaaag actgctggaa accatccaga
     ccgtcgtttc cccttatacc 901 gacagctggt accacatcta catggacaac tactacaatt
     ctgtggccaa ctgcgaggcc 961 ctgatgaaga acaagtttag aatctgcggc acaatcagaa
     aaaacagagg catccctaag 1021 gacttccaga ccatctctct gaagaagggc gaaaccaagt
     tcatcagaaa gaacgacatc 1081 ctgctccaag tgtggcagtc caagaaaccc gtgtacctga
     tcagcagcat ccatagcgcc
```

-continued

```
1141  gagatggaag aaagccagaa catcgacaga acaagcaaga
      agaagatcgt gaagcccaat 1201  gctctgatcg actacaacaa gcacatgaaa ggcgtggacc
      gggccgacca gtacctgtct 1261  tattactcta tcctgagaag aacagtgaaa tggaccaaga
      gactggccat gtacatgatc 1321  aattgcgccc tgttcaacag ctacgccgtg tacaagtccg
      tgcgacaaag aaaaatggga 1381  ttcaagatgt tcctgaagca gacagccatc cactggctga
      cagacgacat tcctgaggac 1441  atggacattg tcccagatct gcaacctgtg cccagcacct
      ctggtatgag agctaagcct 1501  cccaccagcg atcctccatg tagactgagc atggacatgc
      ggaagcacac cctgcaggcc 1561  atcgtcggca gcggcaagaa gaagaacatc cttagacggt
      gcagggtgtg cagcgtgcac 1621  aagctgcgga gcgagactcg gtacatgtgc aagtttttgca
      acattcccct gcacaaggga 1681  gcctgcttcg agaagtacca caccctgaag aattactag,
``` or a nucleotide sequence having at least about 90%, or at least about 93%, or at least about 95%, or at least about 97%, or at least about 98%, or at least about 99% identity thereto (the codon corresponding to the N125K mutation is underlined and bolded).

```
                                              (SEQ ID NO: 7)
  1  MAQHSDYSDD EFCADKLSNY SCDSDLENAS TSDEDSSDDE
     VMVRPRTLRR RRISSSSSDS

61  ESDIEGGREE WSHVDNPPVL EDFLGHQGLN TDAVINNIED
     AVKLFIGDDF FEFLVEESNR

121  YYNQKENNFK LSKKSLKWKD ITPQEMKKFL GLIVLMGQVR
     KDRRDDYWTT EPWTETPYFG

181  KTMTRDRFRQ IWKAWHFNNN ADIVNESDRL CKVRPVLDYF
     VPKFINIYKP HQQLSLDEGI

241  VPWRGRLFFR VYNAGKIVKY GILVRLLCES DTGYICNMEI
     YCGEGKRLLE TIQTVVSPYT

301  DSWYHIYMDN YYNSVANCEA LMKNKFRICG TIRKNRGIPK
     DFQTISLKKG ETKFIRKNDI

361  LLQVWQSKKP VYLISSIHSA EMEESQNIDR TSKKKIVKPN
     ALIDYNKHMK GVDRADQYLS

421  YYSILRRTVK WTKRLAMYMI NCALFNSYAV YKSVRQRKMG
     FKMFLKQTAI HWLTDDIPED

481  MDIVPDLQPV PSTSGMRAKP PTSDPPCRLS MDMRKHTLQA
     IVGSGKKKNI LRRCRVCSVH

541  KLRSETRYMC KFCNIPLHKG ACFEKYHTLK NY,
``` or an amino acid sequence having at least about 90%, or at least about 93%, or at least about 95%, or at least about 97%, or at least about 98%, or at least about 99% identity thereto (the amino acid corresponding to the N125K mutation is underlined and bolded).

In some embodiments, the MLT transposase encoded by the nucleotide sequence of SEQ ID NO: 7 and having the amino acid sequence of SEQ ID NO: 7 is referred to as an MLT transposase 1 (or MLT1).

In some embodiments, an MLT transposase is encoded by a nucleotide sequence (SEQ ID NO: 8) that corresponds to an amino acid (SEQ ID NO: 9) having the S8P and C13R mutations relative to the amino acid sequence of SEQ ID NO: 2 or a functional equivalent thereof:

```
                                              (SEQ ID NO: 8)
  1  atggcccagc acagcgacta ccccgacgac gagttcagag
     ccgataagct gagtaactac 61  agctgcgaca gcgacctgga aaacgccagc acatccgacg
     aggacagctc tgacgacgag 121  gtgatggtgc ggcccagaac cctgagacgg agaagaatca
     gcagctctag cagcgactct 181  gaatccgaca tcgagggcgg ccgggaagag tggagccacg
     tggacaaccc tcctgttctg 241  gaagattttc tgggccatca gggcctgaac accgacgccg
     tgatcaacaa catcgaggat 301  gccgtgaagc tgttcatagg agatgatttc tttgagttcc
     tggtcgagga atccaaccgc 361  tattacaacc agaatagaaa caacttcaag ctgagcaaga
     aaagcctgaa gtggaaggac 421  atcaccctc aggagatgaa aaagttcctg ggactgatcg
     ttctgatggg acaggtgcgg 481  aaggacagaa gggatgatta ctggacaacc gaaccttgga
     ccgagacccc ttactttggc 541  aagaccatga ccagagacag attcagacag atctggaaaa
     cctggcactt caacaacaat 601  gctgatatcg tgaacgagtc tgatagactg tgtaaagtgc
     ggccagtgtt ggattacttc 661  gtgcctaagt tcatcaacat ctataagcct caccagcagc
     tgagcctgga tgaaggcatc 721  gtgccctggc ggggcagact gttcttcaga gtgtacaatg
     ctggcaagat cgtcaaatac 781  ggcatcctgg tgcgccttct gtgcgagagc gatacaggct
     acatctgtaa tatggaaatc 841  tactgcggcg agggcaaaag actgctggaa accatccaga
     ccgtcgtttc cccttatacc 901  gacagctggt accacatcta catggacaac tactacaatt
     ctgtggccaa ctgcgaggcc 961  ctgatgaaga acaagtttag aatctgcggc acaatcagaa
     aaaacagagg catccctaag 1021 gacttccaga ccatctctct gaagaagggc gaaaccaagt
     tcatcagaaa gaacgacatc 1081 ctgctccaag tgtggcagtc caagaaaccc gtgtacctga
     tcagcagcat ccatagcgcc 1141 gagatggaag aaagccagaa catcgacaga acaagcaaga
     agaagatcgt gaagcccaat 1201 gctctgatcg actacaacaa gcacatgaaa ggcgtggacc
     gggccgacca gtacctgtct 1261 tattactcta tcctgagaag aacagtgaaa tggaccaaga
     gactggccat gtacatgatc 1321 aattgcgccc tgttcaacag ctacgccgtg tacaagtccg
     tgcgacaaag aaaaatggga 1381 ttcaagatgt tcctgaagca gacagccatc cactggctga
     cagacgacat tcctgaggac 1441 atggacattg tgccagatct gcaacctgtg cccagcacct
     ctggtatgag agctaagcct
```

-continued

```
1501  cccaccagcg  atcctccatg  tagactgagc  atggacatgc
      ggaagcacac  cctgcaggcc 1561  atcgtcggca  gcggcaagaa  gaagaacatc  cttagacggt
      gcagggtgtg  cagcgtgcac 1621  aagctgcgga  gcgagactcg  gtacatgtgc  aagtttgca
      acattcccct  gcacaaggga 1681  gcctgcttcg  agaagtacca  caccctgaag  aattactag,
``` or a nucleotide sequence having at least about 90%, or at least about 93%, or at least about 95%, or at least about 97%, or at least about 98%, or at least about 99% identity thereto (the codons corresponding to the S8P and C13R mutations are underlined and bolded).

```
                                              (SEQ ID NO: 9)
  1  MAQHSDYPDD  EFRADKLSNY  SCDSDLENAS  TSDEDSSDDE
     VMVRPRTLRR  RRISSSSSDS

61  ESDIEGGREE  WSHVDNPPVL  EDFLGHQGLN  TDAVINNIED
     AVKLFIGDDF  FEFLVEESNR

121  YYNQNRNNFK  LSKKSLKWKD  ITPQEMKKFL  GLIVLMGQVR
     KDRRDDYWTT  EPWTETPYFG

181  KTMTRDRFRQ  IWKAWHFNNN  ADIVNESDRL  CKVRPVLDYF
     VPKFINIYKP  HQQLSLDEGI

241  VPWRGRLFFR  VYNAGKIVKY  GILVRLLCES  DTGYICNMEI
     YCGEGKRLLE  TIQTVVSPYT

301  DSWYHIYMDN  YYNSVANCEA  LMKNKFRICG  TIRKNRGIPK
     DFQTISLKKG  ETKFIRKNDI

361  LLQVWQSKKP  VYLISSIHSA  EMEESQNIDR  TSKKKIVKPN
     ALIDYNKHMK  GVDRADQYLS

421  YYSILRRTVK  WTKRLAMYMI  NCALFNSYAV  YKSVRQRKMG
     FKMFLKQTAI  HWLTDDIPED

481  MDIVPDLQPV  PSTSGMRAKP  PTSDPPCRLS  MDMRKHTLQA
     IVGSGKKKNI  LRRCRVCSVH

541  KLRSETRYMC  KFCNIPLHKG  ACFEKYHTLK  NY,
``` or an amino acid sequence having at least about 90%, or at least about 93%, or at least about 95%, or at least about 97%, or at least about 98%, or at least about 99% identity thereto (the amino acids corresponding to the S8P and C13R mutations are underlined and bolded).

In some embodiments, the MLT transposase encoded by the nucleotide sequence of SEQ ID NO: 8 and having the amino acid sequence of SEQ ID NO: 9 is referred to as an MLT transposase 2 (or MLT2).

In aspects, there is provided a composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto. In embodiments, the substitution is a non-polar aliphatic amino acid, optionally one of G, A, V, L, I and P, optionally S2A. In embodiments, the enzyme does not have additional residues at the C terminus. In embodiments, the enzyme has one or more mutations which confer hyperactivity, e.g. selected from $S8X_1$, $C13X_2$ and/or $N125X_3$, e.g. and where $X_1$ is selected from G, A, V, L, I and P, $X_2$ is selected from K, R, and H, and $X_3$ is selected from K, R, and H, e.g. $X_1$ is P, $X_2$ is R, and/or $X_3$ is K. In embodiments, there is provided a composition comprising a nucleic acid encoding the transposase enzyme (e.g. an MLT transposase) described here, e.g. having a nucleotide sequence of SEQ ID NO: 3, or a nucleotide sequence having at least about 80%, at least about 90%, or at least about 93%, or at least about 95%, or at least about 98% identity thereto. In embodiments, the transposase or nucleic acid is in the form of a lipid nanoparticle (LNP). In embodiments, the enzyme is co-formulated with a nucleic acid encoding a transposon, e.g. in the same lipid nanoparticle (LNP). In embodiments, the co-formulation comprises the nucleic acid encoding the enzyme and the nucleic acid encoding the transposon.

In embodiments, there is provided a method for inserting a gene into the genome of a cell, comprising contacting a cell with the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto, or the nucleotide sequence having at least about 80%, at least about 90%, or at least about 93%, or at least about 95%, or at least about 98% identity thereto. In embodiments, the substitution is a non-polar aliphatic amino acid, optionally one of G, A, V, L, I and P, optionally S2A. In embodiments, the enzyme does not have additional residues at the C terminus. In embodiments, the enzyme has one or more mutations which confer hyperactivity, e.g. selected from $S8X_1$, $C13X_2$ and/or $N125X_3$, e.g. and where $X_1$ is selected from G, A, V, L, I and P, $X_2$ is selected from K, R, and H, and $X_3$ is selected from K, R, and H, e.g. $X_1$ is P, $X_2$ is R, and/or $X_3$ is K. In embodiments, the method further comprises contacting the cell with a construct comprising a transposon and/or the enzyme is co-formulated with a nucleic acid encoding a transposon (e.g. in an LNP). In embodiments, the co-formulation comprises the nucleic acid encoding the enzyme and the nucleic acid encoding the transposon.

In some embodiments, a MLT transposase comprising the amino acid sequence of SEQ ID NO: 2 includes one or more mutations selected from S8P and/or C13R and one of R164N, W168V, M278A, K286A, R287A, R333A, K334A, N335A, K349A, K350A, K368A, K369A, and D416N.

In some embodiments, a MLT transposase comprising the amino acid sequence of SEQ ID NO: 2 includes one or more mutations selected from S8P and/or C13R and one of R164N, W168V, M278A, K286A, R287A, R333A, K334A, N335A, K349A, K350A, K368A, K369A, and D416N and/or one or more of E284A, K286A, R287A, N310A, R333A, K334A, R336A, K349A, K350A, K368A, and K369A.

In some embodiments, a MLT transposase comprising the amino acid sequence of SEQ ID NO: 2 includes one or more mutations selected from S8P and/or C13R and one of R164N, W168V, M278A, K286A, R287A, R333A, K334A, N335A, K349A, K350A, K368A, K369A, and D416N and/or one or more of E284A, K286A, R287A, N310A, R333A, K334A, R336A, K349A, K350A, K368A, and K369A and/or one R336A.

In embodiments, there is provided a method for treating a disease or disorder ex vivo, comprising contacting a cell with the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto or comprising a transposase enzyme (e.g. an MLT transposase) having a nucleotide sequence having a nucleotide sequence of SEQ ID NO: 3, or the nucleotide sequence having at least about 80%, at least about 90%, or at least about 93%, or at least about 95%, or at least about 98% identity thereto.

In embodiments, there is provided a method for treating a disease or disorder in vivo, comprising administering the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto, or comprising a transposase enzyme (e.g. an MLT transposase) having a nucleotide sequence having a nucleotide sequence of SEQ ID NO: 3, or the nucleotide sequence having at least about 80%, at least about 90%, or at least about 93%, or at least about 95%, or at least about 98% identity thereto, or a cell comprising the composition comprising a transposase enzyme (e.g. an MLT transposase) having an amino acid sequence of SEQ ID NO: 2 and a substitution at position S2, or a variant having at least about 90%, or at least about 93%, or at least about 95%, or at least about 97%, or at least about 98%, or at least about 99% identity thereto, or comprising a transposase enzyme (e.g. an MLT transposase) having a nucleotide sequence having a nucleotide sequence of SEQ ID NO: 2, or the nucleotide sequence having at least about 80%, at least about 90%, or at least about 93%, or at least about 95%, or at least about 98% identity thereto.

In embodiments, the present MLT transposase, e.g. with an amino acid sequence of SEQ ID NO: 2, or a variant thereof (and optionally one or more hyperactive mutations) demonstrates improved integration efficiency relative to PiggyBac™ transposase. In embodiments, the present MLT transposase of an amino acid sequence of SEQ ID NO: 2, and S8P, C13R and/or N125K, demonstrates improved integration efficiency relative to PiggyBac™ transposase.

In embodiments, the present MLT transposase, e.g. with an amino acid sequence of SEQ ID NO: 2, or a variant thereof (and optionally one or more hyperactive mutations) can be in the form or an RNA or DNA and have one or two N-terminus nuclear localization signal (NLS) to shuttle the protein more efficiently into the nucleus. For example, in embodiments, the present MLT transposase further comprises one, two, three, four, five, or more NLSs. Examples of NLS are provided in Kosugi et al. (*J. Biol. Chem.* (2009) 284:478-485; incorporated by reference herein). In a particular embodiment, the NLS comprises the consensus sequence K(K/R)X(K/R) (SEQ ID NO: 348). In an embodiment, the NLS comprises the consensus sequence (K/R)(K/R)$X_{10-12}$ (K/R)$_{35}$ (SEQ ID NO: 349), where (K/R)$_{35}$ represents at least three of the five amino acids is either lysine or arginine. In an embodiment, the NLS comprises the c-myc NLS. In a particular embodiment, the c-myc NLS comprises the sequence PAAKRVKLD (SEQ ID NO: 350). In a particular embodiment, the NLS is the nucleoplasmin NLS. In a particular embodiment, the nucleoplasmin NLS comprises the sequence KRPAATKKAGQAKKKK (SEQ ID NO: 351). In a particular embodiment, the NLS comprises the SV40 Large T-antigen NLS. In a particular embodiment, the SV40 Large T-antigen NLS comprises the sequence PKKKRKV (SEQ ID NO: 352). In a particular embodiment, the NLS comprises three SV40 Large T-antigen NLSs (e.g., DPKKKRKVDPKKKRKVDPKKKRKV (SEQ ID NO: 353). In various embodiment, the NLS may comprise mutations/variations in the above sequences such that they contain 1 or more substitutions, additions or deletions (e.g. about 1, or about 2, or about 3, or about 4, or about 5, or about 10 substitutions, additions, or deletions).

In some embodiments, the transposase is from a LEAP-IN 1 type or LEAP-IN transposon system (*Biotechnol J.* 2018 October; 13(10):e 1700748. doi: 10.1002/biot.201700748. Epub 2018 Jun. 11).

In some embodiments, a non-viral vector includes a LEAP-IN 1 type of LEAPIN Transposase (ATUM, Newark, CA). The LEAPIN Transposase system includes a transposase (e.g., a transposase mRNA) and a vector containing one or more genes of interest (transposons), selection markers, regulatory elements, insulators, etc., flanked by the transposon cognate inverted terminal ends and the transposition recognition motif (TTAT). Upon co-transfection of vector DNA and transposase mRNA, the transiently expressed enzyme catalyzes high-efficiency and precise integration of a single copy of the transposon cassette (all sequences between the terminal ends) at one or more sites across the genome of the host cell. Hottentot et al. In Genotyping: Methods and Protocols. White SJ, Cantsilieris S, eds: 185-196. (New York, NY: Springer): 2017. pp. 185-196. The LEAPIN Transposase generates stable transgene integrants with various advantageous characteristics, including single copy integrations at multiple genomic loci, primarily in open chromatin segments; no payload limit, so multiple independent transcriptional units may be expressed from a single construct; the integrated transgenes maintain their structural and functional integrity; and maintenance of transgene integrity ensures the desired chain ratio in every recombinant cell.

Furthermore, the LEAPIN Transposase has a self-inactivating mechanism. The 3'-TRE, located within an intron of the transposase construct, spatially separates the promoter regions. Therefore, enzymatic excision of the transposon located between TTAA sites, from the plasmid during transposition, results in the separation of the promoter from the 5' end of the LEAPIN Transposase construct. The now promoterless transposase residing in the remaining plasmid backbone is inactivated if inserted non-transpositionally into the genome, thereby reducing genotoxic effects in a host cell. This can stop any protein synthesis from the mRNA constructs that may be erroneously synthesized. Urschitz et al., *Proc Natl Acad Sci USA* 2010; 107:8117-22.

In some embodiments, the present dual system comprises a DNA plasmid encoding a transgene, and RNA encoding a transposase (e.g., the LEAPIN Transposase). In some embodiments, the use of mRNA that encodes a transposase can have a number of advantages over delivery of a transposase-encoding DNA molecule. See, e.g. Wilber et al. *Mol Ther* 2006; 13:625-30. The advantages include improved control with respect to the duration of transposase expression, minimizing persistence in the tissue, and the potential for transgene re-mobilization and re-insertion following the initial transposition event. Furthermore, the transposase-encoding RNA sequence is likely incapable of integrating into the host genome, thereby eliminating concerns about long-term transposase expression and destabilizing effects with respect to the gene of interest. Furthermore, in some embodiments, the dual plasmid DNA transposon/RNA transposase system is in the form of a lipid nanoparticle (LNP), to protect from extracellular RNA degradation, which improves the in vivo use.

In some embodiments, a transgene can be associated with various regulatory elements that are selected to ensure stable expression of a construct with the transgene. Thus, in some embodiments, a transgene can be encoded by a non-viral vector (e.g., a DNA plasmid) that can comprise one or more insulator sequences that prevent or mitigate activation or inactivation of nearby genes. The insulators flank the transposon (transgene cassette) to reduce transcriptional silencing and position effects imparted by chromosomal sequences. As an additional effect, the insulators can eliminate functional interactions of the transgene enhancer and promoter sequences with neighboring chromosomal sequences. In some embodiments, the one or more insulator sequences comprise an HS4 insulator (1.2-kb 5'-HS4 chicken β-globin (cHS4) insulator element) and an D4Z4 insulator (tandem macrosatellite repeats linked to Facio-Scapulo-Humeral Dystrophy (FSHD). In some embodiments, the sequences of the HS4 insulator and the D4Z4 insulator are as described in Rival-Gervier et al. *Mol Ther.* 2013 August; 21(8): 1536-50, which is incorporated herein by reference in its entirety.

The described method enhances enzymes capable of targeted genomic integration by transposition (e.g., without limitation, transposases) by fusing them to DNA binding TALEs or dCas9/gRNA to target integrations to GSHS, which can be in areas that have open chromatin. In embodiments, a nucleic acid encoding the enzyme (e.g., DNA) encodes the enzyme in the form of first and second portions with an intein encoded between the first and second portions, such that the first and second portions are fused into a functional enzyme upon post-translational excision of the intein from the enzyme. The described method provides reduced insertional mutagenesis or oncogenesis as compared to a method with a non-chimeric transposase. Also, in some embodiments, the method is used to treat an inherited or acquired disease in a patient in need thereof.

In embodiments, there is provided a transgenic organism that may comprise cells which have been transformed by the methods of the present disclosure. In embodiments, the organism may be a mammal or an insect. When the organism is a mammal, the organism may include, but is not limited to, a mouse, a rat, a monkey, a dog, a rabbit and the like. When the organism is an insect, the organism may include, but is not limited to, a fruit fly, a mosquito, a bollworm and the like.

The compositions can be included in a container, kit, pack, or dispenser together with instructions for administration.

Also provided herein are kits comprising: i) any of the aforementioned gene transfer constructs of this invention, and/or any of the aforementioned cells of this invention and ii) a container. In certain embodiments, the kits further comprise instructions for the use thereof. In certain embodiments, any of the aforementioned kits can further comprise a recombinant DNA construct comprising a nucleic acid sequence that encodes a transposase.

In embodiments, a composition in accordance with embodiments of the present disclosure is in the form of a pharmaceutical composition, in combination with a pharmaceutically acceptable carrier. A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject (e.g., a mammal, such as a human, non-human primate, dog, cat, sheep, pig, horse, cow, mouse, rat, or rabbit), which is nontoxic to the cell or subject being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed, Mack Publishing Company, Easton, PA (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick, *Regul Toxicol Pharmacol* 32:210-218, 2000; Wang, *Int J Pharm* 203:1-60, 2000; Charman *J Pharm Sci* 89:967-978, 2000; and Powell et al. *PDA J Pharm Sci Technol* 52:238-311, 1998), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can contain sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a pharmaceutical composition including a composition as provided herein can be, at least in part, in the form of a solution or powder with or without a diluent to make an injectable suspension. The composition may include additional ingredients including, without limitation, pharmaceutically acceptable vehicles, such as saline, water, lactic acid, mannitol, or combinations thereof, for example.

Any appropriate method can be used to administer a composition as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing a composition as described herein can be administered prior to, after, or in lieu of surgical resection of a tumor.

This invention is further illustrated by the following non-limiting examples.

EXAMPLES

Example 1—Design of Chimeric Transposases with Transcription Activator-Like Effector (TALE) DNA Binding Domains (DBDs) or dCas9/gRNA that Target Human Genomic Safe Harbor Sites (GSHS)

In this example, chimeric transposases were designed using human GSHS TALE or dCas9/gRNA DBD. FIGS. 1A-1D and FIG. 2 depict representations of chimeric transposase designed using human GSHS TALE or dCas9/gRNA DBD. FIG. 1A. TALEs includes nuclear localization signals (NLS) and an activation domain (AD) to function as transcriptional activators. A central tandem repeat domain confers specific DNA-binding and host specificity. Translocation signal (TD) and four cryptic repeats required for initiation of DNA binding and for the recognition of 5'-T⁰ are located at the N-terminus (checkered rectangles). Each 34 amino acid (aa) long repeat in the CRD binds to one nucleotide with specificity determined mainly by aa at position 13. One sample repeat is shown below the protein scheme. Numbers 12/13 refer to aa positions within the repeat. See Jankele et al., *Brief Funct Genomics* 2014; 13:409-19. FIG. 1B. Repeat types are shown that have specificity for one or several nucleotides. Only bases of the DNA leading strand are shown. FIG. 1C. A chimeric transposase having a TALE DNA-binding protein fused thereto by a linker that is greater than 23 amino acids in length (top). See Hew et al., Synth Biol (Oxf) 2019; 4:ysz018. FIG. 1D. Binding of the TALE to GSHS physically sequesters the transposase to the same location and promotes transposition to the nearby TTAA sequences near repeat variable di-residues (RVD) nucleotide sequences. All RVD are preceded by a thymine (T) to bind to the NTR shown in FIG. 1A. All of these GSHS regions are in open chromatin and are susceptible to transposase activity).

FIG. 2 is a non-limiting representation of a system in accordance with embodiments of the present disclosure comprising a nucleic acid (e.g., helper RNA) encoding an enzyme capable of targeted genomic integration by transposition and a nucleic acid encoding a transposase (donor DNA). The helper RNA is translated into a bioengineered enzyme (e.g., integrase, recombinase, or transposase) that recognizes specific ends and seamlessly inserts the donor DNA into the human genome in a site-specific manner without a footprint. The enzyme can form a dimer or a tetramer at open chromatin to insert donor DNA at TTAA recognition sites near DNA binding regions targeted by dCas9/gRNA or TALEs. Binding of the dCas9/gRNA to TALE GSHS physically sequesters the enzyme to the same location and promotes transposition to the nearby TTAA sequences (See FIG. 3 and FIG. 4).

FIG. 1C also illustrates (bottom) a chimeric transposase construct comprising dCas9 linked to one or more guide RNAs. An engineered chimeric transposase may include: a guide RNA (gRNA) and an inactivated Cas protein. The gRNA is a short synthetic RNA composed of a scaffold sequence necessary for Cas-binding and a user-defined ~20 nucleotide spacer that defines the genomic target to be modified. Thus, the genomic target of the Cas protein is based upon the sequence present in the gRNA. FIG. 4 shows gRNA sequences that physically sequester the transposase to GSHS and promotes transposition to the nearby TTAA sequences.

Figure 8A:
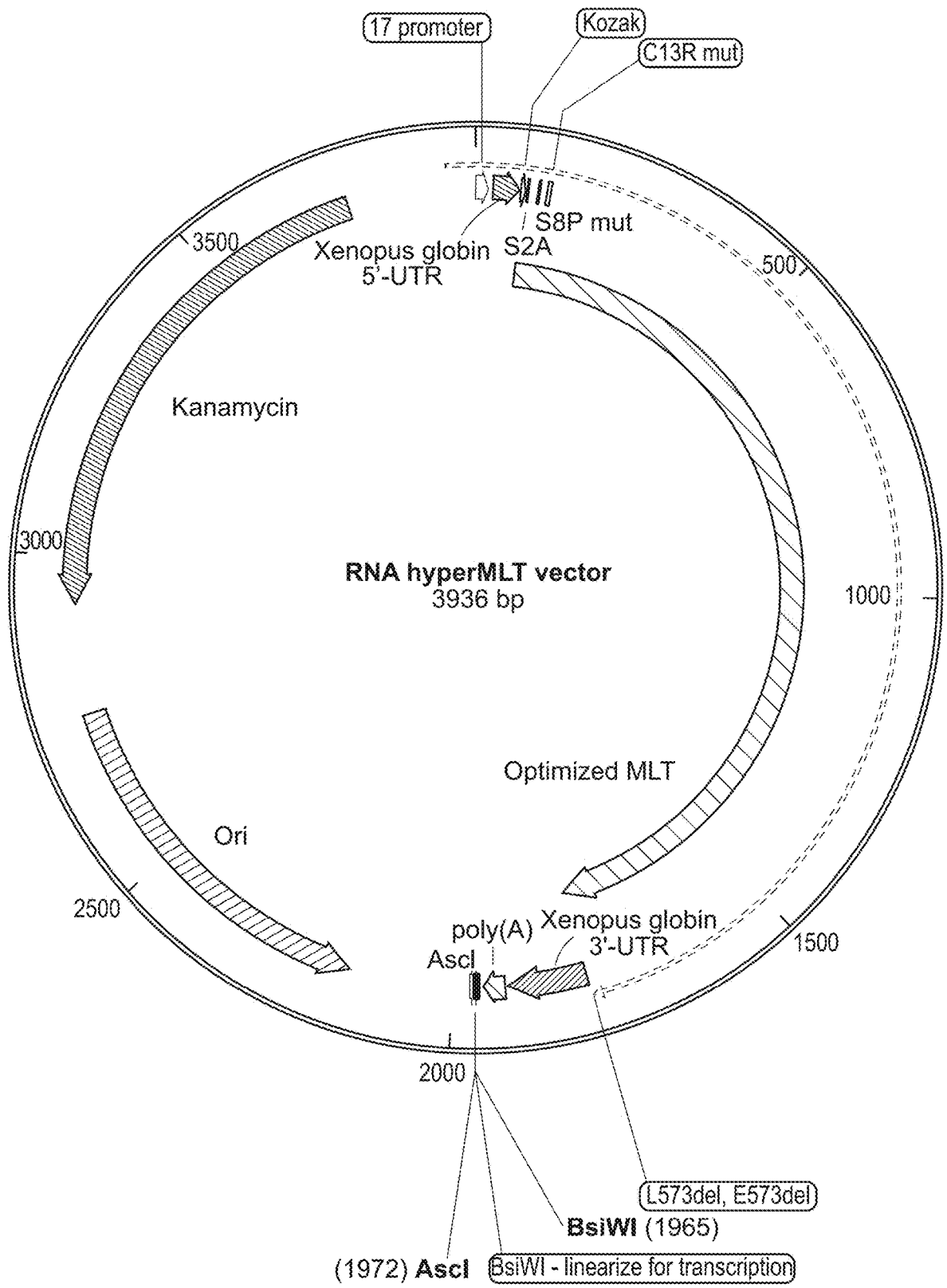
FIGS. 8A and 8B depict non-limiting examples of construct templates.
Figure 8B:
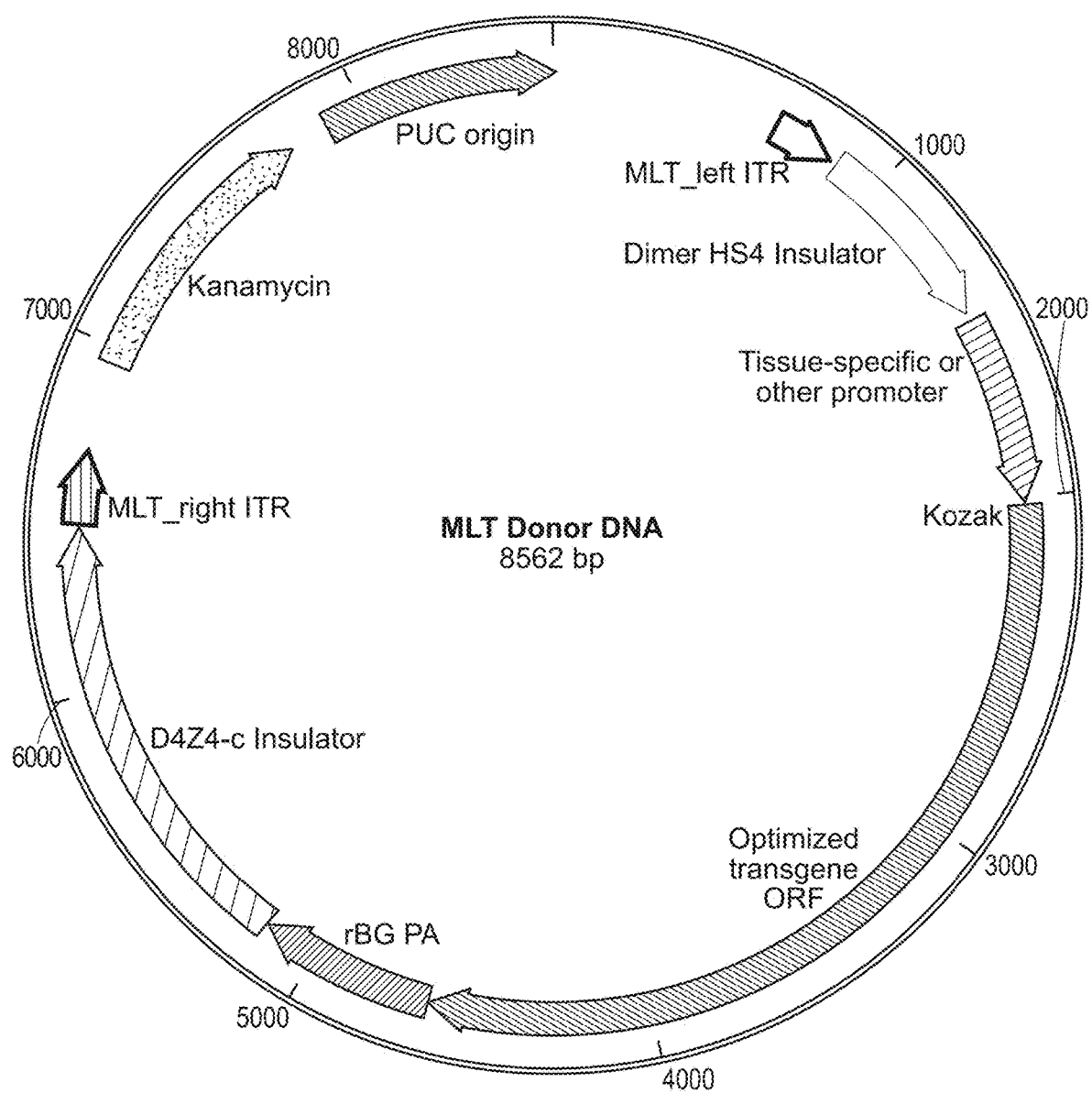

FIGS. 8A-8D depict examples of construct templates. FIG. 8A depicts a plasmid construct template that transcribes transposase RNA that is later processed with a 5'-m7G cap1 and pseudouridine substitution. Other transposases can be substituted. FIG. 8B depicts a (generic) MLT donor DNA construct template that can be used for transfer of any transgene. Other dCas9/gRNAs and transposases can be substituted.

Example 2—Characterizing Transposition Activity of *M. lucifugus* MLT Transposase and its Hyperactive Forms This study, in part, aims at functionally characterizing the transposition activity of *M. lucifugus* (MLT) transposase, including monomer, dimer, tetramer, hyperactive, and Int-forms of MLT transposase. The MLT transposase protein with the L573del, E574del, and S2A mutations, discovered in the present disclosure, can be referred to as an engineered, corrected MLT transposase in accordance with the present disclosure.

FIGS. 5A and 5B depict hyperactive, excision positive, and integration deficient (Int-) MLT mutants from the MLT transposase DNA and MLT transposase protein. For each mutant, FIG. 5A shows nucleotide changes and corresponding amino acid changes relative to a non-mutated wild type MLT transposase, having the amino acid sequence of SEQ ID NO: 4 and that is encoded by the nucleotide sequence of SEQ ID NO: 5. FIG. 5B shows mutations in the MLT transposase backbone and various MLT mutants (1, 2, and 3).

Figure 6A:
FIG. 6A depicts the three dimensional MLT protein structure with 100% confidence that shows DNA binding domains.
Figure 6B:
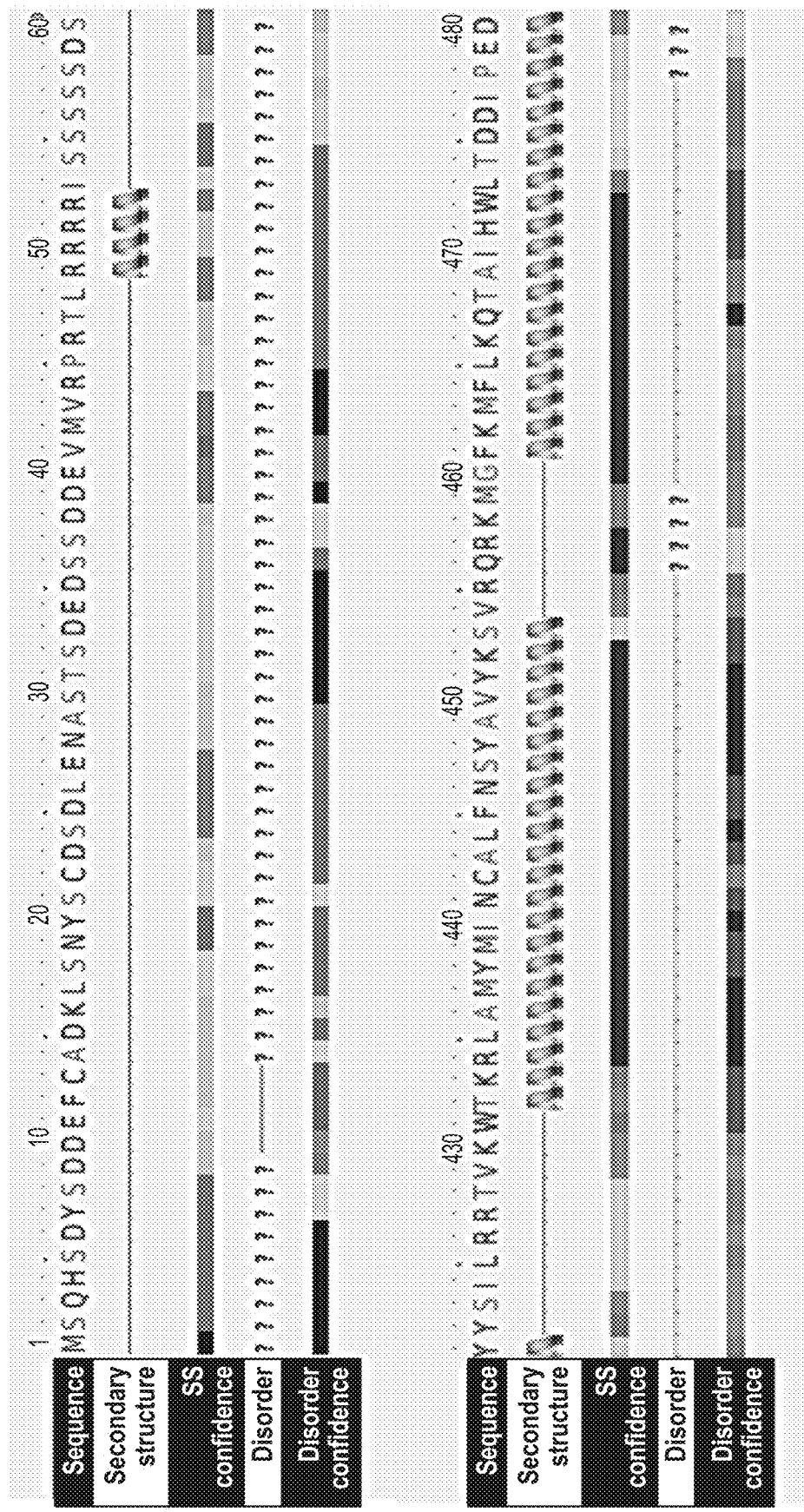
FIG. 6B depicts secondary structure prediction for an MLT transposase comprising the amino acid sequence of SEQ ID NO: 4 encoded by a nucleotide sequence of SEQ ID NO: 5
Figure 6B:

FIG. 6A depicts the three-dimensional MLT protein structure with 100% confidence that shows DNA binding domains. The three dimensional MLT protein structure is generated using Phyre$^2$ (Protein Homology/AnalogY Recognition Engine), Kelley LA et al. *Nature Protocols* 10, 845-858 (2015). FIG. 6B depicts secondary structure prediction for MLT, using Phyre$^2$.

FIG. 7 depicts an amino acid sequence alignment of PiggyBac™ ("*Trichoplusia ni*") transposase to MLT ("*Myotis lucifugus*") transposase (two different sequences), and bat transposases *Myotis myotis* (four different sequences) and *Pteropus vampyrus*. The sequences were obtained from Jebb, et al., *Nature*, volume 583, pages 578-584 (2020), which is incorporated herein by reference in its entirety. In FIG. 7, the alignment, generated using SnapGene® software (from GSL Biotech), is to the consensus sequence. Amino acids that match the reference (consensus), i.e. highly conserved mammalian transposase sequences, are marked with yellow highlighting. Consensus threshold is greater than 50%.

In this example, the sequences shown in FIGS. 3, 4, and 7, or any other sequences, are used in testing varying combinations of MLT mutants, to identify candidates for targeting genomic safe harbor sites with site-specific TALEs or dCas9/gRNA. Hyperactive, excision positive, or Int- MLT mutants can be generated by synthetic DNA synthesis by substituting the mutations in FIGS. 5A and 5B in a MLT transposase described herein, e.g. a nucleotide and amino acid sequence.

In this example, a genetic assay as described, for example, in Example 8 of International Application WO2010085699, which is incorporated herein by reference in its entirety, can be used for screening for an increased frequency of Ura+ reversion. The genetic assay uses a modified version of the yeast URA3 gene as a transposon donor, for the excision of MLT in yeast (*Saccharomyces cerevisiae*).

Example 3—Characterizing Integration Efficiency of PiggyBac™ Transposase, Wild-Type MLT Transposase, and Engineered MLT Transposase of the Disclosure A goal of this study was to assess integration efficiency of known hyperactive PiggyBac™ transposases, including those from published sources, and of an engineered MLT transposase in accordance with the present disclosure. The wild type *Myotis Lucifugus* transposase (MLT) sequence was described in a WO2010/085699 publication (of PCT/US2010/021871) and in Mitra et al., *PNAS* 2013; 110:234. The nucleotide sequence of a transposase from Mitra et al. (2013) has 77% sequence identity to the MLT transposase of the present disclosure (referred to as "MLT") that has the nucleotide sequence of SEQ ID NO: 3. See FIG. 10, which depicts a nucleotide sequence alignment of hyperactive MLT (human codon-optimized for RNA) and published sequence from Mitra et al. (2013) (*Identity* 77.67%, gaps 1.44%). The nucleotide sequence of MLT and the nucleotide sequence from WO2010085699 have 73.68%, identity (gaps 1.16%), as shown in FIG. 11 containing their alignment.

Furthermore, the end sequences of the engineered MLT transposase of the present disclosure are different than those referenced by Mitra et al. (2013) (see Ray et al., *Genome Res* 2008; 18:717). FIG. 14 and FIG. 15 show left and right terminal ends of the engineered MLT transposase, compared to left and right terminal ends of the published sequence from Ray et al., 2018.

FIG. 12 illustrates an amino acid alignment of the engineered hyperactive MLT transposase (L573del/E574del/S2A, with S8P, C13R, and N125K mutations, "MLT") and a published sequence by Mitra et al. (the differences between the amino acid sequences are underlined and bolded). As shown in FIG. 12, the amino acid sequence from Mitra et al. contained two extra C-terminal amino acids relative to the MLT transposase of the present disclosure.

FIG. 13 illustrates an amino acid alignment of the engineered, hyperactive MLT transposase (L573del/E574del/S2A, with S8P and C13R mutations, "MLT") and a published sequence from WO2010085699 (the differences between the amino acid sequences are underlined and bolded). The sequence from the WO2010085699 publication had multiple amino acid residue changes compared to the amino acid sequence of the MLT transposase of the present disclosure. WO2010085699 described hyperactive transposase enzymes comprising amino acid changes in the sequence as shown in FIG. 13, the amino acid changes selected from A14V, D475G, P491Q, A561T, T546T, T300A, T294A, A520T, G239S, S5P, S8F, S54N, D9N, D9G, 1345V, M481V, E11G, K130T, G9G, R427H, S8P, S36G, D10G, S36G and silent.

Figure 9B:
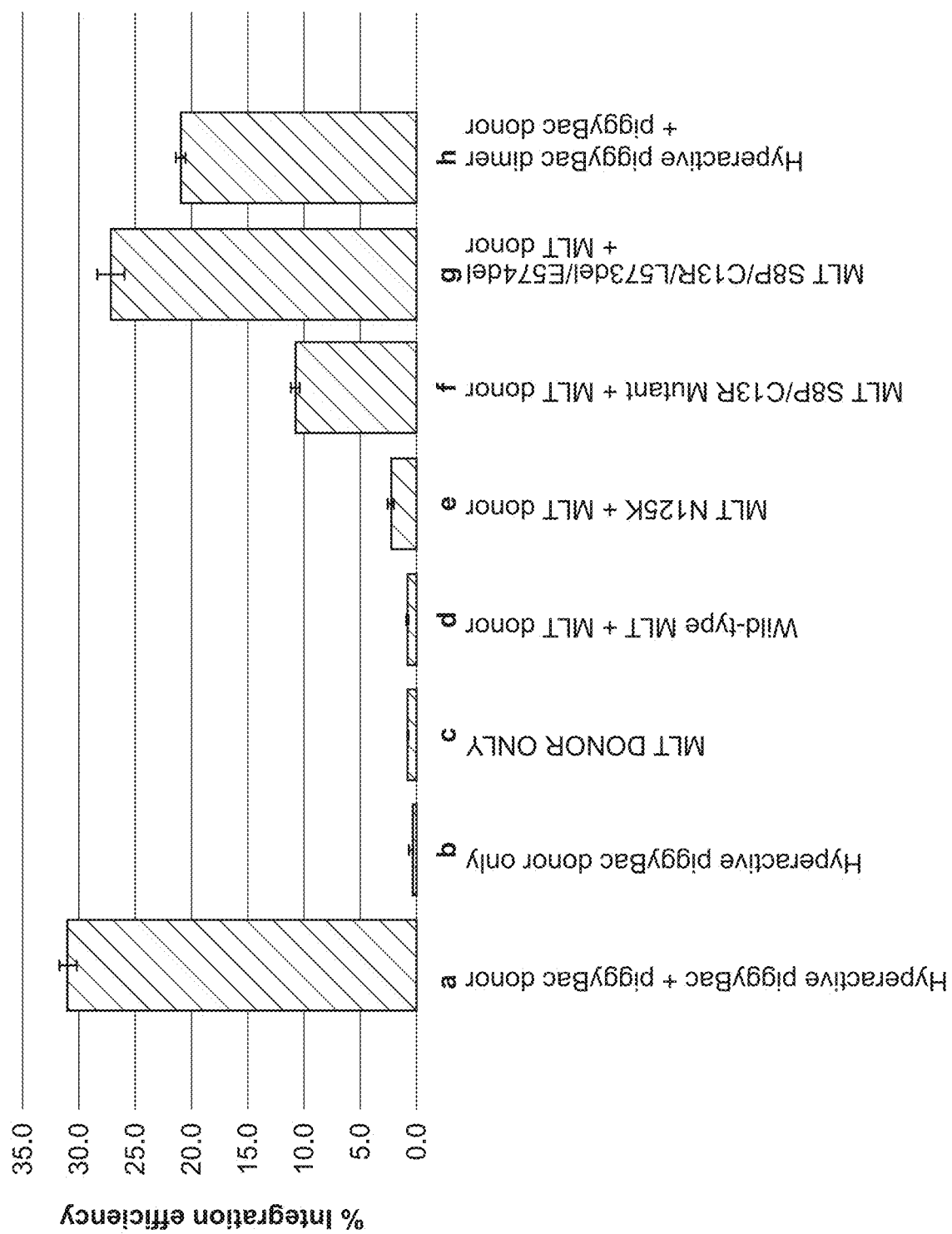
FIG. 9B is a bar chart illustrating integration efficiency of engineered MLT (S8P/C13R double mutant; L573del E574del, S2A) compared to hyperactive PiggyBac™ transposase, using sequences from Yusa et al. (2010).
Figure 16:
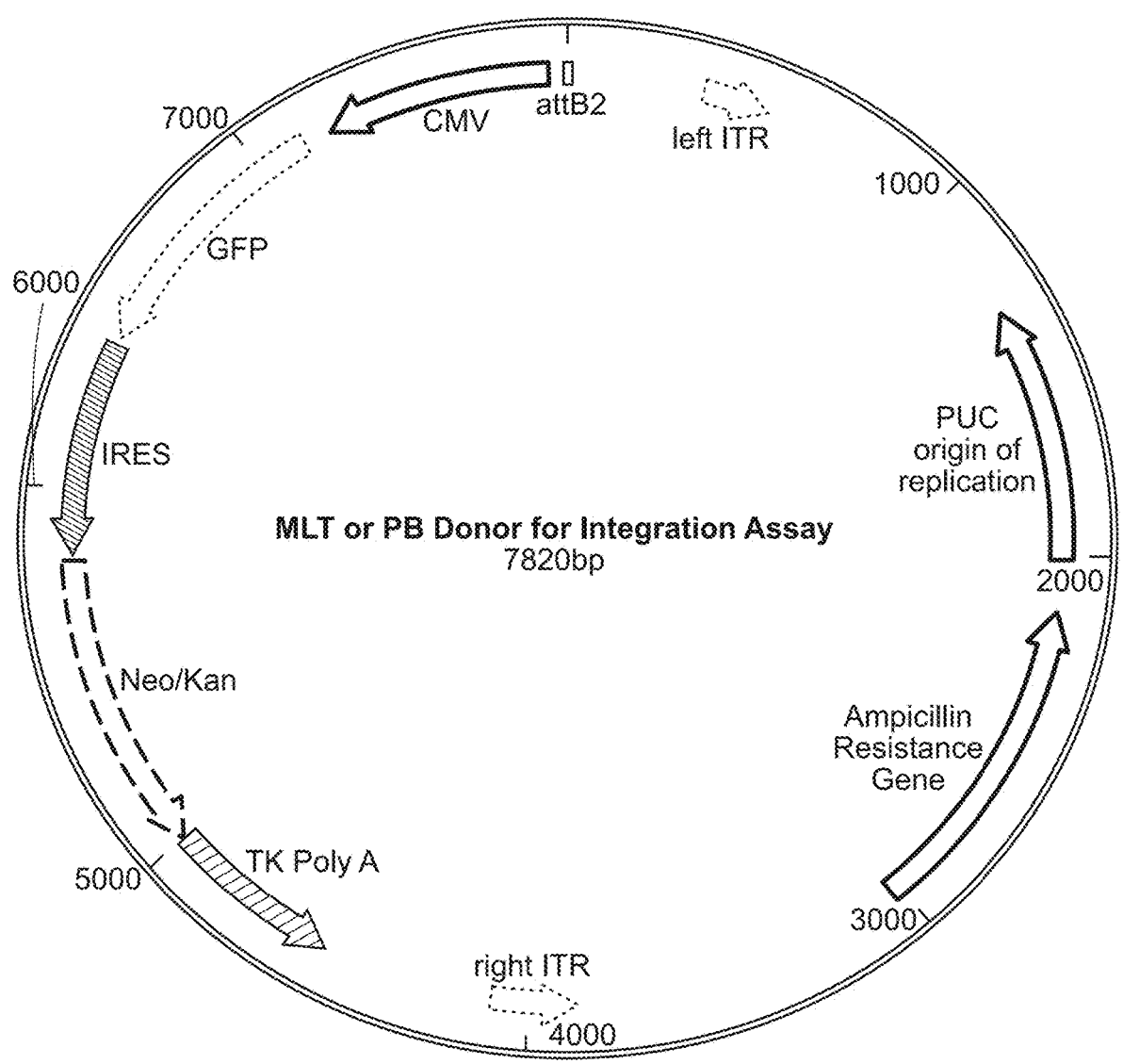
FIG. 16 depicts a DNA donor construct template used with either *Myotis lucifugus* transposase (MLT) or Piggy-Bac™ (PB) transposase, for an integration assay. The DNA donor construct template has a cytomegalovirus (CMV) promoter that drives expression of green fluorescent protein (GFP).

FIGS. 9A and 9B are bar charts illustrating results of assessment of integration efficiency of the engineered MLT transposase of the present disclosure and other (known) transposases. FIG. 9A illustrates integration efficiency of a hyperactive PiggyBac™ transposase from Yusa et al. *PNAS* 2010; 108:1531-1536 (see FIGS. 16A, 16B, 16C, and 16D), used with a PiggyBac™ transposase donor (CMV-GFP, see FIG. 15), versus the engineered MLT transposase of the present disclosure (S8P/C13R/S2A/L573del/E574del MLT) used with an MLT donor (CMV-GFP, see FIG. 16 that shows an example of a DNA donor construct template).

The hyperactive PiggyBac™ transposase amino acid sequence used in the study show in FIG. 9A and FIG. 9B (from Yusa et al. (2010), with 130V, S103P, G165S, M282V, S509G, N538K, and N571S mutations, shown bolded and underlined) is as follows:

```
                                           (SEQ ID NO: 17)
  1  MGSSLDDEHI LSALLQSDDE LVGEDSDSEV SDHVSEDDVQ
     SDTEEAFIDE VHEVQPTSSG

61  SEILDEQNVI EQPGSSLASN RILTLPQRTI RGKNKHCWST
     SKPTRRSRVS ALNIVRSQRG

121  PTRMCRNIYD PLLCFKLFFT DEIISEIVKW TNAEISLKRR
     ESMTSATFRD TNEDEIYAFF

181  GILVMTAVRK DNHMSTDDLF DRSLSMVYVS VMSRDRFDFL
     IRCLRMDDKS IRPTLRENDV

241  FTPVRKIWDL FIHQCIQNYT PGAHLTIDEQ LLGFRGRCPF
     RVYIPNKPSK YGIKILMMCD

301  SGTKYMINGM PYLGRGTQTN GVPLGEYYVK ELSKPVHGSC
     RNITCDNWFT SIPLAKNLLQ
```

```
361  EPYKLTIVGT VRSNKREIPE VLKNSRSRPV GTSMFCFDGP
     LTLVSYKPKP AKMVYLLSSC

421  DEDASINEST GKPQMVMYYN QTKGGVDTLD QMCSVMTCSR
     KTNRWPMALL YGMINIACIN

481  SFIIYSHNVS SKGEKVQSRK KFMRNLYMGL TSSFMRKRLE
     APTLKRYLRD NISNILPKEV

541  PGTSDDSTEE PVMKKRTYCT YCPSKIRRKA SASCKKCKKV
     ICREHNIDMC QSCF
```

The hyperactive PiggyBac™ transposase nucleotide sequence used in the study show in FIG. 9A and FIG. 9B (mutated codons underlined and bolded) is as follows:

```
                                        (SEQ ID NO: 18)
   1 ATGGGCAGCA GCCTGGACGA CGAGCACATC CTGAGCGCCC
     TGCTGCAGAG CGACGACGAG

61 CTGGTCGGCG AGGACAGCGA CAGCGAGGTG AGCGACCACG
     TGAGCGAGGA CGACGTGCAG

121 TCCGACACCG AGGAGGCCTT CATCGACGAG GTGCACGAGG
     TGCAGCCTAC CAGCAGCGGC

181 TCCGAGATCC TGGACGAGCA GAACGTGATC GAGCAGCCCG
     GCAGCTCCCT GGCCAGCAAC

241 AGGATCCTGA CCCTGCCCCA GAGGACCATC AGGGGCAAGA
     ACAAGCACTG CTGGTCCACC

301 TCCAAGCCCA CCAGGCGGAG CAGGGTGTCC GCCCTGAACA
     TCGTGAGAAG CCAGAGGGGC

361 CCCACCAGGA TGTGCAGGAA CATCTACGAC CCCCTGCTGT
     GCTTCAAGCT GTTCTTCACC

421 GACGAGATCA TCAGCGAGAT CGTGAAGTGG ACCAACGCCG
     AGATCAGCCT GAAGAGGCGG

481 GAGAGCATGA CCTCCGCCAC CTTCAGGGAC ACCAACGAGG
     ACGAGATCTA CGCCTTCTTC

541 GGCATCCTGG TGATGACCGC CGTGAGGAAG GACAACCACA
     TGAGCACCGA CGACCTGTTC

601 GACAGATCCC TGAGCATGGT GTACGTGAGC GTGATGAGCA
     GGGACAGATT CGACTTCCTG

661 ATCAGATGCC TGAGGATGGA CGACAAGAGC ATCAGGCCCA
     CCCTGCGGGA GAACGACGTG

721 TTCACCCCCG TGAGAAAGAT CTGGGACCTG TTCATCCACC
     AGTGCATCCA GAACTACACC

781 CCTGGCGCCC ACCTGACCAT CGACGAGCAG CTGCTGGGCT
     TCAGGGGCAG GTGCCCCTTC

841 AGGGTCTATA TCCCCAACAA GCCCAGCAAG TACGGCATCA
     AGATCCTGAT GATGTGCGAC

901 AGCGGCACCA AGTACATGAT CAACGGCATG CCCTACCTGG
     GCAGGGGCAC CCAGACCAAC

961 GGCGTGCCCC TGGGCGAGTA CTACGTGAAG GAGCTGTCCA
     AGCCCGTCCA CGGCAGCTGC

1021 AGAAACATCA CCTGCGACAA CTGGTTCACC AGCATCCCCC
     TGGCCAAGAA CCTGCTGCAG

1081 GAGCCCTACA AGCTGACCAT CGTGGGCACC GTGAGAAGCA
     ACAAGAGAGA GATCCCCGAG

1141 GTCCTGAAGA ACAGCAGGTC CAGGCCCGTG GGCACCAGCA
     TGTTCTGCTT CGACGGCCCC

1201 CTGACCCTGG TGTCCTACAA GCCCAAGCCC GCCAAGATGG
     TGTACCTGCT GTCCAGCTGC

1261 GACGAGGACG CCAGCATCAA CGAGAGCACC GGCAAGCCCC
     AGATGGTGAT GTACTACAAC

1321 CAGACCAAGG GCGGCGTGGA CACCCTGGAC CAGATGTGCA
     GCGTGATGAC CTGCAGCAGA

1381 AAGACCAACA GGTGGCCCAT GGCCCTGCTG TACGGCATGA
     TCAACATCGC CTGCATCAAC

1441 AGCTTCATCA TCTACAGCCA CAACGTGAGC AGCAAGGGCG
     AGAAGGTGCA GAGCCGGAAA

1501 AAGTTCATGC GGAACCTGTA CATGGGCCTG ACCTCCAGCT
     TCATGAGGAA GAGGCTGGAG

1561 GCCCCCACCC TGAAGAGATA CCTGAGGGAC AACATCAGCA
     ACATCCTGCC CAAAGAGGTG

1621 CCCGGCACCA GCGACGACAG CACCGAGGAG CCCGTGATGA
     AGAAGAGGAC CTACTGCACC

1681 TACTGTCCCA GCAAGATCAG AAGAAAGGCC AGCGCCAGCT
     GCAAGAAGTG TAAGAAGGTC

1741 ATCTGCCGGG AGCACAACAT CGACATGTGC CAGAGCTGTT
     TC
```

The hyperactive PiggyBac™ transposase left ITR nucleotide sequence used in the study show in FIG. 9A and FIG. 9B (205 bp) is as follows:

```
                                        (SEQ ID NO: 19)
   1 TTAACCCTAG AAAGATAATC ATATTGTGAC GTACGTTAAA
     GATAATCATG CGTAAAATTG

61 ACGCATGTGT TTTATCGGTC TGTATATCGA GGTTTATTTA
     TTAATTTGAA TAGATATTAA

121 GTTTTATTAT ATTTACACTT ACATACTAAT AATAAATTCA
     ACAAACAATT TATTTATGTT

181 TATTTATTTA TTAAAAAAAA ACAAA
```

The hyperactive PiggyBac™ transposase right ITR nucleotide sequence used in the study show in FIG. 9A and FIG. 9B (310 bp) is as follows:

```
                                        (SEQ ID NO: 20)
   1 ATCTATAACA AGAAAATATA TATATAATAA GTTATCACGT
     AAGTAGAACA TGAAATAACA

61 ATATAATTAT CGTATGAGTT AAATCTTAAA AGTCACGTAA
     AAGATAATCA TGCGTCATTT

121 TGACTCACGC GGTCGTTATA GTTCAAAATC AGTGACACTT
     ACCGCATTGA CAAGCACGCC

181 TCACGGGAGC TCCAAGCGGC GACTGAGATG TCCTAAATGC
     ACAGCGACGG ATTCGCGCTA

241 TTTAGAAAGA GAGAGCAATA TTTCAAGAAT GCATGCGTCA
     ATTTTACGCA GACTATCTTT

301 CTAGGGTTAA
```

As shown in FIG. 9A, the MLT transposase of the present disclosure had a greater integration efficiency that the transposase from Yusa et al. (2010). The inventors have discovered that a transposase sequence without the last two amino acids (L573del, E574del) has a greater efficiency than a transposase with those terminal amino acids present.

FIG. 9B illustrates an integration efficiency of the engineered MLT of the present disclosure, compared to integration efficiencies of PiggyBac™ transposase mutants. FIG. 9B shows percent of integration efficiency for a) hyperactive PiggyBac™ transposase (from Yusa et al. (2010), see SEQ ID NOs: 17, 18, 19, and 20)+PiggyBac™ transposase donor (see FIG. 16); b) hyperactive PiggyBac™ transposase donor only (see FIG. 16); c) MLT donor only (see FIG. 16); d) wild-type MLT+MLT donor; e) MLT N125K+MLT donor; f) MLT S8P/C13R+MLT donor; g) engineered MLT of the present disclosure (MLT S8P/C13R/L573del/E574del)+MLT donor; and h) hyperactive PiggyBac™ transposase dimer+PiggyBac™ transposase donor. The hyperactive PiggyBac™ transposase donor (b) and the MLT donor (c) were used as controls. As shown in FIG. 9A and FIG. 9B, the engineered MLT of the present disclosure has an integration efficiency comparable to the hyperactive PiggyBac™ transposase+PiggyBac™ transposase donor system.

Example 4—In Vitro Analysis of Hyperactive MLT Transposase Variants in HeLa and HEK293 Cells This study showed a discovery of novel mutations in a mammalian transposase in accordance with the present disclosure (an MLT transposase), to improve its excision capabilities (Exc+) by evaluating hyperactive mutants for their relative integration efficiency. This study details the analysis of hyperactive MLT transposase mutants in HeLa and HEK293 cells.

DNAs for the Mammalian Cell Integration Assays.

A two-plasmid transposition assay, using a donor plasmid including a transposon carrying a GFP gene and blasticidin resistance (BsdR) cassette and a helper plasmid expressing the transposase under a cytomegalovirus (CMV) promoter to measure transposition. The insect PiggyBac™ transposase donor plasmid contained GFP and BsdR cassettes driven by a CMV promoter, flanked by end sequences in a ZeoCassette™ Vector (pCMV/Zeo) (Thermo Fisher Scientific) backbone. The insect PiggyBac™ transposase helper plasmid contained the PiggyBac™ transposase ORF cloned into pcDNA3.1 myc His A-His (Invitrogen). For the MLT donor plasmid, the GFP-Bsd cassette from the insect PiggyBac™ transposase mammalian donor pCMV/miniPB-GFP-Bsd was PCR amplified using specific primers. The fragment was digested and cloned into the MLT donor plasmid. In the MLT mammalian helper plasmid, the enzyme was tagged with a HA tag. The MLT ORF was PCR amplified from plasmid- with a primer from the 5' end of the gene and a primer from the 3' end of the gene. The PCR product was digested and cloned into the plasmid. Various mutations in the putative catalytic domains were synthesized and evaluated.

Mammalian Cell Integration Assay.

Hela cells were grown in DMEM+10% FBS+penicillin-streptomycin. Hela cells ($2\times10^5$) were transfected with donor (294 nM) and helper (42 nM) plasmids with FuGENE-HD (Roche) in OPTI-MEM media (Life Technologies) according to the manufacturer's protocol. Cells transfected with donor plasmid and empty pCDNA3.1/myc-His A were the non-transposase control. After 46 h of transfection, cells were trypsinized and serially diluted in the appropriate DMEM as described above+blasticidin (3.5 µg/mL). Fresh media with antibiotics were administered every 24 h and continued for 21 d. After 21 days, cells were fixed with 4% paraformaldehyde and stained with 0.2% methylene blue, and blue colonies were counted.

Results

Figure 17A:
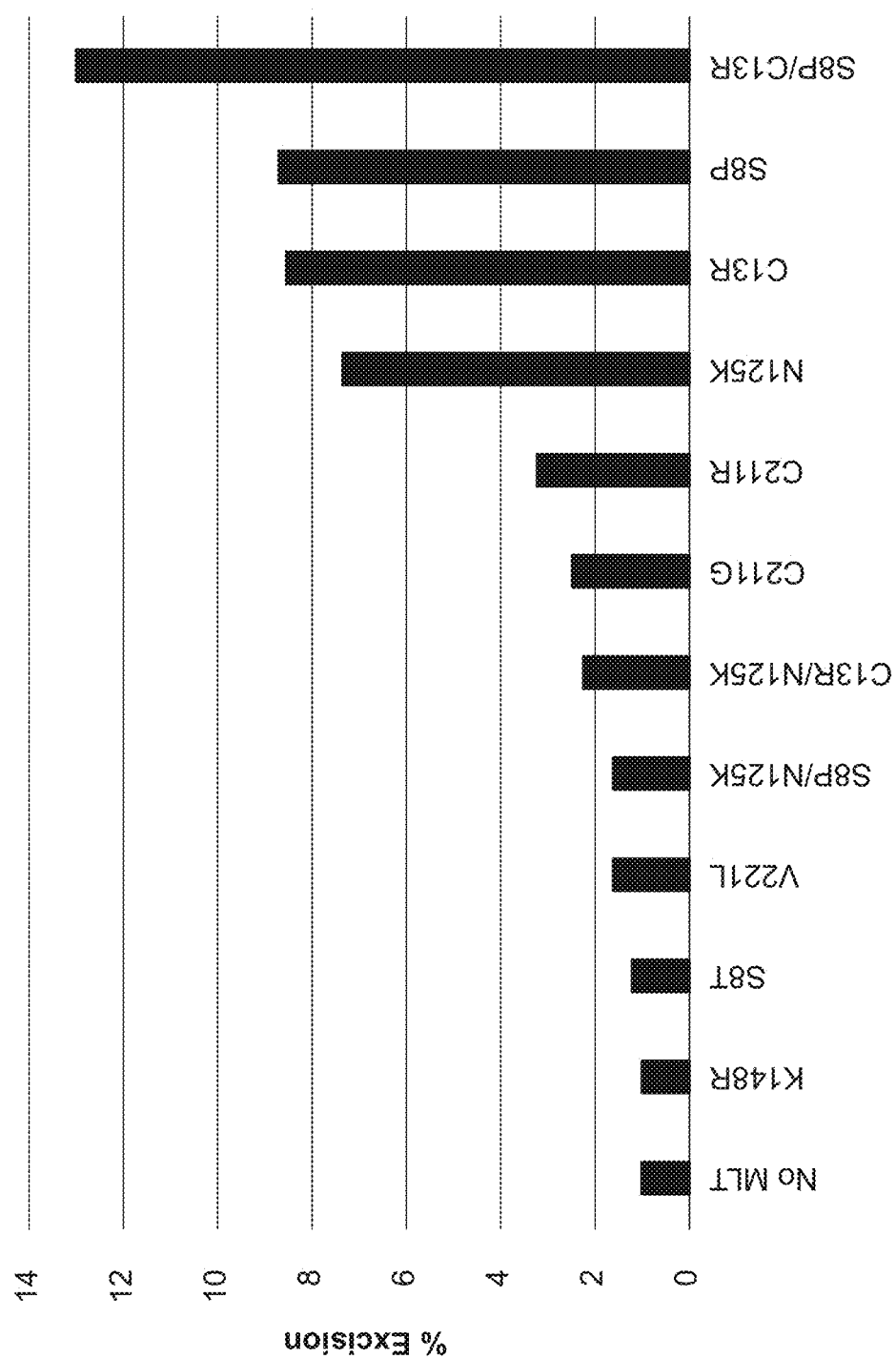
FIGS. 17A and 17B show results of functional assessment of the hyperactive MLT transposase mutants in HeLa cell.
Figure 17B:
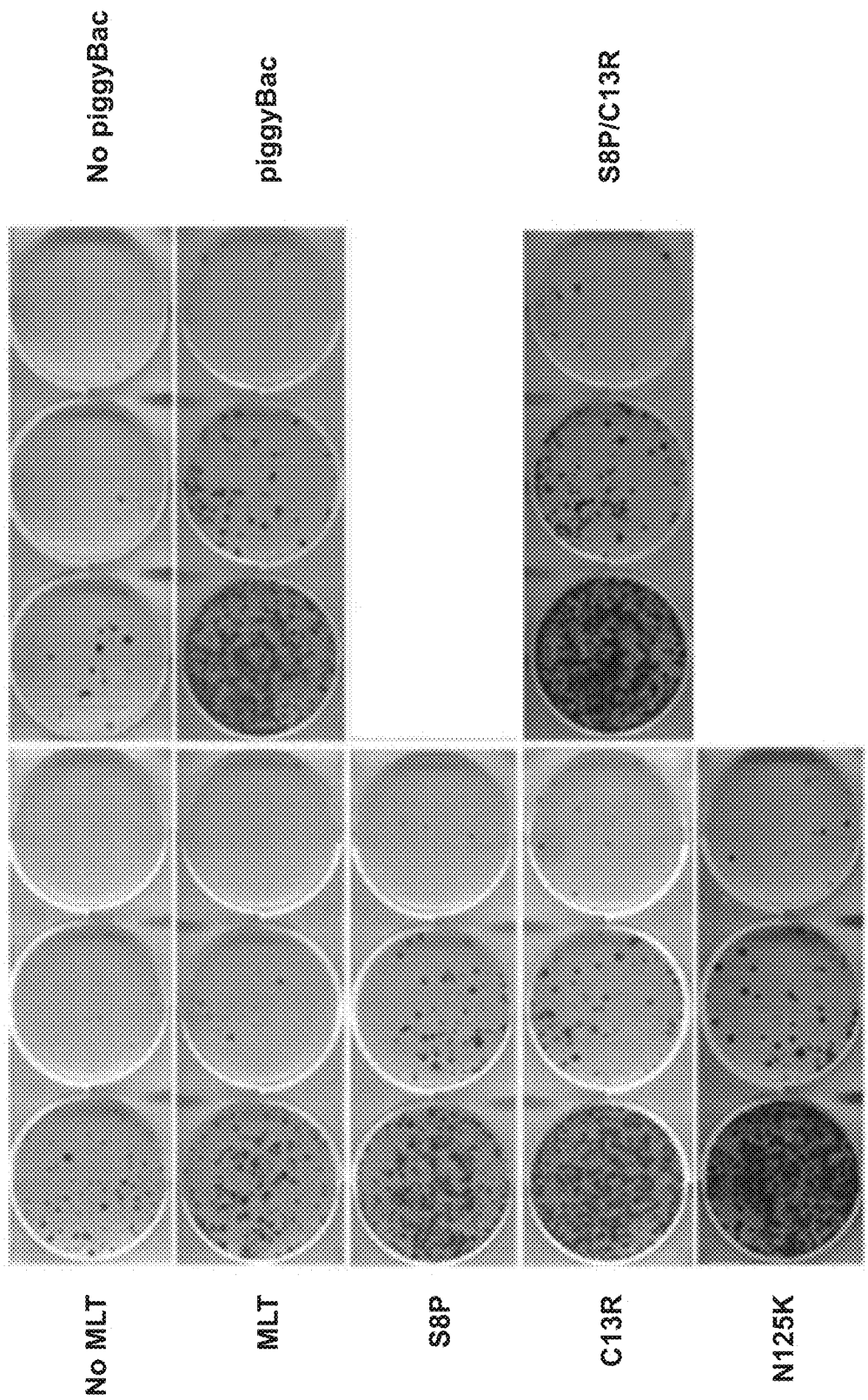

FIGS. 17A and 17B show results of functional assessment of the hyperactive MLT transposase mutants in HeLa cell. FIG. 17A shows that mammalian transposase (Ts) variants S8P, C13R, N125K and S8P/C13R have higher excision and integration frequency than the native enzyme. FIG. 17B shows functional transgene expression in Hela cells transfected with a donor neomycin transgene, 1:20 serial dilutions. The mammalian MLT transposase variant S8P/C13R showed comparable relative integration to the insect PiggyBac™ transposase in Hela cells.

Figure 18:
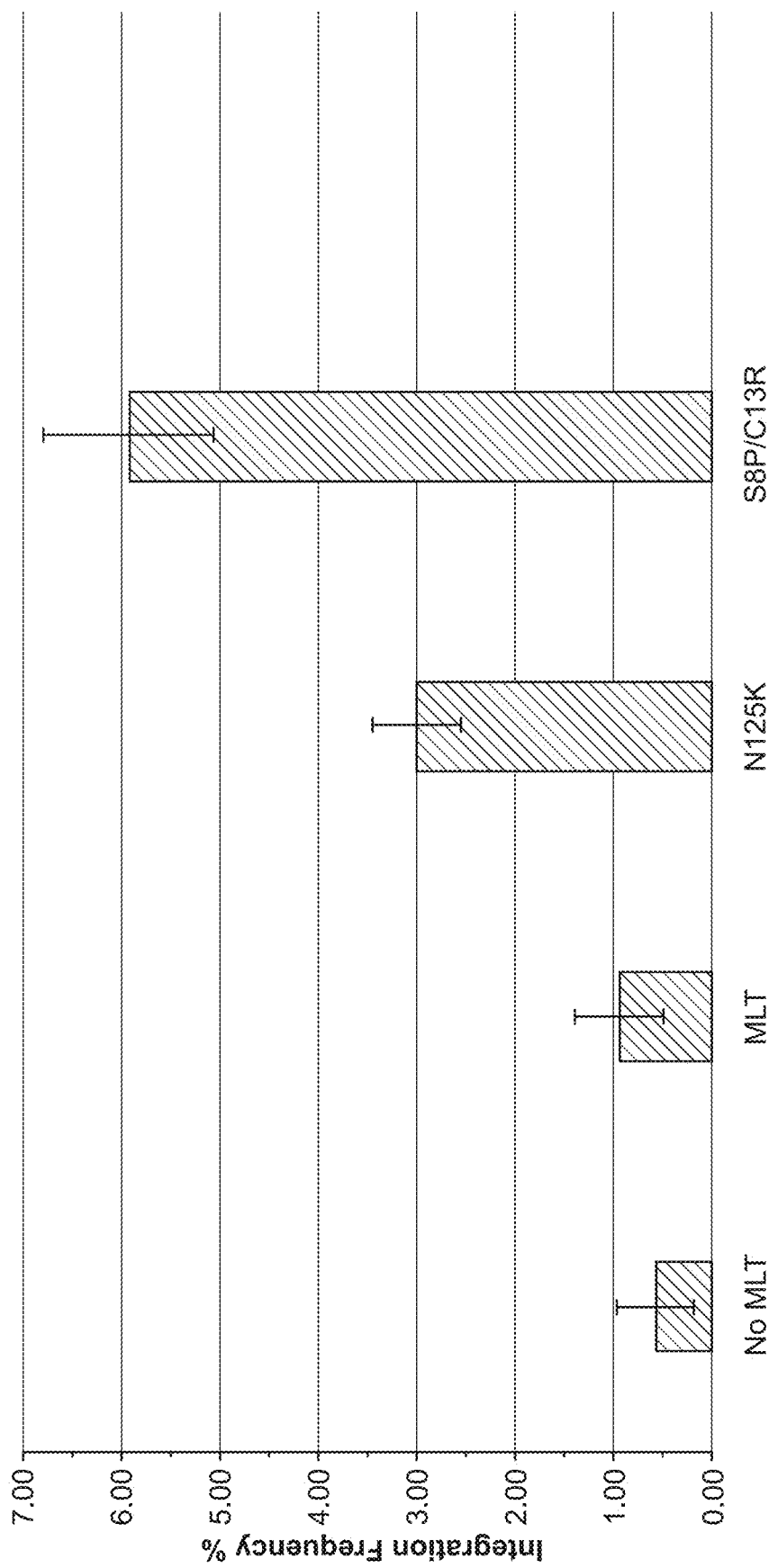
FIG. 18 are bar charts illustrating percent (%) of integration efficiency of MLT transposase hyperactive mutants in HEK293 cells, for no MLT, MLT, N125K mutant, and S8P/C13R mutant. The double mutant S8P/C13R shows that highest integration efficiency was observed in HEK293 cells. The MLT transposase is an MLT transposase comprising the amino acid sequence of SEQ ID NO: 4 and encoded by a nucleotide sequence of SEQ ID NO: 5.

FIG. 18 shows relative integration frequency of MLT transposase hyperactive mutants in HEK293 cells. The double mutant A/C shows that highest integration efficiency was observed in HEK293 cells.

The MLT transposase transposed successfully in human cultured HeLa and HEK293. A two-plasmid co-transfection assay was used in which a donor plasmid carried a transposon comprising an antibiotic resistance marker and a helper plasmid expressing the transposase, measuring the transposase-dependent chromosomal integration of the transposon antibiotic marker. It was found that the relative frequency of integration using the hyperactive MLT transposase was comparable to the insect wild type and hyperactive PiggyBac™ transposase in Hela cells (FIGS. 17A and 17B) but about 50% in HEK293 cells (FIG. 18).

In the present study, the relative integration efficiencies of mammalian MLT transposase hyperactive variants D and A/C were comparable to insect PiggyBac™ transposase in Hela cells. These variants also showed integration hyperactivity in HEK293 cells.

Example 5—MLT Transposase Protein Isolation and Purification

A goal of this study was to isolate an MLT transposase protein.

Protein Expression and Purification

The gene for a full-length MLT transposase of the present disclosure was codon-optimized for mammalian expression and cloned into the pD2610 expression vector between BamHI and Kpnl restriction sites, downstream of an N-terminal maltose-binding protein (MBP) tag followed by a TEV protease cleavage site. The plasmid pD2610-MPB-MLT transposase was transfected into 500 ml EXPI293F cells (Thermo Fisher Scientific) for transient protein expression using a standard PEI transfection protocol. The transfected cells were supplied with 1 L Expi293 expression medium after 24 h. Cells were harvested 3 days after transfection at 300×g and stored at −80° C. Cells expressing MBP-tagged MLT transposase were resuspended in lysis buffer containing 25 mM Tris-Cl, pH 7.5, 500 mM NaCl, 1 mM TCEP, and protease inhibitor cocktail (Roche). The cells were lysed by three cycles of sonication. Cell lysates were centrifuged at ~95,000×g for 30 min at 4° C. (Beckman Coulter Optima L-100 XP Ultracentrifuge, Type 45 Ti rotor). The supernatant was filtered and mixed with 10 ml amylose resin (New England BioLabs) equilibrated with lysis buffer. After one hour of continual rotation, the mixture was loaded onto a gravity flow column and washed with 100 ml lysis buffer. The protein was eluted with 50 ml elution buffer (25 mM Tris-Cl, PH 7.5, 500 mM NaCl, 10 mM maltose, 1 mM TCEP, and protease inhibitor cocktail). The eluate was incubated with TEV protease and dialyzed against dialysis buffer (50 mM Tris-Cl, pH 7.5, 500 mM NaCl, and 1 mM TCEP) for 16-20 h at 4° C. The cleaved MBP tag and the MLT transposase were separated heparin elution. A sample volume onto the Superdex 200™ size exclusion column connected to an AKTA system equipped with an autosampler and installed with the UNICORN system control software. Eluted protein was monitored at 260 nm and 280 nm. For data analysis, the QtiPlot software was used. Purified MLT transposase was stored at −80° C. The yield was 0.45 mL at 2.2 mg/ml or about 1 mg/L cell culture.

Results

Figure 19A:
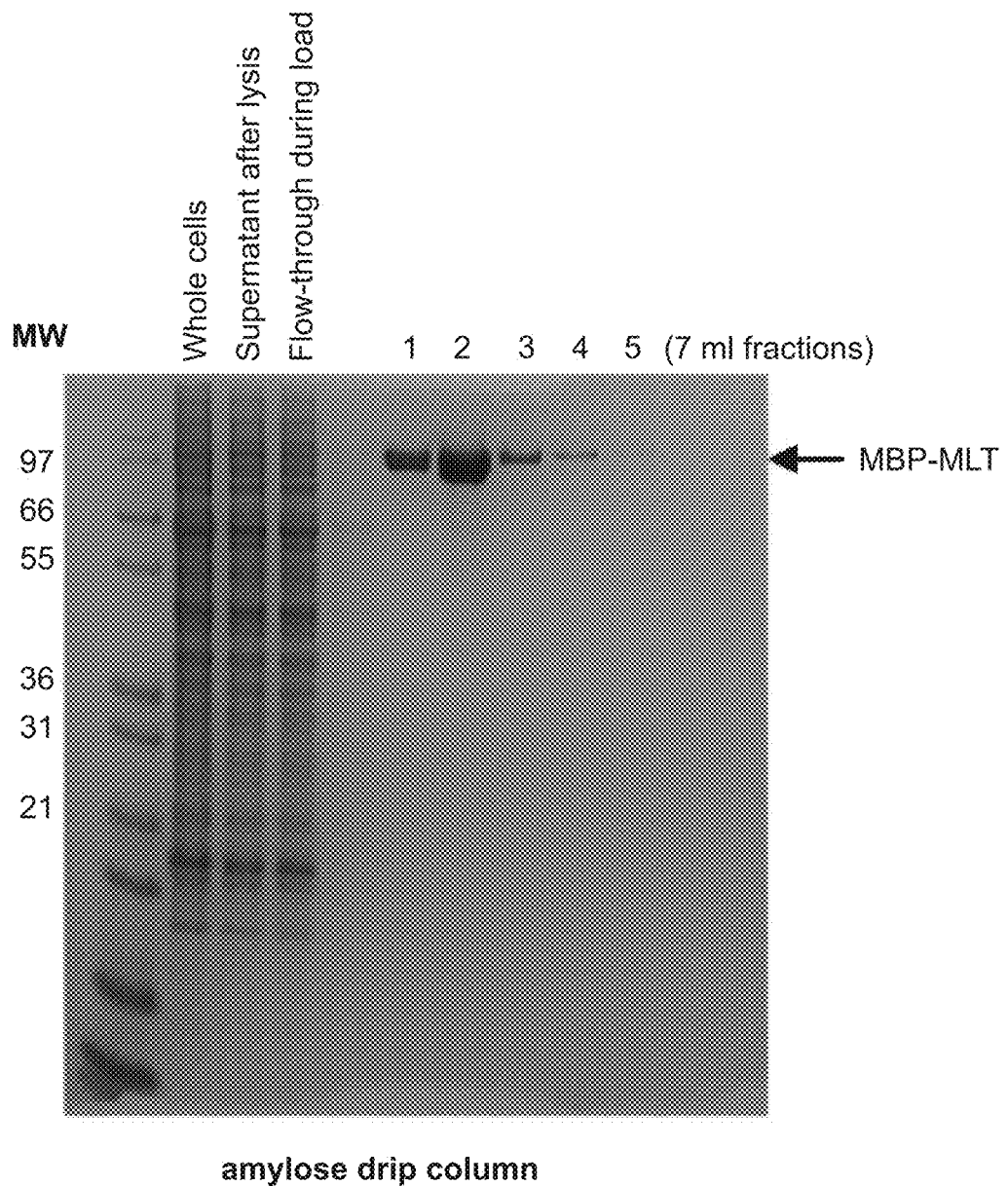
FIGS. 19A and 19B show images of sodium dodecyl sulfate-polyacrylamide gel electrophoresis.
Figure 19B:
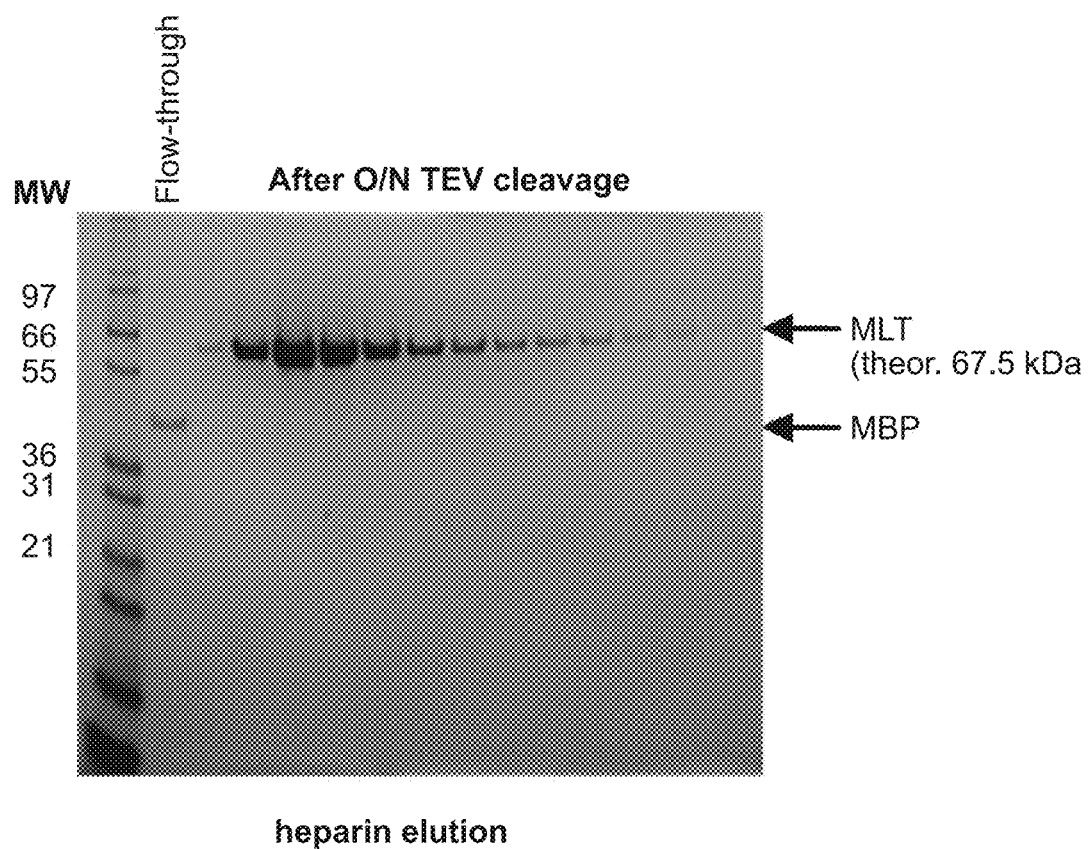

FIGS. 19A and 19B show images of sodium dodecyl sulfate-polyacrylamide gel electrophoresis. FIG. 19A shows analysis of purified MBP-MLT transposase fusion protein by an amylose-resin column. A major protein band of 100+kDa was identified by SDS-PAGE after purification of the expressed protein (MBP-MLT transposase) from the supernatant of the sonicated bacteria on a column of amylose resin. In FIG. 19B, shows a 67.5 kDa MLT transposase-specific band was shown after overnight cleavage of the MBP tag by TEV protease and heparin elution.

Affinity chromatography of the MBP MLT transposase fusion protein was performed with amylose agarose resin, followed by a step elution. The loaded samples, flow through, washes, and eluted proteins were analyzed by SDS-PAGE to show the pool peak fractions containing the MBP-MLT transposase purified protein (FIG. 19A). The MLT transposase was separated from the MBP tag by heparin elution with a size of 66-68 kD by SDS PAGE (FIG. 19B).

Figure 20:
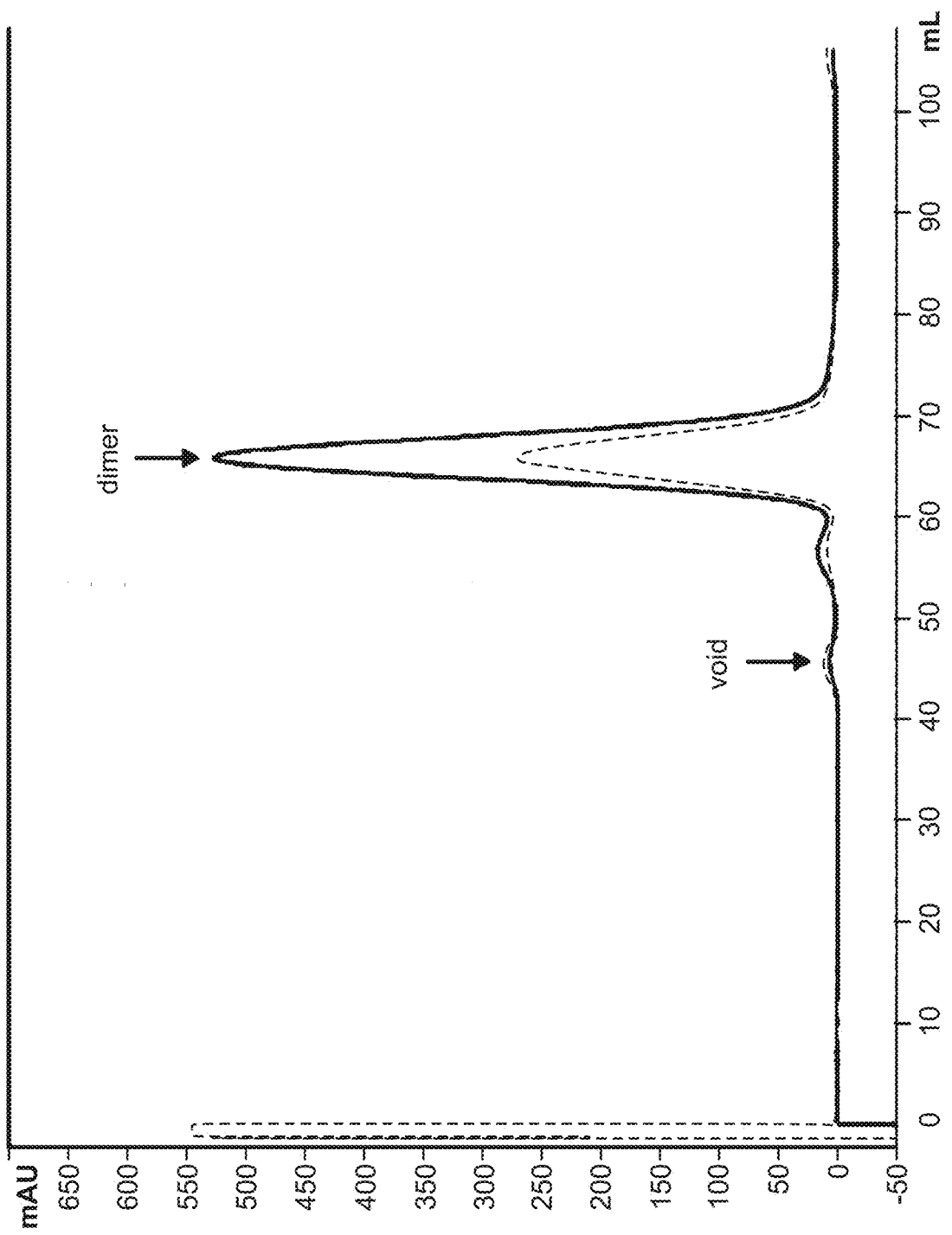
FIG. 20 shows Superdex™ size exclusion chromatography of maltose-binding protein (MBP)-MLT transposase fusion protein.

FIG. 20 shows Superdex™ M size exclusion chromatography. A sample volume of purified MLT transposase was loaded onto the Superdex 200™ size exclusion column. The eluted protein peaks at 260 nm and 280 nm suggest a dimer formation. Thus, the chromatographic profile indicates that the MLT transposase exists as a dimer (FIG. 20).

This study demonstrated that DNA binding proteins can be produced as fusion proteins to enable more specific purification, but their ability to bind DNA also enable affinity purification using heparin as a ligand. This study also showed that the MLT transposase of the present disclosure is a DNA binding protein with a molecular weight of approximately 67.5 kD that exists as a dimer.

Figure 21:
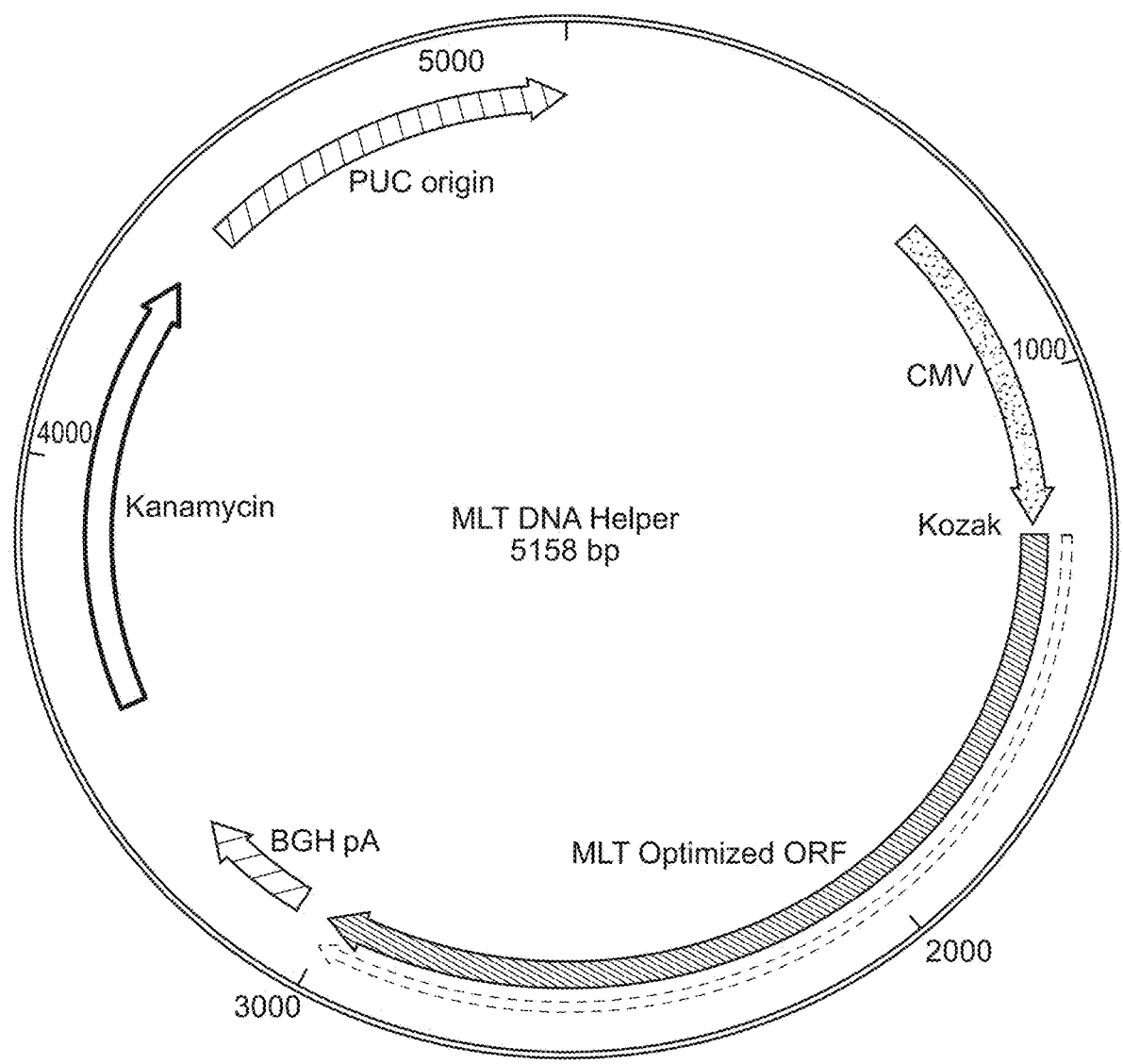
FIG. 21 depicts an example of a donor plasmid comprising an MLT transposon.

Example 6—Assessing Integration Profile Differences Between MLT Transposase and PiggyBac™ Transposase An objective of this study was to assess the integration pattern differences between the insect derived PiggyBac™ (PB) transposase and the non-specific, mammal-derived MLT transposase of the present disclosure. The comparison involved comparison of molecular sizes, protein lengths, recognition ends, integration in RefSeq genes, +5 kb transcription start site, +5 kb from CpG islands, and immunogenicity. An example of a DNA MLT Helper construct is shown in FIG. 21.

In general, the MLT transposase and the PiggyBac™ transposase when delivered as DNA are similar in the integration and molecular characteristics, as shown in Table 1.

TABLE 1

Comparison of certain properties of PiggyBac™ transposase and MLT DNA transposases.

| Characteristics | PiggyBac™ transposase | MLT |
|---|---|---|
| Species of origin | Cabbage looper moth | Mammalian |
| Molecular size | ~2.5 kb in length | 1.9 kb in length |
| Protein length | 594 amino acids | 571 amino acids |
| Recognition Ends | ITRs: 35 bp, 63 bp | Ends: 157 bp; 212 bp |
| Integration in RefSeq genes (random 34%) | ~55% | ~40% |
| ±5 kb transcription start site (random 0.04%) | ~20% | ~10% |
| ±5 kb from CpG islands | ~20% | ~10% |
| immunogenicity | Unknown (insect protein) | Likely low (mammal protein) |

The comparisons made herein showed that the MLT and PiggyBac™ transposase when delivered as DNA have similar characteristics. The comparisons in Table 1 also show that the MLT transposase is safer than the PiggyBac™ transposase and is thus less likely to cause undesired disruption or activation of genes during integration.

Example 7—Comparison of Integration Efficiency of Hyperactive MLT Transposase and Hyperactive PiggyBac™ Transposase An objective of this study was to assess the integration efficiency differences of the most hyperactive form of insect derived transposase PiggyBac™ transposase (PB) (I30V/G165S, S103P, M282V, S509G/N570S, N538K) and the hyperactive, non-specific mammal-derived transposase, MLT transposase in accordance with the present disclosure (with S8P/C13R mutations) (referred to as hypMLT herein).

Hyperactive PiggyBac™ transposase (hypPB) transposase enzyme [containing seven mutations—I30V/G165S, S103P, M282V, S509G/N570S, N538K—(7pB)] is used for gene transfer in human cells in vitro and to somatic cells in mice in vivo. Despite a protein level expression similar to that of a native PB, hypPB significantly increased the gene transfer efficiency of a neomycin resistance cassette transposon in both HEK293 and HeLa cultured human cells. Native PB and SB100X, the most active transposase of the Sleeping Beauty transposon system, exhibited similar transposition efficiency in cultured human cell lines. When delivered to primary human T cells ex vivo, hypPB increased gene delivery two- to threefold compared with PiggyBac™ transposase and SB100X. hypPB was compared with native PB and SB100X in vivo in mice using hydrodynamic tail-vein injection of a limiting dose of transposase DNA combined with luciferase reporter transposons. Transgene expression was monitored for up to 6 months and observed approximately 10-fold greater long-term gene expression in mice injected with a hypPB, compared with mice injected with native PB or SB100X.

Methodology

HEK293 cells were plated in 12-well size plates the day before transfection.
The day of the transfection, the media was exchanged 1 hour and 30 min before the transfection was performed.
The X-tremeGENE™ 9 DNA Transfection Reagent was used, in accordance with manufacturer's protocol (Sigma-Aldrich).

In duplicate, a donor plasmid containing GFP and a helper plasmid (600 ng each), were co-transfected. The donor DNA was mixed for each duplicate transfection, and 1200 ng of helper RNA (transposase) was mixed with 1200 ng of donor DNA for 2400 ng total. A 3:1 ratio of X-tremeGENE™ 9 DNA Transfection Reagent was used; therefore, each duplicate had 2400 ng of DNA and used 7.2 ul of the X-tremeGENE™ 9 DNA Transfection Reagent.

Two different donor plasmids, one for hypPB and one for hypMLT, were used. All PB transposases were mixed with the PB donor but not with an MLT donor.

48 hours after the transfection, the cells were analyzed by flow cytometry, and percent (%) of GFP expressing cells was counted, to measure transient transfection efficiency. The cells were gated to distinguish them from the debris, and 20,000 cells were counted each. GFP gating was liberal, such that even GFP-dim cells were counted as GFP-positive (GFP+) cells.

The cells were cultured for 15-20 days without an antibiotic. The cells were passaged ⅔ times per week.

Flow cytometry was used to percent (%) of GFP-expressing cells, to measure integration efficiency at 2 weeks (80,000 cells were counted). Gating was conservative, such that a gate was drawn around the obvious bright population and excluded very dim cells.

The final integration efficiency was calculated by dividing 2-week % GFP cells by 48 hours.

Results

Figure 22A:
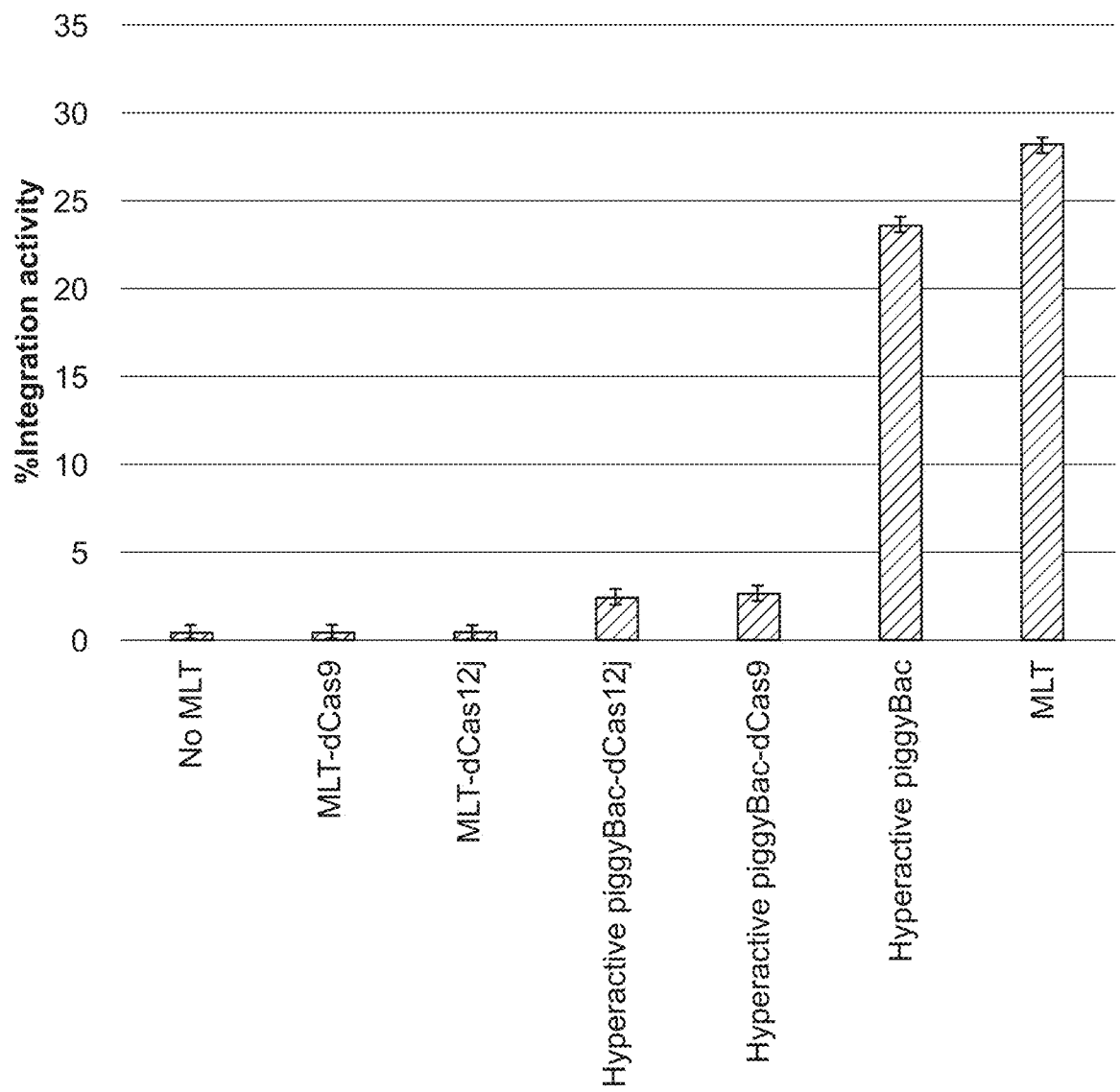
FIGS. 22A, 22B, 22C, 22B, and 22D are bar charts illustrating integration efficiency and excision activity of variants of a hyperactive form of PiggyBac™ transposase (hypPB) compared to a hyperactive MLT transposase (hypMLT) that comprises L573del/E574del/S2A and has the S8P/C13R mutations (the MLT transposase encoded by the nucleotide sequence of SEQ ID NO: 8 and having the amino acid sequence of SEQ ID NO: 9).
Figure 22B:
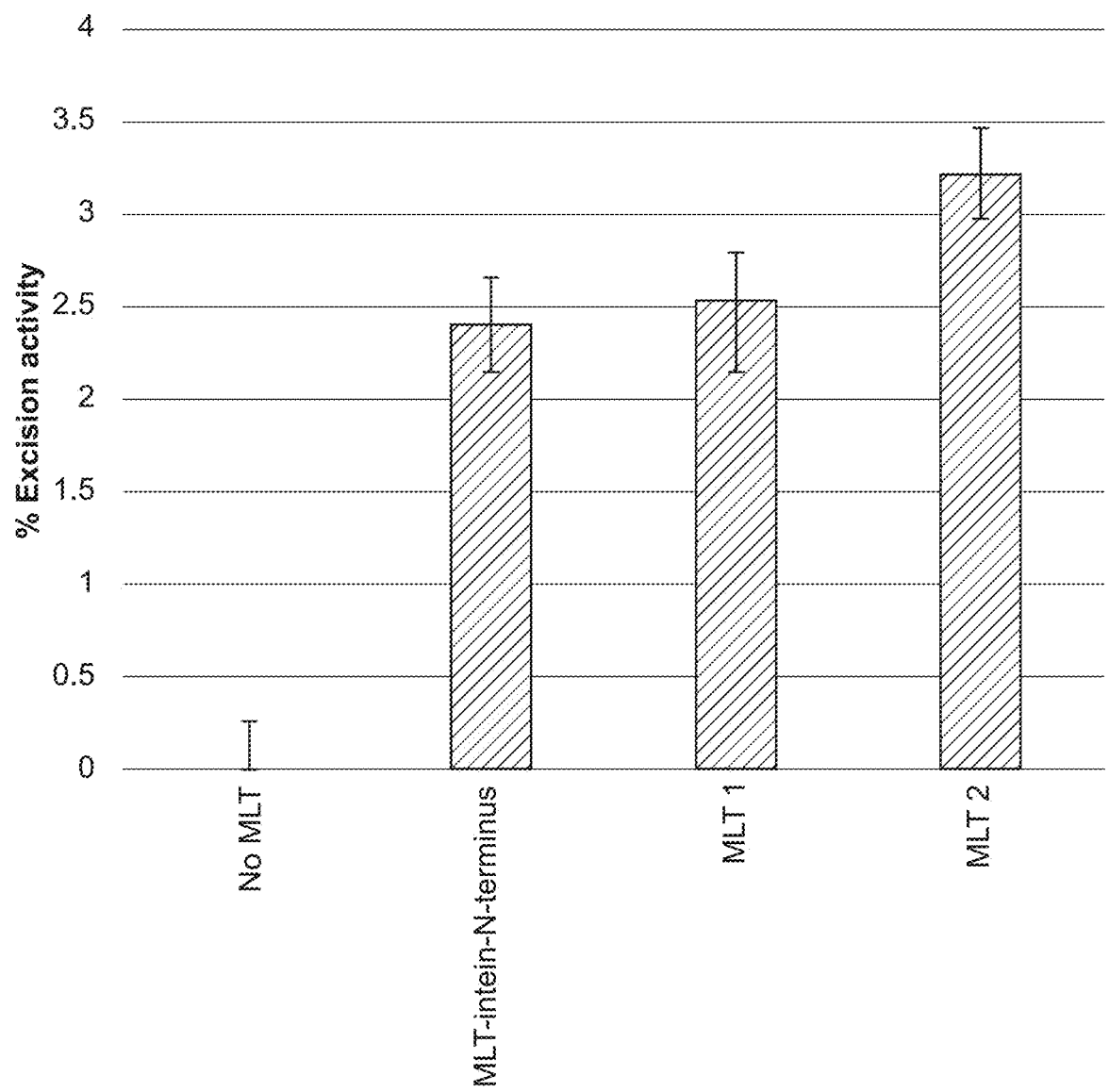
Figure 22C:
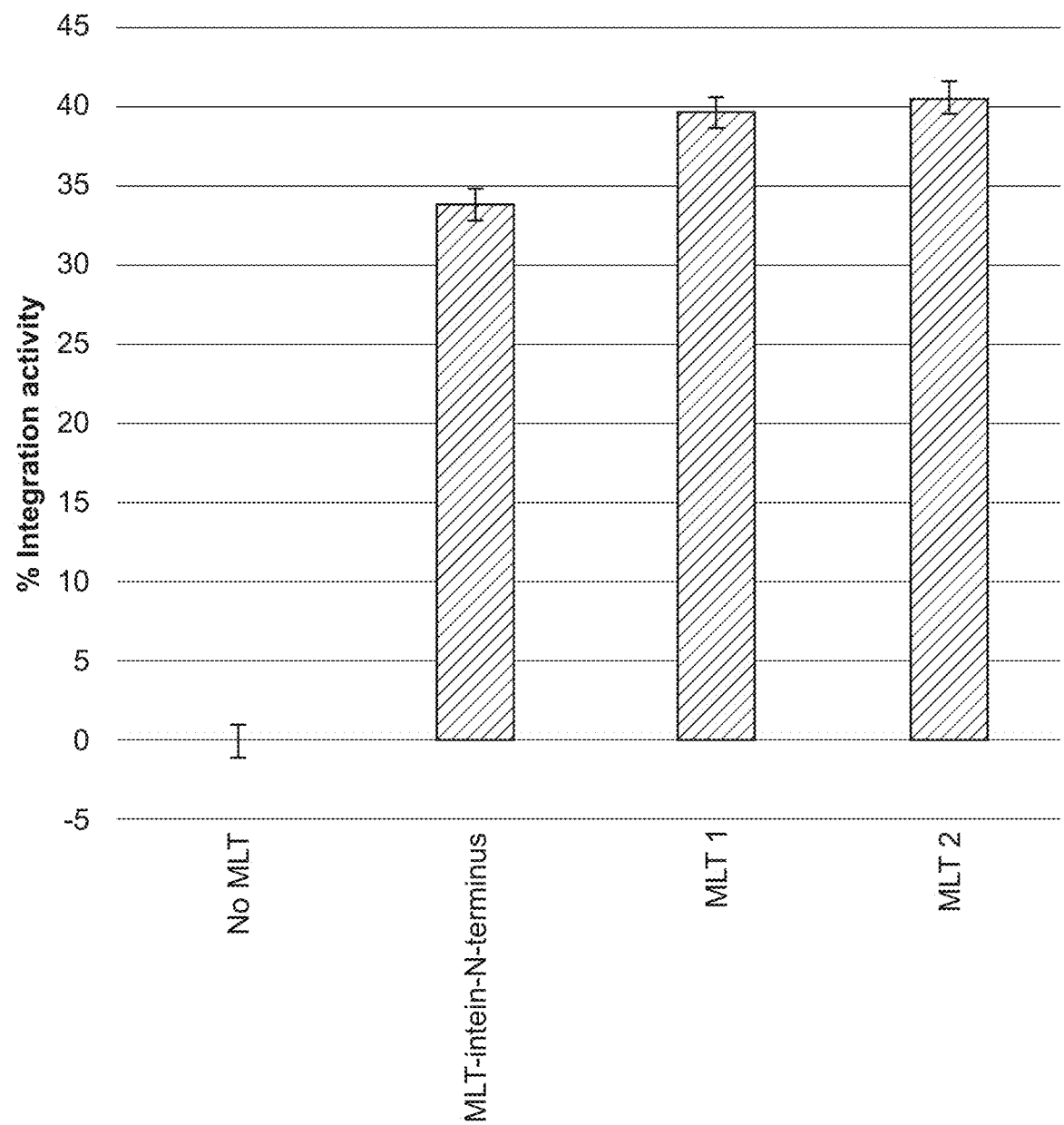
Figure 22D:
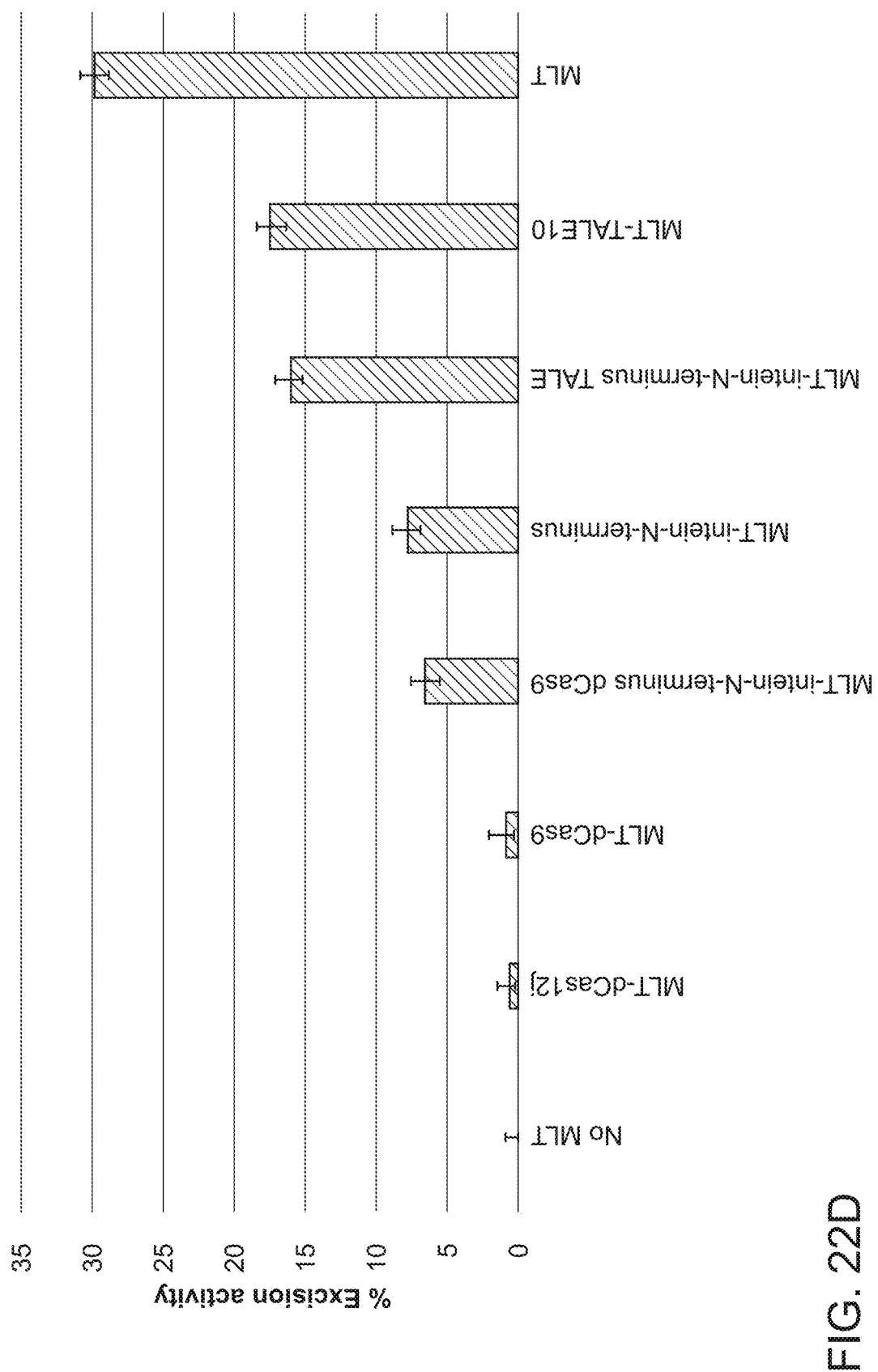

FIG. 22A shows % of integration activity for no MLT, MLT-dCas9, MLT-dCas12j, hyperacive PiggyBac™ transposase-dCas12j, hyperacive PiggyBac™ transposase-dCas9, hyperacive PiggyBac™ transposase, and MLT. FIG. 22B shows % of excision activity for no MLT, MLT-Intein-N-terminus, MLT1, and MLT2. FIG. 22C shows % of integration activity for no MLT, MLT-Intein-N-terminus, MLT1, and MLT2. FIG. 22D shows % of excision activity for no MLT, MLT-Cas12j, MLT-Cas9, MLT-Intein-N-terminus Cas9, MLT-Intein-N-terminus, MLT-Intein-N-terminus TALE, MLT-TALE10, and MLT.

FIG. 22A shows integration efficiency of a hyperactive form of PiggyBac™ transposase (hypPB) compared to MLT transposase (MLT2). The integration efficiency for the hyperactive MLT transposase (about 28%) was greater than the integration efficiency for the hyperactive form of PiggyBac™ transposase (about 24%) that is typically used for cell and gene therapy. Integration efficiency was reduced by the addition of dead Cas (dCas) binders. The addition of reduced excision activity from 30% to 18% (FIG. 22D). The addition of dCas to MLT reduced excision activity to 8% (FIG. 22D).

Example 8—In Vitro Analysis of Human ROSA26 Genomic Safe Harbor Site Targeting

A goal of this study was to assess efficacy of RNA-guided transposition to direct a transposase to the human safe harbor site, ROSA26.

In the present study, a panel of RNA-guided transposase vectors containing mutations in the native PiggyBac™ transposase DBD was studied for their ability to target the human ROSA26 safe harbor site.

Plasmid Development

Representations of targeting PiggyBac™ transposase plasmids are shown in FIGS. 23A, 23B, 23C, 23D, and 23E.

Figure 23A:
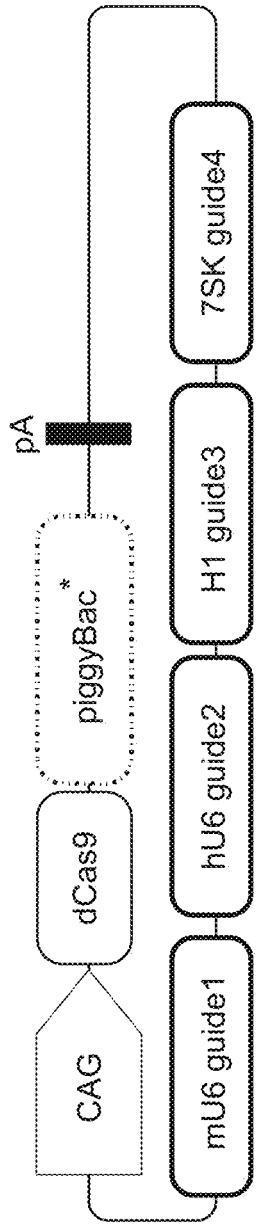
FIGS. 23A, 23B, 23C, 23D, and 23E depict examples of a structure of targeting PiggyBac™ transposase plasmids used in the present study.
Figure 23B:
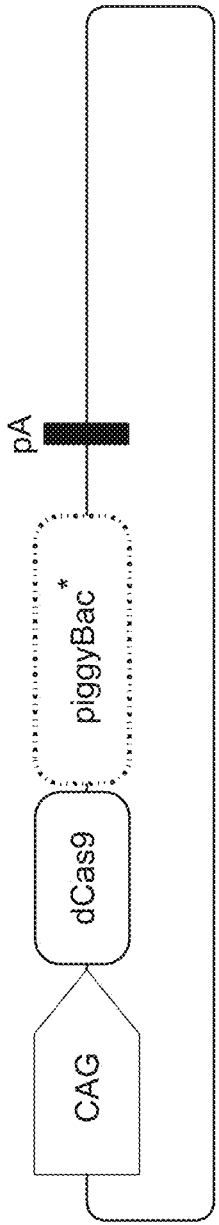
Figure 23C:
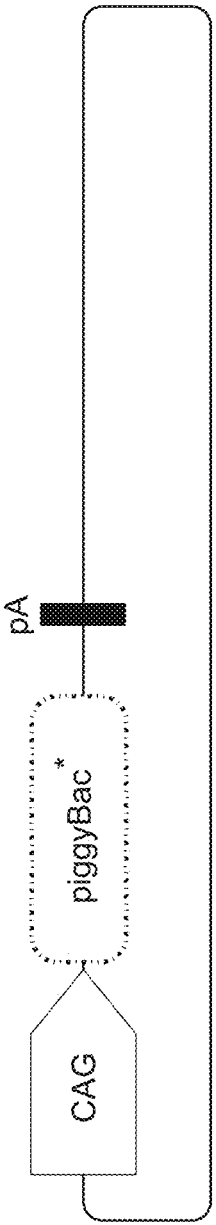
Figure 23D:
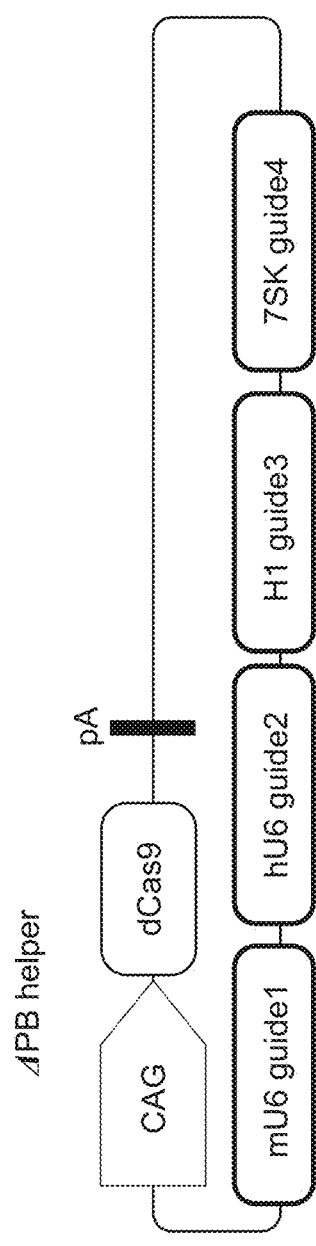
Figure 23E:
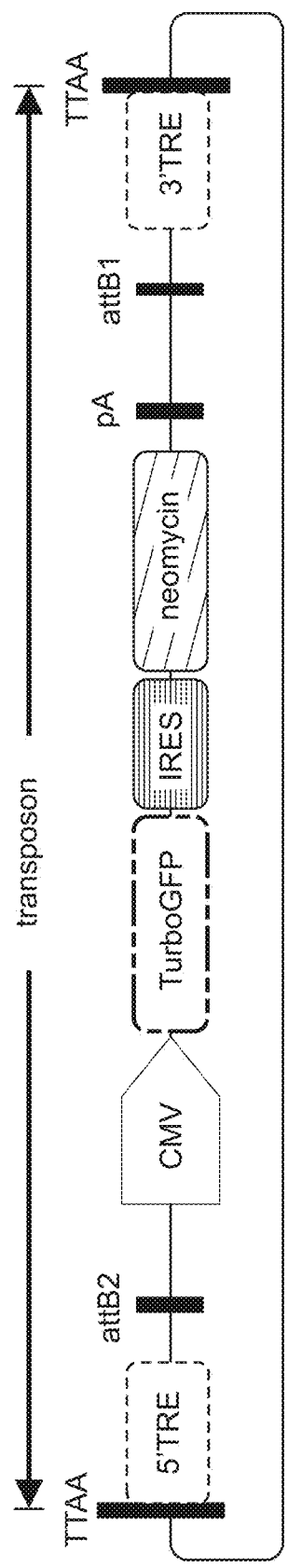

FIG. 23A shows a dCas9-PB-4 guide helper—catalytically inactive dCas9 fused to the transposase (PiggyBac™ transposase) via a flexible linker and placed under control the CAG promoter, with guide RNA. FIG. 23B shows the shows a dCas9-PB-4 guide helper, devoid of guide RNA. FIG. 23C shows a control PB (PiggyBac™ transposase) helper, devoid of the dCas9 DNA-binding protein. FIG. 23D shows a non-insertional control helper (dCas9 under control the CAG promoter) devoid of the transposase (DPB). FIG. 23E shows a donor plasmid including the TurboGFP internal ribosomal entry site (IRES) neomycin transgene under the CMV promoter and flanked by the transposon terminal repeat elements (TREs).

Figure 23F:
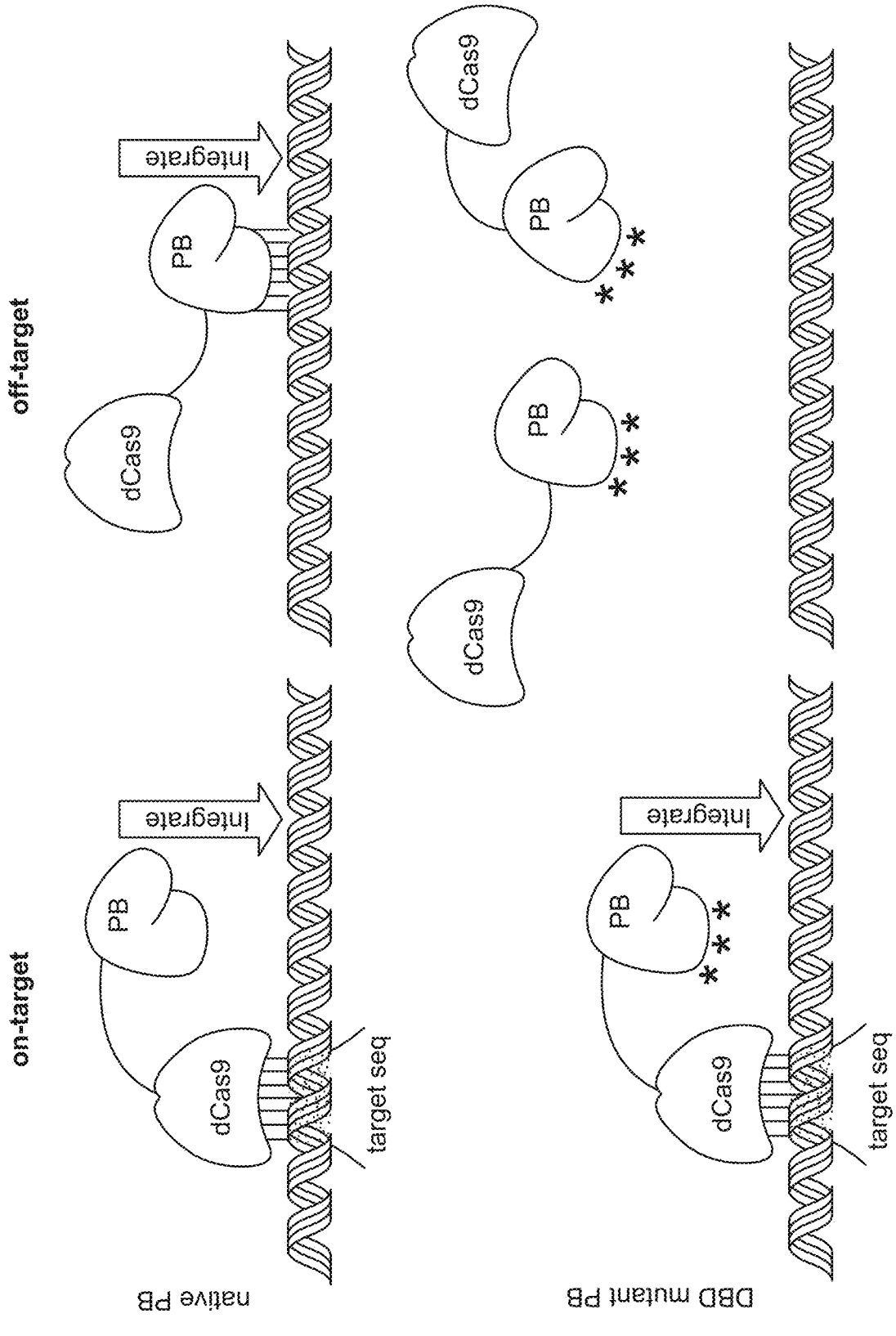
FIG. 23F is a non-limiting schematic of a model for improvement of specificity by disruption of the PiggyBac™ transposase DNA binding domain DBD, in accordance with embodiments of the present invention.

FIG. 23F is a non-limiting schematic of a model for improvement of specificity by disruption of a PiggyBac™ transposase DNA binding domain DBD. The native PB transposase retains full DNA-binding capability and can either integrate following dCas9 targeting (on-target), or integrate following binding to off-target sequences without dCas9 targeting (off-target). Similar to PB, the H2 and H3 mutant transposase integration deficient variants (Int-) can integrate following dCas9 targeting (on-target). However, off-target binding of the transposase is inhibited due to mutations in the DNA binding domain. FIG. 23F illustrates a rationale for using Int- transposase mutants.

Figure 23G:
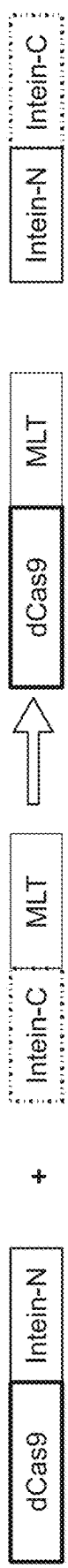
FIG. 23G depicts an MLT transposase attached to dCas by using e.g. NpuN (Intein-N) (SEQ ID NO: 423) and NpuC (Intein-C) (SEQ ID NO: 424) intein protein splicing. Other dCas can be substituted to target specific genomic sites.
Figure 23H:
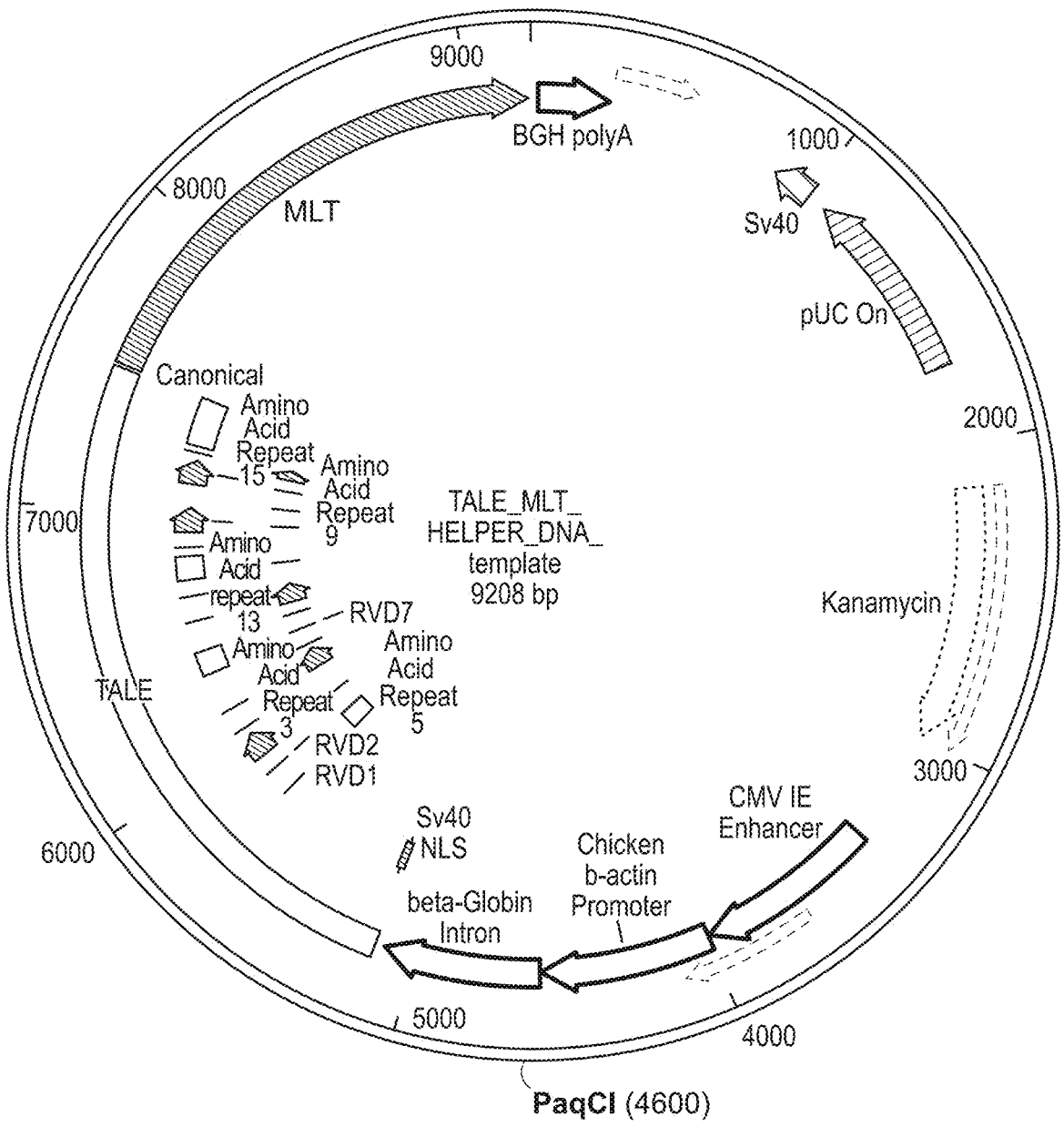
FIG. 23H depicts a chimeric MLT transposase construct attached to a TALE DNA binder. Other TALEs and transposases can be substituted to target specific genomic sites.

FIG. 23H depicts a chimeric MLT transposase construct attached to a TALE DNA binder. Other TALEs and transposases can be substituted to target specific genomic sites.

FIG. 23G depicts a MLT transposase attached to dCas by using NpuN:

(SEQ ID NO: 423)
ggcggatctggcggtagtgctgagtattgtctgagttacgaaacggaaat actcacggttgagtatgggcttcttccaattggcaaaatcgttgaaaagc gcatagagtgtacggtgtattccgtcgataacaacggtaatatctacacc cagccggtagctcagtggcacgaccgaggcgaacaggaagtgttcgagta ttgcttggaagatggctcccttatccgcgccactaaagaccataagttta tgacggttgacgggcagatgctgcctatagacgaaatatttgagagagag ctggacttgatgagagtcgataatctgccaaat and NpuC:

(SEQ ID NO: 424)
ggcggatctggcggtagtgggggttccggatccataaagatagctactag gaaatatcttggcaaacaaaacgtctatgacataggagttgagcgagatc acaattttgctttgaagaatgggttcatcgcgtctaattgcttcaacgct agcggcgggtcaggaggctctggtggaagc The SpCas9-HF1 gene was mutated at the D10A and H840A residues to inactivate the catalytic domain and generate dCas9. The dCas9-PB helper plasmid was generated using Gibson assembly by fusing the a transposase gene (PB) to the dCas9 DNA-binding protein using a flexible linker described previously. The fusion protein was placed under the CAG (cytomegalovirus (CMV) immediate early enhancer, chicken b-actin promoter and b-globin intron) promoter. Two mutant transposase helper plasmids containing codon changes in the DBD were generated using Gibson assembly. First, the transposase was human codon-optimized and synthesized by Genscript. Next, mutations R372A and D450N were introduced to generate the dCas9-

H2 helper plasmid and a third K375A mutation was introduced to generate the dCas9-H3 helper plasmid. Four gRNAs were appended to the helper plasmid backbone using Golden Gate. Briefly, single stranded oligos containing the guide sequence were annealed and ligated into Bbsl linearized expression plasmids containing either the hU6, mU6, H1 or 7SK promoter. One of each of the four resulting guide expression plasmids were first digested with BsmBI and then assembled into a single BsmBI-linearized helper plasmid in a single step. For experiments requiring eight guides, two plasmids each containing four guides were co-transfected in equal amounts. Negative control helper plasmids lacked gRNAs. Control helper plasmids that contained either the PB, H2 or H3 transposase but lacking a DBD were also generated using Gibson assembly. To generate the non-integrating DPB control, the entire PiggyBac™ transposase coding sequence was removed from the dCas9-PB helper plasmid using Gibson assembly. To generate the donor plasmid, Gateway cloning (Thermo Fisher) was used to recombine a pENTR plasmid featuring the CMV promoter driving TurboGFP, internal ribosome entry site (IRES) and neomycin (GIN) gene with a pDONR plasmid containing PiggyBac™ transposase terminal repeat elements (TREs) flanking the transgene.

Cell Transfections

Figure 24C:
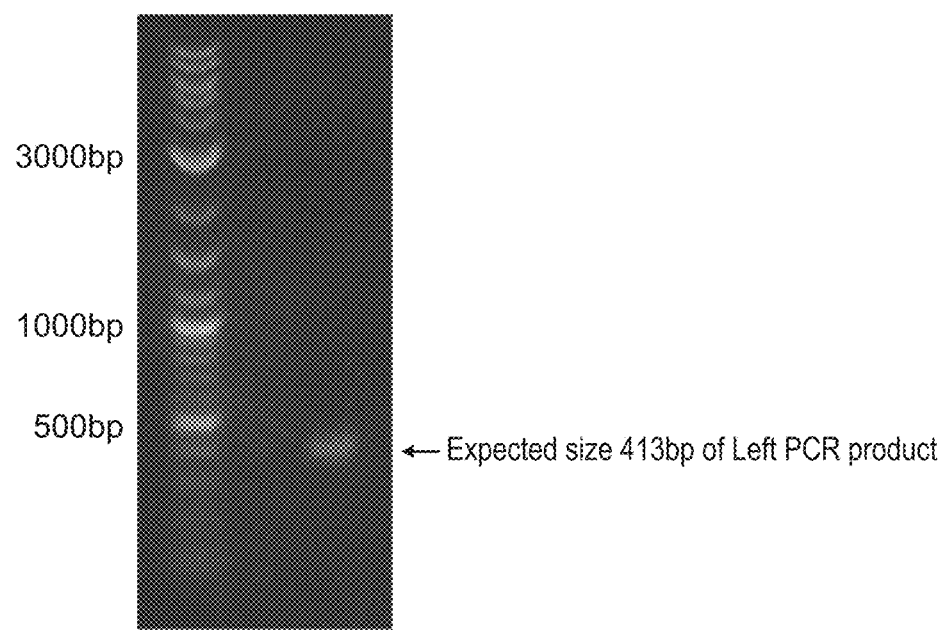
FIG. 24C depicts a 1.0% agarose gel showing the expected nester PCR fragment when an MLT donor is inserted at hROSA26 after transfection with MLT helper with Cas9/gRNA, identified in the present disclosure.

Human embryonic kidney (HEK293) cells were maintained incomplete Dulbecco's modified Eagle's medium (DMEM) supplemented with 10% heat inactivated fetal bovine serum. Prior to transfection, $4 \times 10^5$ cells per well were seeded in 6-well plates. Cells at ~80% confluency were transfected with 2 μg of plasmid DNA using X-tremeGENE 9 (Sigma-Aldrich). Twenty-four hours after transfection, cells were resuspended and 10% of cells were removed for flow cytometry analysis to measure transfection efficiency. Forty-eight hours after transfection, 90% of the cells were transferred to a T75 flask and cultured for 3 weeks under 200 mg/ml G418 at which point the cells were pelleted for lysis and genomic polymerase chain reaction (PCR) analysis. The remaining 10% of cells in the 6-well dish were cultured without antibiotic for 3 weeks and analyzed by flow cytometry to measure stable insertion efficiency. For single-cell isolation, two dCas9-H2-8 guide transfections were repeated. The G418-selected polyclonal populations were each plated into a 96-well poly-D-lysine coated plate (BD Biosciences) resulting in an average of 50 colonies per well. After wells became greater than 40% confluent, media was aspirated, and the cells were manually resuspended in 30 ml of phosphate-buffered saline. A volume of 20 ml of the resuspension was removed and mixed with 30 ml of the DirectPCR Lysis Reagent (Viagen Biotech) for analysis. The remaining cells were cultured further. Two wells identified to contain targeted clones by genomic PCR were expanded and single-cell sorted using serial dilution. Wells were visually monitored until 157 single-cell expansions were obtained. Clonally expanded cells were subsequently resuspended by manual pipetting and lysed for analysis. Positive clonal lines, containing targeted insertions to human ROSA26 (FIG. 24A) were expanded for flow cytometry analysis to detect potential silencing of the transgene.

Flow Cytometry

Green fluorescent protein (GFP) expression of 20,000 live cells from ROSA26-targeted single-cell expansions was analyzed using a FACSAria III cytometer (BD Biosciences) after 13 weeks of culture, following transfection with dCas9-H2-8guide.

Colony Count Assay

In order to determine the number of transposons present in human ROSA26-targeted single clones, a copy number assay was performed by TaqMan quantitative PCR to estimate the number of neomycin genes present in the genome. The human RNase P gene was used to normalize the total genomes per sample. Templates included: genomic DNA from clonal lines, negative control untransfected human genomic DNA and reference control genomic DNA from a clonal cell line with a single neomycin gene insertion. Quantitative PCR using the QuantStudio 12K Flex thermocycler (Applied Biosystems) was performed using the TaqPath ProAmp Master Mix reagent (Thermo Fisher) according to the manufacturer's instructions. Primers and probes were included in the TaqMan Copy Number Reference Assay for human RNase P and the TaqMan NeoR Assay ID:Mr00299300_cn (Thermo Fisher). CopyCaller Software v2.1 was used to predict the number of insertions for each sample.

T7 Endonuclease I Assay

In 12-well plates, HEK293 cells at 80% confluency in DMEM supplemented with 10% heat inactivated fetal bovine serum, were co-transfected with 500 ng of SpCas9-HF1 expression plasmid and 500 ng of one of eight ROSA26 directed gRNA or negative control gRNA expression plasmids, using X-tremeGENE 9 (Sigma-Aldrich). Seventy-two hours later, cells were pelleted and lysed using DirectPCR Cell lysis buffer (Viagen Biotech). Genomic PCR using the KOD Xtreme Hot Start DNA Polymerase (Novagen) was performed using primers designed to flank all eight guide binding sites. Products were purified with the PureLink PCR Micro Kit (Invitrogen) and melted and reannealed to form heteroduplexes. For each sample, identical incubations with or without T7 endonuclease I (T7E1) (New England Biolabs) were performed to cut DNA containing mismatched sequences. Products were separated on a 2% gel for gel imaging. A 2100 Bioanalyzer (Agilent) was used to measure the concentration of products obtained by the T7E1 assay. The fraction of cleaved products was calculated by dividing the total pg/ll of the two expected cleavage products by the total pg/ll of the two expected cleavage products and uncleaved product. Percent of indel occurrence was calculated.

Nested PCR

HEK293 cells were plated in 12-well size plates the day before transfection. The day of the transfection the media is exchanged 1.5 hr before the transfection is performed. The present experiments used X-tremeGENET 9 DNA Transfection Reagent and manufacturer's protocol (Sigma-Aldrich).

In triplicate transfections, a donor plasmid containing GFP and neomycin, a helper plasmid with a DBD fused to either pB or MLT transposase, and a guide RNA expression plasmid or combination of plasmids were co-transfected. The DNA was mixed for each triplicate transfection, i.e. 1500 ng of helper plasmid was mixed with 1500 ng of donor plasmid and 600 ng of guide RNA, with a total of 3600 ng. A 3:1 ratio of XtremeGene9 reagent was used, such that each triplicate transfection had 3600 ng of DNA and used 10.8 ul of reagent. 48 hours after transfection, the cells are resuspended and plated into a T75 flask. 72 hours after transfection, the media was changed from a normal media to a G418-containing media. The cells in the G418-containing media were cultured for 3 weeks, and the cells were then pelleted.

Cell lysis and Proteinase K treatment was then performed (DirectPCR Lysis Reagent, Viagen Biotech), to prepare genomic DNA for template for PCR.

Primary PCR was performed using half the primers extending from the genome and half the primers extending from the transposon insert (FIG. 24B). FIG. 24B depicts a nested PCR strategy to detect the insertion of a donor MLT at a specific TTAA site in human ROSA26 locus using MLT helper with Cas9 and two different sets of gRNA (Set 1: AATCGAGAAGCGACTCGACA (SEQ ID NO: 425), TGCCCTGCAGGGGAGTGAGC (SEQ ID NO: 426); Set 2: GAAGCGACTCGACATGGAGG (SEQ ID NO: 427), CCTGCAGGGGAGTGAGCAGC (SEQ ID NO: 428) that were 61 bp and 62 bp respectively, from the TTAA targeted site.

Figure 24D:
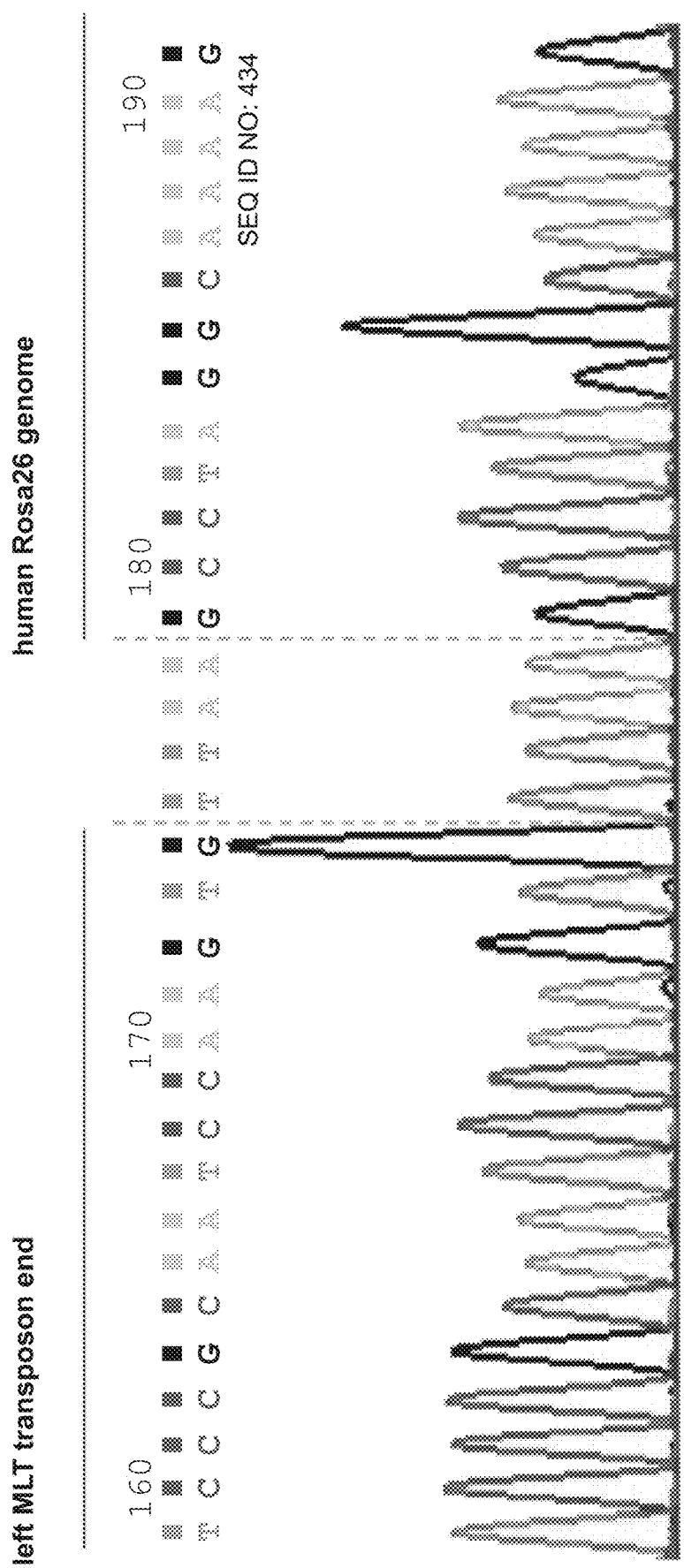
FIG. 24D depicts a DNA sequencing chromatogram that shows the correct junction DNA sequence when a MLT donor is inserted at hROSA26 after transfection with an MLT helper with Cas9/gRNA, identified in the present disclosure.

KOD One polymerase was used: 10 ul reaction, and 1 ul of direct lysis as template. The primary PCR product was diluted 1:50 in water. Then, 1 ul of the 1:50 dilution was used as a template for Nested PCR, using primers that are nested within the Primary products. PrimeStar GXL polymerase was used (20 ul reaction). The nested PCR products were run on a 1% agarose gel (FIG. 24C), a band of the expected size was sequenced. The sequences were aligned and positive insertions were identified—those that include genomic sequence with the TTAA insertions site and the edge of the transposon insert (FIG. 24D).

Targeted Genomic Integration Site Recovery

Pellets from stable transfections of HEK293 cells were lysed using the DirectPCR Cell lysis buffer (Viagen Biotech) for use as template for nested PCR to identify targeted transposon insertions. In order to optimize the PCR, the lysate template was used at three dilutions, 1:1, 1:4 and 1:8. Forward primers were designed to extend outward from the transposon whereas reverse primers were designed to extend from the ROSA26 target sequence (FIG. 24B). A 10 uL primary PCR was performed using the KOD Xtreme Hot Start DNA Polymerase (Novagen) that was diluted 1:50 in $H_2O$ and used as template for a 20 uL nested PCR using PrimeSTAR GXL DNA Polymerase (Clontech). Amplification products were gel purified with the Zymoclean Gel DNA Recovery Kit (Zymo Research) and sequenced directly or cloned into pJet1.2 (Thermo Fisher) for sequencing. Sequences were aligned against the transposon sequence using BLAST and against the human reference genome (hg38) using BLAT to identify insertion site locations.

RNA-Guided Transposition to the Genome

We tested the ability of our dCas9 PiggyBac™ transposase fusion constructs to deliver a transgene to the human ROSA26 safe harbor locus. The donor plasmid was cotransfected with dCas9-PB, dCas9-$H_2$ or dCas9 $H_3$ each with 0, 4 or 8 guides, in duplicate. Following 3 weeks of antibiotic selection, the cultures were lysed for use as template for genomic PCR. To improve the chances of recovering insertions, three dilutions of the lysate template were used. Primary PCR primers were designed to extend out from each side of the transposon. Four additional primary PCR primers were designed to extend towards the target site in ROSA26 (two on each side). Individual PCR reactions were performed using all pair-wise primer combinations (eight total). Products arising from the primary PCR reactions were used as template for nested PCR. Sequenced products included the flanking TRE of the transposon, the canonical TTAA sequence at the junction and the genomic sequence flanking the insertion site.

Results

In the present study, a total of 22 insert junctions were recovered, which are shown in FIG. 24A. The present study demonstrated RNA-guided transposition to ROSA26 in human cells and provided a proof-of-concept for directing integration deficient (Int-) PB transposase mutants to human ROSA26, for gene therapy use.

The present study also demonstrates that the inventors were able to target one specific TTAA site at ROSA26 using MLT fused to dCas9 by intein splicing and gRNA.

It was observed that helper MLT-TALE and MLT-Cas9/gRNA transposases expression targets hROSA26 at a specific TTAA site (FIG. 24B, FIG. 24C, and FIG. 24D) used genomic PCR to recover targeted insertions to human ROSA26. Despite millions of potential TTAA sequences available for insertion throughout the genome, a number of inserted transposons adjacent to the gRNA target sequence were uncovered. Control transfections without gRNA did not result in any targeted insertions. The results shown in FIG. 24B, FIG. 24C, and FIG. 24D demonstrate that a transgene was successfully integrated into the genomic safe harbor site, hROSA26, without a footprint (as shown by DNA sequencing). This indicates that any gene can be placed in that TTAA location.

Example 9—Study of Integration in Various Cell Lines (FACs) Using MLT Transposase (RNA Helper)

An objective of this study was to use the MLT transposase of the present disclosure and CMV-GFP to integrate into four different cell lines (HEK293, Huh7, CHO-K1, and T-cells), to compare the efficiency of integration for various cell lines. A further objective was to integrate CMV-GFP only, to determine whether the MLT transposase had an effect on cell viability. This was quantified by using FACs to measure GFP expression in each cell line, once it was integrated.

The following protocol was used:
CHO-K1, HEK293, HUH7, and-T-cells were seeded at three different cell densities.
Nucleofection efficiency of the three cell lines was tested using the Cell Line 4D-Nucleofector™ Kit and program (Lonza Bioscience) using 0.4 µg of pmaxGFP™ Vector (following the provider's recommendation for each specific cell line) as a positive control.
Measurement of GFP expression was assessed using high-content analysis (visual) and flowcytometry (quantitative) at two timepoints (24 h and 72 h). Nuclei were stained and quantified with Hoechst33342 vital dye. Percentage of GFP positive cells was calculated. As T-cells are suspension cells, only flow cytometry read-out was performed.

Results

All of the studied cell lines (CHO-K1, HEK293, HUH7, and-T-cells) were more than 80% nucleofected. All of the cell lines showed 85-95% GFP expression in presence or absence of the MLT transposase after three days of nucleofection, as shown in FIGS. 25 to 28.

Figure 25:
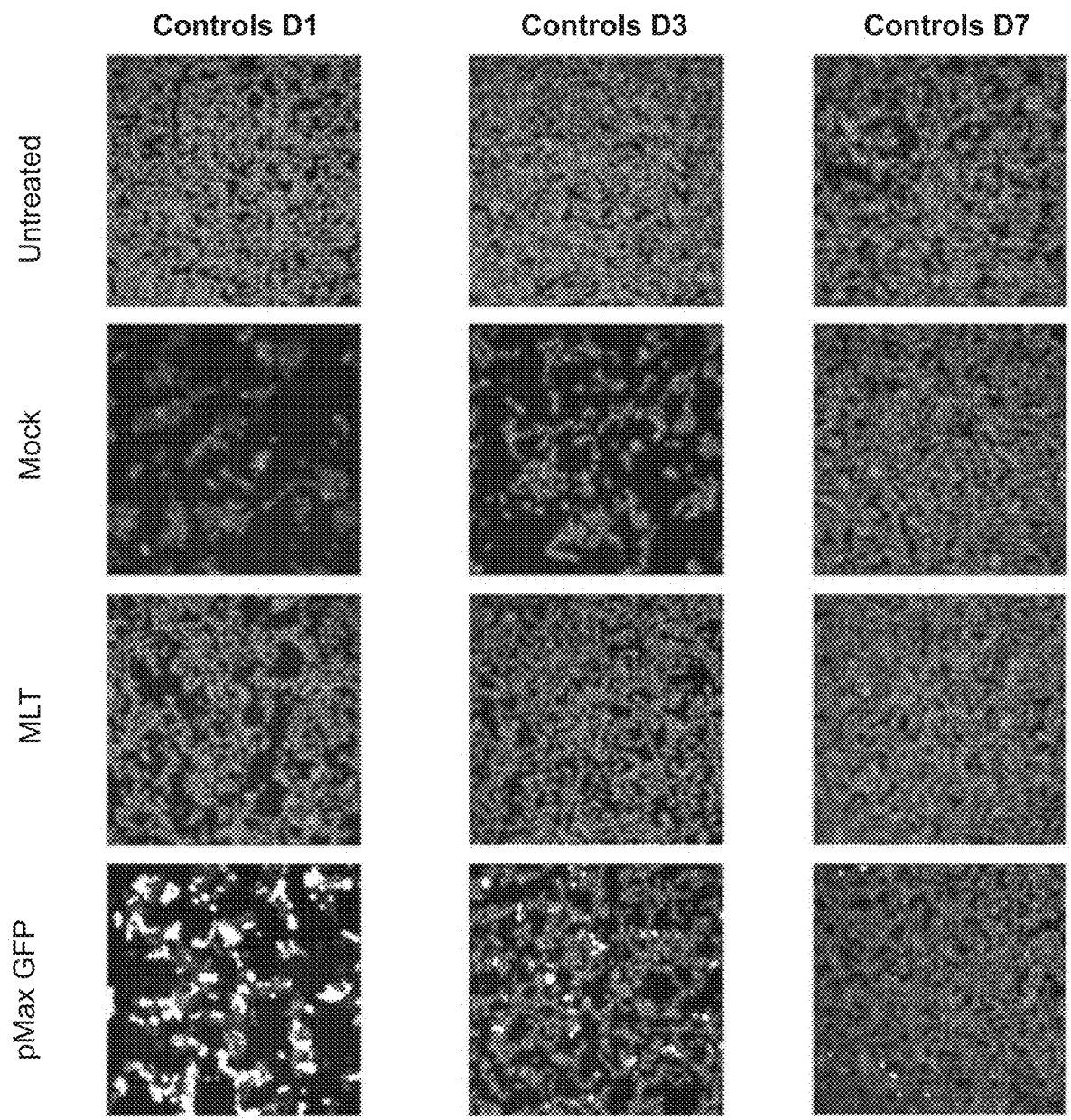
FIG. 25 shows initial Huh7 cell lines transfected under different conditions to show that Huh7 express GFP. The rows show (from the top) untreated cells, mock, cells treated with MLT, and cells treated with pmaxGFP; the columns show controls at day 1 (D1), day 3 (D3), and day 7 (D7).

FIG. 25 shows initial Huh7 cell lines transfected under different conditions to show that Huh7 express GFP. The rows show (from the top) untreated cells, mock transfections (without a nucleic acid), cells treated with MLT, and cells treated with pmaxGFP; the columns show controls at day 1 (D1), day 3 (D3), and day 7 (D7).

Figure 26:
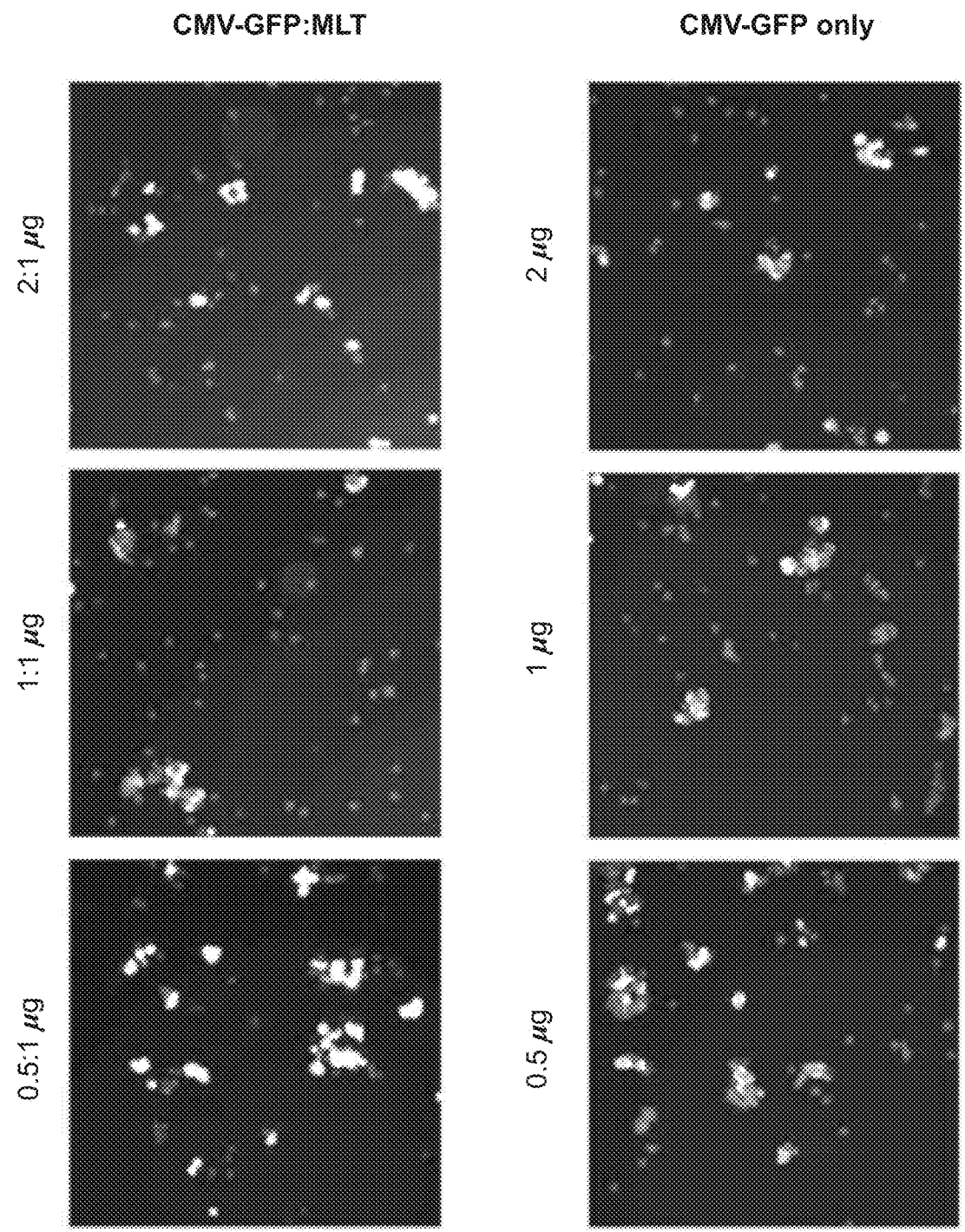
FIG. 26 shows Huh7 cells transfected with CMV-GFP+ MLT, compared to cells transfected with CMV-GFP only, at different ratios, 24 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

FIG. 26 shows Huh7 cells transfected with CMV-GFP+MLT, compared to cells transfected with CMV-GFP only, at different ratios, 24 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

Figure 27:
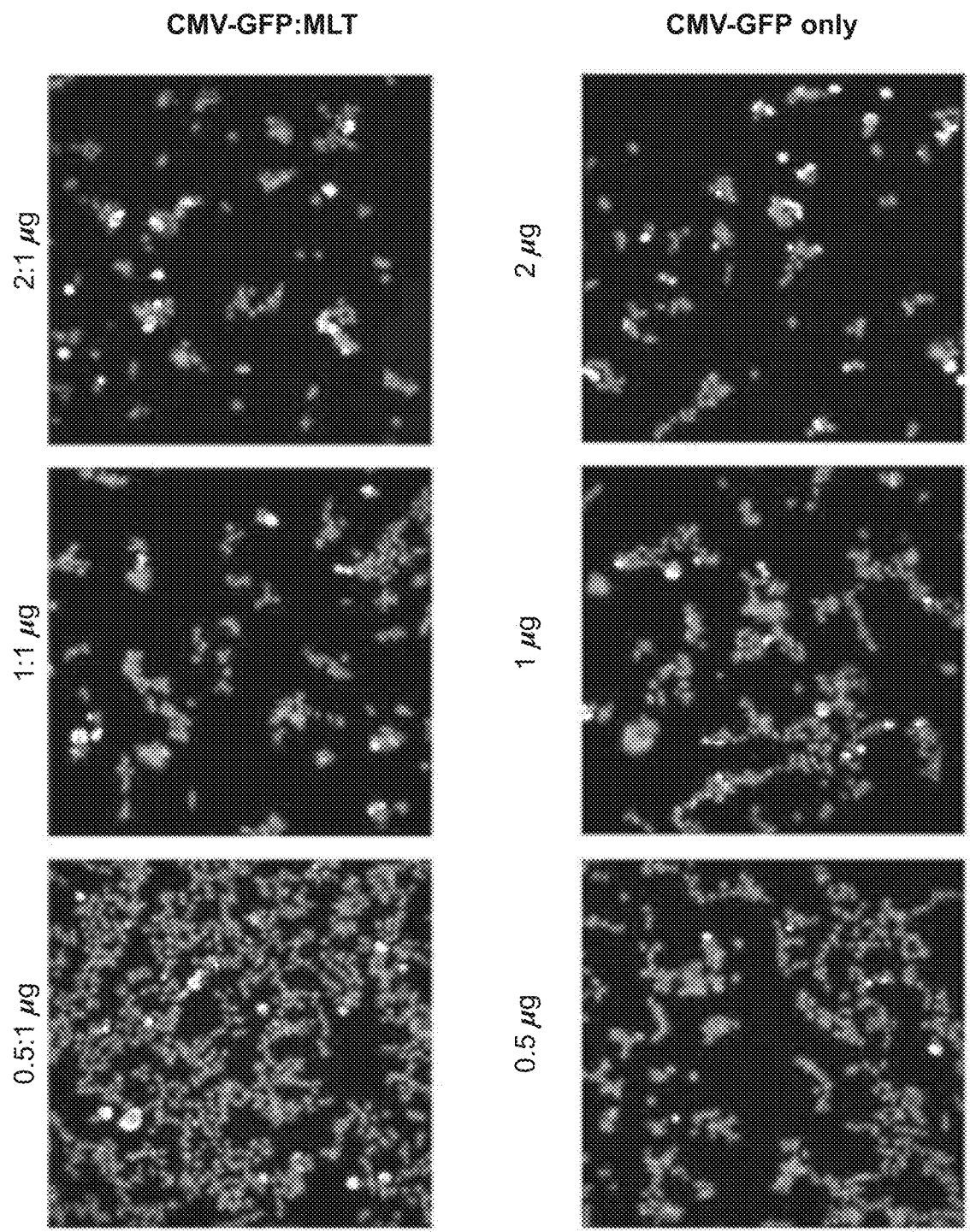
FIG. 27 shows Huh7 cells transfected with CMV-GFP+ MLT, compared to cells transfected with CMV-GFP only at different ratios, 72 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

FIG. 27 shows Huh7 cells transfected with CMV-GFP+MLT, compared to cells transfected with CMV-GFP only at different ratios, 72 hours post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

Figure 28:
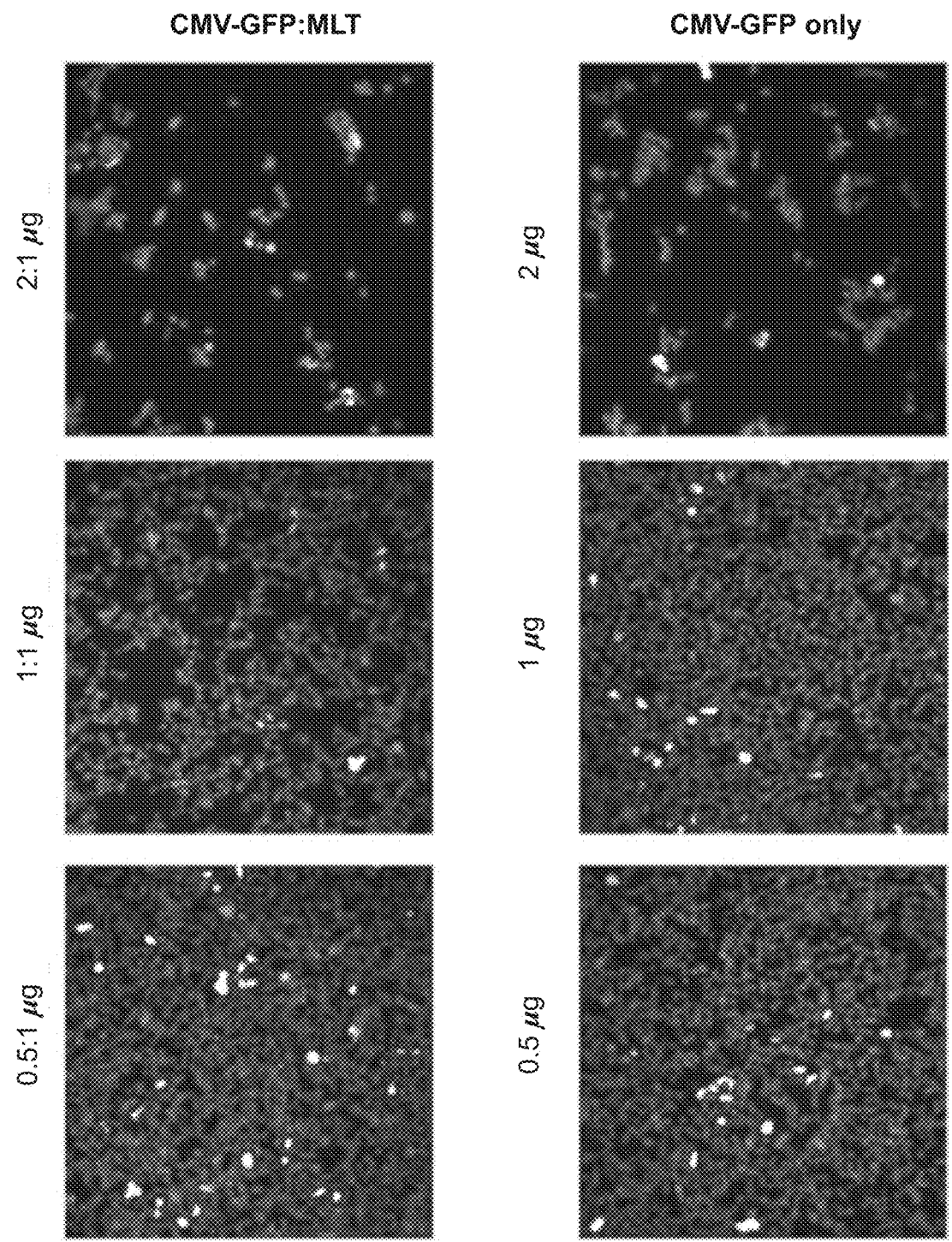
FIG. 28 shows Huh7 cells transfected with CMV-GFP+ MLT, compared to cells transfected with CMV-GFP only at different ratios, 1 week post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP: MLT ratio of 0.5:1 μg, and the cells transfected with CMV-GFP only (0.5 μg).

FIG. 28 shows Huh7 cells transfected with CMV-GFP+MLT, compared to cells transfected with CMV-GFP only at different ratios, 1 week post transfection. The top row shows cells transfected with a CMV-GFP:MLT ratio of 2:1 μg, and cells transfected with CMV-GFP only (2 μg). The middle row shows cells transfected with a CMV-GFP:MLT ratio of 1:1 μg, and the cells transfected with CMV-GFP only (1 μg). The bottom row shows cells transfected with a CMV-GFP:MLT ratio of 0.5:1 μg, and the cells transfected with CMV-GFP only (0.5 μg).

Figure 29A:
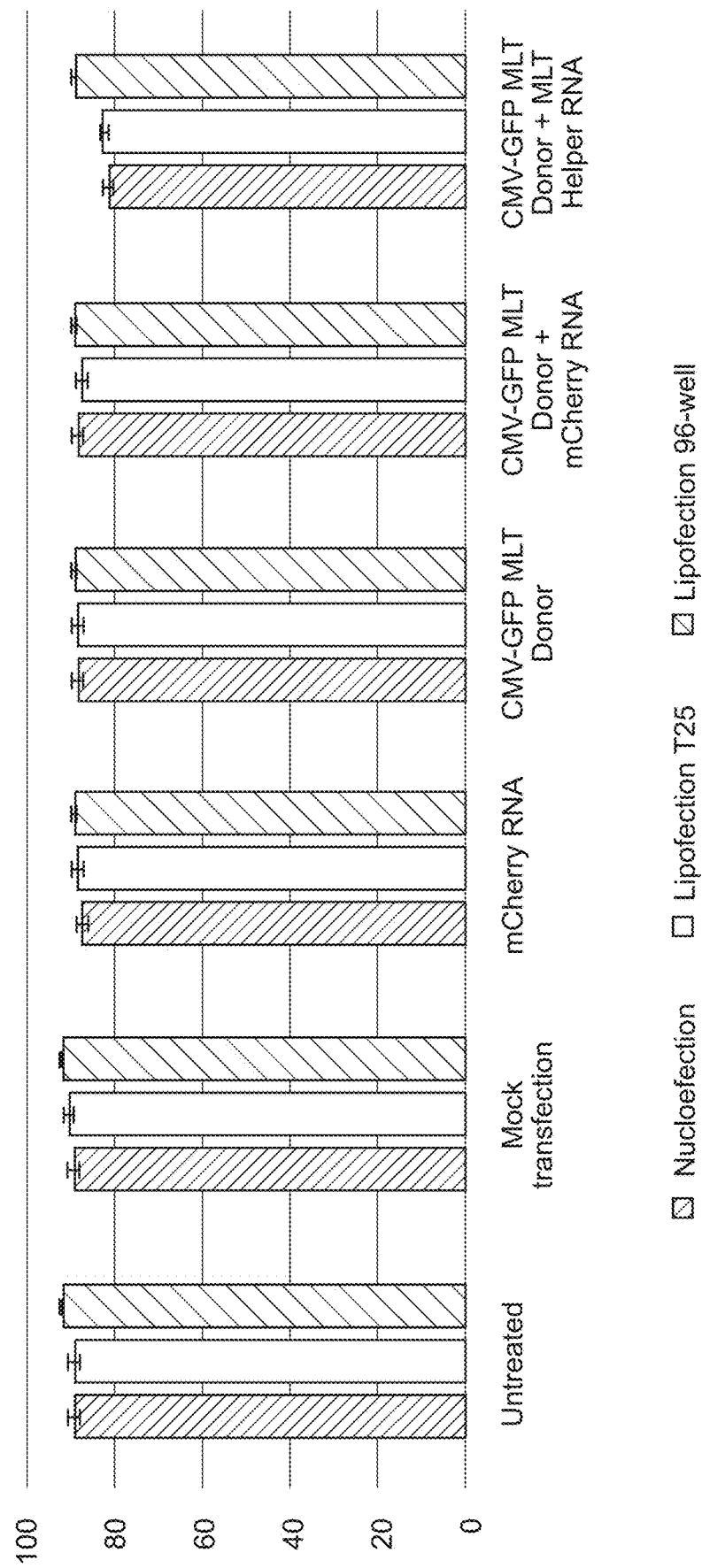
FIGS. 29A and 29B show the viability of HEK293 cells after nucleofection in 96-well plates, lipofection in T25 flasks, and lipofection in 96-well plates, 14 days after transfection (FIG. 29A) and 21 days after transfection (FIG. 29B). Cell viability is slightly better in 96-well plates at 14 days and 21 days after transfection. There are no significant differences in cell viability between the untreated cells and treated cells.
Figure 29B:
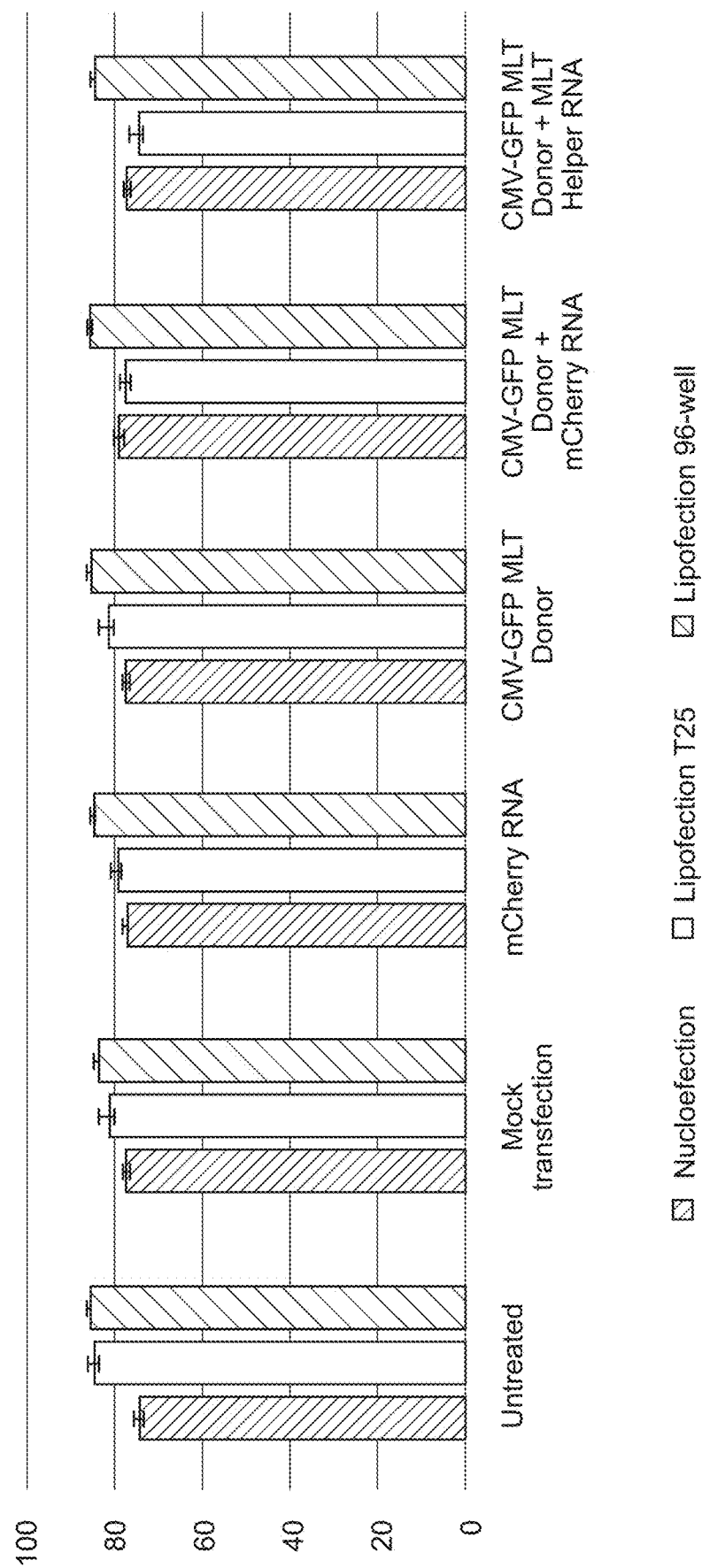
Figure 29C:
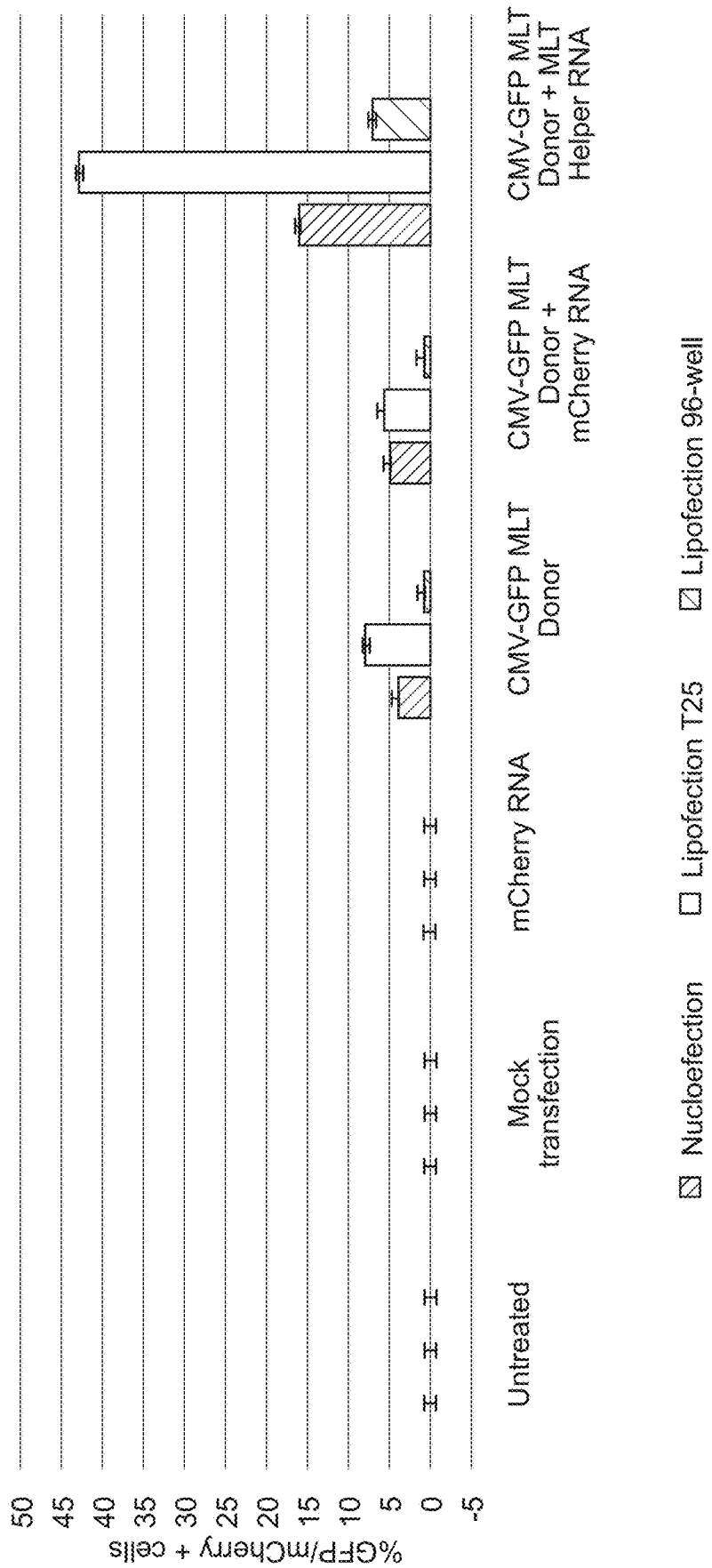
FIGS. 29C and 29D show the percentage of GFP/mCherry positive HEK293 cells after nucleofection in 96-well plates, lipofection in T25 flasks, and lipofection in 96-well plates, 14 days after transfection (FIG. 29C) and 21 days after transfection (FIG. 29D). A FACs gating strategy was applied to samples within each experiment. Selection of GFP-positive and mCherry-positive cell population was obtained. mCherry RNA expression was undetectable at Day 14. The highest % GFP positive cells was observed in the Lipofectamine™ transfection reagent T25 format. The integration efficiency was 35% at 14 days, and 37% at 21 days.
Figure 29D:
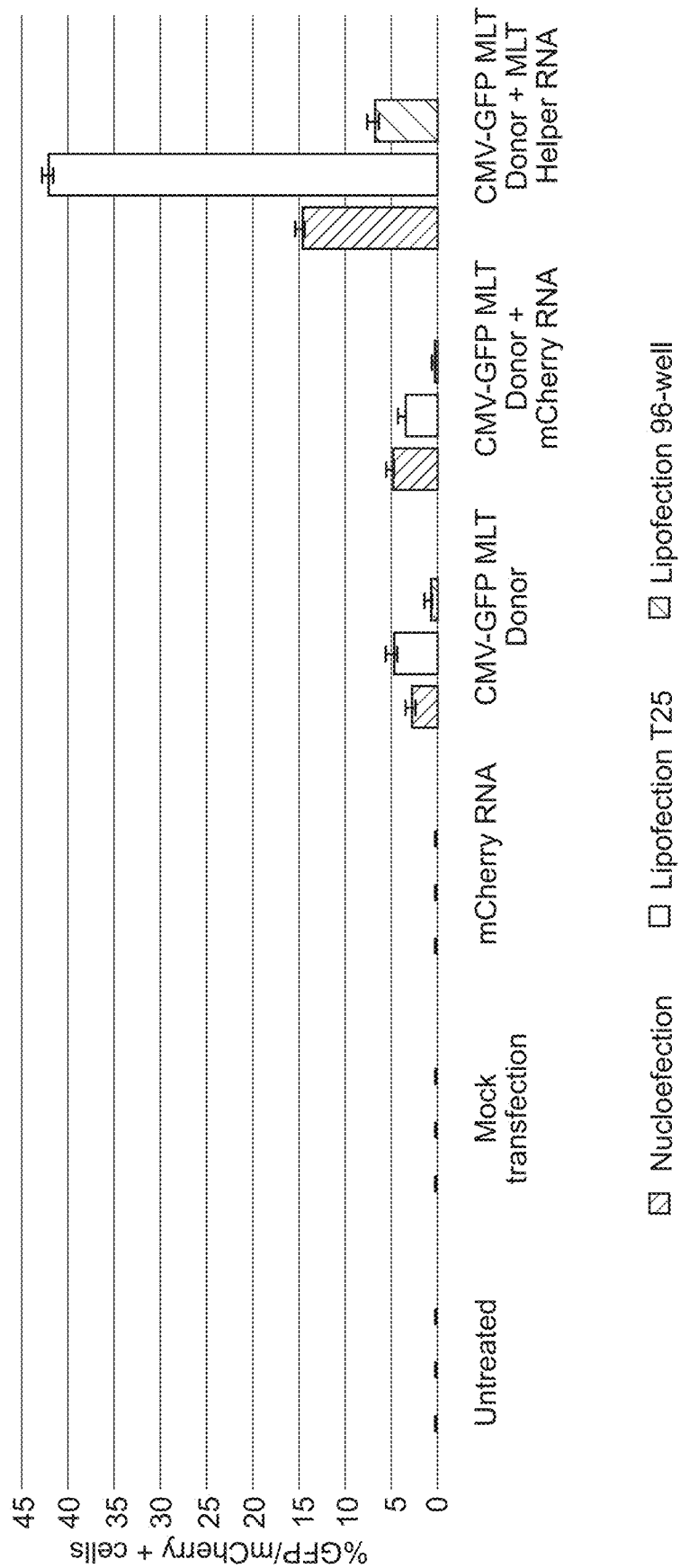
Figure 29E:
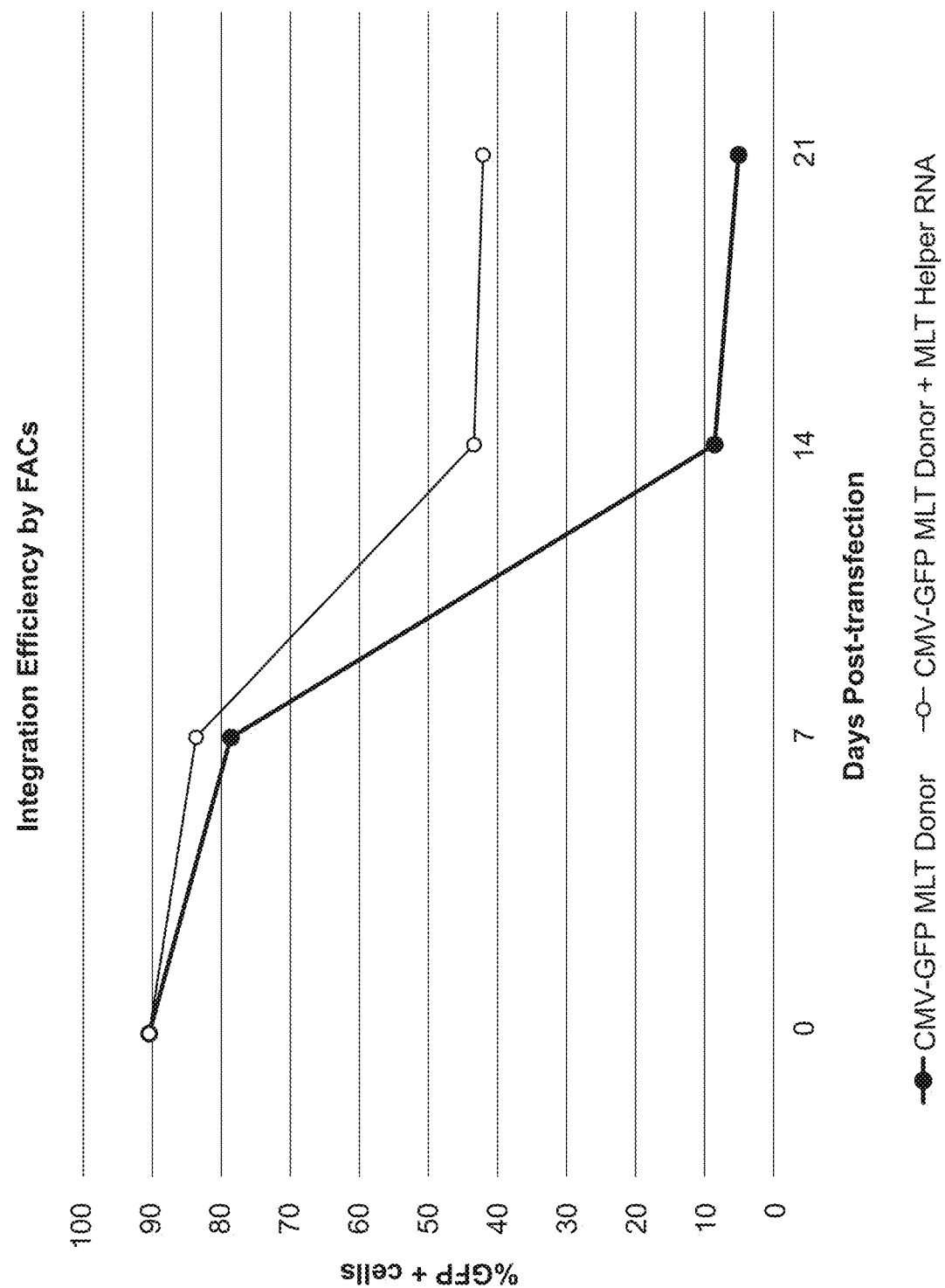
FIG. 29E shows the percentage of GFP positive HEK293 cells after nucleofection lipofection in T25 flasks. The % GFP positive cells was the same in CMV-GFP MLT Donor alone compared to CMV-GFP MLT Donor plus MLT Helper RNA. The % GFP positivity declined rapidly in HEK293 cells transfected with CMV-GFP MLT Donor alone and reached 5% at Day 21. The % GFP positivity stabilized in HEK293 cells transfected with CMV-GFP MLT Donor plus MLT Helper RNA and reached 42% at Day 21. The integration efficiency was calculated at 37%. The top curve is "CMV-GFP Donor".
Figure 30A:
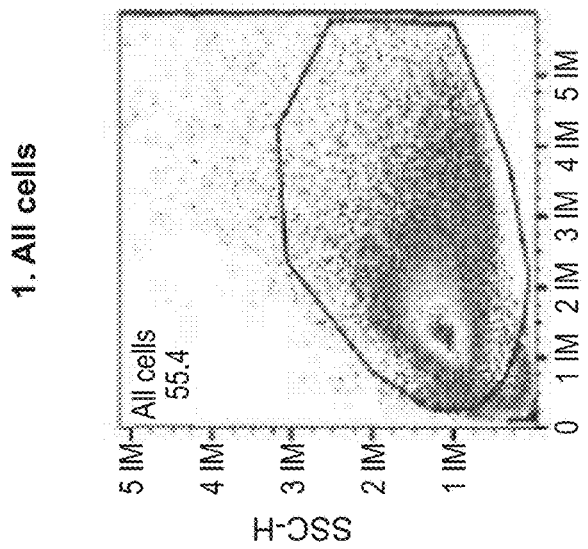
FIGS. 30A, 30B, 30C, and 30D show the FACS gating strategy that determined that neither RNA or DNA affected the viability of HEK293 cells (FIGS. 29A and 29B), RNA expression decreased rapidly after transfection and was undetectable by Day 14 (FIGS. 29C and 29D), and the DNA MLT Donor/MLT RNA Helper system has a high integration efficiency (FIG. 29E).
Figure 30B:
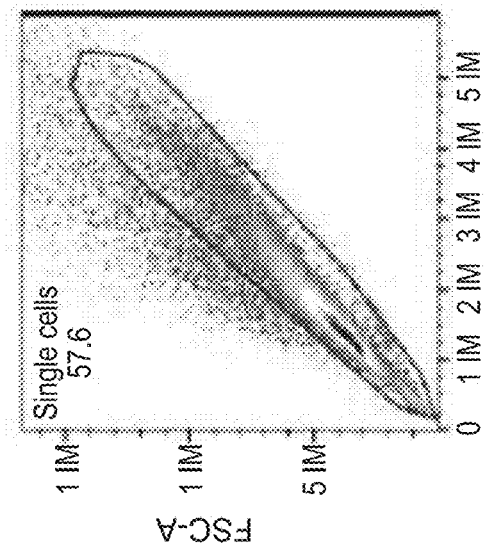
Figure 30C:
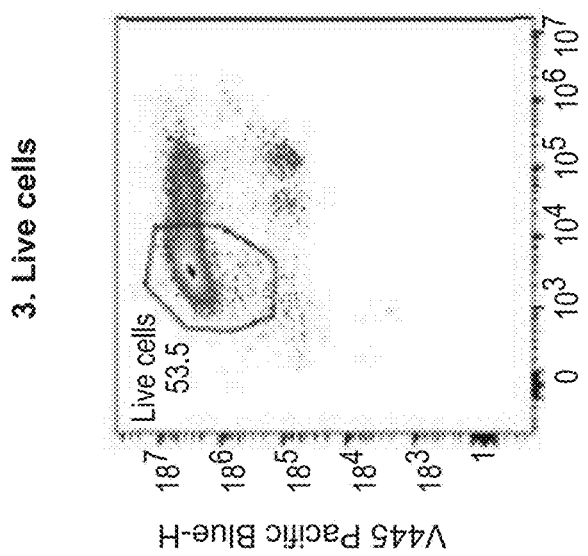
Figure 30D:
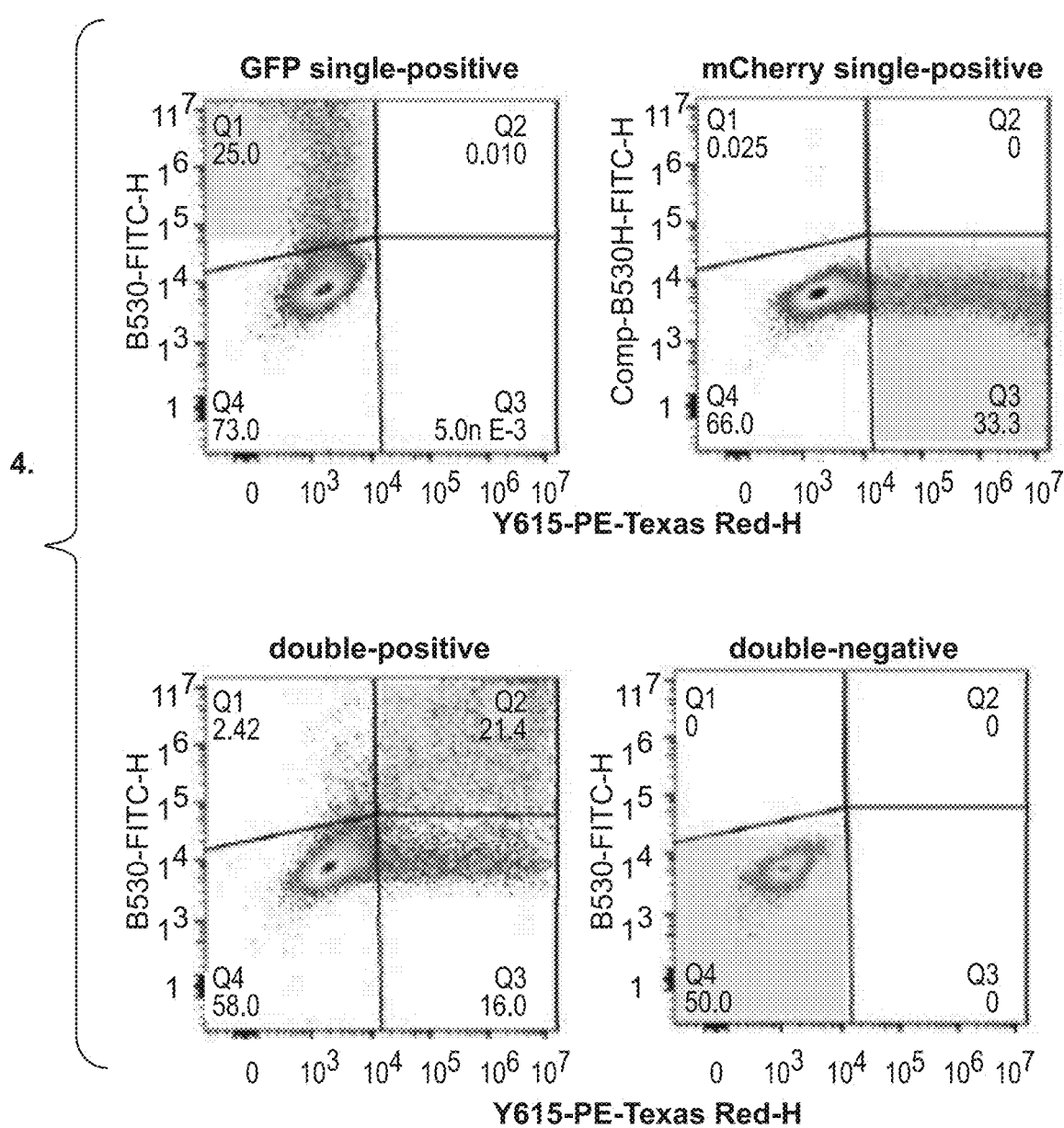

FIG. 29A shows the viability of HEK293 cells at 14 and 21 days after transfection using CMV-GFP MLT DNA donor and a MLT RNA helper. There was no apparent toxicity due to Lipofectamine™ transfection reagent, DNA or RNA. Robust GFP expression was found in over 40% of the cells after 14 and 21 days (FIG. 29B). Integration efficiency was analyzed FACs and showed that 37% of cells were stably integrated with the MLT donor DNA (FIG. 29C and FIG. 29D). FIG. 29E shows the percentage of GFP positive HEK293 cells after nucleofection lipofection in T25 flasks. The % GFP positive cells was the same in CMV-GFP MLT Donor alone compared to CMV-GFP MLT Donor plus MLT Helper RNA. The % GFP positivity declined rapidly in HEK293 cells transfected with CMV-GFP MLT Donor alone and reached 5% at Day 21. The % GFP positivity stabilized in HEK293 cells transfected with CMV-GFP MLT Donor plus MLT Helper RNA and reached 42% at Day 21. The integration efficiency was calculated at 37%. Gated FACs was able to select GFP positive and mnCHerry positive cell populations in order to evaluate the effects of RNA expression (mCherry) (FIG. 30A-D).

Example 10—Transposition of HT1080 Cells Using CMV-GFP/MLT Transposase

An objective of this study was to transfect HT1080 cells with CMV-GFP MLT DNA Donor and MLT DNA Helper transposase 1 or MLT DNA Helper transposase 2, and quantify their transposition efficiency by comparing their GFP expression. HT1080 is a human fibrosarcoma cell line.

Figure 31:
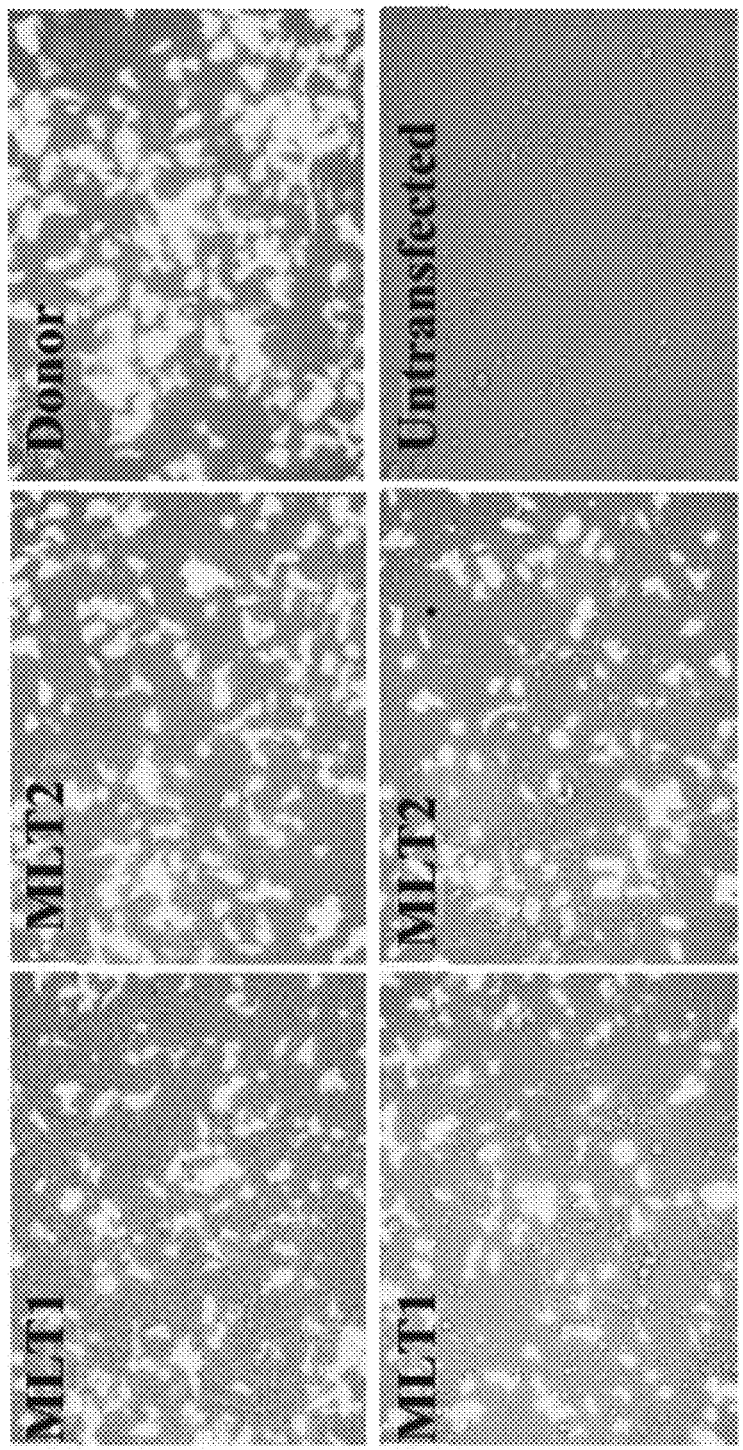
FIG. 31 shows transfection of CMV-GFP MLT Donor plus MLT Helper DNA 24 hours post transfection of HT 1080 cells. The results at 24 hours are similar to the DNA MLT Donor/MLT RNA Helper system.
Figure 32:
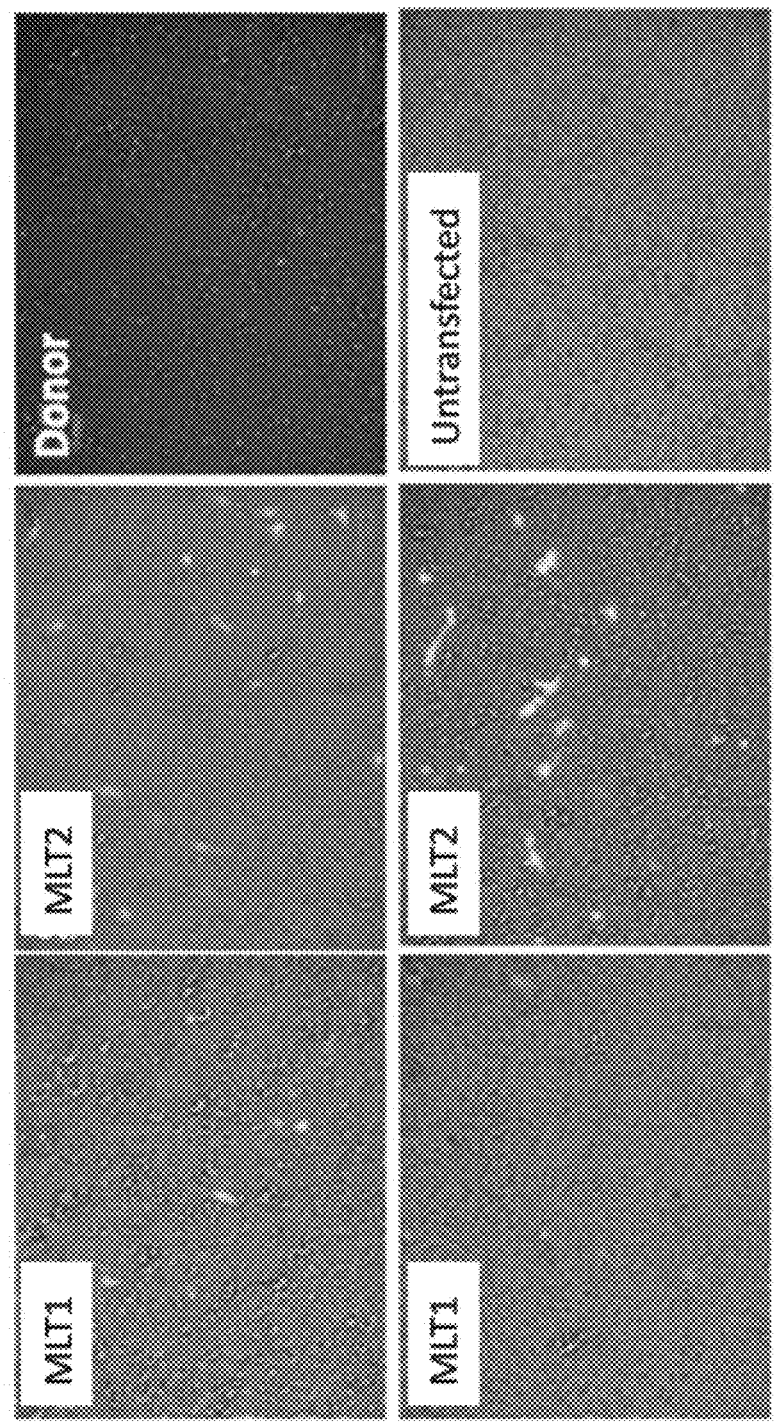
FIG. 32 shows transfection of CMV-GFP MLT Donor plus MLT Helper DNA 2 weeks post transfection of HT 1080 cells. The results suggest that DNA MLT Donor/MLT DNA Helper system (~20% GFP+ cells) has less integration efficiency compared to DNA MLT Donor/MLT DNA Helper system.

FIG. 31 shows CMV-GFP MLT DNA Donor expression 24 hours post transfection of HT 1080 cells, and FIG. 32 shows CMV-GFP MLT DNA Donor expression 2 weeks post transfection of HT1080 cells.

As shown in FIG. 31, both MLT DNA Helper transposase 1 and MLT DNA Helper transposase 2 effectively transfected the HT 1080 cells when combined with CMV-GFP MLT Donor DNA. Both of these transposases expressed very similar levels of GFP, while the donor DNA-only (CMV-GFP only) demonstrated that GFP can be expressed in these cells. The untransfected cell line had no GFP expression, since none is present in this cell line.

After 2 weeks, as shown in FIG. 32, less GFP expression was observed from MLT DNA Helper transposase 1 and MLT DNA Helper transposase 2, while the MLT DNA Helper transposase 2 expressed GFP slightly stronger when compared to the MLT DNA Helper transposase 1. The CMV-GFP only (donor DNA only) and the untransfected cells had no GFP expression, because the donor DNA did not integrate into the cell line while the untransfected cell never expressed GFP to begin with.

In this study, when comparing the transfection efficiency of the MLT DNA Helper transposase 1 and MLT DNA Helper transposase 2 in HT1080 cells, the MLT DNA Helper transposase 2 with CMV-GFP MLT DNA Donor was shown to more effectively transfect the HT1080 cells (FIG. 32, 2 weeks post-transfection). Although the integration efficiency is comparable between The MLT RNA Helper transposase 2 and MLT DNA Helper transposase 2, the MLT DNA Helper transposase 2 is more suitable for transfection of cell lines, including for ex-vivo experiments.

Definitions

The following definitions are used in connection with the invention disclosed herein. Unless defined otherwise, all technical and scientific terms used herein have the same meaning as commonly understood to one of skill in the art to which this invention belongs.

The term "in vivo" refers to an event that takes place in a subject's body.

The term "ex vivo" refers to an event which involves treating or performing a procedure on a cell, tissue and/or organ which has been removed from a subject's body. Aptly, the cell, tissue and/or organ may be returned to the subject's body in a method of treatment or surgery.

As used herein, the term "variant" encompasses but is not limited to nucleic acids or proteins which comprise a nucleic acid or amino acid sequence which differs from the nucleic acid or amino acid sequence of a reference by way of one or more substitutions, deletions and/or additions at certain positions. The variant may comprise one or more conservative substitutions. Conservative substitutions may involve, e.g., the substitution of similarly charged or uncharged amino acids.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, lipid or the like, which is nontoxic and which does not interact with other components of the composition in a deleterious manner.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

SEQUENCE LISTING

```
Sequence total quantity: 436
SEQ ID NO: 1            moltype =    length =
SEQUENCE: 1
000

SEQ ID NO: 2            moltype = AA   length = 572
FEATURE                 Location/Qualifiers
source                  1..572
                        mol_type = protein
                        organism = synthetic construct
SEQUENCE: 2
MAQHSDYSDD EFCADKLSNY SCDSDLENAS TSDEDSSDDE VMVRPRTLRR RRISSSSSDS    60
ESDIEGGREE WSHVDNPPVL EDFLGHQGLN TDAVINNIED AVKLFIGDDF FEFLVEESNR   120
YYNQNRNNFK LSKKSLKWKD ITPQEMKKFL GLIVLMGQVR KDRRDDYWTT EPWTETPYFG   180
KTMTRDRFRQ IWKAWHFNNN ADIVNESDRL CKVRPVLDYF VPKFINIYKP HQQLSLDEGI   240
VPWRGRLFFR VYNAGKIVKY GILVRLLCES DTGYICNMEI YCGEGKRLLE TIQTVVSPYT   300
DSWYHIYMDN YYNSVANCEA LMKNKFRICG TIRKNRGIPK DFQTISLKKG ETKFIRKNDI   360
LLQVWQSKKP VYLISSIHSA EMEESQNIDR TSKKKIVKPN ALIDYNKHMK GVDRADQYLS   420
YYSILRRTVK WTKRLAMYMI NCALFNSYAV YKSVRQRKMG FKMFLKQTAI HWLTDDIPED   480
MDIVPDLQPV PSTSGMRAKP PTSDPPCRLS MDMRKHTLQA IVGSGKKKNI LRRCRVCSVH   540
KLRSETRYMC KFCNIPLHKG ACFEKYHTLK NY                                572

SEQ ID NO: 3            moltype = DNA   length = 1719
FEATURE                 Location/Qualifiers
source                  1..1719
                        mol_type = other DNA
                        organism = synthetic construct
```

SEQUENCE: 3
```
atggcccagc acagcgacta cagcgacgac gagttctgtg ccgataagct gagtaactac   60
agctgcgaca gcgacctgga aaacgccagc acatccgacg aggacagctc tgacgacgag  120
gtgatggtgc ggcccagaac cctgagacgg agaagaatca gcagctctag cagcgactct  180
gaatccgaca tcgagggcgg ccgggaagag tggagccagg tggacaaccc tcctgttctg  240
gaagattttc tgggccatca gggcctgaac accgacgccg tgatcaacaa catcgaggat  300
gccgtgaagc tgttcatagg agatgatttc tttgagttcc tggtcgagga atccaaccgc  360
tattacaacc agaatagaaa caacttcaag ctgagcaaga aaagcctgaa gtggaaggac  420
atcacccctc aggagatgaa aaagttcctg ggactgatcg ttctgatggg acaggtgcgg  480
aaggacagaa gggatgatta ctggacaacc gaaccttgga ccgagacccc ttactttggt  540
aagaccatga ccagagacag attcagacag atctggaaag cctggcactt caacaacaat  600
gctgatatcg tgaacgagtc tgatagactg tgtaaagtgc ggccagtgtt ggattacttc  660
gtgcctaagt tcatcaacat ctataagcct accagcagc tgagcctgga tgaaggcatc  720
gtgccctggc ggggcagact gttcttcaga gtgtacaatg ctggcaagat cgtcaaatac  780
ggcatcctgg tgcgccttct gtgcgagagc gatacaggct acatctgtaa tatgaaaatc  840
tactgcggcg agggcaaaag actgctgaaa accatccaga ccgtcgtttc cccttatacc  900
gacagctggt accacatcta catggacaac tactacaatt ctgtgccaa ctgcgaggcc  960
ctgatgaaga acaagtttag aatctgcggc acaatcagaa aaaacagaga catccctaag 1020
gacttccaga ccatctctct gaagaagggc gaaaccaagt tcatcagaaa gaacgacatc 1080
ctgctccaag tgtggcagtc caagaaaccc gtgtacctga tcagcagcat ccatagcgcc 1140
gagatggaag aaagccagaa catcgacaga acaagcaaga agaagatcgt gaagcccaat 1200
gctctgatcg actacaacaa gcacatgaaa ggcgtggacc gggccgacca gtacctgtct 1260
tattactcta tcctgagaag aacagtgaaa tggaccaaga gactggccat gtacatgatc 1320
aattgcgccc tgttcaacag ctacgccgtg tacaagtccg tgcgacaaag aaaaatggga 1380
ttcaagatgt tcctgaagca gacagccatc cactggctga cagacgacat tcctgaggac 1440
atggacattg tgccagatct gcaacctgtg cccagcacct ctggtatgag actaagcct  1500
cccaccagcg atcctccatg tagactgagc atggacatgc ggaagcacac cctgcaggcc 1560
atcgtcggca gcggcaagaa gaagaacatc cttagacggt gcagggtgtg cagcgtgcac 1620
aagctgcgga gcgagactcg gtacatgtgc aagttttgca acattcccct gcacaaggga 1680
gcctgcttcg agaagtacca caccctgaag aattactag                        1719
```

SEQ ID NO: 4          moltype = AA   length = 568
FEATURE               Location/Qualifiers
source                1..568
                        mol_type = protein
                        organism = synthetic construct SEQUENCE: 4
```
MSQHSDYSDD EFCADKLSNY SCDSDLENAS TSDEDSSDDE VMVRPRTLRR RRISSSSSDS   60
ESDIEGGREE WSHVDNPPVL EDFLGHQGLN TDAVINNIED AVKLFIGDDF FEFLVEESNR  120
YYNQNRNNFK LSKKSLKWKD ITPQEMKKFL GLIVLMGQVR KDRRDDYWTT EPWTETPYFG  180
KTMTRDRFRQ IWKAWHFNNN ADIVNESDRL CKVRPVLDYF VPKFINIYKP HQQLSLDEGI  240
VPWRGRLFFR VYNAGKIVKY GILVRLLCES DTGYICNMEI YCGEGKRLLE TIQTWSPYTD  300
SWYHIYMDNY YNSVANCEAL MKNKFRICGT IRKNRGIPKD FQTISLKKGE TKFIRKNDIL  360
LQVWQSKKPV YLISSHSAEM EESQNIDRTS KKKIVKPNAL IDYNKHMKGV DRADQYLSYY  420
SILRRWKWTK RLAMYMINCA LFNSYAVYKS VRQRKMGFKM FLKQTAHWLT DDIPEDMDIV  480
PDLQPVPSTS GMRAKPPTSD PPCRLSMDMR KHTLQAIVGS GKKKNILRRC RVCSVHKLRS  540
ETRYMCKFCN IPLHKGACFE KYHTLKNY                                    568
```

SEQ ID NO: 5          moltype = DNA   length = 1716
FEATURE               Location/Qualifiers
misc_feature         1..1716
                        note = Synthetic Sequence
source                1..1716
                        mol_type = other DNA
                        organism = synthetic construct SEQUENCE: 5
```
atgtcgcagc attcagacta ttctcatgat gagttttgtg cagacaagtt gtccaattat   60
tcttgtgata gcgatcttga aaatgcgagt acaagtgatg aagattctag tgatgatgaa  120
gtaatggtgc gtcccaggac attgaggcga cgaagaattc cgagctccaa ctctgactca  180
gagtcagata tagaaggcgg gagagaagaa tggtcgcatg ttgataatcc accggtctta  240
gaagattttt tagggcatca aggattaaac acagatgctg ttataaataa tatagaagat  300
gccgtgaaat tatttatcgg agatgatttt tttgaatttc ttgtagagga gtcaaacagg  360
tattataatc aaaataggaa taatttcaaa cttttcaaaa aaagcctaaa gtggaaagat  420
ataccccctc aagagatgaa gaagttttta gggttattc ttctcatggg acaggtgcgc  480
aaagatagaa gagatgacta ttggaccacg gagccatgga cggagacgcc atattttggt  540
aaaacgatga cgagagacag gttccgacag atatggaaag cttggcactt caataataat  600
gcggatatcg taaatgaatc agatagactt tgcaaagtga gaccagtact agattatttt  660
gtgcctaaat tttataaat ttacaaacct catcagcaat tatcactaga tgaagggatc  720
gtaccttgga ggggaagatt attcttttagg gtatataatg ctgcaagat cgttaaatat  780
ggaatattgg ttcgttttgtt gtgcgaaagt gatacaggat atatctgtaa catgaaaatt  840
tattgcggcg aaggaaagcg attattgaa acgatacaaa cagtagtgtc tccatacact  900
gattcgtggt accatatata tatggacaat tattataata gcgtcgcaaa ttgtgaagca  960
cttatgaaaa acaaattcag aatatgtgga acaatccgga aaaatcgagg tatacctaaa 1020
gattttcaaa caatttcttt gaaaaaaggt gaaacaaagt ttataaggaa aaatgatata 1080
ttgttacaag tgtggcaatc aaaaaaagcct gtataccgtga tttcttcgat tcattctgcg 1140
gagatggaag aaagtcagaa tattgacaga acatcaaaa agaaaattgt caaaccgaat 1200
gcactcattg actacaataa acatatgaaa ggtgttgacc gggccgacca ataccttctca 1260
tattattcga tattgcggag acggtcaaa tggacaaaaa ggttggcaat gtatatgata 1320
aattgcgcat tatttaattc ttatgcagtt tacaaatcag tgaggcaaag aaaaatgggt 1380
```

```
tttaaaatgt ttttgaaaca aacagctatc cactggttga cggatgatat tccagaggac 1440
atggacattg ttccagacct tcaaccagta ccgtctactt ctggaatgcg ggctaaacca 1500
cctacatctg atccaccatg caggctatcg atggacatga gaaagcatac gttacaggca 1560
attgtcggaa gtgaaaaaa gaaaacatt ttgagaaggt gtcgcgtatg ttccgttcat 1620
aaattgcgca gtgagacacg ctacatgtgc aaattttgca atatacctct acataaaggg 1680
gcgtgttttg aaaaatatca tacgctaaaa aactat                            1716
```

SEQ ID NO: 6                 moltype = DNA   length = 1719
FEATURE                   Location/Qualifiers
misc_feature          1..1719
                           note = Synthetic Sequence
source                  1..1719
                           mol_type = other DNA
                           organism = synthetic construct
SEQUENCE: 6

```
atggcccagc acagcgacta cagcgacgac gagttctgtg ccgataagct gagtaactac 60
agctgcgaca gcgacctgga aaacgccagc acatccgacg aggacagctc tgacgacgag 120
gtgatggtgc ggcccagaac cctgagacgg agaagaatca gcagctctag cagcgactct 180
gaatccgaca tcgagggcgg ccgggaagag tggagccacg tggacaaccc tcctgttctg 240
gaagattttc tgggccatca gggcctgaac accgacgccg tgatcaacaa catcgaggat 300
gccgtgaagc tgttcatagg agatgatttc tttgagttcc tggtcgagga atccaaccgc 360
tattacaacc agaagagaaa caacttcaag ctgagcaaga aagcctgaa gtggaaggac 420
atcaccctc aggagatgaa aaagttcctg ggactgatcg ttctgatggg acaggtgcgg 480
aaggacagaa gggatgatta ctggacaacc gaaccttgga ccgagacccc ttactttggc 540
aagaccatga ccagagacag attcagacag atctggaaag cctggcactt caacaacaat 600
gctgatatcg tgaacgagtc tgatagactg tgtaaagtgc ggcagtgtt ggattacttc 660
gtgcctaagt tcatcaacat ctataagcct caccagcagc tgagcctgga tgaaggcatc 720
gtgccctggc ggggcagact gttcttcaga gtgtacaatg ctggcaagat cgtcaaatac 780
ggcatcctgg tgcgccttct gtgcgagagc gatacaggct acatctgtaa tatggaaatc 840
tactgcggca agggcaaaag actgctggaa accatccaga ccgtcgtttc cccttatacc 900
gacagctggt accacatcta catggacaac tactacaatt ctgtggccaa ctgcgaggcc 960
ctgatgaaga caagtttag aatctgcggc acaatcagaa aaaacagagg catccctaag 1020
gacttccaga ccatctctct gaagaagggc gaaaccaagt tcatcagaaa gaacgacatc 1080
ctgctccaag tgtggcagtc caagaaaccc gtgtacctga tcagcagcat ccatagcgcc 1140
gagatggaag aaaagccagaa catcgacaga acaagcaaga agaagatcgt gaagcccaat 1200
gctctgatcg actacaacaa gcacatgaaa ggcgtggacc gggccgacca gtacctgtct 1260
tattactcta tcctgagaag aacagtgaaa tggaccaaga gactggccat gtacatgatc 1320
aattgcgccc tgttcaacag ctacgccgtg tacaagtccg tgcgacaaag aaaaatggga 1380
ttcaagatgt tcctgaagca gacagccatc cactggctga cacgacact tcctgaggac 1440
atggacattg tgccagatct gcaacctgtg cccagcacct ctggtatgag agctaagcct 1500
cccaccagcg atcctccatg tagactgagc atggacatgc ggaagcacac cctgcaggcc 1560
atcgtcggca gcggcaagaa gaagaacatc cttagacggt gcagggtgtg cagcgtgcac 1620
aagctgcgga gcgagactcg gtacatgtgc aagtttgca acattcccct gcacaaggga 1680
gcctgcttcg agaagtacca caccctgaag aattactag                         1719
```

SEQ ID NO: 7                 moltype = AA   length = 572
FEATURE                     Location/Qualifiers
source                  1..572
                           mol_type = protein
                           organism = synthetic construct
SEQUENCE: 7

```
MAQHSDYSDD EFCADKLSNY SCDSDLENAS TSDEDSSDDE VMVRPRTLRR RRISSSSSDS  60
ESDIEGGREE WSHVDNPPVL EDFLGHQGLN TDAVINNIED AVKLFIGDDF FEFLVEESNR 120
YYNQKRNNFK LSKKSLWKD ITPQEMKKFL GLIVLMGQVR KDRRDDYWTT EPWTETPYFG 180
KTMTRDRFRQ IWKAWHFNNN ADIVNESDRL CKVRPVLDYF VPKFINIYKP HQQLSLDEGI 240
VPWRGRLFFR VYNAGKIVKY GILVRLLCES DTGYICNMEI YCGEGKRLLE TIQTVVSPYT 300
DSWYHIYMDN YYNSVANCEA LMKNKFRICG TIRKNRGIPK DFQTISLKKG ETKFIRKNDI 360
LLQVWQSKKP VYLISSIHSA EMEESQNIDR TSKKKIVKPN ALIDYNKHMK GVDRADQYLS 420
YYSILRRTVK WTKRLAMYMI NCALFNSYAV YKSVRQRKMG FKMFLKQTAI HWLTDDIPED 480
MDIVPDLQPV PSTSGMRAKP PTSDPPCRLS MDMRKHTLQA IVGSGKKKNI LRRCRVCSVH 540
KLRSETRYMC KFCNIPLHKG ACFEKYHTLK NY                              572
```

SEQ ID NO: 8                 moltype = DNA   length = 1719
FEATURE                     Location/Qualifiers
misc_feature          1..1719
                           note = Synthetic Sequence
source                  1..1719
                           mol_type = other DNA
                           organism = synthetic construct
SEQUENCE: 8

```
atggcccagc acagcgacta ccccgacgac gagttcagag ccgataagct gagtaactac  60
agctgcgaca gcgacctgga aaacgccagc acatccgacg aggacagctc tgacgacgag 120
gtgatggtgc ggcccagaac cctgagacgg agaagaatca gcagctctag cagcgactct 180
gaatccgaca tcgagggcgg ccgggaagag tggagccacg tggacaaccc tcctgttctg 240
gaagattttc tgggccatca gggcctgaac accgacgccg tgatcaacaa catcgaggat 300
gccgtgaagc tgttcatagg agatgatttc tttgagttcc tggtcgagga atccaaccgc 360
tattacaacc agaatagaaa caacttcaag ctgagcaaga aagcctgaa gtggaaggac 420
atcaccctc aggagatgaa aaagttcctg ggactgatcg ttctgatggg acaggtgcgg 480
aaggacagaa gggatgatta ctggacaacc gaaccttgga ccgagacccc ttactttggc 540
```

```
aagaccatga ccagagacag attcagacag atctggaaag cctggcactt caacaacaat    600
gctgatatcg tgaacgagtc tgatagactg tgtaaagtgc ggccagtgtt ggattacttc    660
gtgcctaagt tcatcaacat ctataagcct caccagcagc tgagcctgga tgaaggcatc    720
gtgccctggc ggggcagact gttcttcaga gtgtacaatg ctggcaagat cgtcaaatac    780
ggcatcctgg tgcgccttct gtgcgagagc gatacaggct acatctgtaa tatgaaatc     840
tactgcggcg agggcaaaag actgctggaa accatccaga ccgtcgtttc cccttatacc    900
gacagctggt accacatcta catggacaac tactacaatt ctgtggccaa ctgcgaggcc    960
ctgatgaaga acaagtttag aatctgcggc acaatcagaa aaacagagg catccctaag    1020
gacttccaga ccatctctct gaagaagggc gaaaccaagt tcatcagaaa gaacgacatc   1080
ctgctccaag tgtggcagtc caagaaaccc gtgtacctga tcagcagcat ccatagcgcc   1140
gagatggaag aaagccagaa catcgacaga caagcaagag aagatcgt gaagcccaat    1200
gctctgatcg actacaacaa gcacatgaaa ggcgtggacc gggccgacca gtacctgtct    1260
tattactcta tcctgagaag aacagtgaaa tggaccaaga gactggccat gtacatgatc    1320
aattgcgccc tgttcaacag ctacgccgtg tacaagtccg tgcgacaaag aaaaatggga    1380
ttcaagatgt tcctgaagca gacagccatc cactggctga cagacgacat tcctgaggac    1440
atggacattg tgccagatct gcaacctgtg cccagcaccct tggtatgag agctaagcct    1500
cccaccagcg atcctccatg tagactgagc atggacatgc ggaagcacac cctgcaggcc    1560
atcgtcggca gcggcaagaa gaagaacatc cttagacgt gcagggtgtg cagcgtgcac   1620
aagctgcgga gcgagactcg gtacatgtgc aagttttgca acattcccct gcacaaggga   1680
gcctgcttcg agaagtacca caccctgaag aattactag                         1719

SEQ ID NO: 9            moltype = AA   length = 572
FEATURE                 Location/Qualifiers
source                  1..572
                        mol_type = protein
                        organism = synthetic construct
SEQUENCE: 9
MAQHSDYPDD EFRADKLSNY SCDSDLENAS TSDEDSSDDE VMVRPRTLRR RRISSSSSDS     60
ESDIEGGREE WSHVDNPPVL EDFLGHQGLN TDAVINNIED AVKLFIGDDF FEFLVEESNR    120
YYNQNRNNFK LSKKSLKWKD ITPQEMKKFL GLIVLMDGVR KDRRDDYWTT EPWTETPYFG    180
KTMTRDRFRQ IWKAWHFNNN ADIVNESDRL CKVRPVLDYF VPKFINIYKP HQQLSLDEGI    240
VPWRGRLFFR VYNAGKIVKY GILVRLLCES DTGYICNMEI YCGEGKRLLE TIQTVVSPYT    300
DSWYHIYMDN YYNSVANCEA LMKNKFRICG TIRKNRGIPK DFQTISLKKG ETKFIRKNDI    360
LLQVWQSKKP VYLISSIHSA EMEESQNIDR TSKKKIVKPN AIDYNKHMK GVDRADQYLS     420
YYSILRRTVK WTKRLAMYMI NCALFNSYAV YKSVRQRKMG FKMFLKQTAI HWLTDDIPED    480
MDIVPDLQPV PSTSGMRAKP PTSDPPCRLS MDMRKHTLQA IVGSGKKKNI LRRCRVCSVH    540
KLRSETRYMC KFCNIPLHKG ACFEKYHTLK NY                                  572

SEQ ID NO: 10           moltype = AA   length = 594
FEATURE                 Location/Qualifiers
source                  1..594
                        mol_type = protein
                        organism = synthetic construct
SEQUENCE: 10
MGSSLDDEHI LSALLQSDDE LVGEDSDSEI SDHVSEDDVQ SDTEEAFIDE VHEVQPTSSG     60
SEILDEQNVI EQPGSSLASN KILTLPQRTI RGKNKHCWST SKSTRRSRVS ALNIVRSQRG    120
PTRMCRNIYD PLLCFKLFFT DEIISEIVKW TNAEISLKRR ESMTGATFRD TNEDEIYAFF    180
GILVMTAVRK DNHMSTDDLF DRSLSMVYVS VMSRDRFDPL IRCLRMDDKS IRPTLRENDV    240
FTPVRKIWDL FIHQCIQNYT PGAHLTIDEQ LLGFRGRCPF RMYIPNKPSK YGIKILMMCD    300
SGTKYMINGM PYLGRGTQTN GVPLGEYYVK ELSKPVRGSC RNITCDNWFT SIPLAKNLLQ    360
EPYKLTIVGT VRSNKREIPE VLKNSRSRPV GTSMFCFDGP AKMVYLLSSC                420
DEDASINEST GKPQMVMYYN QTKGGVDTLD QMCSVMTCSR KTNRWPMALL YGMINIACIN    480
SFIIYSHNVS SKGEKVQSRK KFMRNLYMSL TSSFMRKRLE APTLKRYLRD NISNILPNEV    540
PGTSDDSTEE PVTKKRTYCT YCPSKIRRKA NASCKKCKKV ICREHNIDMC QSCF           594

SEQ ID NO: 11           moltype = AA   length = 280
FEATURE                 Location/Qualifiers
source                  1..280
                        mol_type = protein
                        organism = synthetic construct
SEQUENCE: 11
MSNPRKRSIP TCDVNFVLEQ LLAEDSFDES DFSEIDDSDD FSDSASEDYT VRPPSDSESD     60
GNSPTSADSG RALKWSTRVM IPRQRYDFTG TPGRKVDVSD TTDPLQYFEL FFTEELVSKI    120
TSEMNAQAAL LASKPPGPKG FSRMDKWKDT DNDELKVFFA VMLLQGIVQK PELEMFWSTR    180
PLLDIPYLRQ IMTGERFLLL LRCLHFVNNS SISAGQSKAQ ISLQKIKPVF DFLVNKFSTV    240
YTPNRNIAVD ESLMLFKGRL AMKQYIPTKM NLKDSADGLK                          280

SEQ ID NO: 12           moltype = AA   length = 252
FEATURE                 Location/Qualifiers
source                  1..252
                        mol_type = protein
                        organism = synthetic construct
SEQUENCE: 12
MDLRCQHTVL SIRESRGLLP NLKMKTSRMK KGDIIFSRKG DILLLAWKDK RVVRMISIHD     60
TSVSTTGKKN RKTGENIVKP ACIKEYNAHM KGVDRADQFL SCCSILRKMM KWTKKVVLYL    120
INCGLFNSFR VYNVLNPQAK MKYKQFLLSV ARDWIMDDNN EGSPEPETNL SSPSPGGARR    180
APRKDPPKRL SGDMKQHEPT CIPASGKKKF PTRACRVCAH GKRSESRYLC KFCLVPLHRG    240
KCFTQYHTLK KY                                                        252
```

```
SEQ ID NO: 13              moltype = AA  length = 432
FEATURE                    Location/Qualifiers
source                     1..432
                           mol_type = protein
                           organism = synthetic construct
SEQUENCE: 13
MKAFLGVILN MGVLNHPNLQ SYWSMDFESH IPFFRSVFKR ERFLQIFWML HLKNDQKSSK    60
DLRTRTEKVN CFLSYLEMKF RERFCPGREI AVDEAVVGFK GKIHFITYNP KKPTKWGIRL   120
YVLSDSKCGY VHSFVPYYGG ITSETLVRPD LPFTSRIVLE LHERLKNSVP GSQGYHFFTD   180
RYYTSVTLAK ELFKEKTHLT GTIMPNRKDN PPVIKHQKLK KGEIVAFRDE NVMLLAWKDK   240
RIVTLSTWDS ETESVERRVG GGKEIVLKPK VVTNYTKFMG GVDIADYTST YCFMRKTLKW   300
WRTLFFWGLE VSVVNSYILY KECQKRKNEK PITHVKFIRK LVHDLVGEFR DGTLTSRGRL   360
LSTNLEQRLD GKLHIITPHP NKKHKDCVVC SNRKIKGGRR ETIYICETCE CKPGLHVGEC   420
FKKYHTMKNY RD                                                      432

SEQ ID NO: 14              moltype = AA  length = 662
FEATURE                    Location/Qualifiers
source                     1..662
                           mol_type = protein
                           organism = synthetic construct
SEQUENCE: 14
MPSLRKRKET NETDTLPEVF NDNLSDIPSE IEDADDCFDD SGDDSTDSTD SEIIRPVRKR    60
KVAVLSSDSD TDEATDNCWS EIDTPPRLQM FEGHAGVTTF PSQCDSVPSV TNLFFGDELF   120
EMLCKELSNY HDQTAMKRKT PSRTLKWSPV TQKDIKKFLG LIILMGQTRK DSLKDYWSTD   180
PLICTPIFPQ TMSRHRFEQI WTFWHFNDNA KMDSRSGRLF KIQPVLDYFL HKFRTIYKPK   240
QQLSLDEGMI PWRGRFKFRT YNPAKITKYG LLVRMVCESD TGYICSMEIY TAEGRKLQET   300
VLSVLGPYLG IWHHIYQDNY YNATSTAELL LQNKTRVCGT IRESRGLPPN LEMKTSRMKK   360
GDIIFSRKGD ILLLAWKDKR VVRMISTIHD TSVSTTGKKN RKTGENIVKP TCIKEYNAHM   420
KGVDRADQFL SCCSILRKTM KWTKKVVLYL INCGLFNSFR VYNVLNPQAK MKYKQFLLSV   480
ARDWITDDNN EGSPEPETNL SSPSPGGARR APRKDPPKRL SGDMKQHEPT CIPASGKKKF   540
PTRACRVCAA HGKRSESRYL CKFCLVPLHR GKCFTQYHTL KKYMDLRCQH TVLSTVGRGY   600
SVLARFKPRT NERTGSSHCH VQVPAGGQGP PSTIIANGCG CKLEPMVRTR SPTCLVIEFG   660
CM                                                                 662

SEQ ID NO: 15              moltype = AA  length = 673
FEATURE                    Location/Qualifiers
source                     1..673
                           mol_type = protein
                           organism = synthetic construct
SEQUENCE: 15
MPSLRKRKET NETDTLPEVF NDNLSDIPSE IEDADDCFDD SGDDSTDSTE SEIIRPVRKR    60
KVAVLSSDSN TDEATDNCWS EIDTPPRLQM FEGHAGVTTF PSQCDSVPSV TNLFFGDELF   120
EMLCKELSNY HDQTAMKRKT PSRTLKWSPV TQKDIKKFLG LIILMGQTRK DSWKDYWSTD   180
PLICTPIFPQ TMSRHRFEQI WTFWHFNDNA KMDSCSGRLF KIQPVLDYFL HKFRTIYKPK   240
QQLSLDEGMI PWRGRLKFTY NPAITKYGLL VRMVCESDTG YICNMEIYTA ERKKLQETVL   300
SVLGPYLGIW HHIYQDNYYN ATSTAELLLQ NKTRVCGTIR ESRGLPPNLK MKTSRMKKGD   360
IIFSRKGDIL LLAWKDKRVV RMISTIHDTS VSTTGKKNRK TGENIVKPTC IKEYNAHMKG   420
VDRADQFLSC CSILRKTTKW TKKVVLYLIN CGLFNSFRVY NILNPQAMKM YKQFLLSVAR   480
DWITDDNNEG SPEPETNLSS PSSGGARRAP RKDQPKRLSG DMKQHEPTCI PASGKKKFPT   540
ACRVCAAHGK RSESRYLRKF CFVPLRGKCF MYHTLKKYSE LFSLIVVSKI QNVIIYKTTK   600
VYMRYVMRSH CPLSFLVFAP SVKDRSRVFS FFTRHLLWTL DVNTLSCPHR MKRSHWWKPC   660
RSIYEKLYNC TNP                                                     673

SEQ ID NO: 16              moltype = AA  length = 254
FEATURE                    Location/Qualifiers
source                     1..254
                           mol_type = protein
                           organism = synthetic construct
SEQUENCE: 16
MDLRCQHTVL SIRESRGLPP NLKMKTSRMK KGDIIFSRKG DILLLAWKDK RVVRMISTIH    60
DTSVSTTGKK NRKTGENIVK PACIKEYNAH MKGVDRADQF LSCCSILRKT MKWTKKVVLY   120
LINCGLFNSF RVYNVLNPQA KMKYKQFLLS VARDWITDDN NEGSPEPETN LSSPSPGGAR   180
RAPRKDPPKR LSGDMKQHEP TCIPASGKKK FPTRACRVCA AHGKRSESRY LCKFCLVPLH   240
RGKCFTQYHT LKKY                                                    254

SEQ ID NO: 17              moltype = AA  length = 594
FEATURE                    Location/Qualifiers
source                     1..594
                           mol_type = protein
                           organism = synthetic construct
SEQUENCE: 17
MGSSLDDEHI LSALLQSDDE LVGEDSDSEV SDHVSEDDVQ SDTEEAFIDE VHEVQPTSSG    60
SEILDEQNVI EQPGSSLASN RILTLPQRTI RGKNKHCWST SKPTRRSRVS ALNIVRSQRG   120
PTRMCRNIYD PLLCFKLFFT DEIISEIVKW TNAEISLKRR ESMTSATFRD TNEDEIYAFF   180
GILVMTAVRK DNHMSTDDLF DRSLSMVYVS VMSRDRFDFL IRCLRMDDKS IRPTLRENDV   240
FTPVRKIWDL FIHQCIQNYT PGAHLTIDEQ LLGFRGRCPF RVYIPNKPSK YGIKILMMCD   300
SGTKYMINGM PYLGRGTQTN GVPLGEYYVK ELSKPVHGSC RNITCDNWFT SIPLAKNLLQ   360
EPYKLTIVGT VRSNKREIPE VLKNSRSRPV GTSMFCFDGP LTLVSYKPKP AKMVYLLSSC   420
DEDASINEST GKPQMVMYYN QTKGGVDTLD QMCSVMTCSR KTNRWPMALL YGMINIACIN   480
```

```
SFIIYSHNVS SKGEKVQSRK KFMRNLYMGL TSSFMRKRLE APTLKRYLRD NISNILPKEV   540
PGTSDDSTEE PVMKKRTYCT YCPSKIRRKA SASCKKCKKV ICREHNIDMC QSCF         594

SEQ ID NO: 18           moltype = DNA   length = 1782
FEATURE                 Location/Qualifiers
misc_feature            1..1782
                        note = Synthetic Sequence
source                  1..1782
                        mol_type = other DNA
                        organism = synthetic construct
SEQUENCE: 18
atgggcagca gcctggacga cgagcacatc ctgagcgccc tgctgcagag cgacgacgag    60
ctggtcggcg aggacagcga cagcgaggtg agcgaccacg tgagcgagga cgacgtgcag   120
tccgacaccg aggaggcctt catcgacgag gtgcacgagg tgcagcctac cagcagcggc   180
tccgagatcc tggacgagca gaacgtgatc gagcagcccg cagctccct ggccagcaac    240
aggatcctga ccctgcccca gaggaccatc agggggcaaga caagcactg ctggtccacc   300
tccaagccca ccaggcggag cagggtgtcc gccctgaaca tcgtgagaag ccagaggggc   360
cccaccagga tgtgcaggaa catctacgac ccctgctgt gcttcaagct gttcttcacc    420
gacgagatca tcagcgagat cgtgaagtgg accaacgccg agatcagcct gaagaggcgg   480
gagagcatga cctccgccac cttcagggac accaacgagg acgagatcta cgccttcttc   540
ggcatcctgg tgatgaccgc cgtgaggaag gacaaccaca tgagcaccga cgacctgttc   600
gacagatccc tgagctgagc gtacgtgatc gtgatgaggc agacagatt cgacttcctg   660
atcagatgcc tgaggatgga cgacaagagc atcaggccca cctgcggga gaacgacgtg    720
ttcaccccgc tgagaaagat ctgggacctg ttcatccacc agtgcatcca gaactacacc   780
cctggcgccc acctgaccat cgacgagcag ctgctgggct tcaggggcag gtgccccttc   840
agggtctata tcccaaacaa gcccagcaag tacggcatca agatcctgat gatgtgcgac   900
agcggcacca agtacatgat caacggcatg ccctacctgg caggggcac ccagaccaac    960
ggcgtgcccc tgggcgagta ctacgtgaag gagctgtcca agcccgtcca cggcagctgc  1020
agaaacatca ccctgcgaca actggttcacc agcatcccc tggccaagaa cctgctgcag  1080
gagccctaca agctgaccat cgtggagcac cctgaagaga caaagagaga gatccccgag  1140
gtcctgaaga acagcaggtc caggcccgtg gcaccagca tgttctgctt cgacggcccc   1200
ctgaccctgg tgtcctacaa gcccaagccc gccaagatgg tgtacctgct gtccagctgc  1260
gacgaggacc ccagcatcaa cgagagcacc ggcaagcccc agatggtgat gtactacaac  1320
cagaccaagg gcggcgtgga caccctggac cagatgtgca gcgtgatgc ctgcagcaga   1380
aagaccaaca ggtggcccat ggccctgctg tacggcatga tcaacatcgc ctgcatcaac  1440
agcttcatca tctacagcca caacgtgagc agcaagggcg agaaggtgca gagccggaaa  1500
aagttcatgc ggaaccctgta catgggcctg acctccagct tcatgaggaa gaggctggag  1560
gccccacccc tgaagagata cctgagggac aacatcagca catcctgcc caaagaggtg   1620
cccggcacca gcgacgacag caccgaggag ccgtgatga agaagaggac ctactgcacc   1680
tactgtccca gcaagatcag aagaaaggcc agcgccagct gcaagaagtg taagaaggtc  1740
atctgccggg agcacaacat cgacatgtgc cagagctgtt tc                     1782

SEQ ID NO: 19           moltype = DNA   length = 205
FEATURE                 Location/Qualifiers
misc_feature            1..205
                        note = Synthetic Sequence
source                  1..205
                        mol_type = other DNA
                        organism = synthetic construct
SEQUENCE: 19
ttaaccctag aaagataatc atattgtgac gtacgttaaa gataatcatg cgtaaaattg    60
acgcatgtgt tttatcggtc tgtatatcga ggtttattta ttaatttgaa tagatattaa   120
gttttattat atttacactt acatactaat aataaattca acaaacaatt tatttatgtt   180
tatttattta ttaaaaaaaa acaaa                                         205

SEQ ID NO: 20           moltype = DNA   length = 310
FEATURE                 Location/Qualifiers
misc_feature            1..310
                        note = Synthetic Sequence
source                  1..310
                        mol_type = other DNA
                        organism = synthetic construct
SEQUENCE: 20
atctataaca agaaaatata tatataataa gttatcacgt aagtagaaca tgaaataaca    60
atataattat cgtatgagtt aaatcttaaa agtcacgtaa aagataatca tgcgtcattt   120
tgactcacgc ggtcgttata gttcaaaatc agtgacactt accgcattga caagcacgcc   180
tcacgggagc tccaagcggc gactgagatg tcctaaatgc acagcgacgg attcgcgcta   240
tttagaaaga gagagcaata tttcaagaat gcatgcgtca attttacgca gactatcttt   300
ctagggttaa                                                          310

SEQ ID NO: 21           moltype = DNA   length = 157
FEATURE                 Location/Qualifiers
misc_feature            1..157
                        note = Synthetic Sequence
source                  1..157
                        mol_type = other DNA
                        organism = synthetic construct
SEQUENCE: 21
ttaacacttg gattgcggga aacgagttaa gtcggctcgc gtgaattgcg cgtactccgc    60
```

```
gggagccgtc ttaactcggt tcatatagat ttgcggtgga gtgcgggaaa cgtgtaaact    120
cgggccgatt gtaactgcgt attaccaaat atttgtt                             157

SEQ ID NO: 22           moltype = DNA   length = 212
FEATURE                 Location/Qualifiers
misc_feature            1..212
                        note = Synthetic Sequence
source                  1..212
                        mol_type = other DNA
                        organism = synthetic construct
SEQUENCE: 22
aattatttat gtactgaata gataaaaaaa tgtctgtgat tgaataaatt ttcatttttt    60
acacaagaaa ccgaaaattt catttcaatc gaacccatac ttcaaaagat ataggcattt   120
taaactaact ctgattttgc gcgggaaacc taaataattg cccgcgccat cttatatttt   180
ggcgggaaat tcacccgaca ccgtagtgtt aa                                 212

SEQ ID NO: 23           moltype = DNA   length = 19
FEATURE                 Location/Qualifiers
misc_feature            1..19
                        note = Synthetic Sequence
source                  1..19
                        mol_type = other DNA
                        organism = synthetic construct
SEQUENCE: 23
tggccggcct gaccactgg                                                 19

SEQ ID NO: 24           moltype = DNA   length = 19
FEATURE                 Location/Qualifiers
misc_feature            1..19
                        note = Synthetic Sequence
source                  1..19
                        mol_type = other DNA
                        organism = synthetic construct
SEQUENCE: 24
tgaaggcctg gccggcctg                                                 19

SEQ ID NO: 25           moltype = DNA   length = 19
FEATURE                 Location/Qualifiers
misc_feature            1..19
                        note = Synthetic Sequence
source                  1..19
                        mol_type = other DNA
                        organism = synthetic construct
SEQUENCE: 25
tgagcactga aggcctggc                                                 19

SEQ ID NO: 26           moltype = DNA   length = 19
FEATURE                 Location/Qualifiers
misc_feature            1..19
                        note = Synthetic Sequence
source                  1..19
                        mol_type = other DNA
                        organism = synthetic construct
SEQUENCE: 26
tccactgagc actgaaggc                                                 19

SEQ ID NO: 27           moltype = DNA   length = 19
FEATURE                 Location/Qualifiers
misc_feature            1..19
                        note = Synthetic Sequence
source                  1..19
                        mol_type = other DNA
                        organism = synthetic construct
SEQUENCE: 27
tggtttccac tgagcactg                                                 19

SEQ ID NO: 28           moltype = DNA   length = 19
FEATURE                 Location/Qualifiers
misc_feature            1..19
                        note = Synthetic Sequence
source                  1..19
                        mol_type = other DNA
                        organism = synthetic construct
SEQUENCE: 28
tggggaaaat gacccaaca                                                 19

SEQ ID NO: 29           moltype = DNA   length = 19
FEATURE                 Location/Qualifiers
misc_feature            1..19
```

```
                    note = Synthetic Sequence
source              1..19
                    mol_type = other DNA
                    organism = synthetic construct
SEQUENCE: 29
taggacagtg gggaaaatg                                                   19

SEQ ID NO: 30       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 30
tccagggaca cggtgctag                                                   19

SEQ ID NO: 31       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 31
tcagagccag gagtcctgg                                                   19

SEQ ID NO: 32       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 32
tccttcagag ccaggagtc                                                   19

SEQ ID NO: 33       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 33
tcctccttca gagccagga                                                   19

SEQ ID NO: 34       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 34
tccagcccct cctccttca                                                   19

SEQ ID NO: 35       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 35
tccgagcttg acccttgga                                                   19

SEQ ID NO: 36       moltype = DNA   length = 19
FEATURE             Location/Qualifiers
misc_feature        1..19
                    note = Synthetic Sequence
source              1..19
                    mol_type = other DNA
                    organism = synthetic construct
SEQUENCE: 36
tggtttccga gcttgaccc                                                   19

SEQ ID NO: 37       moltype = DNA   length = 38
FEATURE             Location/Qualifiers
```

```
misc_feature              1..38
                          note = Synthetic Sequence
source                    1..38
                          mol_type = other DNA
                          organism = synthetic construct
SEQUENCE: 37
tggggtggtt tccgagcttt ggggtggttt ccgagctt                                38

SEQ ID NO: 38             moltype = DNA  length = 19
FEATURE                   Location/Qualifiers
misc_feature              1..19
                          note = Synthetic Sequence
source                    1..19
                          mol_type = other DNA
                          organism = synthetic construct
SEQUENCE: 38
tctgctgggg tggtttccg                                                     19

SEQ ID NO: 39             moltype = DNA  length = 38
FEATURE                   Location/Qualifiers
misc_feature              1..38
                          note = Synthetic Sequence
source                    1..38
                          mol_type = other DNA
                          organism = synthetic construct
SEQUENCE: 39
tgcagagtat ctgctggggt gcagagtatc tgctgggg                                38

SEQ ID NO: 40             moltype = DNA  length = 14
FEATURE                   Location/Qualifiers
misc_feature              1..14
                          note = Synthetic Sequence
source                    1..14
                          mol_type = other DNA
                          organism = synthetic construct
SEQUENCE: 40
ccaatcccct cagt                                                          14

SEQ ID NO: 41             moltype = DNA  length = 15
FEATURE                   Location/Qualifiers
misc_feature              1..15
                          note = Synthetic Sequence
source                    1..15
                          mol_type = other DNA
                          organism = synthetic construct
SEQUENCE: 41
cagtgctcag tggaa                                                         15

SEQ ID NO: 42             moltype = DNA  length = 18
FEATURE                   Location/Qualifiers
misc_feature              1..18
                          note = Synthetic Sequence
source                    1..18
                          mol_type = other DNA
                          organism = synthetic construct
SEQUENCE: 42
gaaacatccg gcgactca                                                      18

SEQ ID NO: 43             moltype = DNA  length = 19
FEATURE                   Location/Qualifiers
misc_feature              1..19
                          note = Synthetic Sequence
source                    1..19
                          mol_type = other DNA
                          organism = synthetic construct
SEQUENCE: 43
tcgcccctca aatcttaca                                                     19

SEQ ID NO: 44             moltype = DNA  length = 19
FEATURE                   Location/Qualifiers
misc_feature              1..19
                          note = Synthetic Sequence
source                    1..19
                          mol_type = other DNA
                          organism = synthetic construct
SEQUENCE: 44
tcaaatctta cagctgctc                                                     19

SEQ ID NO: 45             moltype = DNA  length = 19
```

| FEATURE | Location/Qualifiers |
|---|---|
| misc_feature | 1..19<br>note = Synthetic Sequence |
| source | 1..19<br>mol_type = other DNA<br>organism = synthetic construct |

SEQUENCE: 45
tcttacagct gctcactcc                                                   19

| SEQ ID NO: 46 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 46
tacagctgct cactcccct                                                   19

| SEQ ID NO: 47 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 47
tgctcactcc cctgcaggg                                                   19

| SEQ ID NO: 48 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 48
tcccctgcag ggcaacgcc                                                   19

| SEQ ID NO: 49 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 49
tgcagggcaa cgcccaggg                                                   19

| SEQ ID NO: 50 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 50
tctcgattat gggcgggat                                                   19

| SEQ ID NO: 51 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 51
tcgcttctcg attatgggc                                                   19

| SEQ ID NO: 52 | moltype = DNA  length = 19 |
|---|---|
| FEATURE | Location/Qualifiers |
| misc_feature | 1..19<br>note = Synthetic Sequence |
| source | 1..19<br>mol_type = other DNA<br>organism = synthetic construct |

SEQUENCE: 52
tgtcgagtcg cttctcgat                                                   19

| | | |
|---|---|---|
| SEQ ID NO: 53<br>FEATURE<br>misc_feature<br><br>source | moltype = DNA   length = 19<br>Location/Qualifiers<br>1..19<br>note = Synthetic Sequence<br>1..19<br>mol_type = other DNA<br>organism = synthetic construct | |
| SEQUENCE: 53<br>tccatgtcga gtcgcttct | | 19 |
| SEQ ID NO: 54<br>FEATURE<br>misc_feature<br><br>source | moltype = DNA   length = 19<br>Location/Qualifiers<br>1..19<br>note = Synthetic Sequence<br>1..19<br>mol_type = other DNA<br>organism = synthetic construct | |
| SEQUENCE: 54<br>tcgcctccat gtcgagtcg | | 19 |
| SEQ ID NO: 55<br>FEATURE<br>misc_feature<br><br>source | moltype = DNA   length = 19<br>Location/Qualifiers<br>1..19<br>note = Synthetic Sequence<br>1..19<br>mol_type = other DNA<br>organism = synthetic construct | |
| SEQUENCE: 55<br>tcgtcatcgc ctccatgtc | | 19 |
| SEQ ID NO: 56<br>FEATURE<br>misc_feature<br><br>source | moltype = DNA   length = 19<br>Location/Qualifiers<br>1..19<br>note = Synthetic Sequence<br>1..19<br>mol_type = other DNA<br>organism = synthetic construct | |
| SEQUENCE: 56<br>tgatctcgtc atcgcctcc | | 19 |
| SEQ ID NO: 57<br>FEATURE<br>misc_feature<br><br>source | moltype = DNA   length = 14<br>Location/Qualifiers<br>1..14<br>note = Synthetic Sequence<br>1..14<br>mol_type = other DNA<br>organism = synthetic construct | |
| SEQUENCE: 57<br>gcttcagctt ccta | | 14 |
| SEQ ID NO: 58<br>FEATURE<br>misc_feature<br><br>source | moltype = DNA   length = 14<br>Location/Qualifiers<br>1..14<br>note = Synthetic Sequence<br>1..14<br>mol_type = other DNA<br>organism = synthetic construct | |
| SEQUENCE: 58<br>ctgtgatcat gcca | | 14 |
| SEQ ID NO: 59<br>FEATURE<br>misc_feature<br><br>source | moltype = DNA   length = 16<br>Location/Qualifiers<br>1..16<br>note = Synthetic Sequence<br>1..16<br>mol_type = other DNA<br>organism = synthetic construct | |
| SEQUENCE: 59<br>acagtggtac acacct | | 16 |
| SEQ ID NO: 60<br>FEATURE<br>misc_feature<br><br>source | moltype = DNA   length = 15<br>Location/Qualifiers<br>1..15<br>note = Synthetic Sequence<br>1..15<br>mol_type = other DNA<br>organism = synthetic construct | |
| SEQUENCE: 60<br>ccacccccca ctaag | | 15 |

| | | |
|---|---|---|
| SEQ ID NO: 61<br>FEATURE<br>misc_feature<br><br>source | moltype = DNA  length = 14<br>Location/Qualifiers<br>1..14<br>note = Synthetic Sequence<br>1..14<br>mol_type = other DNA<br>organism = synthetic construct | |
| SEQUENCE: 61<br>cattggccgg gcac | | 14 |
| SEQ ID NO: 62<br>FEATURE<br>misc_feature<br><br>source | moltype = DNA  length = 16<br>Location/Qualifiers<br>1..16<br>note = Synthetic Sequence<br>1..16<br>mol_type = other DNA<br>organism = synthetic construct | |
| SEQUENCE: 62<br>gcttgaaccc aggaga | | 16 |
| SEQ ID NO: 63<br>FEATURE<br>misc_feature<br><br>source | moltype = DNA  length = 17<br>Location/Qualifiers<br>1..17<br>note = Synthetic Sequence<br>1..17<br>mol_type = other DNA<br>organism = synthetic construct | |
| SEQUENCE: 63<br>acacccgatc cactggg | | 17 |
| SEQ ID NO: 64<br>FEATURE<br>misc_feature<br><br>source | moltype = DNA  length = 14<br>Location/Qualifiers<br>1..14<br>note = Synthetic Sequence<br>1..14<br>mol_type = other DNA<br>organism = synthetic construct | |
| SEQUENCE: 64<br>gctgcatcaa cccc | | 14 |
| SEQ ID NO: 65<br>FEATURE<br>misc_feature<br><br>source | moltype = DNA  length = 16<br>Location/Qualifiers<br>1..16<br>note = Synthetic Sequence<br>1..16<br>mol_type = other DNA<br>organism = synthetic construct | |
| SEQUENCE: 65<br>gccacaaaca gaaata | | 16 |
| SEQ ID NO: 66<br>FEATURE<br>misc_feature<br><br>source | moltype = DNA  length = 15<br>Location/Qualifiers<br>1..15<br>note = Synthetic Sequence<br>1..15<br>mol_type = other DNA<br>organism = synthetic construct | |
| SEQUENCE: 66<br>ggtggctcat gcctg | | 15 |
| SEQ ID NO: 67<br>FEATURE<br>misc_feature<br><br>source | moltype = DNA  length = 16<br>Location/Qualifiers<br>1..16<br>note = Synthetic Sequence<br>1..16<br>mol_type = other DNA<br>organism = synthetic construct | |
| SEQUENCE: 67<br>gatttgcaca gctcat | | 16 |
| SEQ ID NO: 68<br>FEATURE<br>misc_feature<br><br>source | moltype = DNA  length = 15<br>Location/Qualifiers<br>1..15<br>note = Synthetic Sequence<br>1..15<br>mol_type = other DNA<br>organism = synthetic construct | |
| SEQUENCE: 68 | | | aagctctgag gagca                                                                15

SEQ ID NO: 69           moltype = DNA   length = 13
FEATURE                 Location/Qualifiers
misc_feature            1..13
                        note = Synthetic Sequence
source                  1..13
                        mol_type = other DNA
                        organism = synthetic construct
SEQUENCE: 69
ccctagctgt ccc                                                                  13

SEQ ID NO: 70           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 70
gcctagcatg ctag                                                                 14

SEQ ID NO: 71           moltype = DNA   length = 15
FEATURE                 Location/Qualifiers
misc_feature            1..15
                        note = Synthetic Sequence
source                  1..15
                        mol_type = other DNA
                        organism = synthetic construct
SEQUENCE: 71
atgggcttca cggat                                                                15

SEQ ID NO: 72           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 72
gaaactatgc ctgc                                                                 14

SEQ ID NO: 73           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 73
gcaccattgc tccc                                                                 14

SEQ ID NO: 74           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 74
gacatgcaac tcag                                                                 14

SEQ ID NO: 75           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 75
acaccactag gggt                                                                 14

SEQ ID NO: 76           moltype = DNA   length = 14
FEATURE                 Location/Qualifiers
misc_feature            1..14
                        note = Synthetic Sequence
source                  1..14
                        mol_type = other DNA
                        organism = synthetic construct

```
SEQUENCE: 76
gtctgctaga cagg                                                          14

SEQ ID NO: 77          moltype = DNA  length = 15
FEATURE                Location/Qualifiers
misc_feature           1..15
                       note = Synthetic Sequence
source                 1..15
                       mol_type = other DNA
                       organism = synthetic construct
SEQUENCE: 77
ggcctagaca ggctg                                                         15

SEQ ID NO: 78          moltype = DNA  length = 15
FEATURE                Location/Qualifiers
misc_feature           1..15
                       note = Synthetic Sequence
source                 1..15
                       mol_type = other DNA
                       organism = synthetic construct
SEQUENCE: 78
gaggcattct tatcg                                                         15

SEQ ID NO: 79          moltype = DNA  length = 15
FEATURE                Location/Qualifiers
misc_feature           1..15
                       note = Synthetic Sequence
source                 1..15
                       mol_type = other DNA
                       organism = synthetic construct
SEQUENCE: 79
gcctggaaac gttcc                                                         15

SEQ ID NO: 80          moltype = DNA  length = 14
FEATURE                Location/Qualifiers
misc_feature           1..14
                       note = Synthetic Sequence
source                 1..14
                       mol_type = other DNA
                       organism = synthetic construct
SEQUENCE: 80
gtgctctgac aata                                                          14

SEQ ID NO: 81          moltype = DNA  length = 14
FEATURE                Location/Qualifiers
misc_feature           1..14
                       note = Synthetic Sequence
source                 1..14
                       mol_type = other DNA
                       organism = synthetic construct
SEQUENCE: 81
gttttgcagc ctcc                                                          14

SEQ ID NO: 82          moltype = DNA  length = 15
FEATURE                Location/Qualifiers
misc_feature           1..15
                       note = Synthetic Sequence
source                 1..15
                       mol_type = other DNA
                       organism = synthetic construct
SEQUENCE: 82
acagctgtgg aacgt                                                         15

SEQ ID NO: 83          moltype = DNA  length = 15
FEATURE                Location/Qualifiers
misc_feature           1..15
                       note = Synthetic Sequence
source                 1..15
                       mol_type = other DNA
                       organism = synthetic construct
SEQUENCE: 83
ggctctcttc ctcct                                                         15

SEQ ID NO: 84          moltype = DNA  length = 15
FEATURE                Location/Qualifiers
misc_feature           1..15
                       note = Synthetic Sequence
source                 1..15
                       mol_type = other DNA
```

```
                          organism = synthetic construct
SEQUENCE: 84
ctatcccaaa actct                                                              15

SEQ ID NO: 85             moltype = DNA   length = 14
FEATURE                   Location/Qualifiers
misc_feature              1..14
                          note = Synthetic Sequence
source                    1..14
                          mol_type = other DNA
                          organism = synthetic construct
SEQUENCE: 85
gaaaaactat gtat                                                               14

SEQ ID NO: 86             moltype = DNA   length = 15
FEATURE                   Location/Qualifiers
misc_feature              1..15
                          note = Synthetic Sequence
source                    1..15
                          mol_type = other DNA
                          organism = synthetic construct
SEQUENCE: 86
aggcaggctg gttga                                                              15

SEQ ID NO: 87             moltype = DNA   length = 14
FEATURE                   Location/Qualifiers
misc_feature              1..14
                          note = Synthetic Sequence
source                    1..14
                          mol_type = other DNA
                          organism = synthetic construct
SEQUENCE: 87
caatacaacc acgc                                                               14

SEQ ID NO: 88             moltype = DNA   length = 15
FEATURE                   Location/Qualifiers
misc_feature              1..15
                          note = Synthetic Sequence
source                    1..15
                          mol_type = other DNA
                          organism = synthetic construct
SEQUENCE: 88
atgacggact caact                                                              15

SEQ ID NO: 89             moltype = DNA   length = 14
FEATURE                   Location/Qualifiers
misc_feature              1..14
                          note = Synthetic Sequence
source                    1..14
                          mol_type = other DNA
                          organism = synthetic construct
SEQUENCE: 89
cacaacattt gtaa                                                               14

SEQ ID NO: 90             moltype = DNA   length = 14
FEATURE                   Location/Qualifiers
misc_feature              1..14
                          note = Synthetic Sequence
source                    1..14
                          mol_type = other DNA
                          organism = synthetic construct
SEQUENCE: 90
atttccagtg caca                                                               14

SEQ ID NO: 91             moltype = DNA   length = 20
FEATURE                   Location/Qualifiers
misc_feature              1..20
                          note = Synthetic Sequence
source                    1..20
                          mol_type = other DNA
                          organism = synthetic construct
SEQUENCE: 91
gtttagctca cccgtgagcc                                                         20

SEQ ID NO: 92             moltype = DNA   length = 20
FEATURE                   Location/Qualifiers
misc_feature              1..20
                          note = Synthetic Sequence
source                    1..20
```

```
                            mol_type = other DNA
                            organism = synthetic construct
SEQUENCE: 92
cccaatatta ttgttctctg                                                       20

SEQ ID NO: 93               moltype = DNA   length = 20
FEATURE                     Location/Qualifiers
misc_feature                1..20
                            note = Synthetic Sequence
source                      1..20
                            mol_type = other DNA
                            organism = synthetic construct
SEQUENCE: 93
ggggtgggat agggatacg                                                        20

SEQ ID NO: 94               moltype = DNA   length = 20
FEATURE                     Location/Qualifiers
misc_feature                1..20
                            note = Synthetic Sequence
source                      1..20
                            mol_type = other DNA
                            organism = synthetic construct
SEQUENCE: 94
ggatccccct ctacatttaa                                                       20

SEQ ID NO: 95               moltype = DNA   length = 20
FEATURE                     Location/Qualifiers
misc_feature                1..20
                            note = Synthetic Sequence
source                      1..20
                            mol_type = other DNA
                            organism = synthetic construct
SEQUENCE: 95
gtgatcttgt acaaatcatt                                                       20

SEQ ID NO: 96               moltype = DNA   length = 20
FEATURE                     Location/Qualifiers
misc_feature                1..20
                            note = Synthetic Sequence
source                      1..20
                            mol_type = other DNA
                            organism = synthetic construct
SEQUENCE: 96
ctacacagaa tctgttagaa                                                       20

SEQ ID NO: 97               moltype = DNA   length = 20
FEATURE                     Location/Qualifiers
misc_feature                1..20
                            note = Synthetic Sequence
source                      1..20
                            mol_type = other DNA
                            organism = synthetic construct
SEQUENCE: 97
taagctagag aatagatctc                                                       20

SEQ ID NO: 98               moltype = DNA   length = 20
FEATURE                     Location/Qualifiers
misc_feature                1..20
                            note = Synthetic Sequence
source                      1..20
                            mol_type = other DNA
                            organism = synthetic construct
SEQUENCE: 98
tcaatacact taatgattta                                                       20

SEQ ID NO: 99               moltype = DNA   length = 25
FEATURE                     Location/Qualifiers
misc_feature                1..25
                            note = Synthetic Sequence
source                      1..25
                            mol_type = other DNA
                            organism = synthetic construct
SEQUENCE: 99
caccgggagc cacgaaaaca gatcc                                                 25

SEQ ID NO: 100              moltype = DNA   length = 25
FEATURE                     Location/Qualifiers
misc_feature                1..25
                            note = Synthetic Sequence
```

```
                          source              1..25
                                              mol_type = other DNA
                                              organism = synthetic construct
SEQUENCE: 100
caccgcgaaa acagatccag ggaca                                              25

SEQ ID NO: 101            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 101
caccgagatc cagggacacg gtgct                                              25

SEQ ID NO: 102            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 102
caccggacac ggtgctagga cagtg                                              25

SEQ ID NO: 103            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 103
caccggaaaa tgacccaaca gcctc                                              25

SEQ ID NO: 104            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 104
caccggcctg gccggcctga ccact                                              25

SEQ ID NO: 105            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 105
caccgctgag cactgaaggc ctggc                                              25

SEQ ID NO: 106            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 106
caccgtggtt tccactgagc actga                                              25

SEQ ID NO: 107            moltype = DNA   length = 25
FEATURE                   Location/Qualifiers
misc_feature              1..25
                          note = Synthetic Sequence
source                    1..25
                          mol_type = other DNA
                          organism = synthetic construct
SEQUENCE: 107
caccggatag ccaggagtcc tttcg                                              25

SEQ ID NO: 108            moltype = DNA   length = 25
FEATURE                   Location/Qualifiers
misc_feature              1..25
```

```
                    note = Synthetic Sequence
source              1..25
                    mol_type = other DNA
                    organism = synthetic construct
SEQUENCE: 108
caccggcgct tccagtgctc agact                                              25

SEQ ID NO: 109      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 109
caccgcagtg ctcagactag ggaag                                              25

SEQ ID NO: 110      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 110
caccggcccc tcctccttca gagcc                                              25

SEQ ID NO: 111      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 111
caccgtcctt cagagccagg agtcc                                              25

SEQ ID NO: 112      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 112
caccgtggtt tccgagcttg accct                                              25

SEQ ID NO: 113      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 113
caccgctgca gagtatctgc tgggg                                              25

SEQ ID NO: 114      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 114
caccgcgttc ctgcagagta tctgc                                              25

SEQ ID NO: 115      moltype = DNA  length = 25
FEATURE             Location/Qualifiers
misc_feature        1..25
                    note = Synthetic Sequence
source              1..25
                    mol_type = other DNA
                    organism = synthetic construct
SEQUENCE: 115
aaacggatct gttttcgtgg ctccc                                              25

SEQ ID NO: 116      moltype = DNA  length = 25
FEATURE             Location/Qualifiers
```

```
                           -continued misc_feature               1..25
                           note = Synthetic Sequence
source                     1..25
                           mol_type = other DNA
                           organism = synthetic construct
SEQUENCE: 116
aaactgtccc tggatctgtt ttcgc                                         25

SEQ ID NO: 117             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 117
aaacagcacc gtgtccctgg atctc                                         25

SEQ ID NO: 118             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 118
aaaccactgt cctagcaccg tgtcc                                         25

SEQ ID NO: 119             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 119
aaacgaggct gttgggtcat tttcc                                         25

SEQ ID NO: 120             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 120
aaacagtggt caggccggcc aggcc                                         25

SEQ ID NO: 121             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 121
aaacgccagg ccttcagtgc tcagc                                         25

SEQ ID NO: 122             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 122
aaactcagtg ctcagtggaa accac                                         25

SEQ ID NO: 123             moltype = DNA   length = 25
FEATURE                    Location/Qualifiers
misc_feature               1..25
                           note = Synthetic Sequence
source                     1..25
                           mol_type = other DNA
                           organism = synthetic construct
SEQUENCE: 123
aaaccgaaag gactcctggc tatcc                                         25

SEQ ID NO: 124             moltype = DNA   length = 25
```

```
                              -continued
FEATURE              Location/Qualifiers
misc_feature         1..25
                     note = Synthetic Sequence
source               1..25
                     mol_type = other DNA
                     organism = synthetic construct
SEQUENCE: 124
aaacagtctg agcactggaa gcgcc                                    25

SEQ ID NO: 125       moltype = DNA   length = 25
FEATURE              Location/Qualifiers
misc_feature         1..25
                     note = Synthetic Sequence
source               1..25
                     mol_type = other DNA
                     organism = synthetic construct
SEQUENCE: 125
aaaccttccc tagtctgagc actgc                                    25

SEQ ID NO: 126       moltype = DNA   length = 25
FEATURE              Location/Qualifiers
misc_feature         1..25
                     note = Synthetic Sequence
source               1..25
                     mol_type = other DNA
                     organism = synthetic construct
SEQUENCE: 126
aaacggctct gaaggaggag gggcc                                    25

SEQ ID NO: 127       moltype = DNA   length = 25
FEATURE              Location/Qualifiers
misc_feature         1..25
                     note = Synthetic Sequence
source               1..25
                     mol_type = other DNA
                     organism = synthetic construct
SEQUENCE: 127
aaacggactc ctggctctga aggac                                    25

SEQ ID NO: 128       moltype = DNA   length = 25
FEATURE              Location/Qualifiers
misc_feature         1..25
                     note = Synthetic Sequence
source               1..25
                     mol_type = other DNA
                     organism = synthetic construct
SEQUENCE: 128
aaacagggtc aagctcggaa accac                                    25

SEQ ID NO: 129       moltype = DNA   length = 25
FEATURE              Location/Qualifiers
misc_feature         1..25
                     note = Synthetic Sequence
source               1..25
                     mol_type = other DNA
                     organism = synthetic construct
SEQUENCE: 129
aaaccccag cagatactct gcagc                                     25

SEQ ID NO: 130       moltype = DNA   length = 25
FEATURE              Location/Qualifiers
misc_feature         1..25
                     note = Synthetic Sequence
source               1..25
                     mol_type = other DNA
                     organism = synthetic construct
SEQUENCE: 130
aaacgcagat actctgcagg aacgc                                    25

SEQ ID NO: 131       moltype = DNA   length = 20
FEATURE              Location/Qualifiers
misc_feature         1..20
                     note = Synthetic Sequence
source               1..20
                     mol_type = other DNA
                     organism = synthetic construct
SEQUENCE: 131
tcccctccca gaaagacctg                                          20
```

```
SEQ ID NO: 132         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 132
tgggctccaa gcaatcctgg                                                 20

SEQ ID NO: 133         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 133
gtggctcagg aggtacctgg                                                 20

SEQ ID NO: 134         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 134
gagccacgaa aacagatcca                                                 20

SEQ ID NO: 135         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 135
aagtgaacgg ggaagggagg                                                 20

SEQ ID NO: 136         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 136
gacaaaagcc gaagtccagg                                                 20

SEQ ID NO: 137         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 137
gtggttgata aacccacgtg                                                 20

SEQ ID NO: 138         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 138
tgggaacagc cacagcaggg                                                 20

SEQ ID NO: 139         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 139
gcaggggaac ggggatgcag                                                 20
```

```
SEQ ID NO: 140          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 140
gagatggtgg acgaggaagg                                                   20

SEQ ID NO: 141          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 141
gagatggctc caggaaatgg                                                   20

SEQ ID NO: 142          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 142
taaggaatct gcctaacagg                                                   20

SEQ ID NO: 143          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 143
tcaggagact aggaaggagg                                                   20

SEQ ID NO: 144          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 144
tataaggtgg tcccagctcg                                                   20

SEQ ID NO: 145          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 145
ctggaagatg ccatgacagg                                                   20

SEQ ID NO: 146          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 146
gcacagacta gagaggtaag                                                   20

SEQ ID NO: 147          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 147
```

```
                                          -continued
acagactaga gaggtaaggg                                                    20

SEQ ID NO: 148          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 148
gagaggtgac ccgaatccac                                                    20

SEQ ID NO: 149          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 149
gcacaggccc cagaaggaga                                                    20

SEQ ID NO: 150          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 150
ccggagagga cccagacacg                                                    20

SEQ ID NO: 151          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 151
gagaggaccc agacacgggg                                                    20

SEQ ID NO: 152          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 152
gcaacacagc agagagcaag                                                    20

SEQ ID NO: 153          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 153
gaagagggag tggaggaaga                                                    20

SEQ ID NO: 154          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 154
aagacggaac ctgaaggagg                                                    20

SEQ ID NO: 155          moltype = DNA   length = 20
FEATURE                 Location/Qualifiers
misc_feature            1..20
                        note = Synthetic Sequence
source                  1..20
                        mol_type = other DNA
                        organism = synthetic construct
```

```
SEQUENCE: 155
agaaagcggc acaggcccag                                                    20

SEQ ID NO: 156          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 156
gggaaacagt gggccagagg                                                    20

SEQ ID NO: 157          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 157
gtccggactc aggagagaga                                                    20

SEQ ID NO: 158          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 158
ggcacagcaa gggcactcgg                                                    20

SEQ ID NO: 159          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 159
gaagagggga agtcgaggga                                                    20

SEQ ID NO: 160          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 160
gggaatggta aggaggcctg                                                    20

SEQ ID NO: 161          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 161
gcagagtggt cagcacagag                                                    20

SEQ ID NO: 162          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 162
gcacagagtg gctaagccca                                                    20

SEQ ID NO: 163          moltype = DNA  length = 20
FEATURE                 Location/Qualifiers
misc_feature            1..20
                        note = Synthetic Sequence
source                  1..20
                        mol_type = other DNA
```

```
                        -continued
                        organism = synthetic construct
SEQUENCE: 163
gacggggtgt cagcataggg                                               20

SEQ ID NO: 164          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 164
gcccagggcc aggaacgacg                                               20

SEQ ID NO: 165          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 165
ggtggagtcc agcacggcgc                                               20

SEQ ID NO: 166          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 166
acaggccgcc aggaactcgg                                               20

SEQ ID NO: 167          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 167
actaggaagt gtgtagcacc                                               20

SEQ ID NO: 168          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 168
atgaatagca gactgccccg                                               20

SEQ ID NO: 169          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 169
acacccctaa aagcacagtg                                               20

SEQ ID NO: 170          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 170
caaggagttc cagcaggtgg                                               20

SEQ ID NO: 171          moltype = DNA  length = 20
FEATURE                 Location/Qualifiers
misc_feature            1..20
                        note = Synthetic Sequence
source                  1..20
```

```
                        mol_type = other DNA
                        organism = synthetic construct
SEQUENCE: 171
aaggagttcc agcaggtggg                                                   20

SEQ ID NO: 172          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 172
tggaaagagg agggaagagg                                                   20

SEQ ID NO: 173          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 173
tcgaattcct aactgccccg                                                   20

SEQ ID NO: 174          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 174
gacctgccca gcacaccctg                                                   20

SEQ ID NO: 175          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 175
ggagcagctg cggcagtggg                                                   20

SEQ ID NO: 176          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 176
gggagggaga gcttggcagg                                                   20

SEQ ID NO: 177          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 177
gttacgtggc caagaagcag                                                   20

SEQ ID NO: 178          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 178
gctgaacaga gaagagctgg                                                   20

SEQ ID NO: 179          moltype = DNA   length = 20
FEATURE                 Location/Qualifiers
misc_feature            1..20
                        note = Synthetic Sequence
```

```
source                   1..20
                         mol_type = other DNA
                         organism = synthetic construct
SEQUENCE: 179
tctgagggtg gagggactgg                                                   20

SEQ ID NO: 180           moltype = DNA  length = 20
FEATURE                  Location/Qualifiers
misc_feature             1..20
                         note = Synthetic Sequence
source                   1..20
                         mol_type = other DNA
                         organism = synthetic construct
SEQUENCE: 180
ggagaggtga gggacttggg                                                   20

SEQ ID NO: 181           moltype = DNA  length = 20
FEATURE                  Location/Qualifiers
misc_feature             1..20
                         note = Synthetic Sequence
source                   1..20
                         mol_type = other DNA
                         organism = synthetic construct
SEQUENCE: 181
gtgaaccagg cagacaacga                                                   20

SEQ ID NO: 182           moltype = DNA  length = 20
FEATURE                  Location/Qualifiers
misc_feature             1..20
                         note = Synthetic Sequence
source                   1..20
                         mol_type = other DNA
                         organism = synthetic construct
SEQUENCE: 182
caggtacctc ctgagccacg                                                   20

SEQ ID NO: 183           moltype = DNA  length = 20
FEATURE                  Location/Qualifiers
misc_feature             1..20
                         note = Synthetic Sequence
source                   1..20
                         mol_type = other DNA
                         organism = synthetic construct
SEQUENCE: 183
gggggagtag gggcatgcag                                                   20

SEQ ID NO: 184           moltype = DNA  length = 20
FEATURE                  Location/Qualifiers
misc_feature             1..20
                         note = Synthetic Sequence
source                   1..20
                         mol_type = other DNA
                         organism = synthetic construct
SEQUENCE: 184
gcaaatggcc agcaagggtg                                                   20

SEQ ID NO: 185           moltype = DNA  length = 25
FEATURE                  Location/Qualifiers
misc_feature             1..25
                         note = Synthetic Sequence
source                   1..25
                         mol_type = other DNA
                         organism = synthetic construct
SEQUENCE: 185
caccgaatcg agaagcgact cgaca                                             25

SEQ ID NO: 186           moltype = DNA  length = 25
FEATURE                  Location/Qualifiers
misc_feature             1..25
                         note = Synthetic Sequence
source                   1..25
                         mol_type = other DNA
                         organism = synthetic construct
SEQUENCE: 186
caccggtccc tgggcgttgc cctgc                                             25

SEQ ID NO: 187           moltype = DNA  length = 25
FEATURE                  Location/Qualifiers
misc_feature             1..25
```

```
                           note = Synthetic Sequence
source                     1..25
                           mol_type = other DNA
                           organism = synthetic construct
SEQUENCE: 187
caccgccctg ggcgttgccc tgcag                                          25

SEQ ID NO: 188             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 188
caccgccgtg ggaagataaa ctaat                                          25

SEQ ID NO: 189             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 189
caccgtcccc tgcagggcaa cgccc                                          25

SEQ ID NO: 190             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 190
caccggtcga gtcgcttctc gatta                                          25

SEQ ID NO: 191             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 191
caccgctgct gcctcccgtc ttgta                                          25

SEQ ID NO: 192             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 192
caccggagtg ccgcaatacc tttat                                          25

SEQ ID NO: 193             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 193
caccgacact ttggtggtgc agcaa                                          25

SEQ ID NO: 194             moltype = DNA  length = 25
FEATURE                    Location/Qualifiers
misc_feature               1..25
                           note = Synthetic Sequence
source                     1..25
                           mol_type = other DNA
                           organism = synthetic construct
SEQUENCE: 194
caccgtctca aatggtataa aactc                                          25

SEQ ID NO: 195             moltype = DNA  length = 25
FEATURE                    Location/Qualifiers
```

| | | |
|---|---|---|
| misc_feature | 1..25 | |
| | note = Synthetic Sequence | |
| source | 1..25 | |
| | mol_type = other DNA | |
| | organism = synthetic construct | |
| SEQUENCE: 195 | | |
| caccgaatcc cgcccataat cgaga | | 25 |
| | | |
| SEQ ID NO: 196 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 196 | | |
| caccgtcccg cccataatcg agaag | | 25 |
| | | |
| SEQ ID NO: 197 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 197 | | |
| caccgcccat aatcgagaag cgact | | 25 |
| | | |
| SEQ ID NO: 198 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 198 | | |
| caccggagaa gcgactcgac atgga | | 25 |
| | | |
| SEQ ID NO: 199 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 199 | | |
| caccggaagc gactcgacat ggagg | | 25 |
| | | |
| SEQ ID NO: 200 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 200 | | |
| caccggcgac tcgacatgga ggcga | | 25 |
| | | |
| SEQ ID NO: 201 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 201 | | |
| aaactgtcga gtcgcttctc gattc | | 25 |
| | | |
| SEQ ID NO: 202 | moltype = DNA  length = 25 | |
| FEATURE | Location/Qualifiers | |
| misc_feature | 1..25 | |
| | note = Synthetic Sequence | |
| source | 1..25 | |
| | mol_type = other DNA | |
| | organism = synthetic construct | |
| SEQUENCE: 202 | | |
| aaacgcaggg caacgcccag ggacc | | 25 |
| | | |
| SEQ ID NO: 203 | moltype = DNA  length = 25 | |

```
FEATURE                 Location/Qualifiers
misc_feature            1..25
                        note = Synthetic Sequence
source                  1..25
                        mol_type = other DNA
                        organism = synthetic construct
SEQUENCE: 203
aaacctgcag ggcaacgccc agggc                                               25

SEQ ID NO: 204          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 204
aaacattagt ttatcttccc acggc                                               25

SEQ ID NO: 205          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 205
aaacgggcgt tgccctgcag gggac                                               25

SEQ ID NO: 206          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 206
aaactaatcg agaagcgact cgacc                                               25

SEQ ID NO: 207          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 207
aaactacaag acgggaggca gcagc                                               25

SEQ ID NO: 208          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 208
aaacataaag gtattgcggc actcc                                               25

SEQ ID NO: 209          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 209
aaacttgctg caccaccaaa gtgtc                                               25

SEQ ID NO: 210          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 210
aaacgagttt tataccattt gagac                                               25
```

```
SEQ ID NO: 211          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 211
aaactctcga ttatgggcgg gattc                                               25

SEQ ID NO: 212          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 212
aaaccttctc gattatgggc gggac                                               25

SEQ ID NO: 213          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 213
aaacagtcgc ttctcgatta tgggc                                               25

SEQ ID NO: 214          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 214
aaactccatg tcgagtcgct tctcc                                               25

SEQ ID NO: 215          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 215
aaaccctcca tgtcgagtcg cttcc                                               25

SEQ ID NO: 216          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 216
aaactcgcct ccatgtcgag tcgcc                                               25

SEQ ID NO: 217          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 217
caccgacagg gttaatgtga agtcc                                               25

SEQ ID NO: 218          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 218
caccgtcccc ctctacattt aaagt                                               25
```

```
SEQ ID NO: 219          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 219
caccgcattt aaagttggtt taagt                                              25

SEQ ID NO: 220          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 220
caccgttaga aaatataaag aataa                                              25

SEQ ID NO: 221          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 221
caccgtaaat gcttactggt ttgaa                                              25

SEQ ID NO: 222          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 222
caccgtcctg ggtccagaaa aagat                                              25

SEQ ID NO: 223          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 223
caccgttggg tggtgagcat ctgtg                                              25

SEQ ID NO: 224          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 224
caccgcgggg agagtggaga aaaag                                              25

SEQ ID NO: 225          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 225
caccggttaa aactctttag acaac                                              25

SEQ ID NO: 226          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 226
```

```
caccggaaaa tccccactaa gatcc                                        25

SEQ ID NO: 227          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 227
aaacggactt cacattaacc ctgtc                                        25

SEQ ID NO: 228          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 228
aaacacttta aatgtagagg gggac                                        25

SEQ ID NO: 229          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 229
aaacacttaa accaacttta aatgc                                        25

SEQ ID NO: 230          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 230
aaacttattc tttatatttt ctaac                                        25

SEQ ID NO: 231          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 231
aaacttcaaa ccagtaagca tttac                                        25

SEQ ID NO: 232          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 232
aaacatcttt ttctggaccc aggac                                        25

SEQ ID NO: 233          moltype = DNA   length = 25
FEATURE                 Location/Qualifiers
misc_feature            1..25
                        note = Synthetic Sequence
source                  1..25
                        mol_type = other DNA
                        organism = synthetic construct
SEQUENCE: 233
aaaccacaga tgctcaccac ccaac                                        25

SEQ ID NO: 234          moltype = DNA   length = 25
FEATURE                 Location/Qualifiers
misc_feature            1..25
                        note = Synthetic Sequence
source                  1..25
                        mol_type = other DNA
                        organism = synthetic construct
```

```
SEQUENCE: 234
aaacctttt ctccactctc cccgc                                              25

SEQ ID NO: 235          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 235
aaacgttgtc taaagagttt taacc                                             25

SEQ ID NO: 236          moltype = DNA  length = 25
FEATURE                 Location/Qualifiers
misc_feature            1..25
                        note = Synthetic Sequence
source                  1..25
                        mol_type = other DNA
                        organism = synthetic construct
SEQUENCE: 236
aaacggatct tagtggggat tttcc                                             25

SEQ ID NO: 237          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 237
agtagcagta atgaagctgg                                                   20

SEQ ID NO: 238          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 238
atacccagac gagaaagctg                                                   20

SEQ ID NO: 239          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 239
tacccagacg agaaagctga                                                   20

SEQ ID NO: 240          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 240
ggtggtgagc atctgtgtgg                                                   20

SEQ ID NO: 241          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 241
aaatgagaag aagaggcaca                                                   20

SEQ ID NO: 242          moltype = DNA  length = 20
FEATURE                 Location/Qualifiers
misc_feature            1..20
                        note = Synthetic Sequence
source                  1..20
                        mol_type = other DNA
```

```
                        organism = synthetic construct
SEQUENCE: 242
cttgtggcct gggagagctg                                           20

SEQ ID NO: 243          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 243
gctgtagaag gagacagagc                                           20

SEQ ID NO: 244          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 244
gagctggttg ggaagacatg                                           20

SEQ ID NO: 245          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 245
ctggtttggga agacatgggg                                          20

SEQ ID NO: 246          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 246
cgtgaggatg ggaaggaggg                                           20

SEQ ID NO: 247          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 247
atgcagagtc agcagaactg                                           20

SEQ ID NO: 248          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 248
aagacatcaa gcacagaagg                                           20

SEQ ID NO: 249          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 249
tcaagcacag aaggaggagg                                           20

SEQ ID NO: 250          moltype = DNA   length = 20
FEATURE                 Location/Qualifiers
misc_feature            1..20
                        note = Synthetic Sequence
source                  1..20
```

-continued

```
                              mol_type = other DNA
                              organism = synthetic construct
SEQUENCE: 250
aaccgtcaat aggcaaaggg                                                        20

SEQ ID NO: 251                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 251
ccgtatttca gactgaatgg                                                        20

SEQ ID NO: 252                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 252
gagaggacag gtgctacagg                                                        20

SEQ ID NO: 253                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 253
aaccaaggaa gggcaggagg                                                        20

SEQ ID NO: 254                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 254
gacctctggg tggagacaga                                                        20

SEQ ID NO: 255                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 255
cagatgacca tgacaagcag                                                        20

SEQ ID NO: 256                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 256
aacaccagtg agtagagcgg                                                        20

SEQ ID NO: 257                moltype = DNA   length = 20
FEATURE                       Location/Qualifiers
misc_feature                  1..20
                              note = Synthetic Sequence
source                        1..20
                              mol_type = other DNA
                              organism = synthetic construct
SEQUENCE: 257
aggaccttga agcacagaga                                                        20

SEQ ID NO: 258                moltype = DNA   length = 20
FEATURE                       Location/Qualifiers
misc_feature                  1..20
                              note = Synthetic Sequence
```

```
source                       1..20
                             mol_type = other DNA
                             organism = synthetic construct
SEQUENCE: 258
tacagaggca gactaaccca                                                 20

SEQ ID NO: 259               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 259
acagaggcag actaacccag                                                 20

SEQ ID NO: 260               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 260
taaatgacgt gctagacctg                                                 20

SEQ ID NO: 261               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 261
agtaaccact caggacaggg                                                 20

SEQ ID NO: 262               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 262
accacaaaac agaaacacca                                                 20

SEQ ID NO: 263               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 263
gtttgaagac aagcctgagg                                                 20

SEQ ID NO: 264               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 264
gctgaacccc aaaagacagg                                                 20

SEQ ID NO: 265               moltype = DNA  length = 20
FEATURE                      Location/Qualifiers
misc_feature                 1..20
                             note = Synthetic Sequence
source                       1..20
                             mol_type = other DNA
                             organism = synthetic construct
SEQUENCE: 265
gcagctgaga cacacaccag                                                 20

SEQ ID NO: 266               moltype = DNA  length = 20
FEATURE                      Location/Qualifiers
misc_feature                 1..20
```

```
                        note = Synthetic Sequence
source                  1..20
                        mol_type = other DNA
                        organism = synthetic construct
SEQUENCE: 266
aggacacccc aaagaagctg                                                   20

SEQ ID NO: 267          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 267
ggacacccca agaagctga                                                    20

SEQ ID NO: 268          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 268
ccagtgcaat ggacagaaga                                                   20

SEQ ID NO: 269          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 269
agaagaggga gcctgcaagt                                                   20

SEQ ID NO: 270          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 270
gtgtttgggc cctagagcga                                                   20

SEQ ID NO: 271          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 271
catgtgcctg gtgcaatgca                                                   20

SEQ ID NO: 272          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 272
tacaaagagg aagataagtg                                                   20

SEQ ID NO: 273          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 273
gtcacagaat acaccactag                                                   20

SEQ ID NO: 274          moltype = DNA   length = 20
FEATURE                 Location/Qualifiers
```

```
misc_feature            1..20
                        note = Synthetic Sequence
source                  1..20
                        mol_type = other DNA
                        organism = synthetic construct
SEQUENCE: 274
gggttaccct ggacatggaa                                                    20

SEQ ID NO: 275          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 275
catggaaggg tattcactcg                                                    20

SEQ ID NO: 276          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 276
agagtggcct agacaggctg                                                    20

SEQ ID NO: 277          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 277
catgctggac agctcggcag                                                    20

SEQ ID NO: 278          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 278
agtgaaagaa gagaaaattc                                                    20

SEQ ID NO: 279          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 279
tggtaagtct aagaaaccta                                                    20

SEQ ID NO: 280          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 280
cccacagcct aaccaccta                                                     20

SEQ ID NO: 281          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 281
aatatttcaa agccctaggg                                                    20

SEQ ID NO: 282          moltype = DNA  length = 20
```

```
FEATURE                 Location/Qualifiers
source                  1..20
                        mol_type = other DNA
                        organism = synthetic construct
SEQUENCE: 282
gcactcggaa cagggtctgg                                                     20

SEQ ID NO: 283          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 283
agataggagc tccaacagtg                                                     20

SEQ ID NO: 284          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 284
aagttagagc agccaggaaa                                                     20

SEQ ID NO: 285          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 285
tagagcagcc aggaaaggga                                                     20

SEQ ID NO: 286          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 286
tgaataccct tccatgtcca                                                     20

SEQ ID NO: 287          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 287
cctgcattgc accaggcaca                                                     20

SEQ ID NO: 288          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 288
tctagggccc aaacacacct                                                     20

SEQ ID NO: 289          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 289
tccctccatc tatcaaaagg                                                     20

SEQ ID NO: 290          moltype = DNA  length = 20
FEATURE                 Location/Qualifiers
```

```
misc_feature            1..20
                        note = Synthetic Sequence
source                  1..20
                        mol_type = other DNA
                        organism = synthetic construct
SEQUENCE: 290
agccctgaga cagaagcagg                                              20

SEQ ID NO: 291          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 291
gccctgagac agaagcaggt                                              20

SEQ ID NO: 292          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 292
aggagatgca gtgatacgca                                              20

SEQ ID NO: 293          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 293
acaataccaa gggtatccgg                                              20

SEQ ID NO: 294          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 294
tgataaagaa aacaaagtga                                              20

SEQ ID NO: 295          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 295
aaagaaaaca aagtgaggga                                              20

SEQ ID NO: 296          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 296
gtggcaagtg gagaaattga                                              20

SEQ ID NO: 297          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 297
caagtggaga aattgaggga                                              20

SEQ ID NO: 298          moltype = DNA  length = 20
```

```
FEATURE              Location/Qualifiers
misc_feature         1..20
                     note = Synthetic Sequence
source               1..20
                     mol_type = other DNA
                     organism = synthetic construct
SEQUENCE: 298
gtggtgatga ttgcagctgg                                                  20

SEQ ID NO: 299       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 299
ctatgtgcct gacacacagg                                                  20

SEQ ID NO: 300       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 300
gggttggacc aggaaagagg                                                  20

SEQ ID NO: 301       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 301
gatgcctgga aaggaaaga                                                   20

SEQ ID NO: 302       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 302
tagtatgcac ctgcaagagg                                                  20

SEQ ID NO: 303       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 303
tatgcacctg caagaggcgg                                                  20

SEQ ID NO: 304       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 304
agggaagaa gagaagcaga                                                   20

SEQ ID NO: 305       moltype = DNA  length = 20
FEATURE              Location/Qualifiers
misc_feature         1..20
                     note = Synthetic Sequence
source               1..20
                     mol_type = other DNA
                     organism = synthetic construct
SEQUENCE: 305
gctgaatcaa gagacaagcg                                                  20
```

```
SEQ ID NO: 306         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 306
aagcaaataa atctcctggg                                                     20

SEQ ID NO: 307         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 307
agatgagtgc tagagactgg                                                     20

SEQ ID NO: 308         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 308
ctgatggttg agcacagcag                                                     20

SEQ ID NO: 309         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 309
caaatggcca gcaagggtgg                                                     20

SEQ ID NO: 310         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 310
gcagaacctg aggatatgga                                                     20

SEQ ID NO: 311         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 311
aatacacaga atgaaaatag                                                     20

SEQ ID NO: 312         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 312
ctggtgacta gaataggcag                                                     20

SEQ ID NO: 313         moltype = DNA  length = 20
FEATURE                Location/Qualifiers
misc_feature           1..20
                       note = Synthetic Sequence
source                 1..20
                       mol_type = other DNA
                       organism = synthetic construct
SEQUENCE: 313
tggtgactag aataggcagt                                                     20
```

| SEQ ID NO: 314 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 314
taaaagaatg tgaaaagatg                    20

| SEQ ID NO: 315 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 315
tcaggagttc aagaccaccc                    20

| SEQ ID NO: 316 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 316
tgtagtccca gttatgcagg                    20

| SEQ ID NO: 317 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 317
gggttcacac cacaaatgca                    20

| SEQ ID NO: 318 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 318
ggcaaatggc cagcaagggt                    20

| SEQ ID NO: 319 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 319
agaaaccaat cccaaagcaa                    20

| SEQ ID NO: 320 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 320
gccaaggaca ccaaaaccca                    20

| SEQ ID NO: 321 | moltype = DNA length = 20 |
| --- | --- |
| FEATURE | Location/Qualifiers |
| misc_feature | 1..20 |
| | note = Synthetic Sequence |
| source | 1..20 |
| | mol_type = other DNA |
| | organism = synthetic construct |

SEQUENCE: 321

```
agtggtgata aggcaacagt                                               20

SEQ ID NO: 322         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 322
cctgagacag aagtattaag                                               20

SEQ ID NO: 323         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 323
aaggtcacac aatgaatagg                                               20

SEQ ID NO: 324         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 324
caccatacta gggaagaaga                                               20

SEQ ID NO: 325         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 325
aataccctgc ccttagtggg                                               20

SEQ ID NO: 326         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 326
ttagtggggg gtggagtggg                                               20

SEQ ID NO: 327         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 327
caataccctg cccttagtgg                                               20

SEQ ID NO: 328         moltype = DNA   length = 20
FEATURE                Location/Qualifiers
misc_feature           1..20
                       note = Synthetic Sequence
source                 1..20
                       mol_type = other DNA
                       organism = synthetic construct
SEQUENCE: 328
gtgggggtg gagtgggggg                                                20

SEQ ID NO: 329         moltype = DNA   length = 20
FEATURE                Location/Qualifiers
misc_feature           1..20
                       note = Synthetic Sequence
source                 1..20
                       mol_type = other DNA
                       organism = synthetic construct
```

```
SEQUENCE: 329
gggggggtgga gtgggggggtg                                              20

SEQ ID NO: 330          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 330
ggggtggagt gggggtggg                                                 20

SEQ ID NO: 331          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 331
gggtggagtg ggggtgggg                                                 20

SEQ ID NO: 332          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 332
gggggtgggg aaagacatcg                                                20

SEQ ID NO: 333          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 333
gcagctgtga attctgatag                                                20

SEQ ID NO: 334          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 334
gagatcagag aaaccagatg                                                20

SEQ ID NO: 335          moltype = DNA  length = 20
FEATURE                 Location/Qualifiers
misc_feature            1..20
                        note = Synthetic Sequence
source                  1..20
                        mol_type = other DNA
                        organism = synthetic construct
SEQUENCE: 335
tctatactga ttgcagccag                                                20

SEQ ID NO: 336          moltype = DNA  length = 1722
FEATURE                 Location/Qualifiers
misc_feature            1..1722
                        note = Synthetic Sequence
source                  1..1722
                        mol_type = other DNA
                        organism = synthetic construct
SEQUENCE: 336
atggcgcaac actcagatta ctccgacgat gaatttgtg ctgacaaact gtccaattat     60
tcatgcgata gcgacctcga aaacgcttcc acgtctgatg aagatagcag cgatgatgaa  120
gtaatggtga ggcctcgcac cctccgccgt cgccgcatca gctcttcgag ctctgattct  180
gaatccgata ttgagggtgg ccgcgaggag tggtcccacg tagacaatcc gccggtgctg  240
gaggacttcc taggccacca aggtctgaac actgacgcag taatcaacaa tatcgaagat  300
gcagttaaac tgtttatcgg tgacgatttc ttcgagtttc tggtggagga atctaaccgg  360
tactataacc agaatcgtaa taacttcaag ctctctaaaa agtctctgaa gtggaaggac  420
atcaccccctc aggagatgaa aaagttcctc ggtctgatcg ttctgatggg ccaagttcgc  480
```

```
aaggatcgtc gtgacgacta ttggactacc gaaccgtgga cggaaactcc atactttggc   540
aagaccatga ctcgtgaccg tttccgtcag atctggaagg cctggcactt caataacaac   600
gctgacattg tcaacgagtc tgatcgtctg tgtaaggttc gccctgtgct ggattacttc   660
gttccaaaat tcattaacat ttacaaacca catcagcagc tgtccctgga tgagggcatc   720
gtgccgtggc gcggccgcct gttcttccgt gtctataatg ctggcaagat tgtgaagtac   780
ggtatcctgg ttcgcctgct gtgcgaaagc gacactggct acatctgtaa catggaagatc   840
tactgcggcg agggcaaacg tctcctcgaa actatccaga ccgtcgtgtc tccatacacg   900
gattcctggt atcatattta catggataac tattataaca gcgtggctaa ctgtgaagct   960
ctgatgaaaa ataagttccg tatttgcggt actatccgta agaatcgtgg aattccgaaa  1020
gatttccaga ccatctccct gaaaaagggt gaaactaagt tcattcgcaa aaacgacatc  1080
ctcctgcaag tctggcagtc taaaaagcct gtatatctga tctcatctat tcacagcgct  1140
gaaatggaag aatctcagaa cattgatcgc acctccaaga aaaagatcgt caaaccgaat  1200
gcattgattg attacaacaa gcacatgaag ggcgttgatc gtgctgacca gtacctgtct  1260
tactactcta tcctgcgccg tactgtgaag tggactaaga gtctcgctat gtacatgatt  1320
aattgtgcgc tgttcaattc ttacgctgtg tataaaagcg tgcgtcagcg caaaatgggc  1380
tttaaaatgt tcctgaagca gacggctatt cactggctga ccgacgatat tccggaagat  1440
atggacattg tcccggatct ccagccggta ccgagcacca gcggtatgcg tgctaaacct  1500
ccgactagtg atccgccttg ccgtctgtct atggatatgc gtaagcatac cctgcaggca  1560
attgtgggct ctggcaaaaa gaaaaatatc ctgcgtcgtt gccgcgtatg ctctgtacac  1620
aaaactgcgtt ctgagactcg ttatatgtgt aaattttgca atattccact ccacaagggt  1680
gcgtgcttcg agaagtacca tacgctgaag aactatctcg ag                       1722

SEQ ID NO: 337          moltype = DNA  length = 1719
FEATURE                 Location/Qualifiers
misc_feature            1..1719
                        note = Synthetic Sequence
source                  1..1719
                        mol_type = other DNA
                        organism = synthetic construct
SEQUENCE: 337
atggcccagc acagcgacta ccccgacgac gagttcagag ccgataagct gagtaactac    60
agctgcgaca gcgacctgga aaacgccagc acatccgacg aggacagctc tgacgacgag   120
gtgatggtgc ggcccagaac cctgagacgg agaagaatca gcagctctag cagcgactct   180
gaatccgaca tcgagggcgg ccgggaagag tggagccacg tggacaaccc tcctgttctg   240
gaagattttc tgggccatca gggcctgaac accgacgccg tgatcaacaa catcgaggat   300
gccgtgaagc tgttcatagg agatgatttc tttgagttcc tggtcgagga atccaaccgc   360
tattacaacc agaatagaaa caacttcaag ctgagcaaga aaagcctgaa gtggaaggac   420
atcacccctc aggagatgaa aaagttcctg gactgatcg ttctgatggg acaggtgcgg   480
aaggacagaa gggatgatta ctggacaacc gaaccttgga ccgagacccc ttactttggc   540
aagaccatga ccagagacag attcagacag atctggaaag cctggcactt caacaacaat   600
gctgatatcg tgaacgagtc tgatagactg tgtaaagtgc ggccagtgtt ggattacttc   660
gtgcctaagt tcatcaacat ctataagcct caccagcagc tgagcctgga tgaaggcatc   720
gtgccctggc ggggcagact gttcttcaga gtgtacaatg ctggcaagat cgtcaaatac   780
ggcatcctgg tgcgccttct gtgcgagagc gatacaggct acatctgtaa tatggaaatc   840
tactgcggcg agggcaaaag actgctggaa accatccaga ccgtcgtttc cccttatacc   900
gacagctggt accacatcta catggacaac tactacaatt ctgtgcccaa ctgcgaggcc   960
ctgatgaaaa acaagtttag aatctgcggc acaatcagaa aaaacagagg catcctaag   1020
gacttccaga ccatctctct gaagaagggc gaaaccaagt tcatcagaaa gaacgacatc  1080
ctgctccaag tgtggcagtc caagaaaccc gtgtacctga tcagcagcat ccatagcgcc  1140
gagatggaag aaagccagaa cattgacaga acaagcaaga gaaagatcgt gaagcccaat  1200
gctctgatcg actacaacaa gcacatgaag ggcgtggacc gggccgacca gtacctgtct  1260
tattactcta tcctgagaag aacagtgaaa tggaccaaga gactggccat gtacatgatc  1320
aattgcgccc tgttcaacag ctacgccgtg tacaagtccg tgcgacaaag aaaaatggga  1380
ttcaagatgt tcctgaagca gacagccatc cactggctga cagacgacat tcctgaggac  1440
atggacattg tgccagatct gcaacctgtg cccagcacct ctggtatgag ggctaagcct  1500
cccaccagcg atcctccatg tagactgagc atggacatgc ggaagcacac cctgcaggcc  1560
atcgtcggca gcggcaagaa gaagaacatc cttagacggt gcagggtgtg cagcgtgcac  1620
aagctgcgga gcgagactcg gtacatgtgc aagttttgca acattcccct gcacaaggga  1680
gcctgcttcg agaagtacca cacactgaag aattactag                          1719

SEQ ID NO: 338          moltype = DNA  length = 1719
FEATURE                 Location/Qualifiers
misc_feature            1..1719
                        note = Synthetic Sequence
source                  1..1719
                        mol_type = other DNA
                        organism = synthetic construct
SEQUENCE: 338
atggcccagc acagcgacta ccccgacgac gagttcagag ccgataagct gagtaactac    60
agctgcgaca gcgacctgga aaacgccagc acatccgacg aggacagctc tgacgacgag   120
gtgatggtgc ggcccagaac cctgagacgg agaagaatca gcagctctag cagcgactct   180
gaatccgaca tcgagggcgg ccgggaagag tggagccacg tggacaaccc tcctgttctg   240
gaagattttc tgggccatca gggcctgaac accgacgccg tgatcaacaa catcgaggat   300
gccgtgaagc tgttcatagg agatgatttc tttgagttcc tggtcgagga atccaaccgc   360
tattacaacc agaatagaaa caacttcaag ctgagcaaga aaagcctgaa gtggaaggac   420
atcacccctc aggagatgaa aaagttcctg gactgatcg ttctgatggg acaggtgcgg   480
aaggacagaa gggatgatta ctggacaacc gaaccttgga ccgagacccc ttactttggc   540
aagaccatga ccagagacag attcagacag atctggaaag cctggcactt caacaacaat   600
gctgatatcg tgaacgagtc tgatagactg tgtaaagtgc ggccagtgtt ggattacttc   660
```

```
gtgcctaagt tcatcaacat ctataagcct caccagcagc tgagcctgga tgaaggcatc    720
gtgccctggc ggggcagact gttcttcaga gtgtacaatg ctggcaagat cgtcaaatac    780
ggcatcctgg tgcgccttct gtgcgagagc gatacaggct acatctgtaa tatgaaaatc    840
tactgcggcg agggcaaaag actgctggaa accatccaga ccgtcgtttc cccttatacc    900
gacagctggt accacatcta catggacaac tactacagcg tctgtggcca atgcgaggcc    960
ctgatgaaga caagtttag aatctgcggc acaatcagaa aaacagagg catccctaag    1020
gacttccaga ccatctctct gaagaagggg gaaaccaagt tcatcagaaa gaacgacatc    1080
ctgctccaag tgtggcagtc caagaaaccc gtgtacctga tcagcagcat ccatagcgcc    1140
gagatggaag aaagccagaa catcgacaga acaagcaaga agaagatcgt gaagcccaat    1200
gctctgatcg actacaacaa gcacatgaaa ggcgtggacc gggccgacca gtacctgtct    1260
tattactcta tcctgagaag aacagtgaaa tggaccaaga gactggccat gtacatgatc    1320
aattgcgccc tgttcaacag ctacgccgtg tacaagtccg tgcgacaaag aaaaatggga    1380
ttcaagatgt tcctgaagca gacagccatc cactggctga cagacgacat tcctgaggac    1440
atggacattg tgccagatct gcaacctgtg cccagcacct ctggtatgag agctaagcct    1500
cccaccagcg atcctccatg tagactgagc atggacatgc ggaagcacac cctgcaggcc    1560
atcgtcggca gcggcaagaa gaagaacatc cttagacggt gcagggtgtg cagcgtgcac    1620
aagctgcgga gcgagactcg gtacatgtgc aagttttgca acattcccct gcacaaggga    1680
gcctgcttcg agaagtacca caccctgaag aattactag                           1719
```

SEQ ID NO: 339 moltype = DNA length = 1716
FEATURE Location/Qualifiers
misc_feature 1..1716
 note = Synthetic Sequence
source 1..1716
 mol_type = other DNA
 organism = synthetic construct
SEQUENCE: 339

```
atgtcgcagc attcagacta tactcatgat gagttttgtg cagacaagtt gtccaattat     60
tcttgtgata gcgatcttga aaatgcgagt acaagtgatg aagattctag tgatgatgaa    120
gtaatggtgc gtcccaggac attgaggcga cgaagaattt cgagctccag ctctgactca    180
gagtcagata tagaaggcgg gagagaagaa tggtcgcatg ttgataatcc accggtctta    240
gaagattttt tagggcatca aggattaaac acagatgctg ttataaataa tatagaaagt    300
gccgtgaaat tatttatcgg agatgatttt tttgaatttc ttgtagagga gtcaaacagg    360
tattataatc aaaataggaa taatttcaaa cttttcaaaa aaagcctaaa gtggaaagat    420
ataaccctc aagagtgaa gaagttttta gggttaattg ttctcatggg acaggtgcg     480
aaagatagaa gagatgacta ttggaccacg gagccatgga cggagacgcc atattttggt    540
aaaacgatga cgagagacag gttccgacag atatggaaag cttggcactt caataataat    600
gcggatatcg taaatgaatc agatagactt tgcaaagtga gaccagtact agattatttt    660
gtgcctaaat ttataaatat ttacaaacct catcagcaat catcactaga tgaagggatc    720
gtaccttgga ggggaagatt attctttagg tgtatataatg ctggcaagat cgttaaatat    780
ggaatattgg ttcgtttgtt gtgcgaaagt gatacaggat atatctgtaa catggaaatt    840
tattgcggcg aaggaaagcg attattggaa cgatacaaa cagtagtgtc tccatacact    900
gattcgtggt accatatata tatggacaat tattataata gcgtcgcaaa tctgtgaagca    960
cttatgaaaa acaaattcag aatatgtgga acaatccgga aaaatcgagg tataccctaaa   1020
gattttcaaa caatttcttt gaaaaaaggt gaaacaaaat ttataaggaa aaatgatata   1080
ttgttacaag tgtggcaatc aaaaaagcct gtatacctga tttcttcgat tcattctgcg   1140
gagatgaaaa aagtcagaa tattgacaga acatcaaaaa agaaaattgt caaaccgaat   1200
gcactcattg actacaataa acatatgaaa ggtgttgacc gggccgacca ataccttca   1260
tattattcga tattgcggag gacggtcaaa tggacaaaaa ggttggcaat gtatatgata   1320
aattgcgcat tatttaattc ttatgcagtt tacaaatcag tgaggcaaag aaaaatgggt   1380
tttaaaatgt ttttgaaaca aacagctatc cactggttga cggatgatat tccagaggac   1440
atggacattg ttccagacct tcaaccagta ccgtctactt ctggaatgcg ggctaaacca   1500
cctacatctg atcctccatg caggctatcg atgacatga aaagcatac gttacaggca   1560
attgtcggaa gtgaaaaaa gaaaaacatt ttgagaaggt gtcgcgtatg ttccgttcat   1620
aaattgcgca gtgagacacg ctacatgtgc aaatttgca atatacctct acataaaggg   1680
gcgtgttttg aaaaatatca tacgctaaaa aactat                            1716
```

SEQ ID NO: 340 moltype = AA length = 572
FEATURE Location/Qualifiers
source 1..572
 mol_type = protein
 organism = synthetic construct
SEQUENCE: 340

```
MAQHSDYPDD EFRADKLSNY SCDSDLENAS TSDEDSSDDE VMVRPRTLRR RRISSSSSDS     60
ESDIEGGREE WSHVDNPPVL EDFLGHQGLN TDAVINNIED AVKLFIGDDF FEFLVEESNR    120
YYNQKRNNFK LSKKSLKWKD ITPQEMKKFL GLIVLMGQVR KDRRDDYWTT EPWTETPYFG    180
KTMTRDRFRQ IWKAWHFNNN ADIVNESDRL CKVRPVLDYF VPKFINIYKP HQQLSLDEGI    240
VPWRGRLFFR VYNAGKIVKY GILVRLLCES DTGYICNMEI YCGEGKRLLE TIQTVVSPYT    300
DSWYHIYMDN YYNSVANCEA LMKNKFRICG TIRKNRGIPK DFQTISLKKG ETKFIRKNDI    360
LLQVWQSKKP VYLISSIHSA EMEESQNIDR TSKKKIVKPN ALIDYNKHMK GVDRADQYLS    420
YYSILRRTVK WTKRLAMYMI NCALFNSYAV YKSVRQRKMG FKMFLKQTAI HWLTDDIPED    480
MDIVPDLQPV PSTSGMRAKP PTSDPPCRLS MDMRKHTLQA IVGSGKKKNI LRRCRVCSVH    540
KLRSETRYMC KFCNIPLHKG ACFEKYHTLK NY                                  572
```

SEQ ID NO: 341 moltype = AA length = 574
FEATURE Location/Qualifiers
source 1..574
 mol_type = protein
 organism = synthetic construct

```
SEQUENCE: 341
MAQHSDYSDD EFCADKLSNY SCDSDLENAS TSDEDSSDDE VMVRPRTLRR RRISSSSSDS    60
ESDIEGGREE WSHVDNPPVL EDFLGHQGLN TDAVINNIED AVKLFIGDDF FEFLVEESNR   120
YYNQNRNNFK LSKKSLWKD ITPQEMKKFL GLIVLMGQVR KDRRDDYWTT EPWTETPYFG    180
KTMTRDRFRQ IWKAWHFNNN ADIVNESDRL CKVRPVLDYF VPKFINIYKP HQQLSLDEGI   240
VPWRGRLFFR VYNAGKIVKY GILVRLLCES DTGYICNMEI YCGEGKRLLE TIQTVVSPYT   300
DSWYHIYMDN YYNSVANCEA LMKNKFRICG TIRKNRGIPK DFQTISLKKG ETKFIRKNDI   360
LLQVWQSKKP VYLISSIHSA EMEESQNIDR TSKKKIVKPN ALIDYNKHMK GVDRADQYLS   420
YYSILRRTVK WTKRLAMYMI NCALFNSYAV YKSVRQRKMG FKMFLKQTAI HWLTDDIPED   480
MDIVPDLQPV PSTSGMRAKP PTSDPPCRLS MDMRKHTLQA IVGSGKKKNI LRRCRVCSVH   540
KLRSETRYMC KFCNIPLHKG ACFEKYHTLK NYLE                              574

SEQ ID NO: 342        moltype =   length =
SEQUENCE: 342
000

SEQ ID NO: 343        moltype = AA   length = 507
FEATURE               Location/Qualifiers
source                1..507
                      mol_type = protein
                      organism = synthetic construct
SEQUENCE: 343
MSQHSDYSDD EFCADKLSNY SCDSDLENAS TSDEDSSDDE VMVRPRTLRR RRISSSSSDS    60
ESDIEGGREE WSHVDNPPVL EDFLGHQGLN TDAVINNIED AVKLFIGDDF FEFLVEESNR   120
KTMTRDRFRQ IWKAWHFNNN ADIVNESDRL CKVRPVLDYF VPKFINIYKP HQQLSLDEGI   180
VPWRGRLFFR VYNAGKIVKY GILVRLLCES DTGYICNMEI YCGEGKRLLE TIQTWSPYTD   240
SWYHIYMDNY YNSVANCEAL MKNKFRICGT IRKNRGIPKD FQTISLKKGE TKFIRKNDIL   300
LQVWQSKKPV YLISSHSAEM EESQNIDRTS KKKIVKPNAL IDYNKHMKGV DRADQYLSYY   360
SILRRWKWTK RLAMYMINCA LFNSYAVYKS VRQRKMGFKM FLKQTAHWLT DDIPEDMDIV   420
PDLQPVPSTS GMRAKPPTSD PPCRLSMDMR KHTLQAIVGS GKKKNILRRC RVCSVHKLRS   480
ETRYMCKFCN IPLHKGACFE KYHTLKN                                     507

SEQ ID NO: 344        moltype = DNA   length = 153
FEATURE               Location/Qualifiers
misc_feature          1..153
                      note = Synthetic Sequence
source                1..153
                      mol_type = other DNA
                      organism = synthetic construct
SEQUENCE: 344
cacttggatt gcgggaaacg agttaagtcg gctcgcgtga attgcgcgta ctccgcggga    60
gccgtcttaa ctcggttcat atagatttgc ggtggagtgc gggaaacgtg taaactcggg   120
ccgattgtaa ctgcgtatta ccaaatattt gtt                               153

SEQ ID NO: 345        moltype = DNA   length = 158
FEATURE               Location/Qualifiers
misc_feature          1..158
                      note = Synthetic Sequence
source                1..158
                      mol_type = other DNA
                      organism = synthetic construct
SEQUENCE: 345
cacttgggtt gcgggaaacg agttaagtcg gctcgcgtga attgcgcgta ctccgcggga    60
gccgtcttaa actcggttca tatagatttg cggtggagtg cgggaaacgt tgtaaactcg   120
ggccgattgt aactgcgtat taccaaatat ttcatttc                          158

SEQ ID NO: 346        moltype = DNA   length = 181
FEATURE               Location/Qualifiers
misc_feature          1..181
                      note = Synthetic Sequence
source                1..181
                      mol_type = other DNA
                      organism = synthetic construct
SEQUENCE: 346
aaatgtctgt gattgaataa attttcattt tttacacaag aaaccgaaaa tttcatttca    60
atcgaaccca tacttcaaaa gatataggca ttttaaacta actctgattt tgcgcgggaa   120
acctaaaataa ttgcccgcgc catcttatat tttggcggga aattcacccg acaccgtagt   180
g                                                                  181

SEQ ID NO: 347        moltype = DNA   length = 136
FEATURE               Location/Qualifiers
misc_feature          1..136
                      note = Synthetic Sequence
source                1..136
                      mol_type = other DNA
                      organism = synthetic construct
SEQUENCE: 347
aaacgttgta aactcgggcc gattgtaact gcgtattacc aaatatttca tttcaatcga    60
acccatactt aaaagatata ggcatttaa cgcgccatct tatattttgg cgggaaattc   120
```

```
acccgacacc gtagtg                                                       136

SEQ ID NO: 348          moltype = AA  length = 6
FEATURE                 Location/Qualifiers
VARIANT                 4
source                  1..6
                        mol_type = protein
                        organism = synthetic construct
SEQUENCE: 348
KKRXKR                                                                    6

SEQ ID NO: 349          moltype = AA  length = 7
FEATURE                 Location/Qualifiers
VARIANT                 5
source                  1..7
                        mol_type = protein
                        organism = synthetic construct
SEQUENCE: 349
KRKRXKR                                                                   7

SEQ ID NO: 350          moltype = AA  length = 9
FEATURE                 Location/Qualifiers
source                  1..9
                        mol_type = protein
                        organism = synthetic construct
SEQUENCE: 350
PAAKRVKLD                                                                 9

SEQ ID NO: 351          moltype = AA  length = 16
FEATURE                 Location/Qualifiers
source                  1..16
                        mol_type = protein
                        organism = synthetic construct
SEQUENCE: 351
KRPAATKKAG QAKKKK                                                        16

SEQ ID NO: 352          moltype = AA  length = 7
FEATURE                 Location/Qualifiers
source                  1..7
                        mol_type = protein
                        organism = synthetic construct
SEQUENCE: 352
PKKKRKV                                                                   7

SEQ ID NO: 353          moltype = AA  length = 24
FEATURE                 Location/Qualifiers
source                  1..24
                        mol_type = protein
                        organism = synthetic construct
SEQUENCE: 353
DPKKKRKVDP KKKRKVDPKK KRKV                                               24

SEQ ID NO: 354          moltype =     length =
SEQUENCE: 354
000

SEQ ID NO: 355          moltype =     length =
SEQUENCE: 355
000

SEQ ID NO: 356          moltype =     length =
SEQUENCE: 356
000

SEQ ID NO: 357          moltype =     length =
SEQUENCE: 357
000

SEQ ID NO: 358          moltype =     length =
SEQUENCE: 358
000

SEQ ID NO: 359          moltype =     length =
SEQUENCE: 359
000

SEQ ID NO: 360          moltype =     length =
SEQUENCE: 360
000
```

-continued

SEQ ID NO: 361         moltype =    length =
SEQUENCE: 361
000

SEQ ID NO: 362         moltype =    length =
SEQUENCE: 362
000

SEQ ID NO: 363         moltype =    length =
SEQUENCE: 363
000

SEQ ID NO: 364         moltype =    length =
SEQUENCE: 364
000

SEQ ID NO: 365         moltype =    length =
SEQUENCE: 365
000

SEQ ID NO: 366         moltype =    length =
SEQUENCE: 366
000

SEQ ID NO: 367         moltype =    length =
SEQUENCE: 367
000

SEQ ID NO: 368         moltype =    length =
SEQUENCE: 368
000

SEQ ID NO: 369         moltype =    length =
SEQUENCE: 369
000

SEQ ID NO: 370         moltype =    length =
SEQUENCE: 370
000

SEQ ID NO: 371         moltype =    length =
SEQUENCE: 371
000

SEQ ID NO: 372         moltype =    length =
SEQUENCE: 372
000

SEQ ID NO: 373         moltype =    length =
SEQUENCE: 373
000

SEQ ID NO: 374         moltype =    length =
SEQUENCE: 374
000

SEQ ID NO: 375         moltype =    length =
SEQUENCE: 375
000

SEQ ID NO: 376         moltype =    length =
SEQUENCE: 376
000

SEQ ID NO: 377         moltype =    length =
SEQUENCE: 377
000

SEQ ID NO: 378         moltype =    length =
SEQUENCE: 378
000

SEQ ID NO: 379         moltype =    length =
SEQUENCE: 379
000

SEQ ID NO: 380         moltype =    length =
SEQUENCE: 380

-continued

000

SEQ ID NO: 381        moltype =    length =
SEQUENCE: 381
000

SEQ ID NO: 382        moltype =    length =
SEQUENCE: 382
000

SEQ ID NO: 383        moltype =    length =
SEQUENCE: 383
000

SEQ ID NO: 384        moltype =    length =
SEQUENCE: 384
000

SEQ ID NO: 385        moltype =    length =
SEQUENCE: 385
000

SEQ ID NO: 386        moltype =    length =
SEQUENCE: 386
000

SEQ ID NO: 387        moltype =    length =
SEQUENCE: 387
000

SEQ ID NO: 388        moltype =    length =
SEQUENCE: 388
000

SEQ ID NO: 389        moltype =    length =
SEQUENCE: 389
000

SEQ ID NO: 390        moltype =    length =
SEQUENCE: 390
000

SEQ ID NO: 391        moltype =    length =
SEQUENCE: 391
000

SEQ ID NO: 392        moltype =    length =
SEQUENCE: 392
000

SEQ ID NO: 393        moltype =    length =
SEQUENCE: 393
000

SEQ ID NO: 394        moltype =    length =
SEQUENCE: 394
000

SEQ ID NO: 395        moltype =    length =
SEQUENCE: 395
000

SEQ ID NO: 396        moltype =    length =
SEQUENCE: 396
000

SEQ ID NO: 397        moltype =    length =
SEQUENCE: 397
000

SEQ ID NO: 398        moltype =    length =
SEQUENCE: 398
000

SEQ ID NO: 399        moltype =    length =
SEQUENCE: 399
000

SEQ ID NO: 400        moltype =    length =

-continued

| | | |
|---|---|---|
| SEQUENCE: 400 000 | | |
| SEQ ID NO: 401 SEQUENCE: 401 000 | moltype = | length = |
| SEQ ID NO: 402 SEQUENCE: 402 000 | moltype = | length = |
| SEQ ID NO: 403 SEQUENCE: 403 000 | moltype = | length = |
| SEQ ID NO: 404 SEQUENCE: 404 000 | moltype = | length = |
| SEQ ID NO: 405 SEQUENCE: 405 000 | moltype = | length = |
| SEQ ID NO: 406 SEQUENCE: 406 000 | moltype = | length = |
| SEQ ID NO: 407 SEQUENCE: 407 000 | moltype = | length = |
| SEQ ID NO: 408 SEQUENCE: 408 000 | moltype = | length = |
| SEQ ID NO: 409 SEQUENCE: 409 000 | moltype = | length = |
| SEQ ID NO: 410 SEQUENCE: 410 000 | moltype = | length = |
| SEQ ID NO: 411 SEQUENCE: 411 000 | moltype = | length = |
| SEQ ID NO: 412 SEQUENCE: 412 000 | moltype = | length = |
| SEQ ID NO: 413 SEQUENCE: 413 000 | moltype = | length = |
| SEQ ID NO: 414 SEQUENCE: 414 000 | moltype = | length = |
| SEQ ID NO: 415 SEQUENCE: 415 000 | moltype = | length = |
| SEQ ID NO: 416 SEQUENCE: 416 000 | moltype = | length = |
| SEQ ID NO: 417 SEQUENCE: 417 000 | moltype = | length = |
| SEQ ID NO: 418 SEQUENCE: 418 000 | moltype = | length = |
| SEQ ID NO: 419 SEQUENCE: 419 000 | moltype = | length = |

```
SEQ ID NO: 420          moltype =    length =
SEQUENCE: 420
000

SEQ ID NO: 421          moltype =    length =
SEQUENCE: 421
000

SEQ ID NO: 422          moltype =    length =
SEQUENCE: 422
000

SEQ ID NO: 423          moltype = DNA   length = 333
FEATURE                 Location/Qualifiers
misc_feature            1..333
                        note = Synthetic Sequence
source                  1..333
                        mol_type = other DNA
                        organism = synthetic construct
SEQUENCE: 423
ggcggatctg gcggtagtgc tgagtattgt ctgagttacg aaacggaaat actcacggtt    60
gagtatgggc ttcttccaat tggcaaaatc gttgaaaagc gcatagagtg tacggtgtat   120
tccgtcgata caacggtaa tatctacacc cagccggtag ctcagtggca cgaccgaggc   180
gaacaggaag tgttcgagta ttgcttggaa gatggctccc ttatccgcgc cactaaagac   240
cataagttta tgacgttga cgggcagatg ctgcctatag cgaaatatt tgagagagag    300
ctggacttga tgagagtcga taatctgcca aat                                333

SEQ ID NO: 424          moltype = DNA   length = 180
FEATURE                 Location/Qualifiers
misc_feature            1..180
                        note = Synthetic Sequence
source                  1..180
                        mol_type = other DNA
                        organism = synthetic construct
SEQUENCE: 424
ggcggatctg gcggtagtgg gggttccgga tccataaaga tagctactag gaaatatctt    60
ggcaaacaaa acgtctatga cataggagtt gagcgagatc acaattttgc tttgaagaat   120
gggttcatcg cgtctaattg cttcaacgct agcggcgggt caggaggctc tggtggaagc   180

SEQ ID NO: 425          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 425
aatcgagaag cgactcgaca                                                 20

SEQ ID NO: 426          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 426
tgccctgcag gggagtgagc                                                 20

SEQ ID NO: 427          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 427
gaagcgactc gacatggagg                                                 20

SEQ ID NO: 428          moltype = DNA   length = 20
FEATURE                 Location/Qualifiers
misc_feature            1..20
                        note = Synthetic Sequence
source                  1..20
                        mol_type = other DNA
                        organism = synthetic construct
SEQUENCE: 428
cctgcagggg agtgagcagc                                                 20
```

| SEQ ID NO: 429 | moltype = AA length = 34 |
| --- | --- |
| FEATURE | Location/Qualifiers |
| source | 1..34 |
| | mol_type = protein |
| | organism = synthetic construct |

SEQUENCE: 429
LTPEQVVAIA SNGGGKQALE TVQRLLPVLC QAHG                                       34

| SEQ ID NO: 430 | moltype = DNA length = 157 |
| --- | --- |
| FEATURE | Location/Qualifiers |
| misc_feature | 1..157 |
| | note = Synthetic Sequence |
| source | 1..157 |
| | mol_type = other DNA |
| | organism = synthetic construct |

SEQUENCE: 430
ttaacacttg gattgcggga aacgagttaa gtcggctcgc gtgaattgcg cgtactccgc       60
gggagccgtc ttaactcggt tcatatagat ttgcggtgga gtgcgggaaa cgtgtaaact      120
cgggccgatt gtaactgcgt attaccaaat atttgtt                               157

| SEQ ID NO: 431 | moltype = DNA length = 157 |
| --- | --- |
| FEATURE | Location/Qualifiers |
| misc_feature | 1..157 |
| | note = Synthetic Sequence |
| source | 1..157 |
| | mol_type = other DNA |
| | organism = synthetic construct |

SEQUENCE: 431
ttaacacttg gattgcggga aacgagttaa gtcggctcgc gtgaattgcg cgtactccgc       60
gggagccgtc ttaactcggt tcatatagat ttgcggtgga gtgcgggaaa cgtgtaaact      120
cgggccgatt gtaactgcgt attaccaaat atttgtt                               157

| SEQ ID NO: 432 | moltype = DNA length = 212 |
| --- | --- |
| FEATURE | Location/Qualifiers |
| misc_feature | 1..212 |
| | note = Synthetic Sequence |
| source | 1..212 |
| | mol_type = other DNA |
| | organism = synthetic construct |

SEQUENCE: 432
aattatttat gtactgaata gataaaaaaa tgtctgtgat tgaataaatt ttcatttttt       60
acacaagaaa ccgaaaattt catttcaatc gaacccatac ttcaaaagat ataggcattt      120
taaactaact ctgattttgc gcgggaaacc taaataattg cccgcgccat cttatatttt      180
ggcgggaaat tcacccgaca ccgtagtgtt aa                                    212

| SEQ ID NO: 433 | moltype = DNA length = 212 |
| --- | --- |
| FEATURE | Location/Qualifiers |
| misc_feature | 1..212 |
| | note = Synthetic Sequence |
| source | 1..212 |
| | mol_type = other DNA |
| | organism = synthetic construct |

SEQUENCE: 433
aattatttat gtactgaata gataaaaaaa tgtctgtgat tgaataaatt ttcatttttt       60
acacaagaaa ccgaaaattt catttcaatc gaacccatac ttcaaaagat ataggcattt      120
taaactaact ctgattttgc gcgggaaacc taaataattg cccgcgccat cttatatttt      180
ggcgggaaat tcacccgaca ccgtagtgtt aa                                    212

| SEQ ID NO: 434 | moltype = DNA length = 33 |
| --- | --- |
| FEATURE | Location/Qualifiers |
| misc_feature | 1..33 |
| | note = Synthetic Sequence |
| source | 1..33 |
| | mol_type = other DNA |
| | organism = synthetic construct |

SEQUENCE: 434
tcccgcaatc caagtgttaa gcctaggcaa aag                                    33

| SEQ ID NO: 435 | moltype = AA length = 72 |
| --- | --- |
| FEATURE | Location/Qualifiers |
| source | 1..72 |
| | mol_type = protein |
| | organism = synthetic construct |
| VARIANT | 1..5 |
| | note = (Gly4Ser)n, where in n is 1-12 repetitions |

SEQUENCE: 435
GGGGSGGGGG SGGGGGSGGG GGSGGGGSG GGGGSGGGGG SGGGGGSGGG GSGGGGGSG       60
GGGGSGGGGG SG                                                          72

| SEQ ID NO: 436 | moltype = | length = |
|---|---|---|
| SEQUENCE: 436 000 | | |

What is claimed is:

1. A method for inserting a gene into the genome of a cell, comprising contacting the cell with a composition comprising a nucleic acid encoding a transposase enzyme, wherein the transposase enzyme comprises an amino acid sequence having at least 95% sequence identity to SEQ ID NO: 2 and has a non-polar aliphatic amino acid at position 2 of SEQ ID NO: 2,
wherein the transposase enzyme further comprises a substitution C13X2, wherein X2 is selected from lysine (K), arginine (R), and histidine (H).

2. The method of claim 1, wherein the non-polar aliphatic amino acid is selected from alanine (A), glycine (G), valine (V), leucine (L), isoleucine (I), and proline (P).

3. The method of claim 2, wherein the non-polar aliphatic amino acid is alanine (A).

4. The method of claim 1, wherein the transposase enzyme further comprises a substitution S8X1, wherein X1 is selected from alanine (A), glycine (G), valine (V), leucine (L), isoleucine (I), and proline (P).

5. The method of claim 4, wherein X1 is proline (P).

6. The method of claim 1, wherein X2 is arginine (R).

7. The method of claim 1, wherein the transposase enzyme does not have additional amino acid residues at the C terminus relative to SEQ ID NO: 2.

8. The method of claim 1, wherein the transposase enzyme comprises an amino acid sequence having at least 98% identity to SEQ ID NO: 2.

9. The method of claim 1, wherein the nucleic acid further encodes a transcription activator-like effector (TALE) DNA binding domain (DBD), or a nuclease-deficient Cas9 (dCas9) connected to the transposase enzyme.

10. The method of claim 9, wherein the transposase enzyme is capable of inserting a transposon at a TA dinucleotide site or a TTAA tetranucleotide site in a genomic safe harbor site (GSHS) of the genome.

11. The method of claim 10, wherein the TALE DBD or dCas9 is suitable for directing the transposase enzyme to the GSHS sequence.

12. The method of claim 11, wherein the GSHS is selected from adeno-associated virus site 1 (AAVS1), chemokine (C-C motif) receptor 5 (CCR5) gene, and human Rosa26 locus.

13. The method of claim 1, wherein the nucleic acid is co-formulated with a nucleic acid encoding a transposon comprising the gene.

14. The method of claim 13, wherein the composition is in the form of a lipid nanoparticle (LNP).

15. A method for inserting a gene into the genome of a cell, comprising contacting the cell with a composition comprising a nucleic acid encoding a transposase enzyme,
wherein the transposase enzyme comprises an amino acid sequence having at least 95% sequence identity to SEQ ID NO: 2 and has a non-polar aliphatic amino acid at position 2 of SEQ ID NO: 2, wherein the transposase enzyme further comprises a substitution N125X3, wherein X3 is selected from is selected from lysine (K), arginine (R), and histidine (H).

16. The method of claim 15, wherein X3 is lysine (K).

17. The method of claim 15, wherein the non-polar aliphatic amino acid is selected from alanine (A), glycine (G), valine (V), leucine (L), isoleucine (I), and proline (P).

18. The method of claim 15, wherein the nucleic acid further encodes a transcription activator-like effector (TALE) DNA binding domain (DBD), or a nuclease-deficient Cas9 (dCas9) connected to the transposase enzyme.

19. A method for inserting a gene into the genome of a cell, comprising contacting the cell with a composition comprising a nucleic acid encoding a transposase enzyme,
wherein the transposase enzyme comprises an amino acid sequence having at least 95% sequence identity to SEQ ID NO: 2 and has a non-polar aliphatic amino acid at position 2 of SEQ ID NO: 2, wherein the transposase enzyme further comprises two or more of substitutions S8P, C13R, and N125K.

20. The method of claim 19, wherein the non-polar aliphatic amino acid is selected from alanine (A), glycine (G), valine (V), leucine (L), isoleucine (I), and proline (P).

21. The method of claim 20, wherein the nucleic acid further encodes a transcription activator-like effector (TALE) DNA binding domain (DBD), or a nuclease-deficient Cas9 (dCas9) connected to the transposase enzyme.

22. A method for inserting a gene into the genome of a cell, comprising contacting the cell with a composition comprising a first nucleic acid encoding a transposase enzyme and a DNA binding domain and a second nucleic acid encoding a transposon,
wherein the transposase enzyme comprises an amino acid sequence having at least 97% sequence identity to SEQ ID NO: 2 and comprises two or more of substitutions of S8P, C13R, and N125K,
wherein the transposase enzyme is operatively linked to the DNA binding domain, and
wherein the first nucleic acid and second nucleic acid are contained in a LNP.

23. The method of claim 22, wherein the DNA binding domain is a TALE DBD.

24. The method of claim 22, wherein the DNA binding domain is a dCas9.

25. The method of claim 23, wherein the transposase enzyme does not have additional amino acid residues at the C terminus relative to SEQ ID NO: 2.

26. The method of claim 25, wherein the substitutions are S8P and C13R.

27. The method of claim 24, wherein the transposase enzyme does not have additional amino acid residues at the C terminus relative to SEQ ID NO: 2.

28. The method of claim 27, wherein the substitutions are S8P and C13R.

* * * * *